US 12,240,857 B2
Mar. 4, 2025

(12) United States Patent
Plewe et al.

(54) ADAMANTANE DERIVATIVES FOR THE TREATMENT OF FILOVIRUS INFECTION

(71) Applicant: Arisan Therapeutics Inc., Carlsbad, CA (US)

(72) Inventors: Michael Bruno Plewe, San Diego, CA (US); Eric Brown, San Diego, CA (US); Vidyasagar Gantla, San Diego, CA (US); Gregory Henkel, San Diego, CA (US); Kenneth McCormack, San Diego, CA (US); Nadezda Sokolova, San Diego, CA (US)

(73) Assignee: Arisan Therapeutics Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/033,636

(22) Filed: Jul. 12, 2018

(65) Prior Publication Data
US 2020/0017514 A1   Jan. 16, 2020

Related U.S. Application Data

(63) Continuation-in-part of application No. PCT/US2017/013560, filed on Jan. 13, 2017.

(51) Int. Cl.
| | |
|---|---|
| *C07D 487/10* | (2006.01) |
| *A61P 31/14* | (2006.01) |
| *C07C 233/62* | (2006.01) |
| *C07D 205/04* | (2006.01) |
| *C07D 207/12* | (2006.01) |
| *C07D 211/98* | (2006.01) |
| *C07D 295/195* | (2006.01) |
| *C07D 487/08* | (2006.01) |

(52) U.S. Cl.
CPC ............ *C07D 487/10* (2013.01); *A61P 31/14* (2018.01); *C07C 233/62* (2013.01); *C07D 205/04* (2013.01); *C07D 207/12* (2013.01); *C07D 211/98* (2013.01); *C07D 295/195* (2013.01); *C07D 487/08* (2013.01); *C07C 2603/74* (2017.05)

(58) Field of Classification Search
CPC .. C07D 487/10; C07D 205/04; C07D 207/12; C07D 211/98; C07D 295/195; C07D 487/08; A61P 31/14; C07C 233/62; C07C 2603/74

See application file for complete search history.

(56) References Cited

U.S. PATENT DOCUMENTS

| | | |
|---|---|---|
| 3,300,480 A | 1/1967 | Narayanan |
| 3,383,423 A | 5/1968 | Moore |
| 3,663,565 A | 5/1972 | Krimmel |
| 3,816,509 A | 6/1974 | Krimmel |
| 4,052,439 A | 10/1977 | Herrin |
| 4,087,522 A | 5/1978 | Von Esch |
| 4,100,170 A | 7/1978 | Shetty |
| 4,351,847 A | 9/1982 | Griffith |
| 4,357,351 A | 11/1982 | Fancher |
| 4,386,105 A | 5/1983 | Kinsolving |
| 4,486,601 A | 12/1984 | Kinsolving |
| 4,537,908 A | 8/1985 | Griffith |
| 4,829,086 A | 5/1989 | Bodor |
| 4,910,190 A | 3/1990 | Bergeson |
| 5,061,703 A * | 10/1991 | Bormann .................. A61P 9/00 514/662 |
| 5,124,473 A | 6/1992 | Shroot |
| 5,135,926 A | 8/1992 | Bodor |
| 5,424,414 A | 6/1995 | Mattingly |
| 5,486,597 A | 1/1996 | Kalindjian |
| 5,498,795 A | 3/1996 | Song |
| 5,506,256 A | 4/1996 | Kobayashi |
| 5,658,923 A | 8/1997 | Takahashi |
| 5,670,526 A | 9/1997 | Dodd |
| 5,696,267 A | 12/1997 | Reichard |
| 5,872,138 A | 2/1999 | Naylor-Olsen |

(Continued)

FOREIGN PATENT DOCUMENTS

| | | |
|---|---|---|
| CN | 104610112 A | 5/2015 |
| CN | 104693039 A | 6/2015 |

(Continued)

OTHER PUBLICATIONS

CAS Registry No. 377770-50-8 (2001) (Year: 2001).*
CAS Abstract of E. Boreka et al., Mol. Biol. Virusov, Khimioter. Khimioprofil. Virusn. Infekts., Mater. Ob'edin. Sess. Otd. Gig., Mikrobiol. Epidemiol. Akad. Med. Nauk SSSR Beloruss. Inst. Epidemiol. Mikrobiol. (1974) (Year: 1974).*
CAS Registry No. 1317582-53-8 (2011) (Year: 2011).*
STN Registry. Registry No. 2178427-45-5. Published in Registry on Feb. 22, 2018. (Year: 2018).*
STN Registry. Registry No. 134562-65-5. Published in Registry on Jun. 28, 1991. (Year: 1991).*

(Continued)

*Primary Examiner* — Robert H Havlin
*Assistant Examiner* — Lauren Wells

(57) ABSTRACT

Compounds of structural Formula I were developed for the treatment of infections by filoviruses including Ebolavirus and Marburgvirus, wherein, $R^1$, $R^2$, $R^3$, X and Y are defined in the specification.

20 Claims, 1 Drawing Sheet

(56) References Cited

U.S. PATENT DOCUMENTS

| | | | |
|---|---|---|---|
| 5,914,339 A | 6/1999 | Sum | |
| 6,191,165 B1 | 2/2001 | Ognyanov | |
| 6,207,665 B1 | 3/2001 | Bauman | |
| 6,235,737 B1 | 5/2001 | Styczynski | |
| 6,462,064 B1 | 10/2002 | Pfahl | |
| 7,338,961 B2 * | 3/2008 | Smith | C07C 49/323 514/277 |
| 7,511,175 B2 | 3/2009 | Patel | |
| 7,803,559 B1 | 9/2010 | Diamond | |
| 8,030,296 B2 | 10/2011 | Potter | |
| 8,063,248 B2 * | 11/2011 | Smith | C07C 49/323 544/382 |
| 8,557,800 B2 * | 10/2013 | Smith | C07C 49/323 514/195 |
| 9,301,950 B2 | 4/2016 | Degrado | |
| 9,452,992 B2 * | 9/2016 | Cunningham | C07D 295/185 |
| 9,974,800 B2 * | 5/2018 | Fathi | A61K 31/435 |
| 2002/0115883 A1 | 8/2002 | Ogata | |
| 2002/0197285 A1 | 12/2002 | Bonda | |
| 2003/0186967 A1 | 10/2003 | Kees | |
| 2003/0229065 A1 | 12/2003 | Levy | |
| 2004/0048847 A1 | 3/2004 | Lino | |
| 2004/0087658 A1 | 5/2004 | Moebius | |
| 2004/0116423 A1 | 6/2004 | Nivorozhkin | |
| 2004/0204379 A1 | 10/2004 | Cheng | |
| 2004/0209858 A1 | 10/2004 | Bennani | |
| 2005/0113458 A1 | 5/2005 | Gupta | |
| 2005/0124678 A1 | 6/2005 | Levy | |
| 2005/0192358 A1 | 9/2005 | Georgiev | |
| 2006/0149070 A1 | 7/2006 | Rohde | |
| 2006/0241187 A1 | 10/2006 | Chern | |
| 2006/0270630 A1 | 11/2006 | Smith | |
| 2006/0270631 A1 | 11/2006 | Smith | |
| 2006/0287317 A1 | 12/2006 | Smith | |
| 2007/0135388 A1 | 6/2007 | Makriyannis | |
| 2007/0225283 A1 | 9/2007 | Hammock | |
| 2007/0249621 A1 | 10/2007 | Wolf | |
| 2008/0021088 A1 | 1/2008 | Dalavalle | |
| 2008/0206548 A1 | 8/2008 | Enoki | |
| 2008/0234249 A1 | 9/2008 | Ye | |
| 2009/0143390 A1 | 6/2009 | Cincotta | |
| 2009/0163545 A1 | 6/2009 | Goldfarb | |
| 2009/0192198 A1 | 7/2009 | Bitner | |
| 2009/0218935 A1 | 9/2009 | Sotoyama | |
| 2009/0264401 A1 | 10/2009 | Gill | |
| 2010/0160250 A1 | 6/2010 | Douglass | |
| 2010/0216785 A1 | 8/2010 | Lazzari | |
| 2010/0226943 A1 | 9/2010 | Brennan | |
| 2010/0298352 A1 | 11/2010 | Prochownik | |
| 2011/0014699 A1 | 1/2011 | Wender | |
| 2011/0065762 A1 | 3/2011 | Wang | |
| 2011/0065766 A1 | 3/2011 | Wang | |
| 2011/0136861 A1 | 6/2011 | Rao | |
| 2011/0244472 A1 | 10/2011 | Prochownik | |
| 2011/0306552 A1 | 12/2011 | Rao | |
| 2011/0319459 A1 | 12/2011 | Gupta | |
| 2012/0020922 A1 | 1/2012 | Jordan | |
| 2012/0022080 A1 | 1/2012 | Miyata | |
| 2012/0059162 A1 | 3/2012 | Kusakabe | |
| 2012/0095004 A1 | 4/2012 | Smith | |
| 2012/0122870 A1 * | 5/2012 | Smith | A61K 31/425 514/428 |
| 2012/0135954 A1 | 5/2012 | Schang | |
| 2012/0157494 A1 | 6/2012 | Harris | |
| 2012/0202756 A1 | 8/2012 | Franklin | |
| 2012/0252799 A1 | 10/2012 | Yu | |
| 2012/0264708 A1 | 10/2012 | Mitchell | |
| 2012/0289500 A1 | 11/2012 | Brown | |
| 2013/0040953 A1 | 2/2013 | Paller | |
| 2013/0072553 A1 | 3/2013 | Xu | |
| 2013/0108964 A1 | 5/2013 | Ohsawa | |
| 2013/0203775 A1 | 8/2013 | Yeung | |
| 2013/0231391 A1 | 9/2013 | Shetty | |
| 2013/0338145 A1 | 12/2013 | Mitchell | |
| 2013/0345127 A1 | 12/2013 | Boehme | |
| 2014/0073631 A1 | 3/2014 | Shetty | |
| 2014/0243544 A1 | 8/2014 | Wang | |
| 2014/0271996 A1 | 9/2014 | Prakash | |
| 2014/0275263 A1 | 9/2014 | Wassel | |
| 2014/0357611 A1 | 12/2014 | Palczewski | |
| 2015/0018326 A1 | 1/2015 | Jiang | |
| 2015/0056165 A1 | 2/2015 | Or | |
| 2015/0166532 A1 | 6/2015 | Gray | |
| 2015/0175648 A1 | 6/2015 | Kalayanov | |

FOREIGN PATENT DOCUMENTS

| | | | | |
|---|---|---|---|---|
| CN | 104693085 A | | 6/2015 | |
| EP | 0392059 A1 | | 10/1990 | |
| WO | 9429329 A1 | | 12/1994 | |
| WO | 0134610 A1 | | 5/2001 | |
| WO | WO-0134619 A1 * | | 5/2001 | C07H 19/16 |
| WO | 2004056745 A2 | | 7/2004 | |
| WO | 2006048750 A2 | | 5/2006 | |
| WO | 2007112914 A2 | | 10/2007 | |
| WO | 2007113634 A1 | | 10/2007 | |
| WO | WO-2009072643 A1 * | | 6/2009 | C07D 211/58 |
| WO | 2010111713 A2 | | 3/2010 | |
| WO | 2010097641 A1 | | 9/2010 | |
| WO | 2010129954 A1 | | 11/2010 | |
| WO | 2011014009 A2 | | 2/2011 | |
| WO | 2011058582 A1 | | 5/2011 | |
| WO | 2011068927 A2 | | 6/2011 | |
| WO | 2011160024 A2 | | 12/2011 | |
| WO | 2012136859 A1 | | 10/2012 | |
| WO | 2013022550 A2 | | 2/2013 | |
| WO | 2015057068 A1 | | 4/2015 | |
| WO | WO-2017127306 A1 * | | 7/2017 | A61K 31/165 |
| WO | WO-2018006074 A2 * | | 1/2018 | A61K 31/496 |

OTHER PUBLICATIONS

STN Registry. Registry No. 134562-68-8. Published in Registry on Jun. 28, 1991. (Year: 1991).*
PCT International Search Report for PCT International Application No. PCT/US2017/013560.
Search History for PCT Application No. PCT/US2017/013560.
Handa et al., Synthesis of 3-Aryl-1-adamantanemethylamines, Journal of Chemical and Engineering Data, 1984, pp. 223-225, vol. 29, No. 2, American Chemical Society, USA.
Šilhar et al., Evaluation of adamantane hydroxamates as botulinum neurotoxin inhibitors: Synthesis, crystallography, modeling, kinetic and cellular based studies, Bioorganic & Medicinal Chemistry, 2013, pp. 1344-1348, vol. 21, Elsevier, Netherlands.

Shokova et al., p-(3-Carboxy- and 3-carboxymethyl-1-adamantyl)calix[4]arenes: synthesis and arming with amino acid units, Tetrahedron Letters, 2004, pp. 6465-6469, vol. 45, Elsevier, Netherlands.

Safonova et al., Synthesis and Biological Activity of 5-(Adamant-1-YL)Salicylic Acid, 3-(4-Hydroxyphenyl)Adamantanecarboxylic Acid and Some of Their Derivatives, Pharmaceutical Chemistry Journal, 1989, pp. 760-765, vol. 23, No. 9, Kluwer Academic/ Plenum Publishers, USA.

Graf et al., Targeting Ceramide Metabolism with a Potent and Specific Ceramide Kinase Inhibitor, Molecular Pharmacology, 2008, pp. 925-932, vol. 74, No. 4, The American Society for Pharmacology and Experimental Therapeutics, USA.

Min et al., A novel class of highly potent multidrug resistance reversal agents: Disubstituted adamantyl derivatives, Bioorganic & Medicinal Chemistry Letters, 2009, pp. 5376-5379, vol. 19, Elsevier, Netherlands.

Gadhe et al., Various Partial Charge Schemes on 3D-QSAR Models for P-gp Inhibiting Adamantyl Derivatives, Bull. Korean Chem. Soc, 2011, pp. 1604-1612, vol. 32, No. 5, Korean Chemical Society, Korea.

Koperniku et al., Synthesis and trypanocidal action of new adamantane substituted imidazolines, Med. Chem. Commun., 2013, pp. 856-859, vol. 4, The Royal Society of Chemistry, UK.

(56) References Cited

OTHER PUBLICATIONS

Webster et al., Discovery and biological evaluation of adamantyl amide 11b-HSD1 inhibitors, Bioorganic & Medicinal Chemistry Letters, 2007, pp. 2838-2843, vol. 17, Elsevier, Netherlands.
Danilenko et al., Synthesis and biological activity of adamantane derivatives. IV. Viral inhibiting activity of some adamantylamines, Pharmaceutical Chemistry Journal, 1976, pp. 737-741, vol. 10, No. 6, Kluwer Academic/Plenum Publishers, USA.
Danilenko et al., Synthesis and biological activity of adamantane derivatives V. virus-inhibiting action of arylamides of adamantane carboxylic acids, Pharmaceutical Chemistry Journal, 1976, pp. 901-904, vol. 10, No. 7, Kluwer Academic/Plenum Publishers, USA.
Ogawa et al., 3'-Functionalized Adamantyl Cannabinoid Receptor Probes, Journal of Medicinal Chemistry 2015, pp. 3104-3116, vol. 58, American Chemical Society, USA.
Lee et al., Inhibition of Ebola Virus Infection: Identification of Niemann-Pick C1 as the Target by Optimization of a Chemical Probe, ACS Med. Chem. Lett., 2013, pp. 239-243, vol. 4, American Chemical Society, USA.
Adamczyc et al., Synthesis of hapten-phosphoramidites from 2'-deoxyuridine, Tetrahedron, 2003, pp. 5749-5761, vol. 59, Elsevier Science, Netherlands.
Aldrich et al., Antiviral Agents. 2.' Structure-Activity Relationships of Compounds Related to 1-Adamantanamine, Journal of Medicinal Chemistry, 1971, pp. 535-543, vol. 14, No. 6, American Chemical Society, USA.
Badarau et al., Development of Potent and Selective Tissue Transglutaminase Inhibitors: Their Effect on TG2 Function and Application in Pathological Conditions, Chemistry & Biology, 2015, pp. 1-15, vol. 22, Elsevier, Netherlands.
Fino et al., A Convenient Method for the Preparation of Hapten Phosphoramidites, Bioconjugate Chem., 1996, pp. 274-280, vol. 7, American Chemical Society, USA.
Kennedy, A mild and general one-pot preparation of cyanoethyl-protected tetrazoles, Tetrahedron Letters, 2010, pp. 2010-2013, vol. 51, Elsevier, Netherlands.
Motornaya et al., Adamantylcalixarenes with CMPO groups at the wide rim: synthesis and extraction of lanthanides and actinides, Tetrahedron, 2007, pp. 4748-4755, vol. 63, Elsevier, Netherlands.
Shmailov et al., Synthesis of functionalized 5-(3-R-1-adamantyl)uracils and related compounds, Tetrahedron, 2010, pp. 3058-3064, vol. 66, Elsevier, Netherlands.
Danilenko et al., Synthesis and Protective Properties of Phenyladamantane With Respect to Rabies Virus, Pharmaceutical Chemistry Journal, 1998, pp. 83-85, vol. 32, No. 2, Kluwer Academic/Plenum Publishers, USA.
Prokopov et al., Models of Retention of Adamantylamidrazones in Reversed-Phase High-Performance Liquid Chromatography, Russian Journal of Physical Chemistry A, 2011, pp. 845-850, vol. 85, No. 5, Pleiades Publishing, Russia.
Popov et al., Synthesis and Properties of Carbocyclic Schiff Bases, Russian Journal of Organic Chemistry, 2002, p. 350-354, vol. 38, No. 3, Kluwer Academic/Plenum Publishers, USA.
Lavrova et al., Synthesis and Radioprotective Activity of Some Derivatives of N-(3-Aryladamant-1-Ylmethyl) Mercaptoacetamidine, Pharmaceutical Chemistry Journal, 1993, pp. 585-588, vol. 27, No. 8, Kluwer Academic/Plenum Publishers, USA.
Tseng et al., N-[(Aryladamantyl)alkyl]-2-mercaptoacetamidines, their corresponding disulfides and S-phosphorothioates, Tetrahedron, 1988, pp. 1893-1904, vol. 44, Elsevier, UK.
Fan et al., Ligand-Promoted Pd(II)-Catalyzed Functionalization of Unactivated C(sp3)-H Bond: Regio- and Stereoselective Synthesis of Arylated Rimantadine Derivatives, ACS Catalysis, 2016, pp. 769-774, vol. 6, American Chemical Society, USA.
Larrosa et al., C-H Bond Arylation of Diamondoids Catalyzed by Palladium(II) Acetate, Adv. Synth. Catal., 2016, pp. 2163-2171, vol. 358, Wiley-VCH, Germany.
Chakrabarti et al., Chemistry of Adamantane. Part 1II.t The Synthesis and Reactions of 1,2-Disubstituted Adamantane Derivatives, J. Chem. Soc. (C), 1970, pp. 1303-1309, Chemical Society, UK.
Lao et al., Palladium-catalyzed methylene C(sp3)-H arylation of the adamantyl scaffold, Org. Chem. Front., 2015, pp. 1374-1378, vol. 2, Royal Society of Chemistry, UK.
Gopalan et al., Discovery of adamantane based highly potent HDAC inhibitors, Bioorganic & Medicinal Chemistry Letters, 2013, pp. 2532-2537, vol. 23, Elsevier, Netherlands.
Sorenser et al., Adamantane sulfone and sulfonamide 11-b-HSD1 Inhibitors, Bioorganic & Medicinal Chemistry Letters, 2007, pp. 527-532, 17, Elsevier, Netherlands.
Yusuff et al., Lipophilic Isosteres of a π-π Stacking Interaction: New Inhibitors of the Bcl-2-Bak Protein-Protein Interaction, ACS Med. Chem. Lett., 2012, pp. 579-583, vol. 3, American Chemical Society, USA.
Luzhkov et al., Virtual screening and bioassay study of novel inhibitors for dengue virus mRNA cap (nucleoside-2'O)-methyltransferase, Bioorganic & Medicinal Chemistry, 2007, pp. 7795-7802, vol. 15, Elsevier, Netherlands.
Shokova et al., Adamantylation and Adamantylalkylation of Amides, Nitriles and Ureas in Trifluoroacetic Acid, Synthesis, 1997, pp. 1034-1040, No. 9, Thieme Publishing Group, Germany.
Kau et al., A chemical genetic screen identifies inhibitors of regulated nuclear export of a Forkhead transcription factor in PTEN-deficient tumor cells, Cancer Cell, 2003, pp. 463-476, Cell Press, USA.
Goode et al., Identification of Promiscuous Small Molecule Activators in High-Throughput Enzyme Activation Screens, J. Med. Chem., 2008, pp. 2346-2349, vol. 51, American Chemical Society, USA.
Ohta et al., Novel estrogen receptor (ER) modulators containing various hydrophobic bent-core structures, Bioorganic & Medicinal Chemistry 2014, pp. 3508-3514, vol. 22, Elsevier, Netherlands.
Puchnin et al., Calix[4]tubes: An Approach to Functionalization, Chem. Eur. J., 2012, pp. 10954-10968, vol. 18, Wiley-VCH, Germany.
Wintgens et al., Smart DNA Vectors Based on Cyclodextrin Polymers: Compaction and Endosomal Release, Pharm. Res., 2012, pp. 384-396, vol. 29, Springer, USA.
Korotkii et al., Synthesis and Antimicrobial and Antifungal Activities of Quaternary Salts of Adamantane-Containing Alkoxydialkylaminopropanols, Pharmaceutical Chemistry Journal, 2011, pp. 19-21, vol. 45, No. 1, Kluwer Academic/Plenum Publishers, USA.
Wennekes et al., Synthesis and evaluation of dimeric lipophilic iminosugars as inhibitors of glucosylceramide metabolism, Tetrahedron: Asymmetry 2009, pp. 836-846, vol. 20, Elsevier, Netherlands.
Ilies et al., Carbonic anhydrase inhibitors: aromatic and heterocyclic sulfonamides incorporating adamantyl moieties with strong anticonvulsant activity, Bioorganic & Medicinal Chemistry, 2004, pp. 2717-2726, vol. 12, Elsevier, Netherlands.
Smith et al., Novel Carvedilol Analogues That Suppress Store-Overload-Induced Ca2+ Release, J. Med. Chem., 2013, pp. 8626-8655, vol. 56, American Chemical Society, USA.
Shiryaev et al., Synthesis and Antiviral Activity of Adamantyloxiranes and Their Derivatives, Pharmaceutical Chemistry Journal, 1990, pp. 339-343, vol. 24, No. 5, Kluwer Academic/Plenum Publishers, USA.
Wang et al., Organocatalytic asymmetric Michael addition of aldehydes and ketones to nitroalkenes catalyzed by adamantoyl L-prolinamide, RSC Adv., 2015, pp. 5863-5874, vol. 5, The Royal Society of Chemistry, UK.
Giannini et al., New retinoid derivatives as back-ups of Adarotene, Bioorganic & Medicinal Chemistry, 2012, pp. 2405-2415, vol. 20, Elsevier, Netherlands.
Šolaja et al., Novel 4-Aminoquinolines Active against Chloroquine-Resistant and Sensitive P. falciparum Strains that also Inhibit Botulinum Serotype A, J. Med. Chem., 2008, pp. 4388-4391, vol. 51, American Chemical Society, USA.
Kolocouris et al., Synthesis and Antiviral Activity Evaluation of Some Aminoadamantane Derivatives, J. Med. Chem., 1994, pp. 2896-2902, vol. 37, American Chemical Society, USA.
Supplementary Partial European Search Report for Application No. EP 17741793.

(56) References Cited

OTHER PUBLICATIONS

Côté et al., Small molecule inhibitors reveal Niemann-Pick C1 is essential for Ebola virus infection, Nature, 2011, pp. 344-348, vol. 477, Nature Research, UK.
De Clercq, Ebola virus (EBOV) infection: Therapeutic strategies, Biochemical Pharmacology, 2015, pp. 1-10, vol. 93, Elsevier, Netherlands.

* cited by examiner

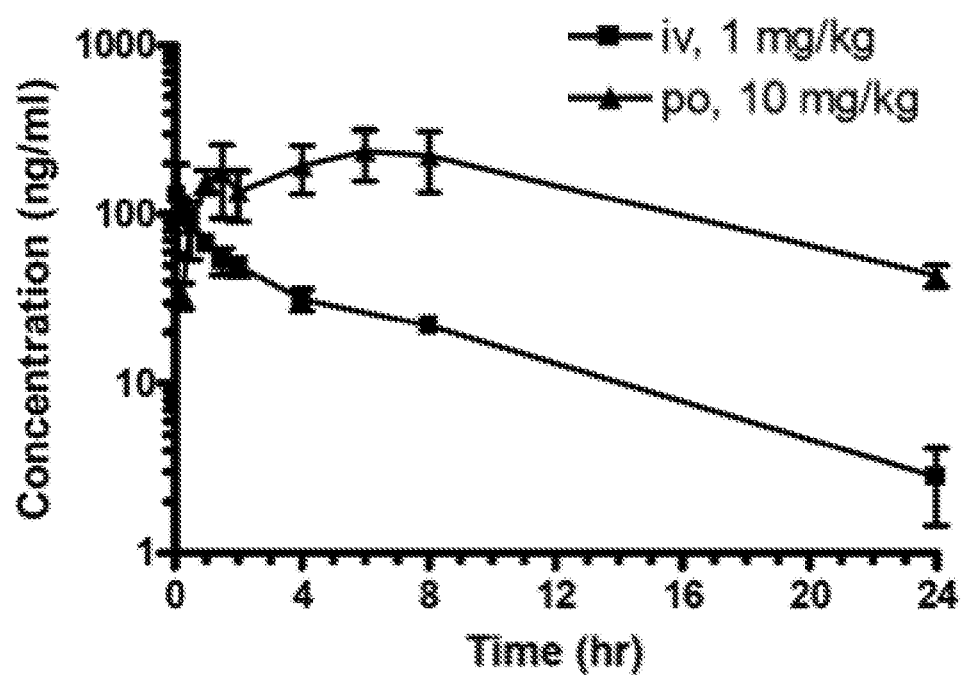

ADAMANTANE DERIVATIVES FOR THE TREATMENT OF FILOVIRUS INFECTION

CROSS REFERENCES TO RELATED APPLICATIONS

This patent application is a continuation in part of and claims the benefit of priority to United States Provisional Patent Applications serial numbers 62/279,917 filed Jan. 18, 2016 and 62/351,839 filed Jun. 17, 2017, both applications are herein incorporated by reference for all purposes, and PCT Application number PCT/US2017/013560 filed Jan. 13, 2017, herein incorporated by reference for all purposes.

GOVERNMENT SUPPORT

This invention was made with government support under R43 AI118207 awarded by U.S. National Institutes of Health. The government has certain rights in the invention.

REFERENCE TO A "SEQUENCE LISTING, A TABLE, OR A COMPUTER PROGRAM LISTING APPENDIX SUBMITTED ON A COMPACT DISK

NOT APPLICABLE

FIELD OF THE INVENTION

The present invention relates to methods of inhibiting infection by viruses of the Filoviridae family (filoviruses) in humans, other mammals, or in cell culture, to treating infection by filoviruses, to methods of inhibiting the replication of filoviruses, to methods of reducing the amount of filoviruses, and to compositions that can be employed for such methods. These methods, applications, and compositions apply not only to Filoviridae viruses but also to any virus, whether naturally emerging or engineered, whose cell entry properties are determined by filovirus glycoproteins.

BACKGROUND OF THE INVENTION

The invention relates to the use of compounds for the treatment and/or prophylaxis of infection of humans or other mammals by one or more of a number of enveloped viruses of the Filoviridae family (filoviruses) or any other native or engineered enveloped virus utilizing filovirus glycoproteins to mediate cell entry. Enveloped viruses are comprised of an outer host-derived lipid membrane and an inner nucleoprotein core, which contains the viral genetic material (whether RNA or DNA). Virus-cell fusion is the means by which all enveloped viruses enter cells and initiate disease-causing cycles of replication. In all cases virus-cell fusion is executed by one or more viral surface glycoproteins that are anchored within the lipid membrane envelope. One or more glycoproteins from a given virus may form a glycoprotein complex that interacts with a number of different surface and/or intracellular receptors of infected host cells to initiate the association between virus and host cell. However, one glycoprotein is generally denoted as the protein primarily driving the fusion of viral and host cell membranes. At least three distinct classes of viral membrane fusion proteins have been determined (classes I, II, and III) [Weissenhorn, W.; Carfi, A.; Lee, K. H.; Skehel, J. J., and Wiley, D. C. *Crystal structure of the Ebola virus membrane fusion subunit, GP2, from the envelope glycoprotein ectodomain.* Mol. Cell (1998) 2:605-616; White, J. M.; Delos, S. E.; Brecher, M.; Schornberg K. *Structures and mechanisms of viral membrane fusion proteins: multiple variations on a common theme.* Crit. Rev. Biochem. Mol. Biol. (2008) 43:189-219; Igonet, S.; Vaney, M. C.; Vonrhein, C.; Bricogne, G.; Stura, E. A.; Hengartner H.; Eschli, B.; Rey, F. A. *X-ray structure of the arenavirus glycoprotein GP2 in its postfusion hairpin conformation*, Proc. Natl. Acad. Sci. (2011) 108:19967-19972]. Class I fusion proteins are found in viruses from the Orthomyxoviridae, Retroviridae, Paramyxoviridae, Coronaviridae, Filoviridae, and Arenaviridae families, Class II proteins from Togaviridae, Flaviviridae, and Bunyaviridae while Class III or other types are from Rhadboviridae, Herpesviridae, Poxviridae, and Hepadnaviridae.

Given that viral cell entry is an essential step in the viral replication process the identification of compounds that inhibit virus cell entry could provide attractive antivirals for viruses that are pathogenic to humans and/or other mammals. Chemical compounds that act as inhibitors of one enveloped virus may also act as inhibitors of other enveloped viruses. However, while enveloped

TABLE 1

Family and Genera of Envelope Viruses and Glycoprotein Classification

| Envelope Virus Family | Genera | Examples of pathogenic species | Glycoprotein Class |
|---|---|---|---|
| Orthomyxoviridae | Influenza virus A, B, C | Influenza A virus | I |
| Filoviridae | Ebolavirus | Zaire virus: Bundibugyo; Sudan; Tai Forest | I |
| | Marburgvirus | Marburg virus | |
| Arenaviridae | Mammarenavirus | Lassa virus; Junin; Machupo; Guanarito | I |
| Coronaviridae | Batacoronaviruses | SARS virus; MERS; HKU-1; OC43 | I |
| Flaviviridae | Flavivirus | Dengue virus; Yellow Fever; West Nile; Japanese encephalitis | II |
| Bunyaviridae | Hantavirus | Andes virus | II |
| | Orthobunyavirus | Bunyamwera virus | |
| | Phlebovirus | Rift Valley fever virus | |
| | Nairovirus | Crimean-Congo hemorrhagic fever virus | |
| Togaviridae | Alphavirus | Chikungunya virus; Sindbis virus | II |
| Paramyxoviridae | Rubulavirus | Mumps virus | I |
| | Morbillivirus | Measles virus | |
| | Pneumovirus | Respiratory syncitial virus | |
| | Henipavirus | Hendra virus; Nipah | |
| Herpesviridae | Cytomegalovirus | Human CMV | III |
| | Simplexvirus | HSV-1; HSV-2 | |
| | Varicellovirus | HHV-3 (Varicella zoster virus) | |
| | Roseolovirus | HHV-6; HHV-7 | |
| | Lymphocryptovirus | Epstein-Barr virus | |
| | Rhadinovirus | Kaposi's sarcoma-associated herpesvirus | | viruses share some common functional and structural features with regard to glycoprotein-dependent cell entry and fusion the specific host targets and mechanisms of cell entry differ among enveloped viruses: between and even within different virus families as a function of their unique glycoprotein (GP) sequences and structures, and the cellular host proteins that they interact with [White, J. M.; Delos, S. E.; Brecher, M., Schornberg K. *Structures and mechanisms of viral membrane fusion proteins: multiple variations on a common theme.* Crit. Rev. Biochem. Mol. Biol. (2008)

43:189-219]. The invention described herein relates to the use of compounds for the treatment and/or prophylaxis of infection as mediated by the cell entry and fusion process of filovirus glycoproteins whether native or engineered.

One viral expression system that may be utilized to identify inhibitors of enveloped viruses based on their glycoprotein sequences and functional properties is the vesicular stomatitis virus (VSV) system. This approach uses VSV, a virus in the Rhadboviridae family (expressing Class III fusion proteins), lacking a native VSV glycoprotein. "Pseudotyped" viruses that are infective and functionally replicative in cell culture can be generated by substituting the VSV glycoprotein with a glycoprotein originating from other enveloped viruses. The cell entry properties and functions of these pseudotyped viruses are determined by the viral glycoprotein that has been introduced. The cell entry and infectivity properites of pseudotyped VSV viruses have been shown to be determined by the introduced glycoprotein from a host of envelope viruses including Ebola, Lassa, Hanta, Hepatitis B, and other viruses [Ogino, M., et al. *Use of vesicular stomatitis virus pseudotypes bearing hantaan or seoul virus envelope proteins in a rapid and safe neutralization test*. Clin. Diagn. Lab. Immunol (2003) 10(1):154-60; Saha, M. N., et al., *Formation of vesicular stomatitis virus pseudotypes bearing surface proteins of hepatitis B virus*. J. Virol (2005) 79(19):12566-74; Takada, A., et al., *A system for functional analysis of Ebola virus glycoprotein*, Proc. Natl. Acad. Sci. (1997) 94:14764-69; Garbutt, M., et al., *Properties of replication-competent vesicular stomatitis virus vectors expressing glycoproteins of filoviruses and arenaviruses*. J. Virol. (2004) 78(10):5458-65]. When the pseudotype virion also expresses a reporter gene such as green fluorescent protein (GFP) or *Renilla* luciferase, virion infectivity and replication may be monitored using high-throughput optical methods in cultured mammalian cell lines, including Vero and HEK-293 cells [Cote, M.; Misasi, J.; Ren, T.; Bruchez, A., Lee, K., Filone, C. M.; Hensley, L.; Li, Q.; Ory, D.; Chandran, K.; Cunningham, J., *Small molecule inhibitors reveal Niemann-Pick C1 is essential for Ebola virus infection*, Nature (2011) 477: 344-348]. While VSV does not infect humans and may not be a virus of particular interest for the development of therapeutic antivirals, VSV pseudotyped viruses expressing glycoproteins from other enveloped viruses may be used to screen chemical libraries to identify compounds that inhibit the glycoproteins, cell entry, and infectivity of enveloped viruses associated with significant human health concerns. [Cunningham, J. et al. US patent application, publication number US2013/0231332; WO 2012/031090, 8 Mar. 2012; WO2013/022550, 14 Feb. 2013; Warren, T. K., et al. *Antiviral activity of a small-molecule inhibitor of Filovirus infection*. Antimicrob. Agents Chemother. (2010) 54: 2152-2159; Yermolina, M., et al. *Discovery, synthesis, and biological evaluation of a novel group of selective inhibitors of filovirus entry*. J. Med. Chem. (2011) 54: 765-781; Basu, A., et al. *Identification of a small-molecule entry inhibitor for Filoviruses*. J. Virol. (2011) 85: 3106-3119; Lee, K., et al., *Inhibition of Ebola virus infection: identification of Niemann-Pick as the target by optimization of a chemical probe*. ACS Med. Chem. Lett. (2013) 4: 239-243; Madrid, P. B., et al. *A Systematic screen of FDA-approved drugs for inhibitors of biological threat agents* Plos One (2013) 8: 1-14; Elshabrawy, H. A., et al. *Identification of a broad-spectrum antiviral amall molecule against severe scute respiratory syndrome Coronavirus and Ebola, Hendra, and Nipah Viruses by using a novel high-throughput screening assay*. J. Virol. (2014) 88: 4353-4365].

Filovirus infections are associated with hemorrhagic fevers, the clinical manifestations of which may be severe and/or fatal. As described herein, for the current invention, VSV pseudotyped viruses expressing filovirus glycoproteins can be generated and screened with a collection of chemical compounds to identify those compounds that inhibit infectivity. The identification of inhibitors of filovirus glycoprotein-mediated virus cell entry may may be utilized to treat infections of filoviruses to provide effective therapeutic regimens for the prophylaxis and/or treatment of filoviruses or any newly emerging virus, whether native or engineered, whose cell entry properties may be determined by filovirus glycoproteins.

The Filoviridae virus family is comprised of at least three genera: Ebolavirus, which currently includes five species Zaire (EBOV), Sudan (SUDV), Bundibygo (BDBV), Tai Forest (TAFV) and Reston (RESTV), Marburgvirus, which currently includes two species Marburg (MARV) and Ravn (RAVV), and Cuervavirus, which currently includes a single species LLovia virus (LLOV). RAVV and LLOV are examples of filoviruses that have been identified only recently and a number of additional new species and genera may continue to emerge.

TABLE 2

Family Filoviridae: currently identified fiiovirus genera, species, and nomenclature

| Genus name | Species name | Virus name (Abbreviation) |
|---|---|---|
| Cuevavirus | Lloviu cuevavirus | Lloviu virus (LLOV) |
| Ebolavirus | Bundibugyo ebolavirus | Bundibugyo virus (BDBV) |
| | Reston ebolavirus | Reston virus (RESTV) |
| | Sudan ebolavirus | Sudan virus (SUDV) |
| | Taï Forest ebolavirus | Taï Forest virus (TAFV) |
| | Zaire ebolavirus | Ebola virus (EBOV) |
| Marburgvirus | Marburg marburgvirus | Marburg virus (MARV) |
| | | Raven virus (RAVV) |

Glycoproteins from Filoviridae family members can be expressed in pseudotyped viruses (e.g. VSV pseudotype) to identify compounds that inhibit filovirus infection. Based on the structural similarities and/or differences between the viral glycoprotein target and/or host cell targets, the inhibitor compounds may act on only a single filovirus glycoprotein or on a broad spectrum of filoviruses. Furthermore, given the basic functional and structural similarities of glycoproteins among different families of enveloped viruses it is proable that a given compound class may act across a broad range of enveloped viruses.

Alignments of representative filovirus glycoprotein sequences were generated to illustrate the amino acid homology among different filovirus species.

TABLE 3

Homology of filovirus glycoproteins - created by Clustal2.1

| Species/Genbank ID | Zaire | Bundi | T Forest | Reston | Sudan | Marburg |
|---|---|---|---|---|---|---|
| Zaire/AAB81004 | 100 | 68.0 | 66.5 | 59.9 | 56.8 | 32.7 |
| Bundibugyo/AGL73453 | 68.0 | 100 | 73.6 | 60.4 | 57.7 | 33.0 |
| Tai Forest/YP_003815426 | 66.5 | 73.6 | 100 | 59.5 | 57.7 | 33.9 |
| Reston/BAB69006 | 59.9 | 60.4 | 59.5 | 100 | 61.4 | 32.7 |

TABLE 3-continued

Homology of filovirus glycoproteins - created by Clustal2.1

| Species/Genbank ID | Zaire | Bundi | T Forest | Reston | Sudan | Marburg |
|---|---|---|---|---|---|---|
| Sudan/AAB37096 | 56.8 | 57.7 | 57.7 | 61.4 | 100 | 33.0 |
| Marburg/AAC40460 | 32.7 | 33.0 | 33.9 | 32.7 | 33.0 | 100 |

A matrix comparison of the amino acid homology (homology is defined as the number of identities between any two sequences, divided by the length of the alignment, and represented as a percentage) as determined from the Clustal2.1 program among and between distinct filovirus genus and species is illustrated in Table 3. Glycoproteins among virus species within the same filovirus genus (e.g., Ebolavirus) are more homologous to each other than to those in another genus (Marburgvirus). However, currently available filovirus glycoproteins exhibit significant homology (>30% identity from any one member to another). Given this homology for some chemical series it is possible to identify compounds that exhibit activity against a broad-spectrum of filoviruses.

Similar alignments were subsequently carried out with a number of class I glycoproteins from other enveloped virus families. Each of the glycoproteins from the other enveloped viruses exhibit <20% identity with any of the filovirus glycoproteins. Although there are similarities in functional and structural characteristics among the class I glycoproteins, there are clear distinctions including dependence on low pH, receptor binding, location of the fusion peptide [White, J. M.; Delos, S. E.; Brecher, M.; Schornberg, K. *Structures and mechanisms of viral membrane fusion proteins: multiple variations on a common theme.* Crit. Rev. Biochem. Mol., Biol. (2008) 43:189-219] and given the low amino acid sequence homology across class I virus families it becomes unlikely that a given chemical series that inhibits filovirus cell entry/fusion would also exhibit similar inhibitory activities with other envelope class I glycoprotein virus families.

TABLE 4

Homology matrix between filoviruses and other class 1 glycoprotein viruses-created by Clustal2.1

| | | | | | | | | | | | |
|---|---|---|---|---|---|---|---|---|---|---|---|
| Z AAB81004 | 100 | 66.5 | 68.0 | 56.8 | 59.9 | 32.7 | 17.0 | 12.8 | 13.4 | 14.2 | 13.7 |
| T YP_003815426 | 66.5 | 100 | 73.6 | 57.7 | 59.5 | 33.9 | 17.7 | 12.0 | 12.0 | 13.8 | 14.2 |
| B AGL73453 | 68.0 | 73.6 | 100 | 57.7 | 60.4 | 33.0 | 17.9 | 12.3 | 12.3 | 13.4 | 14.7 |
| S AAB37096 | 56.8 | 57.7 | 57.7 | 100 | 61.4 | 33.0 | 16.4 | 12.9 | 13.0 | 14.8 | 12.8 |
| R BAB69006 | 59.9 | 59.5 | 60.4 | 61.4 | 100 | 32.7 | 19.8 | 12.9 | 11.8 | 14.6 | 13.5 |
| M AAC40460 | 32.7 | 33.9 | 33.0 | 33.0 | 32.7 | 100 | 15.7 | 10.7 | 8.7 | 12.2 | 14.1 |
| INF ACP41105 | 17.0 | 17.7 | 17.9 | 16.4 | 19.8 | 15.7 | 100 | 14.5 | 12.6 | 11.8 | 11.2 |
| LASV NP_694870 | 12.8 | 12.0 | 12.3 | 12.9 | 12.9 | 10.7 | 14.5 | 100 | 43.2 | 18.8 | 18.3 |
| JUNV AY619641 | 13.4 | 12.0 | 12.3 | 13.0 | 11.8 | 8.7 | 12.6 | 43.2 | 100 | 15.2 | 14.3 |
| Nipah AP238467 | 14.2 | 13.8 | 13.4 | 14.8 | 14.6 | 12.2 | 11.8 | 18.8 | 15.2 | 100 | 20.8 |
| Measles AF21882 | 13.7 | 14.2 | 14.7 | 12.8 | 11.2 | 14.1 | 13.5 | 18.3 | 14.3 | 20.8 | 100 |

Abbreviations: M: *Marburg*, Z: *Zaire*, T: *Tai Forest*, B: *Bundibugyo*, S: *Sudan*, R: *Reston*, INF: *Influenza*, LASV: Lassa virus, JUNV: Junin virus; Genbank ID in bold Abbreviations: M: Marburg, Z: Zaire, T: Tai Forest, B: Bundibugyo, S: Sudan, R: Reston, INF: Influenza, LASV: Lassa virus, JUNV: Junin virus; Genbank ID in bold

BRIEF SUMMARY OF THE INVENTION

The present invention relates to methods of inhibiting filoviruses (or any virus whose cell entry is mediated by filovirus glycoproteins) infection in humans, other mammals, or in cell culture, to treating filovirus infection, to methods of inhibiting the replication of filoviruses, to methods of reducing the amount of filoviruses, and to compositions that can be employed for such methods. These methods, applications, and compositions apply not only to Filoviridae viruses but also to any virus, whether naturally emerging or engineered, whose cell entry properties are determined by filovirus glycoproteins.

In one embodiment, the method comprises administering to humans, other mammals, cell culture, or biological sample an effective amount of a compound represented by Structural Formula I for treatment of filovirus infection

I or a pharmaceutically acceptable salt, and a pharmaceutically acceptable carrier, diluent, or vehicle thereof, wherein:

X is C-A-D, and Y is a bond or $CR^4R^5$; or

X is $CR^5$ and Y is $CR^4$-A-D;

A is $-C(R^{6a}R^{6b})_j-$, ($C_6$ to $C_{10}$) arylene, or ($C_2$ to $C_9$) heteroarylene, wherein each of the said ($C_6$ to $C_{10}$) arylene or ($C_2$ to $C_9$) heteroarylene is optionally substituted with at least one $R^{6a}$ group;

D is selected from the group consisting of

-continued

-continued

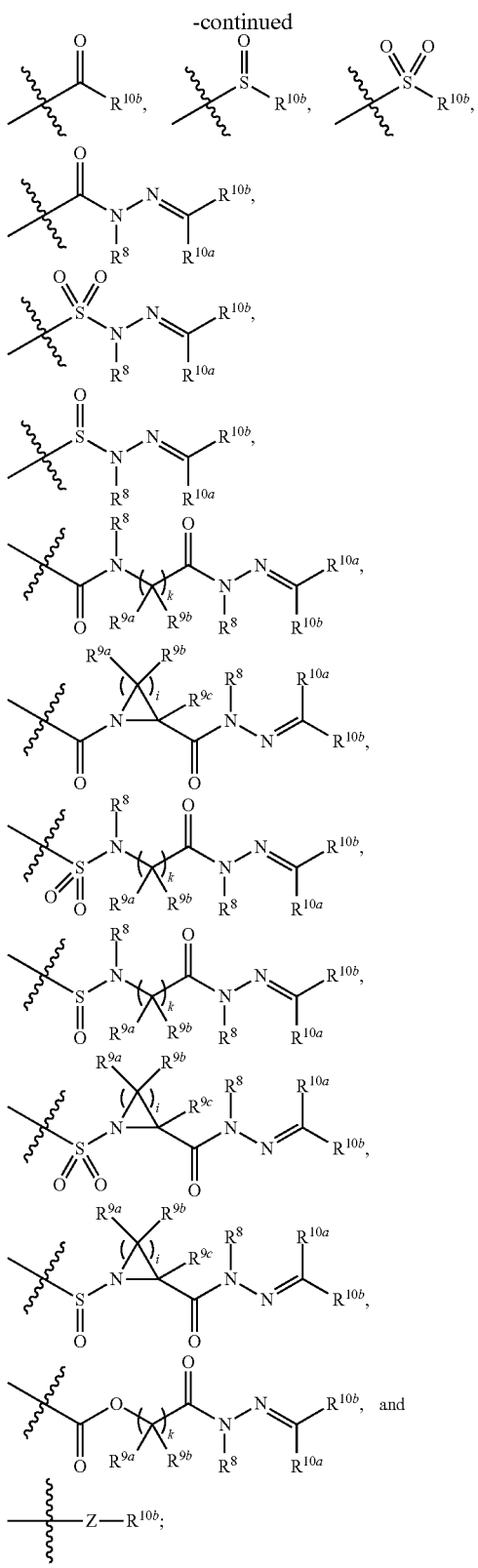

R¹ is selected from hydrogen, halogen, OH, nitro, CF₃, —NR$^{11a}$R$^{11b}$, (C₁ to C₁₀) alkyl, (C₁ to C₁₀) alkenyl, (C₁ to C₁₀) alkynyl, (C₁ to C₁₀) alkoxy, aryloxy, cyano, (C₃ to C₁₀) cycloalkyl, (C₅ to C₁₀) cycloalkenyl, (C₂ to C₉) cycloheteroalkyl, (C to C₁₀) aryl, (C₂ to C₉) heteroaryl, —C(O)R¹², —C(O)NR$^{11a}$R$^{11b}$, —S(O)$_m$R¹², —S(O)$_m$NR$^{11a}$R$^{11b}$, —NR$^{11a}$S(O)$_m$R¹², —(CH₂)$_n$C(O)OR¹², —(CH₂)$_n$C(O)N(R$^{11a}$R$^{11b}$), —(CH₂)$_n$N(R$^{11a}$R$^{11b}$), —OC(O)R¹², —NR$^{11a}$C(O)R¹², and —NR$^{11a}$C(O)N(R$^{11a}$R$^{11b}$), wherein
each of the said (C₁ to C₁₀) alkyl, (C₁ to C₁₀) alkenyl, (C₁ to C₁₀) alkynyl, (C₁ to C₁₀) alkoxy, aryloxy, (C₃ to C₁₀) cycloalkyl, (C₅ to C₁₀) cycloalkenyl, (C₂ to C₉) cycloheteroalkyl, (C₆ to C₁₀) aryl, and (C₂ to C₉) heteroaryl is optionally substituted with at least one R¹³ group;

R² is selected from hydrogen, halogen, OH, nitro, CF₃, —NR$^{11a}$R$^{11b}$, (C₁ to C₁₀) alkyl, (C₁ to C₁₀) alkenyl, (C₁ to C₁₀) alkynyl, (C₁ to C₁₀) alkoxy, aryloxy, cyano, (C₃ to C₁₀) cycloalkyl, (C₅ to C₁₀) cycloalkenyl, (C₂ to C₉) cycloheteroalkyl, (C₆ to C₁₀) aryl, (C₂ to C₉) heteroaryl, —C(O)R¹², —C(O)NR$^{11a}$R$^{11b}$, —S(O)$_m$R¹², —S(O)$_m$NR$^{11a}$R$^{11b}$, —NR$^{11a}$S(O)$_m$R¹², —(CH₂)$_n$C(O)OR¹², —(CH₂)$_n$C(O)N(R$^{11a}$R$^{11b}$), —(CH₂)$_n$N(R$^{11a}$R$^{11b}$), —OC(O)R¹², —NR$^{11a}$C(O)R¹², and —NR$^{11a}$C(O)N(R$^{11a}$R$^{11b}$), wherein
each of the said (C₁ to C₁₀) alkyl, (C₁ to C₁₀) alkenyl, (C₁ to C₁₀) alkynyl, (C₁ to C₁₀) alkoxy, aryloxy, (C₃ to C₁₀) cycloalkyl, (C₅ to C₁₀) cycloalkenyl, (C₂ to C₉) cycloheteroalkyl, (C₆ to C₁₀) aryl, and (C₂ to C₉) heteroaryl is optionally substituted with at least one R¹³ group;

R³ is selected from hydrogen, halogen, OH, nitro, CF₃, —NR$^{11a}$R$^{11b}$, (C₁ to C₁₀) alkyl, (C₁ to C₁₀) alkenyl, (C₁ to C₁₀) alkynyl, (C₁ to C₁₀) alkoxy, aryloxy, cyano, (C₃ to C₁₀) cycloalkyl, (C₅ to C₁₀) cycloalkenyl, (C₂ to C₉) cycloheteroalkyl, (C to C₁₀) aryl, (C₂ to C₉) heteroaryl, —C(O)R¹², —C(O)NR$^{11a}$R$^{11b}$, —S(O)$_m$R¹², —S(O)$_m$NR$^{11a}$R$^{11b}$, —NR$^{11a}$S(O)$_m$R¹², —(CH₂)$_n$C(O)OR¹², —(CH₂)$_n$C(O)N(R$^{11a}$R$^{11b}$), —(CH₂)$_n$N(R$^{11a}$R$^{11b}$), —OC(O)R¹², —NR$^{11a}$C(O)R¹², and —NR$^{11a}$C(O)N(R$^{11a}$R$^{11b}$), wherein
each of the said (C₁ to C₁₀) alkyl, (C₁ to C₁₀) alkenyl, (C₁ to C₁₀) alkynyl, (C₁ to C₁₀) alkoxy, aryloxy, (C₃ to C₁₀) cycloalkyl, (C₅ to C₁₀) cycloalkenyl, (C₂ to C₉) cycloheteroalkyl, (C₆ to C₁₀) aryl, and (C₂ to C₉) heteroaryl is optionally substituted with at least one R¹³ group;

R⁴ is selected from hydrogen, halogen, OH, nitro, CF₃, —NR$^{11a}$R$^{11b}$, (C₁ to C₁₀) alkyl, (C₁ to C₁₀) alkenyl, (C₁ to C₁₀) alkynyl, (C₁ to C₁₀) alkoxy, aryloxy, cyano, (C₃ to C₁₀) cycloalkyl, (C₅ to C₁₀) cycloalkenyl, (C₂ to C₉) cycloheteroalkyl, (C₆ to C₁₀) aryl, (C₂ to C₉) heteroaryl, —C(O)R¹², —C(O)NR$^{11a}$R$^{11b}$, —S(O)$_m$R¹², —S(O)$_m$NR$^{11a}$R$^{11b}$, —NR$^{11a}$S(O)$_m$R¹², —(CH₂)$_n$C(O)OR¹², —(CH₂)$_n$C(O)N(R$^{11a}$R$^{11b}$), —(CH₂)$_n$N(R$^{11a}$R$^{11b}$), —OC(O)R¹², —NR$^{11a}$C(O)R¹², and —NR$^{11a}$C(O)N(R$^{11a}$R$^{11b}$), wherein
each of the said (C₁ to C₁₀) alkyl, (C₁ to C₁₀) alkenyl, (C₁ to C₁₀) alkynyl, (C₁ to C₁₀) alkoxy, aryloxy, (C₃ to C₁₀) cycloalkyl, (C₅ to C₁₀) cycloalkenyl, (C₂ to C₉) cycloheteroalkyl, (C₆ to C₁₀) aryl, and (C₂ to C₉) heteroaryl is optionally substituted with at least one R¹³ group;

R⁵ is selected from hydrogen, halogen, OH, nitro, CF₃, —NR$^{11a}$R$^{11b}$, (C₁ to C₁₀) alkyl, (C₁ to C₁₀) alkenyl, (C₁ to C₁₀) alkynyl, (C₁ to C₁₀) alkoxy, aryloxy, cyano, (C₃ to C₁₀) cycloalkyl, (C₅ to C₁₀) cycloalkenyl, (C₂ to C₉) cycloheteroalkyl, (C₆ to C₁₀) aryl, (C₂ to C₉) heteroaryl, —C(O)R¹², —C(O)NR$^{11a}$R$^{11b}$, —S(O)$_m$R¹², —S(O)$_m$NR$^{11a}$R$^{11b}$, —NR$^{11a}$S(O)$_m$R¹², —(CH₂)$_n$C(O)OR¹², —(CH₂)$_n$C(O)N(R$^{11a}$R$^{11b}$), —(CH₂)$_n$N(R$^{11a}$R$^{11b}$), —OC(O)R¹², —NR$^{11a}$C(O)R¹², and —NR$^{11a}$C(O)N(R$^{11a}$R$^{11b}$), wherein
each of the said (C₁ to C₁₀) alkyl, (C₁ to C₁₀) alkenyl, (C₁ to C₁₀) alkynyl, (C₁ to C₁₀) alkoxy, aryloxy, (C₃ to C₁₀)

cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

each of the $R^{6a}$ and $R^{6b}$ is independently selected from hydrogen, halogen, OH, nitro, $CF_3$, —$NR^{11a}R^{11b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —$C(O)R^{12}$, —$C(O)NR^{11a}R^{11b}$, —$S(O)_mR^{12}$, —$S(O)_mNR^{11a}R^{11b}$, —$NR^{11a}S(O)_mR^{12}$, —$(CH_2)_nC(O)OR^{12}$, —$(CH_2)_nC(O)N(R^{11a}R^{11b})$, —$(CH_2)_nN(R^{11a}R^{11b})$, —$OC(O)R^{12}$, —$NR^{11a}C(O)R^{12}$, and —$NR^{11a}C(O)N(R^{11a}R^{11b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

each of the $R^{7a}$ and $R^{7b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, $NR^{11a}R^{11b}$, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{13}$ group, or $R^{7a}$ and $R^{7b}$ may be taken together with the nitrogen atom to which they are attached to form a ($C_2$ to $C_{10}$) cycloheteroalkyl ring, wherein said ($C_2$ to $C_{10}$) membered cycloheteroalkyl ring has 1 to 3 ring heteroatoms selected from the group consisting of N, O, and S, and wherein the said ($C_2$ to $C_{10}$) membered cycloheteroalkyl ring is optionally substituted with at least one $R^{13}$ group;

each $R^8$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, (C to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{13}$ group;

each of the $R^{9a}$, $R^{9b}$, and $R^{9c}$ is independently selected from hydrogen, halogen, OH, nitro, $CF_3$, —$NR^{11a}R^{11b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, —$C(O)R^{12}$, —$C(O)NR^{11a}R^{11b}$, —$S(O)_mR^{12}$, —$S(O)_mNR^{11a}R^{11b}$, —$NR^{11a}S(O)_mR^{12}$, —$(CH_2)_nC(O)OR^{12}$, —$(CH_2)_nC(O)N(R^{11a}R^{11b})$, —$(CH_2)_nN(R^{11a}R^{11b})$, —$OC(O)R^{12}$, —$NR^{11a}C(O)R^{12}$, and —$NR^{11a}C(O)N(R^{11a}R^{11b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

each of the $R^{10a}$ and $R^{10b}$ is independently selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl is optionally substituted with at least one $R^{13}$ group;

each of the $R^{11a}$ and $R^{11b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_{2\,to\,C9}$) heteroaryl, ($C_6$ to $C_{10}$) arylene, and ($C_2$ to $C_9$) heteroarylene is optionally substituted with at least one $R^{13}$ group, or $R^{11a}$ and $R^{11b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{13}$ group;

each of the $R^{12}$ is independently selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

each $R^{13}$ is independently selected from hydrogen, halogen, OH, nitro, $CF_3$, —$NR^{14a}R^{14b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{15}$, —$C(O)NR^{14a}R^{14b}$, —$S(O)_mR^{15}$, —$S(O)_mNR^{14a}R^{14b}$, —$NR^{14a}S(O)_mR^{15}$, —$(CH_2)_nC(O)OR^{15}$, —$(CH_2)_nC(O)N(R^{14a}R^{14b})$, —$(CH_2)_nN(R^{14a}R^{14b})$, —$OC(O)R^{15}$, —$O(CH_2)_nO$—, —$NR^{14a}C(O)R^{15}$, and —$NR^{14a}C(O)N(R^{14a}R^{14b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{16}$ group;

each of the $R^{14a}$ and $R^{14b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{16}$ group, or $R^{14a}$ and $R^{14b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{16}$ group;

each $R^{15}$ is independently selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl is optionally substituted with at least one $R^{16}$ group;

each $R^{16}$ is independently selected from hydrogen, halogen, OH, nitro, $CF_3$, —$NR^{17a}R^{17b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{18}$, —$C(O)NR^{17a}R^{17b}$, —$S(O)_mR^{18}$, —$S(O)_mNR^{17a}R^{17b}$, —$NR^{17a}S(O)_mR^{18}$, —$(CH_2)_nC(O)OR^{18}$, —$(CH_2)_nC(O)N(R^{17a}R^{17b})$, —$(CH_2)_nN(R^{17a}R^{17b})$, —$OC(O)R^{18}$, —$NR^{17a}C(O)R^{18}$, and —$NR^{17a}C(O)N(R^{17a}R^{17b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, ($C_6$ to $C_{10}$) aryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{19}$ group;

each of the $R^{17a}$ and $R^{17b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, $C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{19}$ group, or $R^{17a}$ and $R^{17b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{19}$ group;

each $R^{18}$ is independently selected from hydrogen, halogen, OH, nitro, $CF_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_6$ to $C_{10}$) aryl is optionally substituted with at least one $R^{19}$ group;

each $R^{19}$ is independently selected from hydrogen, halogen, OH, nitro, $CF_3$, —$NR^{20a}R^{20b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{21}$, —$C(O)NR^{20a}R^{20b}$, —$S(O)_mR^{21}$, —$S(O)_mNR^{20a}R^{20b}$, —$NR^{20a}S(O)_mR^{21}$, —$(CH_2)_nC(O)OR^{21}$, —$(CH_2)_nC(O)N(R^{20a}R^{20b})$, —$(CH_2)_nN(R^{20a}R^{20b})$, —$OC(O)R^{21}$, —$NR^{20a}C(O)R^{21}$, and —$NR^{20a}C(O)N(R^{20a}R^{20b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{22}$ group;

each of the $R^{20a}$ and $R^{20b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, (C to $C_{10}$) cycloalkenyl, ($C_2$ to $C_{10}$) cycloheteroalkyl, ($C_6$ to $C_{10}$) aryl, and ($C_2$ to $C_9$) heteroaryl is optionally substituted with at least one $R^{22}$ group, or $R^{20a}$ and $R^{20b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{22}$ group;

each $R^{21}$ is independently selected from hydrogen, halogen, OH, nitro, $CF_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl; each $R^{22}$ is independently selected from hydrogen, halogen, OH, nitro, $CF_3$, —$NR^{23a}R^{23b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{24}$, —$C(O)NR^{23a}R^{23b}$, —$S(O)_mR^{24}$, —$S(O)_mNR^{23a}R^{23b}$, —$NR^{23a}S(O)_mR^{24}$, —$(CH_2)_nC(O)OR^{24}$, —$(CH_2)_nC(O)N(R^{23a}R^{23b})$, —$(CH_2)_nN(R^{23a}R^{23b})$, —$OC(O)R^{24}$, —$NR^{23a}C(O)R^{24}$, and —$NR^{23a}C(O)N(R^{23a}R^{23b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{25}$ group;

each of the $R^{23a}$ and $R^{23b}$ is independently selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_6$ to $C_{10}$) aryl;

each $R^{24}$ is independently selected from hydrogen, halogen, OH, nitro, $CF_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl;

each $R^{25}$ is independently selected from hydrogen, halogen, OH, nitro, $CF_3$, $-NR^{26a}R^{26b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, $-C(O)R^{27}$, $-C(O)NR^{26a}R^{26b}$, $-S(O)_mR^{27}$, $-S(O)_mNR^{26a}R^{26b}$, $-NR^{26a}S(O)_mR^{27}$, $-(CH_2)_nC(O)OR^{27}$, $-(CH_2)_nC(O)N(R^{26a}R^{26b})$, $-(CH_2)_nN(R^{26a}R^{26b})$, $-OC(O)R^{27}$, $-NR^{26a}C(O)R^{27}$, and $-NR^{26a}C(O)N(R^{26a}R^{26b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{27}$ group;

each of the $R^{26a}$ and $R^{26b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, or $R^{26a}$ and $R^{26b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S;

each $R^{27}$ is independently selected from hydrogen, halogen, OH, nitro, $CF_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl;

h is 1 or 2;
i is 2, 3, 4, 5, or 6;
j is 0, 1, 2, 3, 4, or 5;
k is 1, 2, 3, 4, or 5;
m is 0, 1 or 2;
n is 0, 1, 2, 3, or 4;
Z is selected from the group consisting of $-O-$, $-S-$, $-S(O)-$, and $-S(O)_2-$;
with the proviso that
when $R^1$, $R^2$, or $R^3$ is alkyl or hydrogen, X is C—C($R^{6a}R^{6b}$)$_j$-D, Y is $CH_2$, and D is then $NR^{7a}R^{7b}$ cannot be an optionally substituted piperazine or 1,4-diazepane, and with the proviso that when X is $CR^5$, Y is $CR^4$-D, D is $-NR^{7a}R^{7b}$, and $R^{7a}$ and $R^{7b}$ are taken together with the nitrogen atom to which they are attached to form a ($C_2$ to $C_{10}$) cycloheteroalkyl ring, the said ($C_2$ to $C_{10}$) membered cycloheteroalkyl ring cannot be selected from the group consisting of

DESCRIPTION OF THE DRAWINGS

FIG. 1: Depicts results of a pharmacokinetics (PK) study of compound A78 in male CD-1 mice. Shown are plasma concentrations of A78 after intravenous (iv) administration of 1 mg/kg or oral (po) administration at 10 mg/kg dose over a 24 h period.

DETAILED DESCRIPTION OF THE INVENTION

The present invention relates to methods of inhibiting filoviruses (or any virus whose cell entry is mediated by filovirus glycoproteins) infection in humans, other mammals, or in cell culture, to treating filovirus infection, to methods of inhibiting the replication of filoviruses, to methods of reducing the amount of filoviruses, and to compositions that can be employed for such methods. These methods, applications, and compositions apply not only to Filoviridae viruses but also to any virus, whether naturally emerging or engineered, whose cell entry properties are determined by filovirus glycoproteins.

In one embodiment, the method comprises administering to humans, other mammals, cell culture, or biological sample an effective amount of a compound represented by Structural Formula I for treatment of filovirus infection
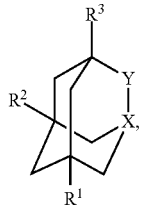

I or a pharmaceutically acceptable salt, and a pharmaceutically acceptable carrier, diluent, or vehicle thereof, wherein:

X is C-A-D, and Y is a bond or $CR^4R^5$; or

X is $CR^5$ and Y is $CR^4$-A-D;

A is $—C(R^{6a}R^{6b})_j—$, ($C_6$ to $C_{10}$) arylene, or ($C_2$ to $C_9$) heteroarylene, wherein each of the said ($C_6$ to $C_{10}$) arylene or ($C_2$ to $C_9$) heteroarylene is optionally substituted with at least one $R^{6a}$ group;

D is selected from the group consisting of

-continued

-continued

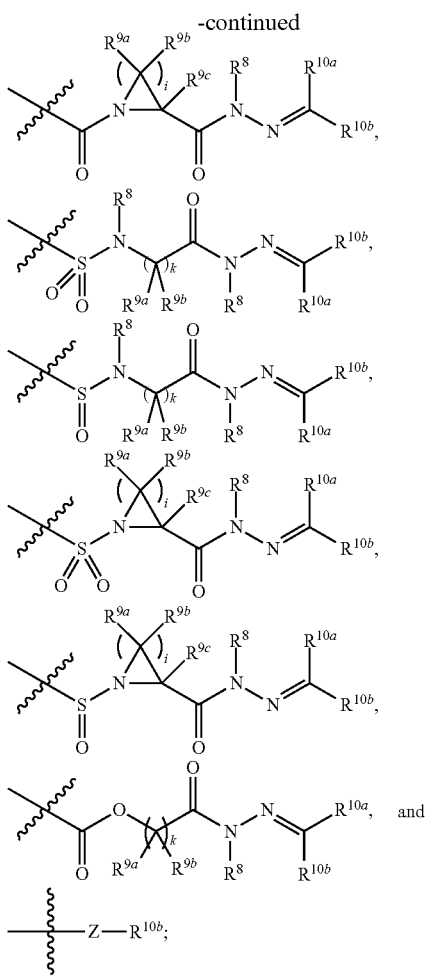

$\text{---}Z\text{---}R^{10b};$ $R^1$ is selected from hydrogen, halogen, OH, nitro, $CF_3$, $-NR^{11a}R^{11b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, (C to $C_{10}$) aryl, ($C_2$ to $C_9$) heteroaryl, $-C(O)R^{12}$, $-C(O)NR^{11a}R^{11b}$, $-S(O)_mR^{12}$, $-S(O)_mNR^{11a}R^{11b}$, $-NR^{11a}S(O)_mR^{12}$, $-(CH_2)_nC(O)OR^{12}$, $-(CH_2)_nCO)N(R^{11a}R^{11b})$, $-(CH_2)_nN(R^{11a}R^{11b})$, $-OC(O)R^{12}$, $-NR^{11a}C(O)R^{12}$, and $-NR^{11a}C(O)N(R^{11a}R^{11b})$, wherein
each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

$R^2$ is selected from hydrogen, halogen, OH, nitro, $CF_3$, $-NR^{11a}R^{11b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, (C to $C_{10}$) aryl, ($C_2$ to $C_9$) heteroaryl, $-C(O)R^{12}$, $-C(O)NR^{11a}R^{11b}$, $-S(O)_mR^{12}$, $-S(O)_mNR^{11a}R^{11b}$, $-NR^{11a}S(O)_mR^{12}$, $-(CH_2)_nC(O)OR^{12}$, $-(CH_2)_nC(O)N(R^{11a}R^{11b})$, $-(CH_2)_nN(R^{11a}R^{11b})$, $-OC(O)R^{12}$, $-NR^{11a}C(O)R^{12}$, and $-NR^{11a}C(O)N(R^{11a}R^{11b})$, wherein
each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

$R^3$ is selected from hydrogen, halogen, OH, nitro, $CF_3$, $-NR^{11a}R^{11b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, $-C(O)R^{12}$, $-C(O)NR^{11a}R^{11b}$, $-S(O)_mR^{12}$, $-S(O)_mNR^{11a}R^{11b}$, $-NR^{11a}S(O)_mR^{12}$, $-(CH_2)_nC(O)OR^{12}$, $-(CH_2)_nC(O)N(R^{11a}R^{11b})$, $-(CH_2)_nN(R^{11a}R^{11b})$, $-OC(O)R^{12}$, $-NR^{11a}C(O)R^{12}$, and $-NR^{11a}C(O)N(R^{11a}R^{11b})$, wherein
each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

$R^4$ is selected from hydrogen, halogen, OH, nitro, $CF_3$, $-NR^{11a}R^{11b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, $-C(O)R^{12}$, $-C(O)NR^{11a}R^{11b}$, $-S(O)_mR^{12}$, $-S(O)_mNR^{11a}R^{11b}$, $-NR^{11a}S(O)_mR^{12}$, $-(CH_2)_nC(O)OR^{12}$, $-(CH_2)_nC(O)N(R^{11a}R^{11b})$, $-(CH_2)_nN(R^{11a}R^{11b})$, $-OC(O)R^{12}$, $-NR^{11a}C(O)R^{12}$, and $-NR^{11a}C(O)N(R^{11a}R^{11b})$, wherein
each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

$R^5$ is selected from hydrogen, halogen, OH, nitro, $CF_3$, $-NR^{11a}R^{11b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, $-C(O)R^{12}$, $-C(O)NR^{11a}R^{11b}$, $-S(O)_mR^{12}$, $-S(O)_mNR^{11a}R^{11b}$, $-NR^{11a}S(O)_mR^{12}$, $-(CH_2)_nC(O)OR^{12}$, $-(CH_2)_nC(O)N(R^{11a}R^{11b})$, $-(CH_2)_nN(R^{11a}R^{11b})$, $-OC(O)R^{12}$, $-NR^{11a}C(O)R^{12}$, and $-NR^{11a}C(O)N(R^{11a}R^{11b})$, wherein
each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

each of the $R^{6a}$ and $R^{6b}$ is independently selected from hydrogen, halogen, OH, nitro, $CF_3$, $-NR^{11a}R^{11b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, $-C(O)R^{12}$, $-C(O)NR^{11a}R^{11b}$, $-S(O)_mR^{12}$, $-S(O)_mNR^{11a}R^{11b}$, $-NR^{11a}S(O)_mR^{12}$, $-(CH_2)_nC(O)OR^{12}$, $-(CH_2)_nC(O)N(R^{11a}R^{11b})$, $-(CH_2)_nN(R^{11a}R^{11b})$, $-OC(O)R^{12}$, $-NR^{11a}C(O)R^{12}$, and $-NR^{11a}C(O)N(R^{11a}R^{11b})$, wherein
each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

each of the $R^{7a}$ and $R^{7b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, $NR^{11a}R^{11b}$, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{13}$ group, or $R^{7a}$ and $R^{7b}$ may be taken together with the nitrogen atom to which they are attached to form a ($C_2$ to $C_{10}$) cycloheteroalkyl ring, wherein said ($C_2$ to $C_{10}$) membered cycloheteroalkyl ring has 1 to 3 ring heteroatoms selected from the group consisting of N, O, and S, and wherein the said ($C_2$ to $C_{10}$) membered cycloheteroalkyl ring is optionally substituted with at least one $R^{13}$ group;

each $R^8$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{13}$ group;

each of the $R^{9a}$, $R^{9b}$, and $R^{9c}$ is independently selected from hydrogen, halogen, OH, nitro, $CF_3$, $-NR^{11a}R^{11b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, $-C(O)R^{12}$, $-C(O)NR^{11a}R^{11b}$, $-S(O)_mR^{12}$, $-S(O)_mNR^{11a}R^{11b}$, $-NR^{11a}S(O)_mR^{12}$, $-(CH_2)_nC(O)OR^{12}$, $-(CH_2)_nC(O)N(R^{11a}R^{11b})$, $-(CH_2)_nN(R^{11a}R^{11b})$, $-OC(O)R^{12}$, $-NR^{11a}C(O)R^{12}$, and $-NR^{11a}C(O)N(R^{11a}R^{11b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

each of the $R^{10a}$ and $R^{10b}$ is independently selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, (C to $C_{10}$) cycloalkenyl, ($C_2$ to $C_9$) cycloheteroalkyl, ($C_6$ to $C_{10}$) aryl, ($C_2$ to $C_9$) heteroaryl is optionally substituted with at least one $R^{13}$ group;

each of the $R^{11a}$ and $R^{11b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{13}$ group, or $R^{11a}$ and $R^{11b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{13}$ group;

each of the $R^{12}$ is independently selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

each $R^{13}$ is independently selected from hydrogen, halogen, OH, nitro, $CF_3$, $-NR^{14a}R^{14b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, $-C(O)R^{15}$, $-C(O)NR^{14a}R^{14b}$, $-S(O)_mR^{15}$, $-S(O)_mNR^{14a}R^{14b}$, $-NR^{14a}S(O)_mR^{15}$, $-(CH_2)_nC(O)OR^{15}$, $-(CH_2)_nC(O)N(R^{14a}R^{14b})$, $-(CH_2)_nN(R^{14a}R^{14b})$, $-OC(O)R^{15}$, $-O(CH_2)_nO-$, $-NR^{14a}C(O)R^{15}$, and $-NR^{14a}C(O)N(R^{14a}R^{14b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{16}$ group;

each of the $R^{14a}$ and $R^{14b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{16}$ group, or $R^{14a}$ and $R^{14b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{16}$ group;

each $R^{15}$ is independently selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$)

aryl, and ($C_2$ to $C_9$) heteroaryl is optionally substituted with at least one $R^{16}$ group;

each $R^{16}$ is independently selected from hydrogen, halogen, OH, nitro, $CF_3$, —$NR^{17a}R^{17b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{18}$, —$C(O)NR^{17a}R^{17b}$, —$S(O)_mR^{18}$, —$S(O)_mNR^{17a}R^{17b}$, —$NR^{17a}S(O)_mR^{18}$, —$(CH_2)_nC(O)OR^{18}$, —$(CH_2)_nC(O)N(R^{17a}R^{17b})$, —$(CH_2)_nN(R^{17a}R^{17b})$, —$OC(O)R^{18}$, —$NR^{17a}C(O)R^{18}$, and —$NR^{17a}C(O)N(R^{17a}R^{17b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, ($C_6$ to $C_{10}$) aryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{19}$ group;

each of the $R^{17a}$ and $R^{17b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, $C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{19}$ group, or $R^{17a}$ and $R^{17b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{19}$ group;

each $R^{18}$ is independently selected from hydrogen, halogen, OH, nitro, $CF_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_6$ to $C_{10}$) aryl is optionally substituted with at least one $R^{19}$ group;

each $R^{19}$ is independently selected from hydrogen, halogen, OH, nitro, $CF_3$, —$NR^{20a}R^{20b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{21}$, —$C(O)NR^{20a}R^{20b}$, —$S(O)_mR^{21}$, —$S(O)_mNR^{20a}R^{20b}$, —$NR^{20a}S(O)_mR^{21}$, —$(CH_2)_nC(O)OR^{21}$, —$(CH_2)_nC(O)N(R^{20a}R^{20b})$, —$(CH_2)_nN(R^{20a}R^{20b})$, —$OC(O)R^{21}$, —$NR^{20a}C(O)R^{21}$, and —$NR^{20a}C(O)N(R^{20a}R^{20b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{22}$ group;

each of the $R^{20a}$ and $R^{20b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl is optionally substituted with at least one $R^{22}$ group, or $R^{20a}$ and $R^{20b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{22}$ group;

each $R^{21}$ is independently selected from hydrogen, halogen, OH, nitro, $CF_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl;

each $R^{22}$ is independently selected from hydrogen, halogen, OH, nitro, $CF_3$, —$NR^{23a}R^{23b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —$C(O)R^{24}$, —$C(O)NR^{23a}R^{23b}$, —$S(O)_mR^{24}$, —$S(O)_mNR^{23a}R^{23b}$, —$NR^{23a}S(O)_mR^{24}$, —$(CH_2)_nC(O)OR^{24}$, —$(CH_2)_nC(O)N(R^{23a}R^{23b})$, —$(CH_2)_nN(R^{23a}R^{23b})$, —$OC(O)R^{24}$, —$NR^{23a}C(O)R^{24}$, and —$NR^{23a}C(O)N(R^{23a}R^{23b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{25}$ group;

each of the $R^{23a}$ and $R^{23b}$ is independently selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C$ to $C_{10}$) cycloalkenyl, ($C_2$ to $C_{10}$) cycloheteroalkyl, ($C_2$ to $C_9$) heteroaryl, and ($C_6$ to $C_{10}$) aryl;

each $R^{24}$ is independently selected from hydrogen, halogen, OH, nitro, $CF_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl;

each $R^{25}$ is independently selected from hydrogen, halogen, OH, nitro, $CF_3$, —$NR^{26a}R^{26b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —C(O)$R^{27}$, —C(O)N$R^{26a}R^{26b}$, —S(O)$_m R^{27}$, —S(O)$_m$N$R^{26a}R^{26b}$, —N$R^{26a}$S(O)$_m R^{27}$, —(CH$_2$)$_n$C(O)O$R^{27}$, —(CH$_2$)$_n$C(O)N($R^{26a}R^{26b}$), —(CH$_2$)$_n$N($R^{26a}R^{26b}$), —OC(O)$R^{27}$, —N$R^{26a}$C(O)$R^{27}$, and —N$R^{26a}$C(O)N($R^{26a}R^{26b}$), wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{27}$ group;

each of the $R^{26a}$ and $R^{26b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, or $R^{26a}$ and $R^{26b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S;

each $R^{27}$ is independently selected from hydrogen, halogen, OH, nitro, CF$_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl;

h is 1 or 2;
i is 2, 3, 4, 5, or 6;
j is 0, 1, 2, 3, 4, or 5;
k is 1, 2, 3, 4, or 5;
m is 0, 1 or 2;
n is 0, 1, 2, 3, or 4;
Z is selected from the group consisting of —O—, —S—, —S(O)—, and —S(O)$_2$—;
with the proviso that
when $R^1$, $R^2$, or $R^3$ is alkyl or hydrogen, X is C—C($R^{6a}R^{6b}$)$_j$-D, Y is CH$_2$, and D is then N$R^{7a}R^{7b}$ cannot be an optionally substituted piperazine or 1,4-diazepane, and with the proviso that when X is C$R^5$, Y is C$R^4$-D, D is —N$R^{7a}R^{7b}$, and $R^{7a}$ and $R^{7b}$ are taken together with the nitrogen atom to which they are attached to form a ($C_2$ to $C_{10}$) cycloheteroalkyl ring, the said ($C_2$ to $C_{10}$) membered cycloheteroalkyl ring cannot be selected from the group consisting of In another embodiment, the method comprises administering to humans, other mammals, cell culture, or biological sample an effective amount of a compound represented by Structural Formula I for treatment of Ebolavirus infection.

In another embodiment, the method comprises administering to humans, other mammals, cell culture, or biological sample an effective amount of a compound represented by Structural Formula I for treatment of Marburgvirus infection.

In another embodiment, the method comprises of inhibiting Ebolavirus.

In another embodiment, the method comprises of including administrating a therapeutic amount of a therapeutic agent selected from the group consisting of Ribavirin, viral RNA-dependent-RNA-polymerase inhibitors, Favipiravir, Triazavirin, GS-5734, small interfering RNAs (siRNAs) and microRNAs, vaccines, and immunomodulators.

In another embodiment, the method comprises of inhibiting of Ebolavirus glycoprotein.

In another embodiment, the invention relates to compounds of Structural Formula I,

I or a pharmaceutically acceptable salt, and a pharmaceutically acceptable carrier, diluent, or vehicle thereof, wherein:

X is C-A-D and Y is C$R^4R^5$, wherein A-D is defined as before.

In another embodiment, the invention relates to compounds of Structural Formula I, or a pharmaceutically acceptable salt, and a pharmaceutically acceptable carrier, diluent, or vehicle thereof, wherein:

X is C-A-D and Y is a bond, wherein A-D is defined as before.

In another embodiment, the invention relates to compounds of Structural Formula I, or a pharmaceutically acceptable salt, and a pharmaceutically acceptable carrier, diluent, or vehicle thereof, wherein:

X is $CR^5$ and Y is $CR^4$-A-D, wherein A-D is defined as before.

In another embodiment, the invention relates to compounds of Structural Formula I, or a pharmaceutically acceptable salt, and a pharmaceutically acceptable carrier, diluent, or vehicle thereof, wherein:

X is C-A-D and Y is $CR^4R^5$;

A is $—C(R^{6a}R^{6b})_j—$; and

D is selected from the group consisting of

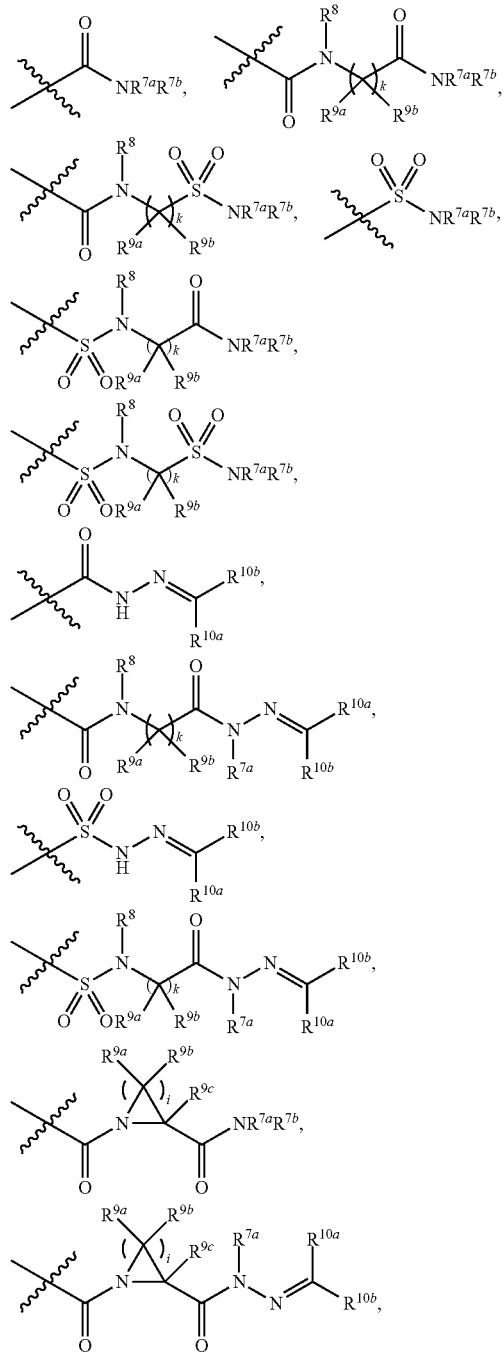

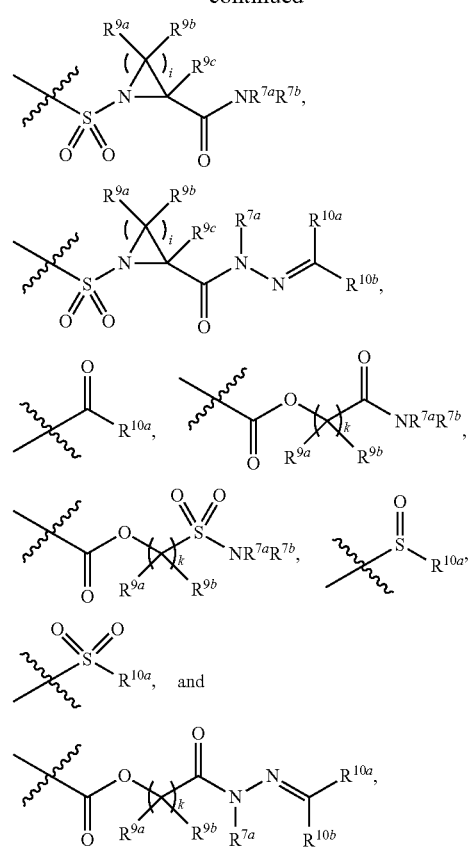

In another embodiment, the invention relates to compounds of Structural Formula I, or a pharmaceutically acceptable salt, and a pharmaceutically acceptable carrier, diluent, or vehicle thereof, wherein:

X is C-A-D and Y is $CR^4R^5$;

A is $—C(R^{6a}R^{6b})_j—$; and

D is selected from the group consisting of

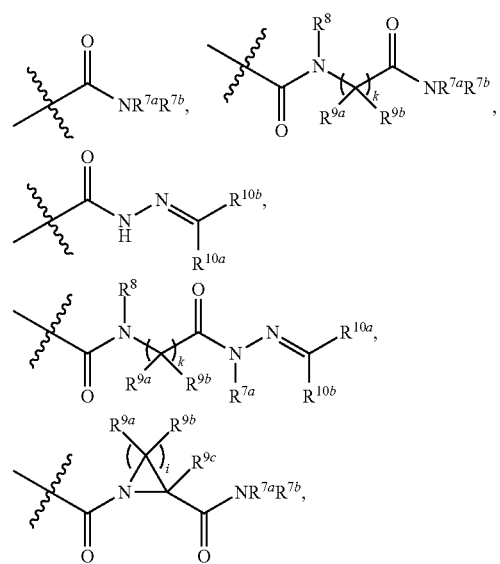

-continued

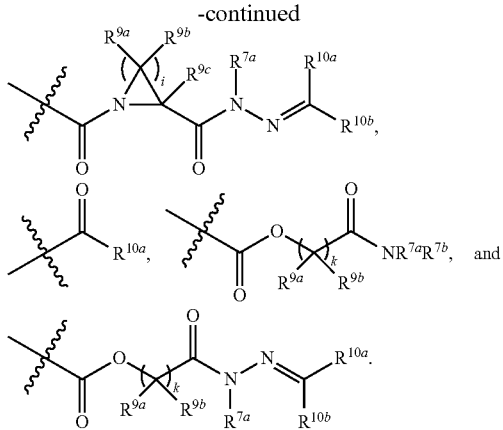

In another embodiment, the invention relates to compounds of Structural Formula I, or a pharmaceutically acceptable salt, and a pharmaceutically acceptable carrier, diluent, or vehicle thereof, wherein:

X is C-A-D and Y is a bond;

A is —C(R$^{6a}$R$^{6b}$)$_j$—; and

D is selected from the group consisting of

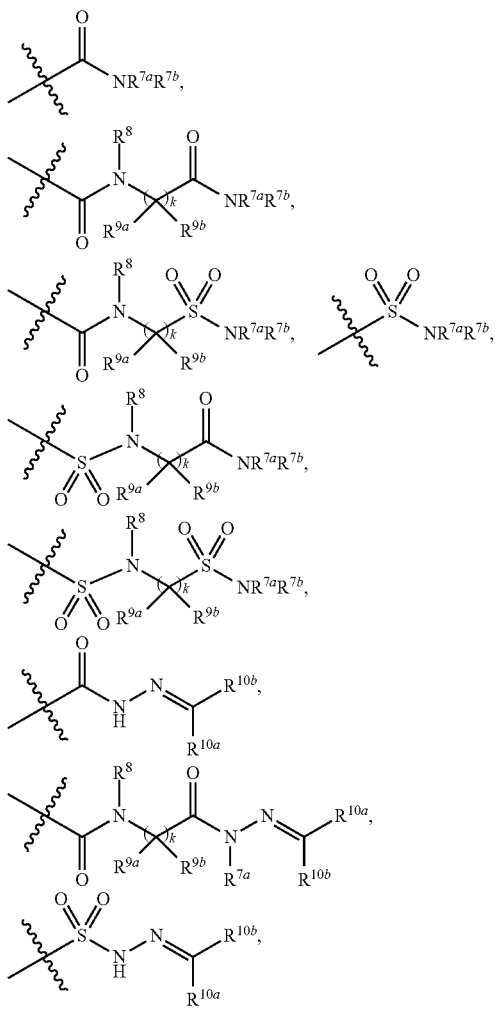

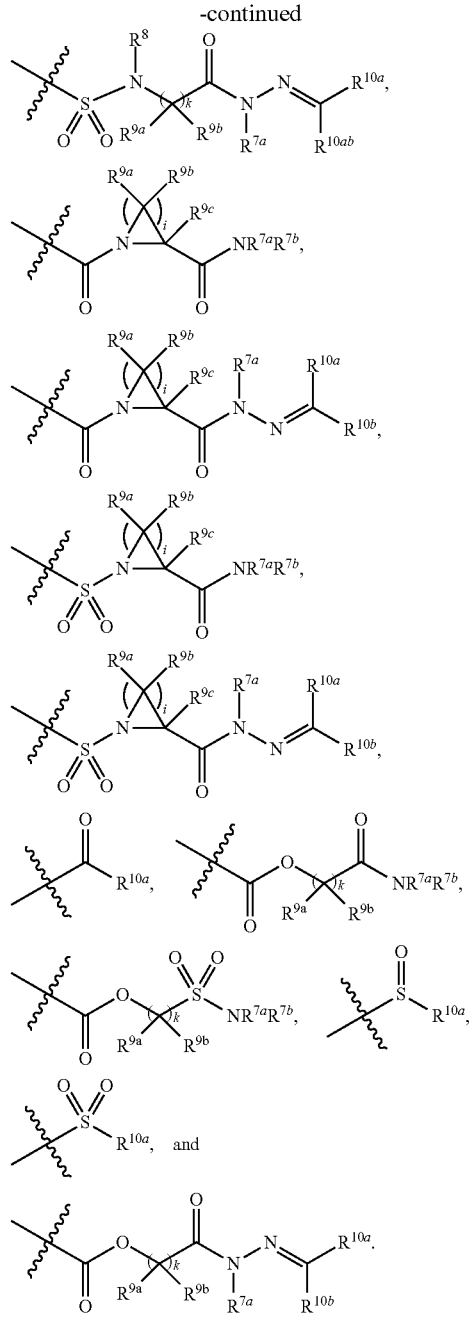

In another embodiment, the invention relates to compounds of Structural Formula I, or a pharmaceutically acceptable salt, and a pharmaceutically acceptable carrier, diluent, or vehicle thereof, wherein:

X is C-A-D and Y is a bond;

A is —C(R$^{6a}$R$^{6b}$)$_j$—; and

D is selected from the group consisting of

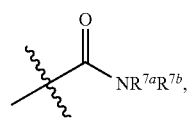

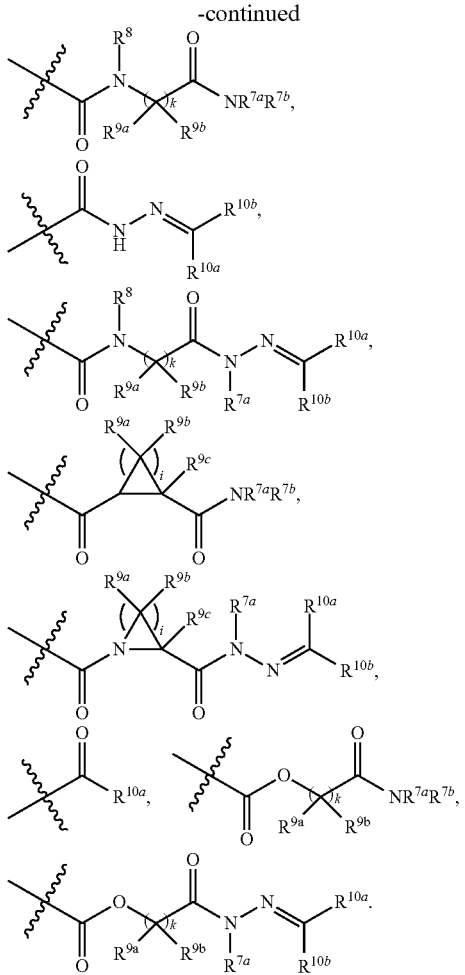
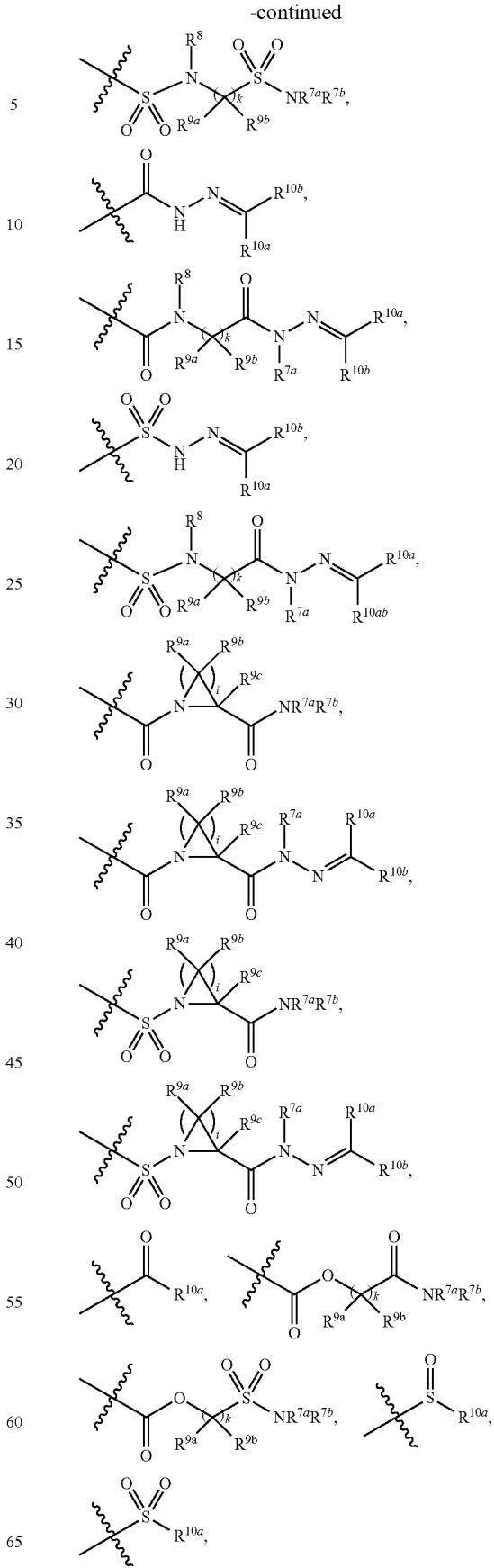
In another embodiment, the invention relates to compounds of Structural Formula I, or a pharmaceutically acceptable salt, and a pharmaceutically acceptable carrier, diluent, or vehicle thereof, wherein:
X is $CR^5$ and Y is $CR^4$-A-D;
A is —$C(R^{6a}R^{6b})_j$—; and
D is selected from the group consisting of
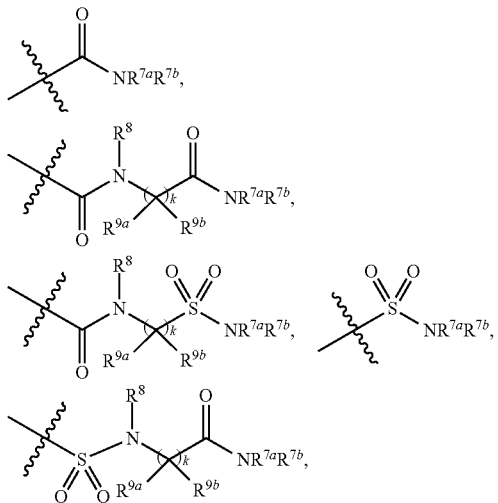

-continued

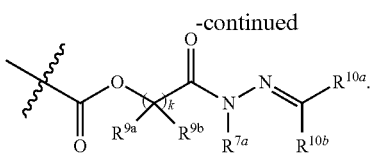

In another embodiment, the invention relates to compounds of Structural Formula I, or a pharmaceutically acceptable salt, and a pharmaceutically acceptable carrier, diluent, or vehicle thereof, wherein:

X is $CR^5$ and Y is $CR^4$-A-D;
A is —$C(R^{6a}R^{6b})_j$—; and
D is selected from the group consisting of

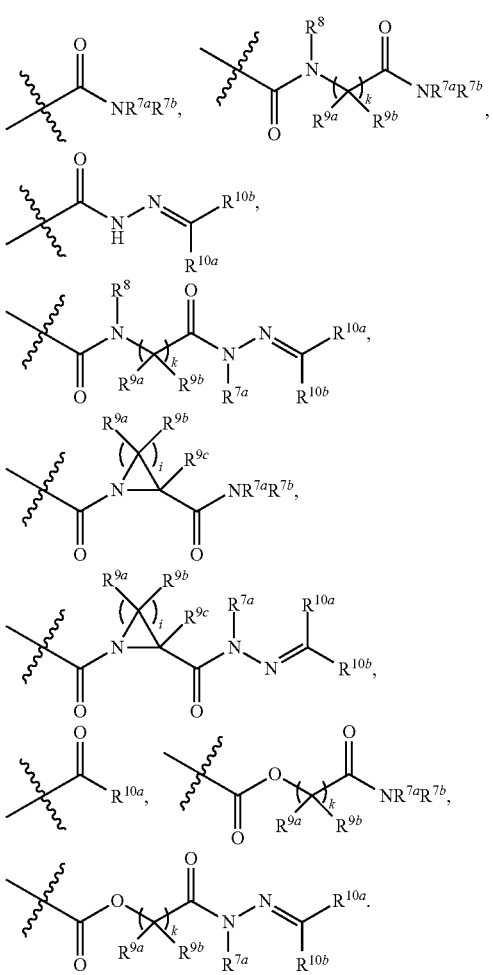

In another embodiment, the invention relates to compounds of Structural Formula I, or a pharmaceutically acceptable salt, and a pharmaceutically acceptable carrier, diluent, or vehicle thereof, wherein:

X is C-A-D and Y is $CR^4R^5$;
A is —$C(R^{6a}R^{6b})_j$—;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^2$ is hydrogen;
$R^3$ is hydrogen;
$R^4$ is hydrogen;
$R^5$ is hydrogen; and
D is selected from the group consisting of

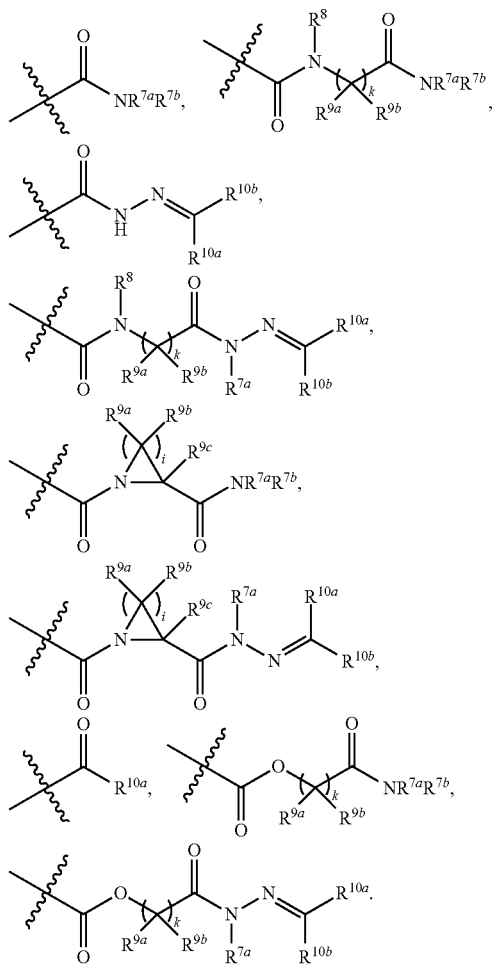

In another embodiment, the invention relates to compounds of Structural Formula I, or a pharmaceutically acceptable salt, and a pharmaceutically acceptable carrier, diluent, or vehicle thereof, wherein:

X is C-A-D and Y is a bond;
A is —$C(R^{6a}R^{6b})_j$—;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^2$ is hydrogen;
$R^3$ is hydrogen;
$R^4$ is hydrogen;
$R^5$ is hydrogen; and
D is selected from the group consisting of

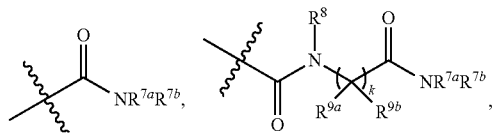

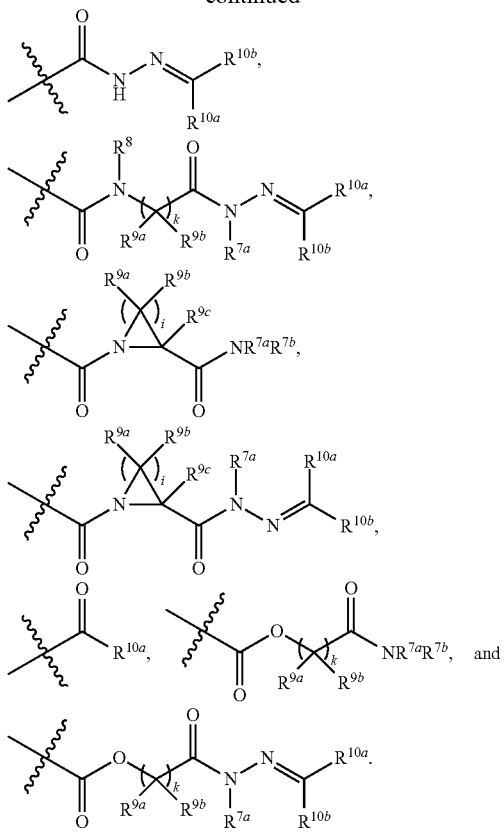

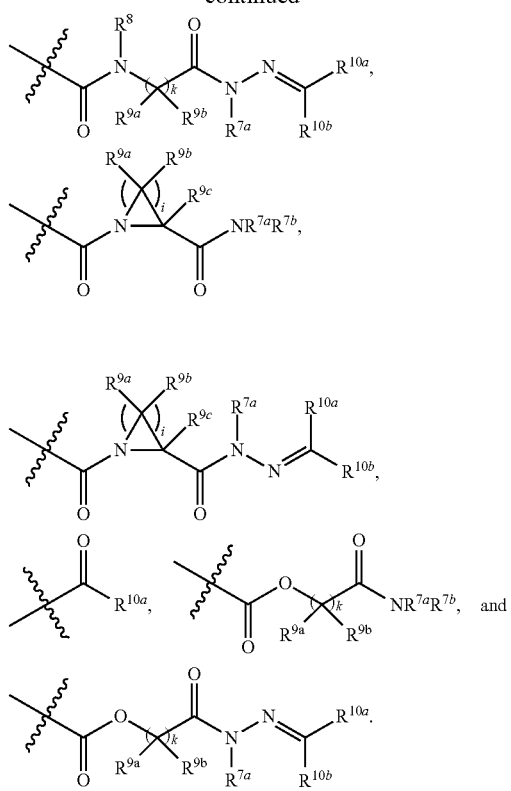

In another embodiment, the invention relates to compounds of Structural Formula I, or a pharmaceutically acceptable salt, and a pharmaceutically acceptable carrier, diluent, or vehicle thereof, wherein:

X is $CR^5$ and Y is $CR^4$-A-D;
A is $-C(R^{6a}R^{6b})_j-$;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^2$ is hydrogen;
$R^3$ is hydrogen;
$R^4$ is hydrogen;
$R^5$ is hydrogen; and
D is selected from the group consisting of

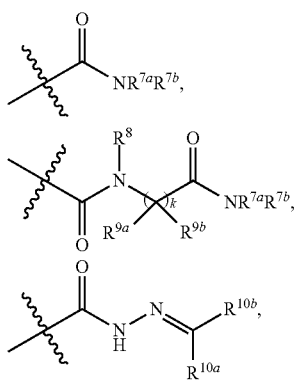

In another embodiment, the invention relates to compounds of Structural Formula I, or a pharmaceutically acceptable salt, and a pharmaceutically acceptable carrier, diluent, or vehicle thereof, wherein:

X is C-A-D and Y is a bond or $CR^4R^5$; or
X is $CR^5$ and Y is $CR^4$-A-D;
A is $-C(R^{6a}R^{6b})_j-$; and
D is selected from the group consisting of

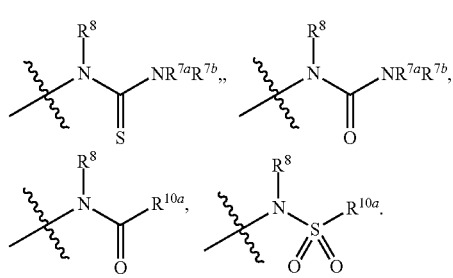

In another embodiment, the invention relates to compounds of Structural Formula I, or a pharmaceutically acceptable salt, and a pharmaceutically acceptable carrier, diluent, or vehicle thereof, wherein:

X is C-A-D and Y is a bond or $CR^4R^5$;
A is $-C(R^{6a}R^{6b})_j-$, ($C_6$ to $C_{10}$) arylene, or ($C_2$ to $C_9$) heteroarylene, wherein
each of the said ($C_6$ to $C_{10}$) arylene or ($C_2$ to $C_9$) heteroarylene is optionally substituted with at least one $R^{6a}$ group; and D is selected from the group consisting of

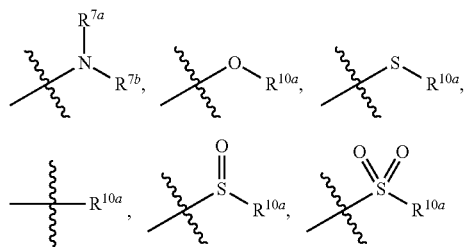

In another embodiment, the invention relates to compounds of Structural Formula I, or a pharmaceutically acceptable salt, and a pharmaceutically acceptable carrier, diluent, or vehicle thereof, wherein:

X is C-A-D and Y is a bond or $CR^4R^5$;

A is ($C_6$ to $C_{10}$) arylene or ($C_2$ to $C_9$) heteroarylene, wherein each of the said ($C_6$ to $C_{10}$) arylene or ($C_2$ to $C_9$) heteroarylene is optionally substituted with at least one $R^{6a}$ group; and D is selected from the group consisting of

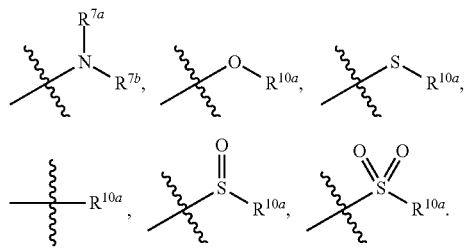

In another embodiment, the invention relates to compounds of Structural Formula I, or a pharmaceutically acceptable salt, and a pharmaceutically acceptable carrier, diluent, or vehicle thereof, wherein:

D is selected from the group consisting of

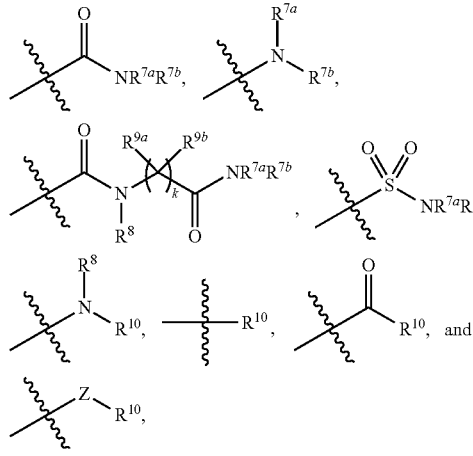

wherein $NR^{7a}R^{7b}$ is selected from the group consisting of

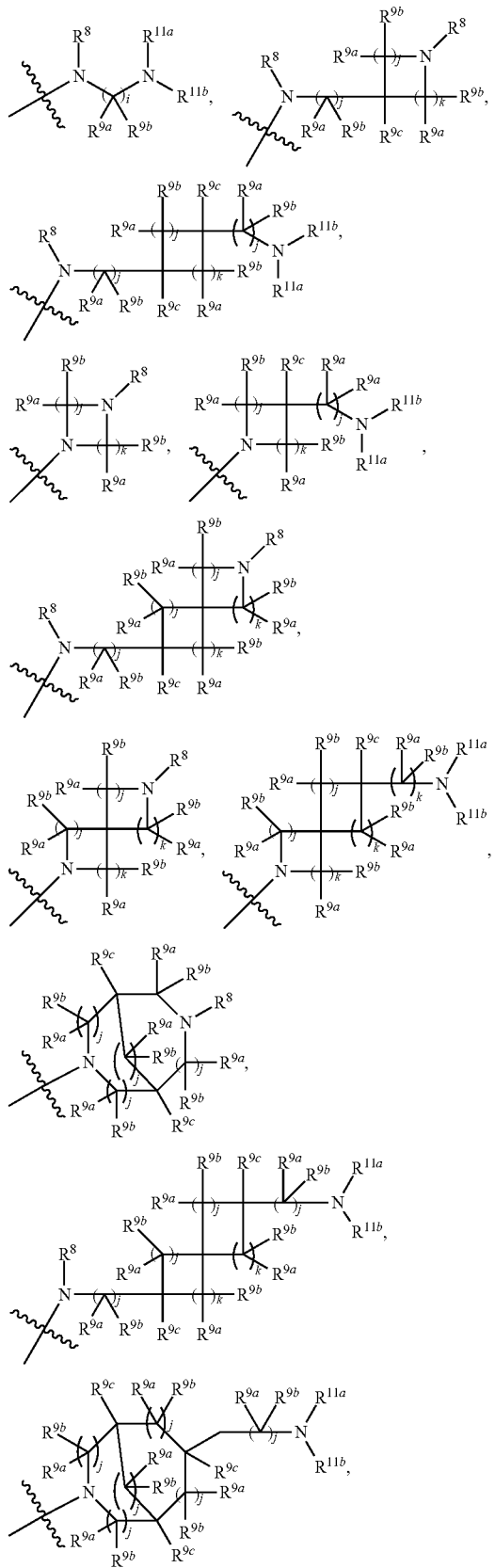

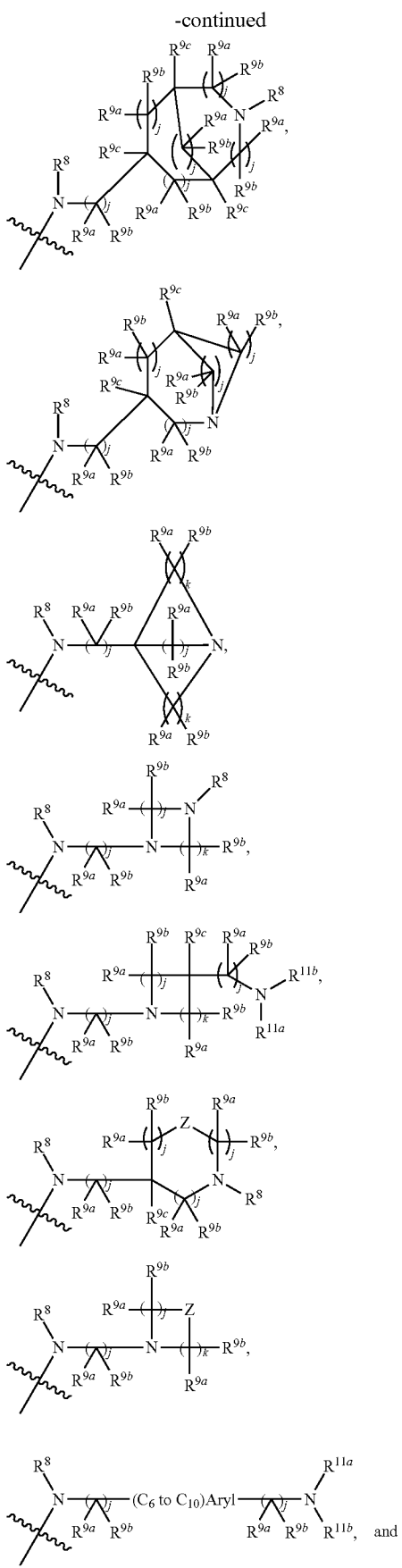

$R^1$ is selected from hydrogen, halogen, OH, nitro, $CF_3$, $-NR^{11a}R^{11b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, $-C(O)R^{12}$, $-C(O)NR^{11a}R^{11b}$, $-S(O)_m R^{12}$, $-S(O)_m NR^{11a}R^{11b}$, $-NR^{11a}S(O)_m R^{12}$, $-(CH_2)_n C(O)OR^{12}$, $-(CH_2)_n C(O)N(R^{11a}R^{11b})$, $-(CH_2)_n N(R^{11a}R^{11b})$, $-OC(O)R^{12}$, $-NR^{11a}C(O)R^{12}$, and $-NR^{11a}C(O)N(R^{11a}R^{11b})$, wherein
  each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

$R^2$ is selected from hydrogen, halogen, OH, nitro, $CF_3$, $-NR^{11a}R^{11b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, $-C(O)R^{12}$, $-C(O)NR^{11a}R^{11b}$, $-S(O)_m R^{12}$, $-S(O)_m NR^{11a}R^{11b}$, $-NR^{11a}S(O)_m R^{12}$, $-(CH_2)_n C(O)OR^{12}$, $-(CH_2)_n C(O)N(R^{11a}R^{11b})$, $-(CH_2)_n N(R^{11a}R^{11b})$, $-OC(O)R^{12}$, $-NR^{11a}C(O)R^{12}$, and $-NR^{11a}C(O)N(R^{11a}R^{11b})$, wherein
  each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

$R^3$ is selected from hydrogen, halogen, OH, nitro, $CF_3$, $-NR^{11a}R^{11b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, $-C(O)R^{12}$, $-C(O)NR^{11a}R^{11b}$, $-S(O)_m R^{12}$, $-S(O)_m NR^{11a}R^{11b}$, $-NR^{11a}S(O)_m R^{12}$, $-(CH_2)_n C(O)OR^{12}$, $-(CH_2)_n C(O)N(R^{11a}R^{11b})$, $-(CH_2)_n N(R^{11a}R^{11b})$, $-OC(O)R^{12}$, $-NR^{11a}C(O)R^{12}$, and $-NR^{11a}C(O)N(R^{11a}R^{11b})$, wherein
  each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

$R^4$ is selected from hydrogen, halogen, OH, nitro, $CF_3$, $-NR^{11a}R^{11b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, $-C(O)R^{12}$, $-C(O)NR^{11a}R^{11b}$, $-S(O)_m R^{12}$, $-S(O)_m NR^{11a}R^{11b}$, $-NR^{11a}S(O)_m R^{12}$, $-(CH_2)_n C(O)OR^{12}$, $-(CH_2)_n C(O)N(R^{11a}R^{11b})$, $-(CH_2)_n N(R^{11a}R^{11b})$, $-OC(O)R^{12}$, $-NR^{11a}C(O)R^{12}$, and $-NR^{11a}C(O)N(R^{11a}R^{11b})$, wherein
  each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

$R^5$ is selected from hydrogen, halogen, OH, nitro, $CF_3$, $-NR^{11a}R^{11b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, $-C(O)R^{12}$, $-C(O)NR^{11a}R^{11b}$, $-S(O)_mR^{12}$, $-S(O)_mNR^{11a}R^{11b}$, $-NR^{11a}S(O)_mR^{12}$, $-(CH_2)_nC(O)OR^{12}$, $-(CH_2)_nC(O)N(R^{11a}R^{11b})$, $-(CH_2)_nN(R^{11a}R^{11b})$, $-OC(O)R^{12}$, $-NR^{11a}C(O)R^{12}$, and $-NR^{11a}C(O)N(R^{11a}R^{11b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

each of the $R^{6a}$ and $R^{6b}$ is independently selected from hydrogen, halogen, OH, nitro, $CF_3$, $-NR^{11a}R^{11b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, $-C(O)R^{12}$, $-C(O)NR^{11a}R^{11b}$, $-S(O)_mR^{12}$, $-S(O)_mNR^{11a}R^{11b}$, $-NR^{11a}S(O)_mR^{12}$, $-(CH_2)_nC(O)OR^{12}$, $-(CH_2)_nC(O)N(R^{11a}R^{11b})$, $-(CH_2)_nN(R^{11a}R^{11b})$, $-OC(O)R^{12}$, $-NR^{11a}C(O)R^{12}$, and $-NR^{11a}C(O)N(R^{11a}R^{11b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

each $R^a$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{13}$ group;

each of the $R^{9a}$, $R^{9b}$, and $R^{9c}$ is independently selected from hydrogen, halogen, OH, nitro, $CF_3$, $-NR^{11a}R^{11b}$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, $-C(O)R^{12}$, $-C(O)NR^{11a}R^{11b}$, $-S(O)_mR^{12}$, $-S(O)_mNR^{11a}R^{11b}$, $-NR^{11a}S(O)_mR^{12}$, $-(CH_2)_nC(O)OR^{12}$, $-(CH_2)_nC(O)N(R^{11a}R^{11b})$, $-(CH_2)_nN(R^{11a}R^{11b})$, $-OC(O)R^{12}$, $-NR^{11a}C(O)R^{12}$, and $-NR^{11a}C(O)N(R^{11a}R^{11b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

$R^{10}$ is selected from the group consisting of each of the $R^{11a}$ and $R^{11b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{13}$ group, or $R^{11a}$ and $R^{11b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{13}$ group;

each $R^{12}$ is independently selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, and ($C_2$ to $C_9$) heteroaryl is optionally substituted with at least one $R^{13}$ group;

each $R^{13}$ is independently selected from hydrogen, halogen, OH, nitro, $CF_3$, $-NR^{14a}R^{14b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, $-C(O)R^{15}$, $-C(O)NR^{14a}R^{14b}$, $-S(O)_mR^{15}$, $-S(O)_mNR^{14a}R^{14b}$, $-NR^{14a}S(O)_mR^{15}$, $-(CH_2)_nC(O)OR^{15}$, $-(CH_2)_nC(O)N(R^{14a}R^{14b})$, $-(CH_2)_nN(R^{14a}R^{14b})$, $-OC(O)R^{15}$, $-O(CH_2)_nO-$, $-NR^{14a}C(O)R^{15}$, and $-NR^{14a}C(O)N(R^{14a}R^{14b})$, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{16}$ group;

each of the $R^{14a}$ and $R^{14b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_9$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{16}$ group, or $R^{14a}$ and $R^{14b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{16}$ group;

each $R^{15}$ is independently selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl is optionally substituted with at least one $R^{16}$ group;

each $R^{16}$ is independently selected from hydrogen, halogen, OH, nitro, $CF_3$, —$NR^{17a}R^{17b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —C(O)$NR^{17a}R^{17b}$, C(O)$R^{18}$, S(O)$_m R^{18}$, —S(O)$_m NR^{17a}R^{17b}$, —$NR^{17a}$S(O)$_m R^{18}$, —(CH$_2$)$_n$C(O)O$R^{18}$, —(CH$_2$)$_n$C(O)N($R^{17a}R^{17b}$), —(CH$_2$)$_n$N($R^{17a}R^{17b}$), —OC(O)$R^{18}$, —$NR^{17a}$C(O)$R^{18}$, and —$NR^{17a}$C(O)N($R^{17a}R^{17b}$) wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, ($C_6$ to $C_{10}$) aryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{19}$ group;

each of the $R^{17a}$ and $R^{17b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, $C_6$ to $C_{10}$) aryl, ($C_2$ to $C_9$) heteroaryl, ($C_6$ to $C_{10}$) arylene, and ($C_2$ to $C_9$) heteroarylene, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, and ($C_2$ to $C_9$) heteroarylene is optionally substituted with at least one $R^{19}$ group, or $R^{17a}$ and $R^{17b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{19}$ group;

each $R^{18}$ is independently selected from hydrogen, halogen, OH, nitro, $CF_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_2$ to $C_{10}$) cycloheteroalkyl, ($C_2$ to $C_9$) heteroaryl, and ($C_6$ to $C_{10}$) aryl is optionally substituted with at least one $R^{19}$ group;

each $R^{19}$ is independently selected from hydrogen, halogen, OH, nitro, $CF_3$, —$NR^{20a}R^{20b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —C(O)$R^{21}$, —C(O)$NR^{20a}R^{20b}$, —S(O)$_m R^{21}$, —S(O)$_m NR^{20a}R^{20b}$, —$NR^{20a}$S(O)$_m R^{21}$, —(CH$_2$)$_n$C(O)O$R^{21}$, —(CH$_2$)$_n$C(O)N($R^{20a}R^{20b}$), —(CH$_2$)$_n$N($R^{20a}R^{20b}$), —OC(O)$R^{21}$, —$NR^{20a}$C(O)$R^{21}$, and —$NR^{20a}$C(O)N($R^{20a}R^{20b}$), wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, and ($C_2$ to $C_{10}$) cycloheteroalkylene is optionally substituted with at least one $R^{22}$ group;

each of the $R^{20a}$ and $R^{20b}$ is independently selected from hydrogen, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl, wherein each of the said ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, ($C_3$ to $C_{10}$) cycloalkyl, (C to $C_{10}$) cycloalkenyl, ($C_2$ to $C_{10}$) cycloheteroalkyl, ($C_6$ to $C_{10}$) aryl, and ($C_2$ to $C_9$) heteroaryl is optionally substituted with at least one $R^{22}$ group, or $R^{20a}$ and $R^{20b}$ may be taken together with the nitrogen atom to which they are attached to form a ($C_2$ to $C_{10}$) cycloheteroalkyl ring, wherein said ($C_2$ to $C_{10}$) cycloheteroalkyl ring has 1 to 3 ring heteroatoms selected from the group consisting of N, O, and S, and wherein the said ($C_2$ to $C_{10}$) cycloheteroalkyl ring is optionally substituted with at least one $R^{22}$ group;

each $R^{21}$ is independently selected from hydrogen, halogen, OH, nitro, $CF_3$, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, and ($C_2$ to $C_9$) heteroaryl;

each $R^{22}$ is independently selected from hydrogen, halogen, OH, nitro, $CF_3$, —$NR^{23a}R^{23b}$, oxo, ($C_1$ to $C_{10}$) alkyl, ($C_1$ to $C_{10}$) alkenyl, ($C_1$ to $C_{10}$) alkynyl, ($C_1$ to $C_{10}$) alkoxy, aryloxy, cyano, ($C_3$ to $C_{10}$) cycloalkyl, ($C_5$ to $C_{10}$) cycloalkenyl, ($C_2$ to $C_{10}$) cycloheteroalkyl, ($C_6$ to $C_{10}$) aryl, ($C_2$ to $C_9$) heteroaryl, ($C_6$ to $C_{10}$) arylene, ($C_2$ to $C_9$) heteroarylene, ($C_3$ to $C_{10}$) cycloalkylene, ($C_2$ to $C_{10}$) cycloheteroalkylene, —C(O)$NR^{23a}R^{23b}$, —C(O)$R^{24}$, —S(O)$_m R^{24}$, —S(O)$_m NR^{23a}R^{23b}$, —$NR^{23a}$S(O)$_m R^{24}$, —(CH$_2$)$_n$C(O)O$R^{24}$, —(CH$_2$)$_n$C (O)N($R^{23a}R^{23b}$), —(CH$_2$)$_n$N($R^{23a}R^{23b}$), —OC(O)$R^{24}$, —N$R^{23a}$C(O)$R^{24}$, and —N$R^{23a}$C(O)N($R^{23a}R^{23b}$), wherein each of the said (C$_1$ to C$_{10}$) alkyl, (C$_1$ to C$_{10}$) alkenyl, (C$_1$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, (C$_2$ to C$_9$) heteroaryl, (C$_6$ to C$_{10}$) arylene, (C$_2$ to C$_9$) heteroarylene, (C$_3$ to C$_{10}$) cycloalkylene, and (C$_2$ to C$_{10}$) cycloheteroalkylene is optionally substituted with at least one $R^{25}$ group;

each of the $R^{23a}$ and $R^{23b}$ is independently selected from hydrogen, (C$_1$ to C$_{10}$) alkyl, (C$_1$ to C$_{10}$) alkenyl, (C$_1$ to C$_{10}$) alkynyl, (C$_3$ to C$_{10}$) cycloalkyl, (C$_5$ to C$_{10}$) cycloalkenyl, (C$_2$ to C$_{10}$) cycloheteroalkyl, (C$_2$ to C$_9$) heteroaryl, and (C$_6$ to C$_{10}$) aryl;

each $R^{24}$ is independently selected from hydrogen, halogen, OH, nitro, CF$_3$, (C$_1$ to C$_{10}$) alkyl, (C$_1$ to C$_{10}$) alkenyl, (C$_1$ to C$_{10}$) alkynyl, (C$_1$ to C$_{10}$) alkoxy, aryloxy, cyano, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, and (C$_2$ to C$_9$) heteroaryl;

$R^{25}$ is selected from hydrogen, halogen, OH, nitro, CF$_3$, —N$R^{26a}R^{26b}$, oxo, (C$_1$ to C$_{10}$) alkyl, (C$_1$ to C$_{10}$) alkenyl, (C$_1$ to C$_{10}$) alkynyl, (C$_1$ to C$_{10}$) alkoxy, aryloxy, cyano, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, (C$_2$ to C$_9$) heteroaryl, (C$_6$ to C$_{10}$) arylene, (C$_2$ to C$_9$) heteroarylene, (C$_3$ to C$_{10}$) cycloalkylene, (C$_2$ to C$_{10}$) cycloheteroalkylene, —C(O)$R^{27}$, —C(O)N$R^{26a}R^{26b}$, —S(O)$_m$$R^{27}$, —S(O)$_m$N$R^{26a}R^{26b}$, —N$R^{26a}$S(O)$_m$$R^{27}$, —(CH$_2$)$_n$C(O)O$R^{27}$, —(CH$_2$)$_n$C(O)N($R^{26a}R^{26b}$), —(CH$_2$)$_n$N($R^{26a}R^{26b}$), —OC(O)$R^{27}$, —N$R^{26a}$C(O)$R^{27}$, and —N$R^{26a}$C(O)N($R^{26a}R^{26b}$), wherein each of the said (C$_1$ to C$_{10}$) alkyl, (C$_1$ to C$_{10}$) alkenyl, (C$_1$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, (C$_2$ to C$_9$) heteroaryl, (C$_6$ to C$_{10}$) arylene, (C$_2$ to C$_9$) heteroarylene, (C$_3$ to C$_{10}$) cycloalkylene, and (C$_2$ to C$_{10}$) cycloheteroalkylene is optionally substituted with at least one $R^{27}$ group;

each of the $R^{26a}$ and $R^{26b}$ is independently selected from hydrogen, (C$_1$ to C$_{10}$) alkyl, (C$_1$ to C$_{10}$) alkenyl, (C$_1$ to C$_{10}$) alkynyl, (C$_1$ to C$_{10}$) alkoxy, aryloxy, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, and (C$_2$ to C$_9$) heteroaryl, or $R^{26a}$ and $R^{26b}$ may be taken together with the nitrogen atom to which they are attached to form a (C$_2$ to C$_{10}$) cycloheteroalkyl ring, wherein said (C$_2$ to C$_{10}$) cycloheteroalkyl ring has 1 to 3 ring heteroatoms selected from the group consisting of N, O, and S;

each $R^{27}$ is independently selected from hydrogen, halogen, OH, nitro, CF$_3$, (C$_1$ to C$_{10}$) alkyl, (C$_1$ to C$_{10}$) alkenyl, (C$_1$ to C$_{10}$) alkynyl, (C$_1$ to C$_{10}$) alkoxy, aryloxy, cyano, (C$_3$ to C$_{10}$) cycloalkyl, (C$_5$ to C$_{10}$) cycloalkenyl, (C$_2$ to C$_{10}$) cycloheteroalkyl, (C$_6$ to C$_{10}$) aryl, and (C$_2$ to C$_9$) heteroaryl;

h is 1 or 2;
i is 2, 3, 4, 5, or 6;
j is 0, 1, 2, 3, 4, or 5;
k is 1, 2, 3, 4, or 5;
m is 0, 1 or 2;
n is 0, 1, 2, 3, or 4;
Z is selected from the group consisting of —O—, —S—, —S(O)—, and —S(O)$_2$—;

with the proviso that
when $R^1$, $R^2$, or $R^3$ is alkyl or hydrogen, X is C—C ($R^{6a}R^{6b}$)$_j$-D, Y is CH$_2$, and D is

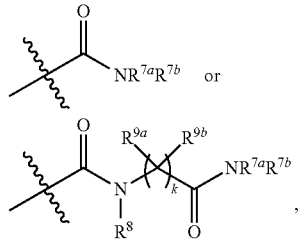

then N$R^{7a}R^{7b}$ cannot be an optionally substituted piperazine or 1,4-diazepane.

In another embodiment, the invention relates to compounds of Structural Formula I, or a pharmaceutically acceptable salt, and a pharmaceutically acceptable carrier, diluent, or vehicle thereof, wherein:

X is C-A-D and Y is CR$^4$R$^5$, wherein A-D is defined as above.

In another embodiment, the invention relates to compounds of Structural Formula I, or a pharmaceutically acceptable salt, and a pharmaceutically acceptable carrier, diluent, or vehicle thereof, wherein:

X is C-A-D and Y is CR$^4$R$^5$;
A is —C($R^{6a}R^{6b}$)$_j$—; and

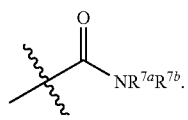

In another embodiment, the invention relates to compounds of Structural Formula I, or a pharmaceutically acceptable salt, and a pharmaceutically acceptable carrier, diluent, or vehicle thereof, wherein:

X is C-A-D and Y is CR$^4$R$^5$;
A is —C($R^{6a}R^{6b}$)$_j$—;
$R^1$ is selected from (C$_6$ to C$_{10}$) aryl and (C$_2$ to C$_9$) heteroaryl, wherein
each of the said (C$_6$ to C$_{10}$) aryl and (C$_2$ to C$_9$) heteroaryl is optionally substituted with at least one $R^{13}$ group;
$R^4$ is hydrogen;
$R^5$ is hydrogen; and
D is

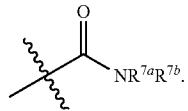

In another embodiment, the invention relates to compounds of Structural Formula I, or a pharmaceutically acceptable salt, and a pharmaceutically acceptable carrier, diluent, or vehicle thereof, wherein:

X is C-A-D and Y is CR$^4$R$^5$;
A is —C($R^{6a}R^{6b}$)$_j$—;
$R^1$ is selected from (C$_6$ to C$_{10}$) aryl and (C$_2$ to C$_9$) heteroaryl, wherein
each of the said (C$_6$ to C$_{10}$) aryl and (C$_2$ to C$_9$) heteroaryl is optionally substituted with at least one $R^{13}$ group;

$R^2$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, ($C_1$ to $C_{10}$) alkoxy, —$(CH_2)_nC(O)N(R^{11a}R^{11b})$, and —$C(O)R^{12}$, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group;

$R^3$ is selected from hydrogen, $C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group;

$R^4$ is hydrogen;
$R^5$ is hydrogen; and
D is

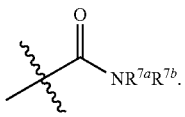

In another embodiment, the invention relates to compounds of Structural Formula I, or a pharmaceutically acceptable salt, and a pharmaceutically acceptable carrier, diluent, or vehicle thereof, wherein:

X is C-A-D and Y is $CR^4R^5$;
A is —$C(R^{6a}R^{6b})_j$—;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;

$R^2$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, ($C_1$ to $C_{10}$) alkoxy, —$(CH_2)_nC(O)N(R^{11a}R^{11b})$, and —$C(O)R^{12}$, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group;

$R^3$ is selected from hydrogen, $C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group;

$R^4$ is hydrogen;
$R^5$ is hydrogen; and
D is

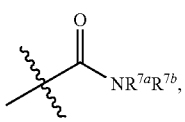

except when $R^1$ is phenyl, $R^2$ is hydrogen, and j is 0, then $NR^{7a}R^{7b}$ cannot be

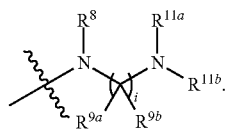

and when $R^1$ is hydrogen, halogen, or hydroxy, $R^2$ is hydrogen, $R^3$ is hydrogen, X is C-A-D, Y is $CH_2$, A is —$C(R^{6a}R^{6b})_j$—, and D is

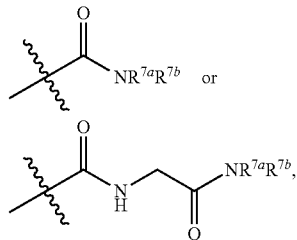

then j is 2, 3, 4, or 5, but not 0 or 1.

In another embodiment, the invention relates to compounds of Structural Formula I, or a pharmaceutically acceptable salt, and a pharmaceutically acceptable carrier, diluent, or vehicle thereof, wherein:

X is C-A-D and Y is $CR^4R^5$;
A is —$C(R^{6a}R^{6b})_j$—;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;

$R^2$ is ($C_1$ to $C_{10}$) alkyl, wherein the said ($C_1$ to $C_{10}$) alkyl is optionally substituted with at least one $R^{13}$ group;

$R^3$ is hydrogen;
$R^4$ is hydrogen;
$R^5$ is hydrogen; and
D is

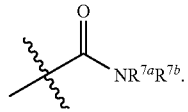

In another embodiment, the invention relates to compounds of Structural Formula I, or a pharmaceutically acceptable salt, and a pharmaceutically acceptable carrier, diluent, or vehicle thereof, wherein:

X is C-A-D and Y is $CR^4R^5$;
A is —$C(R^{6a}R^{6b})_j$—; and
D is

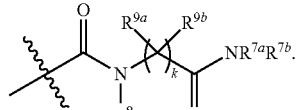

In another embodiment, the invention relates to compounds of Structural Formula I, or a pharmaceutically acceptable salt, and a pharmaceutically acceptable carrier, diluent, or vehicle thereof, wherein:

X is C-A-D and Y is CR$^4$R$^5$;
A is —C(R$^{6a}$R$^{6b}$)$_j$—;
R$^1$ is selected from (C$_6$ to C$_{10}$) aryl and (C$_2$ to C$_9$) heteroaryl, wherein
each of the said (C$_6$ to C$_{10}$) aryl and (C$_2$ to C$_9$) heteroaryl is optionally substituted with at least one R$^{13}$ group;
R$^4$ is hydrogen;
R$^5$ is hydrogen; and
D is

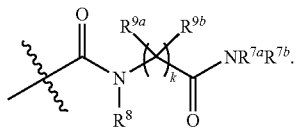

In another embodiment, the invention relates to compounds of Structural Formula I, or a pharmaceutically acceptable salt, and a pharmaceutically acceptable carrier, diluent, or vehicle thereof, wherein:
X is C-A-D and Y is CR$^4$R$^5$;
A is —C(R$^{6a}$R$^{6b}$)$_j$—;
R$^1$ is selected from (C$_6$ to C$_{10}$) aryl and (C$_2$ to C$_9$) heteroaryl, wherein
each of the said (C$_6$ to C$_{10}$) aryl and (C$_2$ to C$_9$) heteroaryl is optionally substituted with at least one R$^{13}$ group;
R$^2$ is selected from hydrogen, (C$_1$ to C$_{10}$) alkyl, (C$_1$ to C$_{10}$) alkenyl, (C$_1$ to C$_{10}$) alkynyl, (C$_3$ to C$_{10}$) cycloalkyl, and (C$_5$ to C$_{10}$) cycloalkenyl, (C$_1$ to C$_{10}$) alkoxy, —(CH$_2$)$_n$C(O)N(R$^{11a}$R$^{11b}$), and —C(O)R$^{12}$, wherein
each of the said (C$_1$ to C$_{10}$) alkyl, (C$_1$ to C$_{10}$) alkenyl, (C$_1$ to C$_{10}$) alkynyl, (C$_3$ to C$_{10}$) cycloalkyl, (C$_5$ to C$_{10}$) cycloalkenyl is optionally substituted with at least one R$^{13}$ group;
R$^3$ is selected from hydrogen, C$_1$ to C$_{10}$) alkyl, (C$_1$ to C$_{10}$) alkenyl, (C$_1$ to C$_{10}$) alkynyl, (C$_3$ to C$_{10}$) cycloalkyl, and (C$_5$ to C$_{10}$) cycloalkenyl, wherein
each of the said (C$_1$ to C$_{10}$) alkyl, (C$_1$ to C$_{10}$) alkenyl, (C$_1$ to C$_{10}$) alkynyl, (C$_3$ to C$_{10}$) cycloalkyl, (C$_5$ to C$_{10}$) cycloalkenyl is optionally substituted with at least one R$^{13}$ group;
R$^4$ is hydrogen;
R$^5$ is hydrogen; and
D is

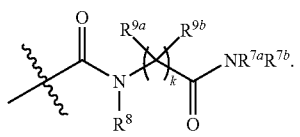

In another embodiment, the invention relates to compounds of Structural Formula I, or a pharmaceutically acceptable salt, and a pharmaceutically acceptable carrier, diluent, or vehicle thereof, wherein:
X is C-A-D and Y is CR$^4$R$^5$;
A is —C(R$^{6a}$R$^{6b}$)$_j$—;
R$^1$ is selected from (C$_6$ to C$_{10}$) aryl and (C$_2$ to C$_9$) heteroaryl, wherein
each of the said (C$_6$ to C$_{10}$) aryl and (C$_2$ to C$_9$) heteroaryl is optionally substituted with at least one R$^{13}$ group;
R$^2$ is selected from hydrogen and (C$_1$ to C$_{10}$) alkyl, wherein the said (C$_1$ to C$_{10}$) alkyl is optionally substituted with at least one R$^{13}$ group;

R$^3$ is hydrogen;
R$^4$ is hydrogen;
R$^5$ is hydrogen; and
D is

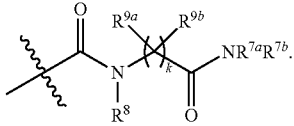

In another embodiment, the invention relates to compounds of Structural Formula I, or a pharmaceutically acceptable salt, and a pharmaceutically acceptable carrier, diluent, or vehicle thereof, wherein:
X is C-A-D and Y is CR$^4$R$^5$;
A is —C(R$^{6a}$R$^{6b}$)$_j$—; and
D is

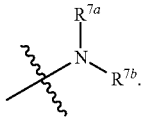

In another embodiment, the invention relates to compounds of Structural Formula I, or a pharmaceutically acceptable salt, and a pharmaceutically acceptable carrier, diluent, or vehicle thereof, wherein:
X is C-A-D and Y is CR$^4$R$^5$;
A is —C(R$^{6a}$R$^{6b}$)$_j$—;
R$^1$ is selected from (C$_6$ to C$_{10}$) aryl and (C$_2$ to C$_9$) heteroaryl, wherein
each of the said (C$_6$ to C$_{10}$) aryl and (C$_2$ to C$_9$) heteroaryl is optionally substituted with at least one R$^{13}$ group;
R$^4$ is hydrogen;
R$^5$ is hydrogen; and
D is

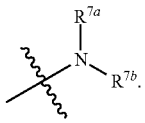

In another embodiment, the invention relates to compounds of Structural Formula I, or a pharmaceutically acceptable salt, and a pharmaceutically acceptable carrier, diluent, or vehicle thereof, wherein:
X is C-A-D and Y is CR$^4$R$^5$;
A is —C(R$^{6a}$R$^{6b}$)$_j$—;
R$^1$ is selected from (C to C$_{10}$) aryl and (C$_2$ to C$_9$) heteroaryl, wherein
each of the said (C$_6$ to C$_{10}$) aryl and (C$_2$ to C$_9$) heteroaryl is optionally substituted with at least one R$^{13}$ group;
R$^2$ is selected from hydrogen, (C$_1$ to C$_{10}$) alkyl, (C$_1$ to C$_{10}$) alkenyl, (C$_1$ to C$_{10}$) alkynyl, (C$_3$ to C$_{10}$) cycloalkyl, and (C$_5$ to C$_{10}$) cycloalkenyl, (C$_1$ to C$_{10}$) alkoxy, —(CH$_2$)$_n$C(O)N(R$^{11a}$R$^{11b}$), and —C(O)R$^{12}$, wherein
each of the said (C$_1$ to C$_{10}$) alkyl, (C$_1$ to C$_{10}$) alkenyl, (C$_1$ to C$_{10}$) alkynyl, (C$_3$ to C$_{10}$) cycloalkyl, (C$_5$ to C$_{10}$) cycloalkenyl is optionally substituted with at least one R$^{13}$ group;

$R^3$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group;

$R^4$ is hydrogen;
$R^5$ is hydrogen; and
D is

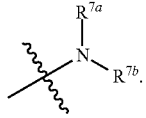

In another embodiment, the invention relates to compounds of Structural Formula I, or a pharmaceutically acceptable salt, and a pharmaceutically acceptable carrier, diluent, or vehicle thereof, wherein:

X is C-A-D and Y is $CR^4R^5$;
A is $—C(R^{6a}R^{6b})_j—$;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^2$ is selected from hydrogen and ($C_1$ to $C_{10}$) alkyl, wherein the said ($C_1$ to $C_{10}$) alkyl is optionally substituted with at least one $R^{13}$ group;
$R^3$ is hydrogen;
$R^4$ is hydrogen;
$R^5$ is hydrogen; and
D is

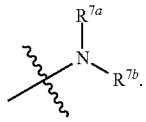

In another embodiment, the invention relates to compounds of Structural Formula I, or a pharmaceutically acceptable salt, and a pharmaceutically acceptable carrier, diluent, or vehicle thereof, wherein:

X is C-A-D and Y is $CR^4R^5$;
A is $—C(R^{6a}R^{6b})_j—$; and
D is

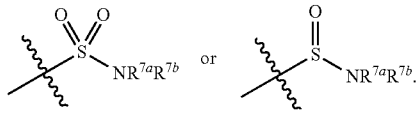

In another embodiment, the invention relates to compounds of Structural Formula I, or a pharmaceutically acceptable salt, and a pharmaceutically acceptable carrier, diluent, or vehicle thereof, wherein:

X is C-A-D and Y is $CR^4R^5$;
A is $—C(R^{6a}R^{6b})_j—$;
$R^1$ is selected from ($C_6$ to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^{13}$ group;
$R^4$ is hydrogen;
$R^5$ is hydrogen; and
D is

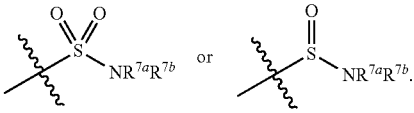

In another embodiment, the invention relates to compounds of Structural Formula I, or a pharmaceutically acceptable salt, and a pharmaceutically acceptable carrier, diluent, or vehicle thereof, wherein:

X is C-A-D and Y is $CR^4R^5$;
A is $—C(R^{6a}R^{6b})_j—$;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^2$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, ($C_1$ to $C_{10}$) alkoxy, $—(CH_2)_nC(O)N(R^{11a}R^{11b})$, and $—C(O)R^{12}$, wherein
each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group;
$R^3$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, wherein
each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group;
$R^4$ is hydrogen;
$R^5$ is hydrogen; and
D is

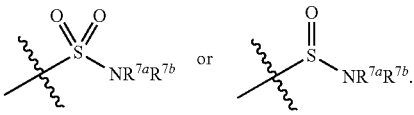

In another embodiment, the invention relates to compounds of Structural Formula I, or a pharmaceutically acceptable salt, and a pharmaceutically acceptable carrier, diluent, or vehicle thereof, wherein:

X is C-A-D and Y is $CR^4R^5$;
A is $—C(R^{6a}R^{6b})_j—$;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^2$ is selected from hydrogen and ($C_1$ to $C_{10}$) alkyl, wherein the said ($C_1$ to $C_{10}$) alkyl is optionally substituted with at least one $R^{13}$ group;
$R^3$ is hydrogen;
$R^4$ is hydrogen;
$R^5$ is hydrogen; and

53

D is

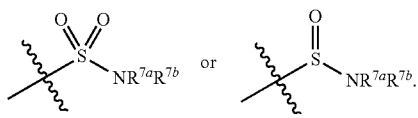

In another embodiment, the invention relates to compounds of Structural Formula I, or a pharmaceutically acceptable salt, and a pharmaceutically acceptable carrier, diluent, or vehicle thereof, wherein:
X is C-A-D and Y is $CR^4R^5$;
A is $—C(R^{6a}R^{6b})_j—$;
D is

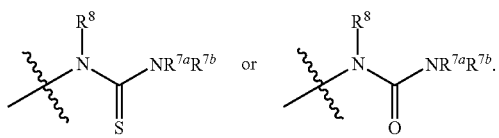

In another embodiment, the invention relates to compounds of Structural Formula I, or a pharmaceutically acceptable salt, and a pharmaceutically acceptable carrier, diluent, or vehicle thereof, wherein:
X is C-A-D and Y is $CR^4R^5$;
A is $—C(R^{6a}R^{6b})_j—$;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^4$ is hydrogen;
$R^5$ is hydrogen; and
D is

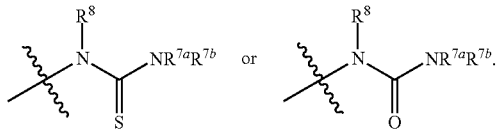

In another embodiment, the invention relates to compounds of Structural Formula I, or a pharmaceutically acceptable salt, and a pharmaceutically acceptable carrier, diluent, or vehicle thereof, wherein:
X is C-A-D and Y is $CR^4R^5$;
A is $—C(R^{6a}R^{6b})_j—$;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^2$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, ($C_1$ to $C_{10}$) alkoxy, $—(CH_2)_nC(O)N(R^{11a}R^{11b})$, and $—C(O)R^{12}$, wherein
each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group;
$R^3$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, wherein

54 each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group;
$R^4$ is hydrogen;
$R^5$ is hydrogen; and
D is

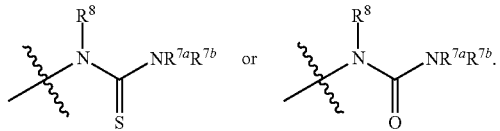

In another embodiment, the invention relates to compounds of Structural Formula I, or a pharmaceutically acceptable salt, and a pharmaceutically acceptable carrier, diluent, or vehicle thereof, wherein:
X is C-A-D and Y is $CR^4R^5$;
A is $—C(R^{6a}R^{6b})_j—$;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^2$ is selected from hydrogen and ($C_1$ to $C_{10}$) alkyl, wherein the said ($C_1$ to $C_{10}$) alkyl is optionally substituted with at least one $R^{13}$ group;
$R^3$ is hydrogen;
$R^4$ is hydrogen;
$R^5$ is hydrogen; and
D is

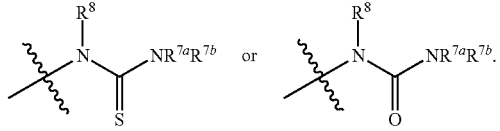

In another embodiment, the invention relates to compounds of Structural Formula I, or a pharmaceutically acceptable salt, and a pharmaceutically acceptable carrier, diluent, or vehicle thereof, wherein:
X is C-A-D, and Y is a bond or $CR^4R^5$; or
X is $CR^5$ and Y is $CR^4$-A-D;
A is $—C(R^{6a}R^{6b})_j—$; and
D is

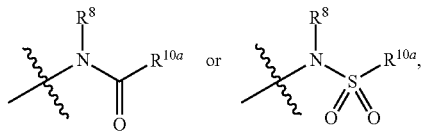

wherein $R^{10a}$ is selected from the group consisting of

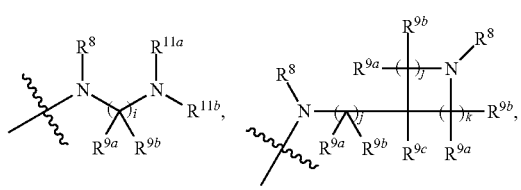

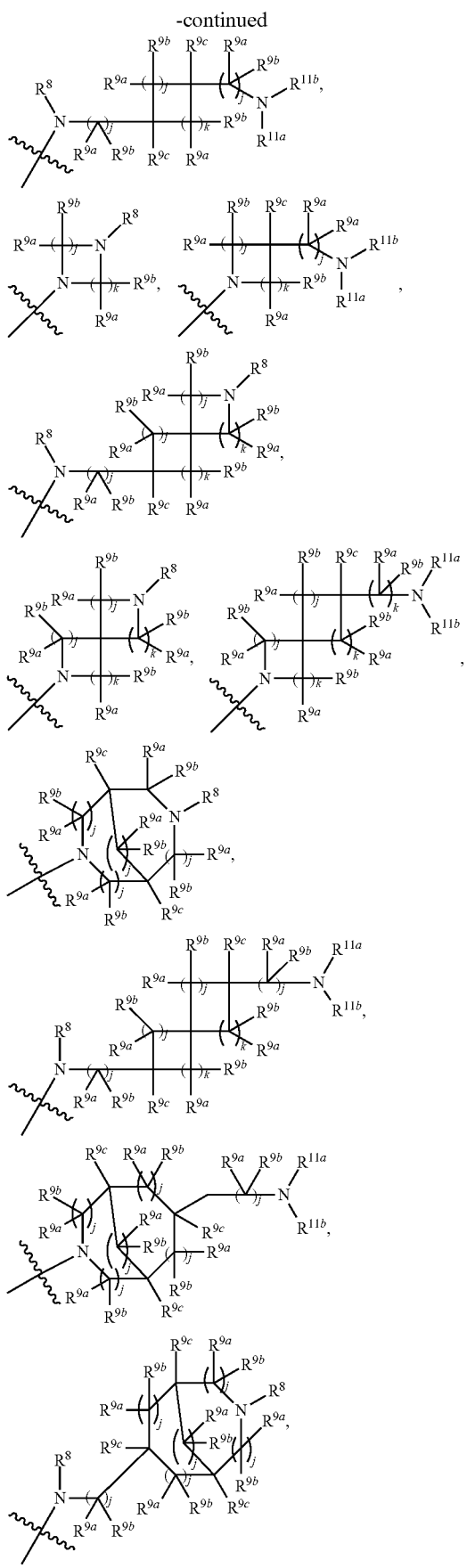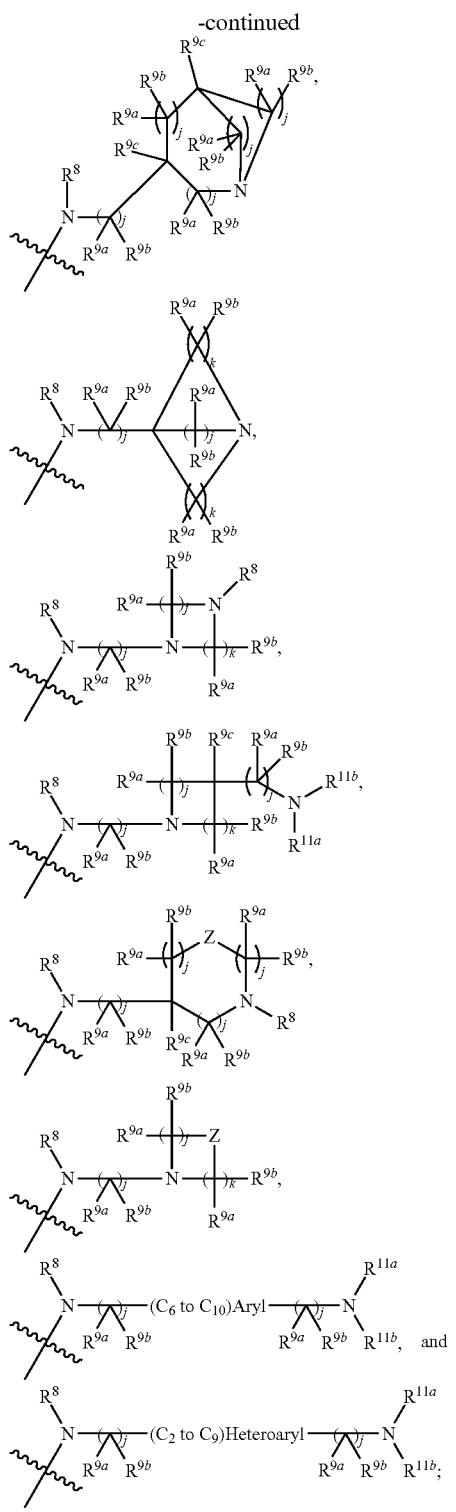

$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;

$R^2$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_1$ to $C_{10}$) alkoxy, —$(CH_2)_nC(O)N(R^{11a}R^{11b})$, and —$C(O)R^{12}$, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, and ($C_1$ to $C_{10}$) alkoxy is optionally substituted with at least one $R^{13}$ group;

$R^3$ is hydrogen;

$R^4$ is hydrogen; and $R^5$ is hydrogen.

In another embodiment, the invention relates to compounds of Structural Formula I, or a pharmaceutically acceptable salt, and a pharmaceutically acceptable carrier, diluent, or vehicle thereof, wherein:

X is C-A-D and Y is a bond.

In another embodiment, the invention relates to compounds of Structural Formula I, or a pharmaceutically acceptable salt, and a pharmaceutically acceptable carrier, diluent, or vehicle thereof, wherein:

X is C-A-D and Y is a bond;

A is —$C(R^{6a}R^{6b})_j$—; and

D is

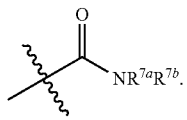

In another embodiment, the invention relates to compounds of Structural Formula I, or a pharmaceutically acceptable salt, and a pharmaceutically acceptable carrier, diluent, or vehicle thereof, wherein:

X is C-A-D and Y is a bond;

A is —$C(R^{6a}R^{6b})_j$—;

$R^1$ is selected from (C to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^{13}$ group;

D is

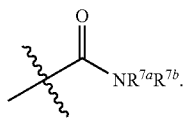

In another embodiment, the invention relates to compounds of Structural Formula I, or a pharmaceutically acceptable salt, and a pharmaceutically acceptable carrier, diluent, or vehicle thereof, wherein:

X is C-A-D and Y is a bond;

A is —$C(R^{6a}R^{6b})_j$—;

$R^1$ is selected from ($C_6$ to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^{13}$ group;

$R^2$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, ($C_1$ to $C_{10}$) alkoxy, —$(CH_2)_nC(O)N(R^{11a}R^{11b})$, and —$C(O)R^{12}$, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group;

$R^3$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group;

D is

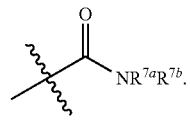

In another embodiment, the invention relates to compounds of Structural Formula I, or a pharmaceutically acceptable salt, and a pharmaceutically acceptable carrier, diluent, or vehicle thereof, wherein:

X is C-A-D and Y is a bond;

A is —$C(R^{6a}R^{6b})_j$—;

$R^1$ is selected from (C to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^{13}$ group;

$R^2$ is selected from hydrogen and ($C_1$ to $C_{10}$) alkyl, wherein the said ($C_1$ to $C_{10}$) alkyl is optionally substituted with at least one $R^{13}$ group;

$R^3$ is hydrogen; and

D is

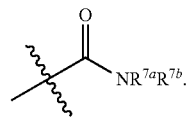

In another embodiment, the invention relates to compounds of Structural Formula I, or a pharmaceutically acceptable salt, and a pharmaceutically acceptable carrier, diluent, or vehicle thereof, wherein:

X is C-A-D and Y is a bond;

A is —$C(R^{6a}R^{6b})_j$—; and

D is

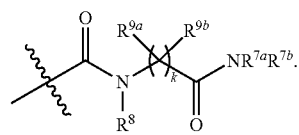

In another embodiment, the invention relates to compounds of Structural Formula I, or a pharmaceutically acceptable salt, and a pharmaceutically acceptable carrier, diluent, or vehicle thereof, wherein:

X is C-A-D and Y is a bond;

A is —$C(R^{6a}R^{6b})_j$—;

$R^1$ is selected from (C to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^{13}$ group; and D is

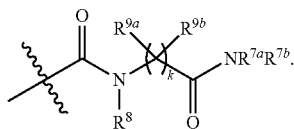

In another embodiment, the invention relates to compounds of Structural Formula I, or a pharmaceutically acceptable salt, and a pharmaceutically acceptable carrier, diluent, or vehicle thereof, wherein:
X is C-A-D and Y is a bond;
A is —C($R^{6a}R^{6b}$)$_j$—;
$R^1$ is selected from (C to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^2$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, ($C_1$ to $C_{10}$) alkoxy, —(CH$_2$)$_n$C(O)N($R^{11a}R^{11b}$), and —C(O)$R^{12}$, wherein
each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group;
$R^3$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, wherein
each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group; and
D is

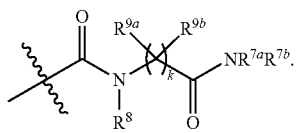

In another embodiment, the invention relates to compounds of Structural Formula I, or a pharmaceutically acceptable salt, and a pharmaceutically acceptable carrier, diluent, or vehicle thereof, wherein:
X is C-A-D and Y is a bond;
A is —C($R^{6a}R^{6b}$)$_j$—;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^2$ is selected from hydrogen and ($C_1$ to $C_{10}$) alkyl, wherein the said ($C_1$ to $C_{10}$) alkyl is optionally substituted with at least one $R^{13}$ group;
$R^3$ is hydrogen; and
D is

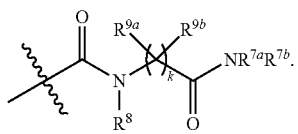

In another embodiment, the invention relates to compounds of Structural Formula I, or a pharmaceutically acceptable salt, and a pharmaceutically acceptable carrier, diluent, or vehicle thereof, wherein:
X is C-A-D and Y is a bond;
A is —C($R^{6a}R^{6b}$)$_j$—; and
D is

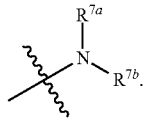

In another embodiment, the invention relates to compounds of Structural Formula I, or a pharmaceutically acceptable salt, and a pharmaceutically acceptable carrier, diluent, or vehicle thereof, wherein:
X is C-A-D and Y is a bond;
A is —C($R^{6a}R^{6b}$)$_j$—;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
D is

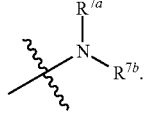

In another embodiment, the invention relates to compounds of Structural Formula I, or a pharmaceutically acceptable salt, and a pharmaceutically acceptable carrier, diluent, or vehicle thereof, wherein:
X is C-A-D and Y is a bond;
A is —C($R^{6a}R^{6b}$)$_j$—;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^2$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, ($C_1$ to $C_{10}$) alkoxy, —(CH$_2$)$_n$C(O)N($R^{11a}R^{11b}$), and —C(O)$R^{12}$, wherein
each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group;
$R^3$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, wherein
each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group; and
D is

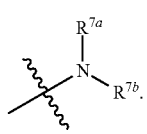

In another embodiment, the invention relates to compounds of Structural Formula I, or a pharmaceutically acceptable salt, and a pharmaceutically acceptable carrier, diluent, or vehicle thereof, wherein:
X is C-A-D and Y is a bond;
A is —C($R^{6a}R^{6b}$)$_j$—;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^2$ is selected from hydrogen and ($C_1$ to $C_{10}$) alkyl, wherein the said ($C_1$ to $C_{10}$) alkyl is optionally substituted with at least one $R^{13}$ group; and
$R^3$ is hydrogen;
D is

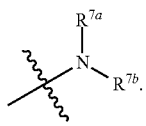

In another embodiment, the invention relates to compounds of Structural Formula I, or a pharmaceutically acceptable salt, and a pharmaceutically acceptable carrier, diluent, or vehicle thereof, wherein:
X is $CR^5$ and Y is $CR^4$-A-D.

In another embodiment, the invention relates to compounds of Structural Formula I, or a pharmaceutically acceptable salt, and a pharmaceutically acceptable carrier, diluent, or vehicle thereof, wherein:
X is $CR^5$ and Y is $CR^4$-A-D;
A is —C($R^{6a}R^{6b}$)$_j$—; and
D is

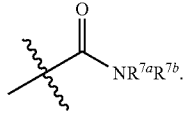

In another embodiment, the invention relates to compounds of Structural Formula I, or a pharmaceutically acceptable salt, and a pharmaceutically acceptable carrier, diluent, or vehicle thereof, wherein:
X is $CR^5$ and Y is $CR^4$-A-D;
A is —C($R^{6a}R^{6b}$)$_j$—;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^4$ is hydrogen;
$R^5$ is hydrogen; and
D is

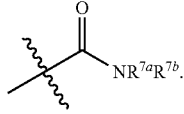

In another embodiment, the invention relates to compounds of Structural Formula I, or a pharmaceutically acceptable salt, and a pharmaceutically acceptable carrier, diluent, or vehicle thereof, wherein:
X is $CR^5$ and Y is $CR^4$-A-D;
A is —C($R^{6a}R^{6b}$)$_j$—;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^2$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, ($C_1$ to $C_{10}$) alkoxy, —(CH$_2$)$_n$C(O)N($R^{11a}R^{11b}$), and —C(O)$R^{12}$, wherein
each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group;
$R^3$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, wherein
each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group;
$R^4$ is hydrogen;
$R^5$ is hydrogen; and
D is

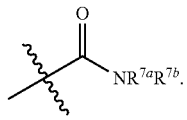

In another embodiment, the invention relates to compounds of Structural Formula I, or a pharmaceutically acceptable salt, and a pharmaceutically acceptable carrier, diluent, or vehicle thereof, wherein:
X is $CR^5$ and Y is $CR^4$-A-D;
A is —C($R^{6a}R^{6b}$)$_j$—;
$R^1$ is selected from (C to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^2$ is selected from hydrogen and ($C_1$ to $C_{10}$) alkyl, wherein the said ($C_1$ to $C_{10}$) alkyl is optionally substituted with at least one $R^{13}$ group;
$R^3$ is hydrogen;
$R^4$ is hydrogen;
$R^5$ is hydrogen; and
D is

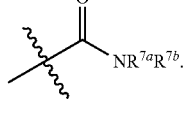

In another embodiment, the invention relates to compounds of Structural Formula I, or a pharmaceutically acceptable salt, and a pharmaceutically acceptable carrier, diluent, or vehicle thereof, wherein:
X is $CR^5$ and Y is $CR^4$-A-D;
A is —C($R^{6a}R^{6b}$)$_j$—; and D is

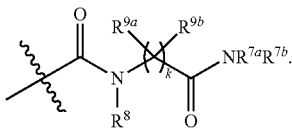

In another embodiment, the invention relates to compounds of Structural Formula I, or a pharmaceutically acceptable salt, and a pharmaceutically acceptable carrier, diluent, or vehicle thereof, wherein:
X is $CR^5$ and Y is $CR^4$-A-D;
A is —$C(R^{6a}R^{6b})_j$—;
$R^1$ is selected from ($C_6$ to $C_{10}$) aryland ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^4$ is hydrogen;
$R^5$ is hydrogen; and
D is

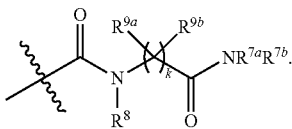

In another embodiment, the invention relates to compounds of Structural Formula I, or a pharmaceutically acceptable salt, and a pharmaceutically acceptable carrier, diluent, or vehicle thereof, wherein:
X is $CR^5$ and Y is $CR^4$-A-D;
A is —$C(R^{6a}R^{6b})_j$—;
$R^1$ is selected from ($C_6$ to $C_{10}$) aryland ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^2$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, ($C_1$ to $C_{10}$) alkoxy, —$(CH_2)_nC(O)N(R^{11a}R^{11b})$, and —$C(O)R^{12}$, wherein
each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group;
$R^3$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, wherein
each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group;
$R^4$ is hydrogen;
$R^5$ is hydrogen; and
D is

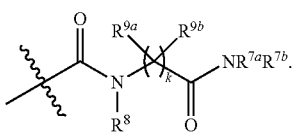

In another embodiment, the invention relates to compounds of Structural Formula I, or a pharmaceutically acceptable salt, and a pharmaceutically acceptable carrier, diluent, or vehicle thereof, wherein:
X is $CR^5$ and Y is $CR^4$-A-D;
A is —$C(R^{6a}R^{6b})_j$—;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^2$ is selected from hydrogen and ($C_1$ to $C_{10}$) alkyl, wherein the said ($C_1$ to $C_{10}$) alkyl is optionally substituted with at least one $R^{13}$ group;
$R^3$ is hydrogen; and
D is

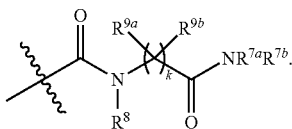

In another embodiment, the invention relates to compounds of Structural Formula I, or a pharmaceutically acceptable salt, and a pharmaceutically acceptable carrier, diluent, or vehicle thereof, wherein:
X is $CR^5$ and Y is $CR^4$-A-D;
A is —$C(R^{6a}R^{6b})_j$—; and
D is

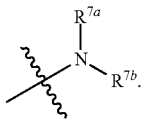

In another embodiment, the invention relates to compounds of Structural Formula I, or a pharmaceutically acceptable salt, and a pharmaceutically acceptable carrier, diluent, or vehicle thereof, wherein:
X is $CR^5$ and Y is $CR^4$-A-D;
A is —$C(R^{6a}R^{6b})_j$—;
$R^1$ is selected from ($C_6$ to $C_{10}$) aryl and ($C_2$ to $C_9$) heteroaryl, wherein
each of the said ($C_6$ to $C_{10}$) aryl and ($C_2$ to $C_9$) heteroaryl is optionally substituted with at least one $R^{13}$ group;
$R^4$ is hydrogen;
$R^5$ is hydrogen; and
D is

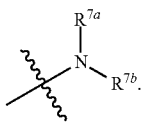

In another embodiment, the invention relates to compounds of Structural Formula I, or a pharmaceutically acceptable salt, and a pharmaceutically acceptable carrier, diluent, or vehicle thereof, wherein:
X is $CR^5$ and Y is $CR^4$-A-D;
A is —$C(R^{6a}R^{6b})_j$—;
$R^1$ is selected from ($C_6$ to $C_{10}$) aryland ($C_2$ to $C_9$) heteroaryl, wherein each of the said ($C_6$ to $C_{10}$) aryl and ($C_2$ to $C_9$) heteroaryl is optionally substituted with at least one $R^{13}$ group;

$R^2$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, ($C_1$ to $C_{10}$) alkoxy, —$(CH_2)_nC(O)N(R^{11a}R^{11b})$, and —$C(O)R^{12}$, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group;

$R^3$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group;

$R^4$ is hydrogen;
$R^5$ is hydrogen; and
D is

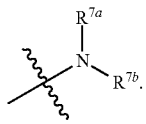

In another embodiment, the invention relates to compounds of Structural Formula I, or a pharmaceutically acceptable salt, and a pharmaceutically acceptable carrier, diluent, or vehicle thereof, wherein:

X is $CR^5$ and Y is $CR^4$-A-D;
A is —$C(R^{6a}R^{6b})_j$—;
$R^1$ is selected from ($C_6$ to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^{13}$ group;

$R^2$ is selected from hydrogen and ($C_1$ to $C_{10}$) alkyl, wherein the said ($C_1$ to $C_{10}$) alkyl is optionally substituted with at least one $R^{13}$ group;

$R^3$ is hydrogen;
$R^4$ is hydrogen;
$R^5$ is hydrogen; and
D is

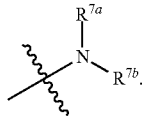

In another embodiment, the invention relates to compounds of Structural Formula I, or a pharmaceutically acceptable salt, and a pharmaceutically acceptable carrier, diluent, or vehicle thereof, wherein:

X is $CR^5$ and Y is $CR^4$-A-D;
A is —$C(R^{6a}R^{6b})_j$—;
D is selected from the group consisting of

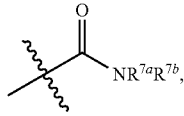

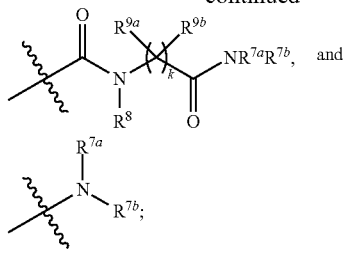

$R^1$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_1$ to $C_{10}$) alkoxy, —$(CH_2)_nC(O)N(R^{11a}R^{11b})$, and —$C(O)R^{12}$, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, and ($C_1$ to $C_{10}$) alkoxy is optionally substituted with at least one $R^{13}$ group;

$R^2$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, ($C_1$ to $C_{10}$) alkoxy, —$(CH_2)_nC(O)N(R^{11a}R^{11b})$, and —$C(O)R^{12}$, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl, and ($C_1$ to $C_{10}$) alkoxy is optionally substituted with at least one $R^{13}$ group;

$R^3$ is selected from hydrogen, ($C_1$ to $C_{10}$) alkyl, ($C_1$ to $C_{10}$) alkenyl, ($C_1$ to $C_{10}$) alkynyl, ($C_3$ to $C_{10}$) cycloalkyl, and ($C_5$ to $C_{10}$) cycloalkenyl, wherein each of the said ($C_1$ to $C_{10}$) alkyl, ($C_1$ to $C_{10}$) alkenyl, ($C_1$ to $C_{10}$) alkynyl, ($C_3$ to $C_{10}$) cycloalkyl, ($C_5$ to $C_{10}$) cycloalkenyl is optionally substituted with at least one $R^{13}$ group.

$R^4$ is selected from (C to $C_{10}$) aryl and ($C_2$ to $C_9$) heteroaryl, wherein each of the said ($C_6$ to $C_{10}$) aryl and ($C_2$ to $C_9$) heteroaryl is optionally substituted with at least one $R^{13}$ group;

$R^5$ is hydrogen.

In another embodiment, the invention relates to compounds of Structural Formula I, or a pharmaceutically acceptable salt, and a pharmaceutically acceptable carrier, diluent, or vehicle thereof, wherein:

X is C-A-D and Y is $CR^4R^5$;
A is —$C(R^{6a}R^{6b})_j$—, ($C_6$ to $C_{10}$) arylene, or ($C_2$ to $C_9$) heteroarylene, wherein each of the said ($C_6$ to $C_{10}$) arylene or ($C_2$ to $C_9$) heteroarylene is optionally substituted with at least one $R^{6a}$ group; and D is selected from the group consisting of

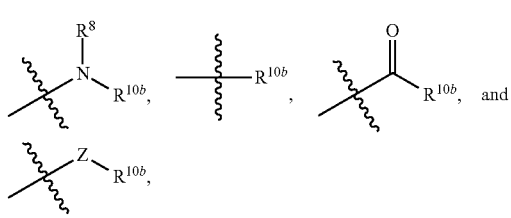

wherein
R$^{10b}$ is selected from the group consisting of

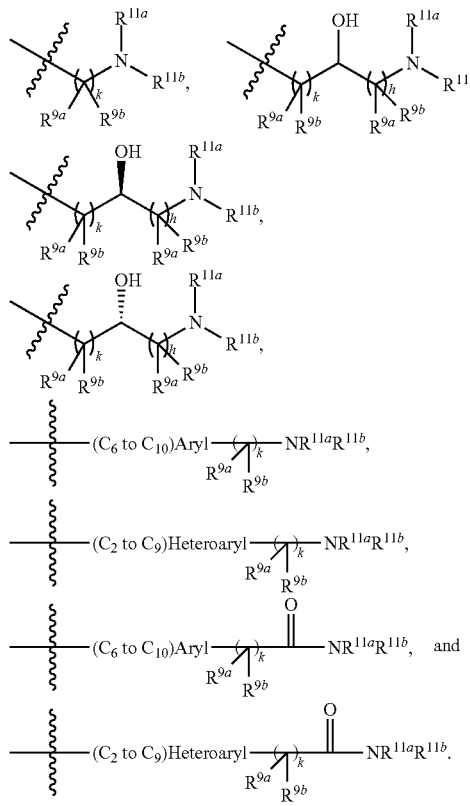

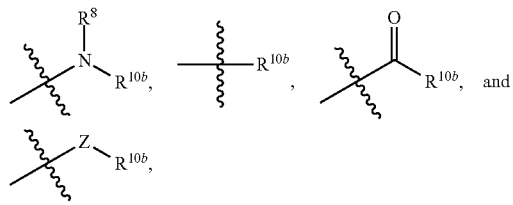

In another embodiment, the invention relates to compounds of Structural Formula I, or a pharmaceutically acceptable salt, and a pharmaceutically acceptable carrier, diluent, or vehicle thereof, wherein:
X is C-A-D and Y is a bond;
A is —C(R$^{6a}$R$^{6b}$)$_j$—, (C$_6$ to C$_{10}$) arylene, or (C$_2$ to C$_9$) heteroarylene, wherein
each of the said (C$_6$ to C$_{10}$) arylene or (C$_2$ to C$_9$) heteroarylene is optionally substituted with at least one R$^{6a}$ group; and
D is selected from the group consisting of

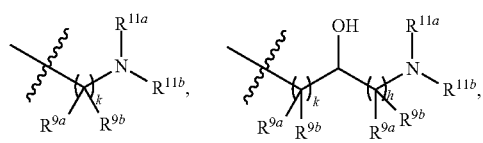

wherein
R$^{10b}$ is selected from the group consisting of

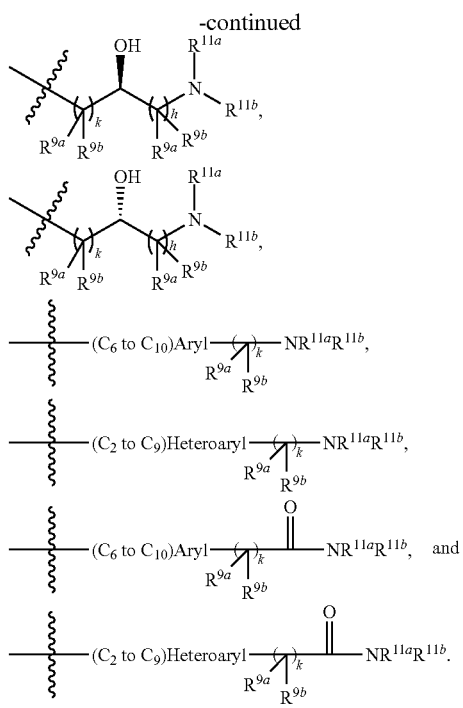

In another embodiment, the invention relates to compounds of Structural Formula I, or a pharmaceutically acceptable salt, and a pharmaceutically acceptable carrier, diluent, or vehicle thereof, wherein:
X is CR$^5$ and Y is CR$^4$-A-D;
A is —C(R$^{6a}$R$^{6b}$)$_j$—, (C$_6$ to C$_{10}$) arylene, or (C$_2$ to C$_9$) heteroarylene, wherein
each of the said (C$_6$ to C$_{10}$) arylene or (C$_2$ to C$_9$) heteroarylene is optionally substituted with at least one R$^{6a}$ group; and
D is selected from the group consisting of

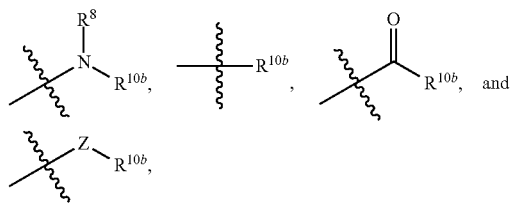

wherein
R$^{10b}$ is selected from the group consisting of

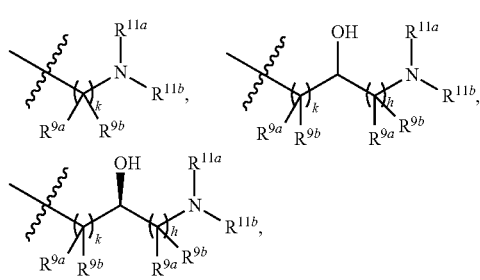

-continued

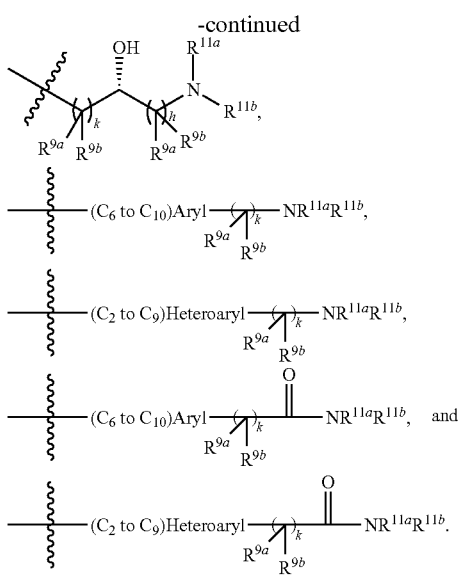

In another embodiment, the invention relates to compounds, or a pharmaceutically acceptable salt, and a pharmaceutically acceptable carrier, diluent, or vehicle thereof, selected from the group consisting the compounds described as examples A1 to A116, A201 to A205, C1 to C19, E1 to E6 in the method of preparation section, and examples B1 to B19 in table 5 and D1 to D47 in Table 7.

Definitions

As used herein, the terms "comprising" and "including" are used in their open, non-limiting sense.

The terms "halo" and/or "halogen" refer to fluorine, chlorine, bromine or iodine.

The term "($C_1$ to $C_{10}$) alkyl" refers to a saturated aliphatic hydrocarbon radical including straight chain and branched chain groups of 1 to 8 carbon atoms. Examples of ($C_1$ to $C_{10}$) alkyl groups include methyl, ethyl, propyl, 2-propyl, n-butyl, iso-butyl, tert-butyl, pentyl, and the like. The terms "Me" and "methyl," as used herein, mean a —$CH_3$ group. The terms "Et" and "ethyl," as used herein, mean a —$C_2H_5$ group.

The term "($C_2$ to $C_{10}$) alkenyl", as used herein, means an alkyl moiety comprising 2 to 10 carbons having at least one carbon-carbon double bond. The carbon-carbon double bond in such a group may be anywhere along the 2 to 10 carbon chain that will result in a stable compound. Such groups include both the E and Z isomers of said alkenyl moiety. Examples of such groups include, but are not limited to, ethene, propene, 1-butene, 2-butene, 1-pentene, 2-pentene, 1-hexene, 2-hexene, and 3-hexene Examples of such groups include, but are not limited to, ethenyl, propenyl, butenyl, allyl, and pentenyl.

The term "allyl," as used herein, means a —$CH_2CH$=$CH_2$ group.

As used herein, the term "($C_2$ to $C_{10}$) alkynyl" means an alkyl moiety comprising from 2 to 8 carbon atoms and having at least one carbon-carbon triple bond. The carbon-carbon triple bond in such a group may be anywhere along the 2 to 10 carbon chain that will result in a stable compound. Examples of such groups include, but are not limited to, ethyne, propyne, 1-butyne, 2-butyne, 1-pentyne, 2-pentyne, 1-hexyne, 2-hexyne, and 3-hexyne.

The term "($C_1$ to $C_{10}$) alkoxy", as used herein, means an O-alkyl group wherein said alkyl group contains from 1 to 8 carbon atoms and is straight, branched, or cyclic. Examples of such groups include, but are not limited to, methoxy, ethoxy, n-propyloxy, iso-propyloxy, n-butoxy, iso-butoxy, tert-butoxy, cyclopentyloxy, and cyclohexyloxy.

The term "($C_6$ to $C_{10}$) aryl", as used herein, means a group derived from an aromatic hydrocarbon containing from 6 to 10 carbon atoms. Examples of such groups include, but are not limited to, phenyl or naphthyl. The terms "Ph" and "phenyl," as used herein, mean a —$C_6H_5$ group. The term "benzyl," as used herein, means a —$CH_2C_6H_5$ group.

The term "($C_6$ to $C_{10}$) arylene" is art-recognized, and as used herein pertains to a bivalent moiety obtained by removing a hydrogen atom from a ($C_6$ to $C_{10}$) aryl ring, as defined above.

"($C_2$ to $C_9$) heteroaryl", as used herein, means an aromatic heterocyclic group having a total of from 5 to 10 atoms in its ring, and containing from 2 to 9 carbon atoms and from one to four heteroatoms each independently selected from O, S and N, and with the proviso that the ring of said group does not contain two adjacent O atoms or two adjacent S atoms. The heterocyclic groups include benzo-fused ring systems. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The $C_2$ to $C_9$ heteroaryl groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached).

The term "($C_2$ to $C_{10}$) heteroarylene" is art-recognized, and as used herein pertains to a bivalent moiety obtained by removing a hydrogen atom from a ($C_6$ to $C_{10}$) heteroaryl ring, as defined above.

The term "($C_2$ to $C_{10}$) cycloheteroalkyl", as used herein, means a non-aromatic, monocyclic, bicyclic, tricyclic, spirocyclic, or tetracyclic group having a total of from 4 to 13 atoms in its ring system, and containing from 5 to 10 carbon atoms and from 1 to 4 heteroatoms each independently selected from O, S and N, and with the proviso that the ring of said group does not contain two adjacent O atoms or two adjacent S atoms. Furthermore, such ($C_2$ to $C_{10}$) cycloheteroalkyl groups may contain an oxo substituent at any available atom that will result in a stable compound. For example, such a group may contain an oxo atom at an available carbon or nitrogen atom. Such a group may contain more than one oxo substituent if chemically feasible. In addition, it is to be understood that when such a ($C_2$ to $C_{10}$) cycloheteroalkyl group contains a sulfur atom, said sulfur atom may be oxidized with one or two oxygen atoms to afford either a sulfoxide or sulfone. An example of a 4 membered cycloheteroalkyl group is azetidinyl (derived from azetidine). An example of a 5 membered cycloheteroalkyl group is pyrrolidinyl. An example of a 6 membered cycloheteroalkyl group is piperidinyl. An example of a 9 membered cycloheteroalkyl group is indolinyl. An example of a 10 membered cycloheteroalkyl group is 4H-quinolizinyl. Further examples of such ($C_2$ to $C_{10}$) cycloheteroalkyl groups include, but are not limited to, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, 3-oxopiperazinyl, 4-methylpiperazinyl, 4-ethylpiperazinyl, and 1-oxo-2,8,diazaspiro[4.5]dec-8-yl. The ($C_2$ to $C_{10}$)heteroaryl groups may be C-attached or N-attached where such is possible. For instance, a group derived from piperazine may be piperazin-1-yl (N-attached) or piperazin-2-yl (C-attached).

The term "($C_2$ to $C_{10}$) cycloheteroalkylene" is art-recognized, and as used herein pertains to a bidentate moiety obtained by removing a hydrogen atom from a (Ceto $C_{10}$) cycloheteroalkyl ring, as defined above.

The term "($C_3$ to $C_{10}$) cycloalkyl group" means a saturated, monocyclic, fused, spirocyclic, or polycyclic ring structure having a total of from 3 to 10 carbon 5 ring atoms. Examples of such groups include, but are not limited to, cyclopropyl, cyclobutyl, cyclopentyl, cyclopentenyl, cyclohexyl, cycloheptyl, and adamantyl.

The term "($C_3$ to $C_{10}$) cycloalkylene" is art-recognized, and as used herein pertains to a bidentate moiety obtained by removing a hydrogen atom from a ($C_3$ to $C_{10}$) cycloalkyl ring, as defined above.

The term "spirocyclic" as used herein has its conventional meaning, that is, any compound containing two or more rings wherein two of the rings have one ring carbon in common. The rings of a spirocyclic compound, as herein defined, independently have 3 to 20 ring atoms. Preferably, they have 3 to 10 ring atoms. Non-limiting examples of a spirocyclic compound include spiro[3.3]heptane, spiro[3.4]octane, and spiro[4.5]decane.

The term "($C_5$ to $C_8$) cycloalkenyl" means an unsaturated, monocyclic, fused, spirocyclic ring structures having a total of from 5 to 8 carbon ring atoms. Examples of such groups include, but not limited to, cyclopentenyl, cyclohexenyl.

The term cyano" refers to a —C≡N group.

An "aldehyde" group refers to a carbonyl group where R is hydrogen.

An "alkoxy" group refers to both an —O-alkyl and an —O-cycloalkyl group, as defined herein.

An "alkoxycarbonyl" refers to a —C(O)OR.

An "alkylaminoalkyl" group refers to an -alkyl-NR-alkyl group.

An "alkylsulfonyl" group refer to a —SO$_2$alkyl.

An "amino" group refers to an —NH$_2$ or an —NRR' group.

An "aminoalkyl" group refers to an -alky-NRR' group.

An "aminocarbonyl" refers to a —C(O)NRR'.

An "arylalkyl" group refers to -alkylaryl, where alkyl and aryl are defined herein.

An "aryloxy" group refers to both an —O-aryl and an —O-heteroaryl group, as defined herein.

An "aryloxycarbonyl" refers to —C(O)Oaryl.

An "arylsulfonyl" group refers to a —SO$_2$aryl.

A "C-amido" group refers to a —C(O)NRR' group.

A "carbonyl" group refers to a —C(O)R.

A "C-carboxyl" group refers to a —C(O)OR groups.

A "carboxylic acid" group refers to a C-carboxyl group in which R is hydrogen.

A "cyano" group refers to a —CN group.

A "dialkylamionalkyl" group refers to an -(alkyl)N(alkyl)$_2$ group.

A "halo" or "halogen" group refers to fluorine, chlorine, bromine or iodine.

A "haloalkyl" group refers to an alkylgroup substituted with one or more halogen atoms.

A "heteroalicycloxy" group refers to a heteroalicyclic-O group with heteroalicyclic as defined herein.

A "heteroaryloxyl" group refers to a heteroaryl-O group with heteroaryl as defined herein.

A "hydroxy" group refers to an —OH group.

An "N-amido" group refers to a —R'C(O)NR group.

An "N-carbamyl" group refers to a —ROC(O)NR group.

A "nitro" group refers to a —NO$_2$ group.

An "N-Sulfonamido" group refers to a —NR—S(O)$_2$R group.

An "N-thiocarbamyl" group refers to a ROC(S)NR' group.

An "O-carbamyl" group refers to a —OC(O)NRR' group.

An "O-carboxyl" group refers to a RC(O)O— group.

An "O-thiocarbamyl" group refers to a —OC(S)NRR' group.

An "oxo" group refers to a carbonyl moiety such that alkyl substituted by oxo refers to a ketone group.

A "perfluoroalkyl" group refers to an alkyl group where all of the hydrogen atoms have been replaced with fluorine atoms.

A "phosphonyl" group refers to a —P(O)(OR)$_2$ group.

A "silyl" group refers to a —SiR$_3$ group.

An "S-sulfonamido" group refers to a —S(O)$_2$NR.

A "sulfinyl" group refers to a —S(O)R group.

A "sulfonyl" group refers to a —S(O)$_2$R group.

A "thiocarbonyl" group refers to a —C(=S)—R group.

A "trihalomethanecarbonyl" group refers to a Z$_3$CC(O)— group, where Z is halogen.

A "trihalomethanesulfonamido" group refers to a Z$_3$CS(O)$_2$NR— group, where Z is halogen.

A "trihalomethanesulfonyl" group refers to a Z$_3$CS(O)$_2$— group, where Z is halogen.

A "trihalomethyl" group refers to a —CZ$_3$ group.

A "C-carboxyl" group refers to a —C(O)OR groups.

The term "substituted," means that the specified group or moiety bears one or more substituents.

The term "unsubstituted," means that the specified group bears no substituents. The term "optionally substituted" means that the specified group is unsubstituted or substituted by one or more substituents. It is to be understood that in the compounds of the present invention when a group is said to be"unsubstituted," or is "substituted" with fewer groups than would fill the valencies of all the atoms in the compound, the remaining valencies on such a group are filled by hydrogen. For example, if a C$_6$ arylgroup, also called "phenyl" herein, is substituted with one additional substituent, one of ordinary skill in the art would understand that such a group has 4 open positions left on carbon atoms of the C6 aryl ring (6 initial positions, minus one to which the remainder of the compound of the present invention is bonded, minus an additional substituent, to leave 4). In such cases, the remaining 4 carbon atoms are each bound to one hydrogen atom to fill their valencies. Similarly, if a C$_6$ aryl group in the present compounds is said to be "disubstituted," one of ordinary skill in the art would understand it to mean that the C$_6$ aryl has 3 carbon atoms remaining that are unsubstituted. Those three unsubstituted carbon atoms are each bound to one hydrogen atom to fill their valencies.

The term "solvate," is used to describe a molecular complex between compounds of the presentinvention and solvent molecules. Examples of solvates include, but are not limited to, compounds of the invention in combination water, isopropanol, ethanol, methanol, dimethylsulfoxide (DMSO), ethyl acetate, acetic acid, ethanolamine, or mixtures thereof.

The term "hydrate" can be used when said solvent is water. It is specifically contemplated that in the present invention one solvent molecule can be associated with one molecule of the compounds of the present invention, such as a hydrate. Furthermore, it is specifically contemplated that in the present invention, more than one solvent molecule may be associated with one molecule of the compounds of the present invention, such as a dihydrate.

Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-hydrate form of the compounds.

The term "pharmaceutically acceptable salt," as used herein, means a salt of a compound of the present invention that retains the biological effectiveness of the free acids and bases of the specified derivative and that is not biologically or otherwise undesirable.

The term "pharmaceutically acceptable formulation", as used herein, means a combination of a compound of the invention, or a salt or solvate thereof, and a carrier, diluent, and/or excipient(s) that are compatible with a compound of the present invention, and is not deleterious to the recipient thereof. Pharmaceutical formulations can be prepared by procedures known to those of ordinary skill in the art. For example, the compounds of the present invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as povidone, sodium starch glycolate, sodium carboxymethylcellulose, agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be pills, tablets, powders, lozenges, saches, cachets, or sterile packaged powders, and the like, depending on the type of excipient used. Additionally, it is specifically contemplated that pharmaceutically acceptable formulations of the present invention can contain more than one active ingredient. For example, such formulations may contain more than one compound according to the present invention. Alternatively, such formulations may contain one or more compounds of the present invention and one or more additional agents that reduce abnormal cell growth.

The term "virus inhibiting amount" as used herein, refers to the amount of a compound of the present invention, or a salt or solvate thereof, required to inhibit the cell entry of an enveloped virus in vivo, such as in a mammal, or in vitro. The amount of such compounds required to cause such inhibition can be determined without undue experimentation using methods described herein and those known to those of ordinary skill in the art.

The terms "treat", "treating", and "treatment" with reference to enveloped virus infection, in mammals, particularly a human, include: (i) preventing the disease or condition from occurring in a subject which may be predisposed to the condition, such that the treatment constitutes prophylactic treatment for the pathologic condition; (ii) modulating or inhibiting the disease or condition, i.e., arresting its development; (iii) relieving the disease or condition, i.e., causing regression of the disease or condition; or (iv) relieving and/or alleviating the disease or condition or the symptoms resulting from the disease or condition.

The compositions are delivered in effective amounts. The term "effective amount" refers to the amount necessary or sufficient to realize a desired biologic effect and/or reduce the viral load. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is effective to treat the particular subject. In addition, based on testing, toxicity of the inhibitor is expected to be low. The effective amount for any particular application can vary depending on such factors as the disease or condition being treated, the particular inhibitor being administered, the size of the subject, or the severity of the disease or condition. One of ordinary skill in the art can empirically determine the effective amount of a particular inhibitor and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug.

"Dose" and "dosage" are used interchangeably herein. For any compound described herein, the therapeutically effective amount can be initially determined from preliminary in vitro studies and/or animal models. A therapeutically effective dose can also be determined from human data for inhibitors that have been tested in humans and for compounds, which are known to exhibit similar pharmacological activities, such as other related active agents. The applied dose can be adjusted based on the relative bioavailability and potency of the administered compound. Adjusting the dose to achieve maximal efficacy based on the methods described above and other methods well-known in the art, is well within the capabilities of the ordinarily skilled artisan. In certain embodiments, the methods of the invention are useful for treating infection with enveloped viruses.

Unless indicated otherwise, all references herein to the inventive compounds include references to salts, solvates, and complexes thereof, including polymorphs, stereoisomers, tautomers, and isotopically labeled versions thereof. For example, compounds of the present invention can be pharmaceutically acceptable salts and/or pharmaceutically acceptable solvates.

The term "stereoisomers" refers to compounds that have identical chemical constitution, but differ with regard to the arrangement of their atoms or groups in space. In particular, the term "enantiomers" refers to two stereoisomers of a compound that are non-superimposable mirror images of one another.

A pure enantiomer can be contaminated with up to 2% of the opposite enantiomer.

The terms "racemic" or "racemic mixture," as used herein, refer to a 1:1 mixture of enantiomers of a particular compound. The term "diastereomers", on the other hand, refers to the relationship between a pair of stereoisomers that comprise two or more asymmetric centers and are not mirror images of one another. In accordance with a convention used in the art, the symbol is used in structural formulas herein to depict the bond that is the point of attachment of the moiety or substituent to the core or backbone structure.

In accordance with another convention, in some structural formulae herein the carbon atoms and their bound hydrogen atoms are not explicitly depicted, e.g.,

represents a methyl group,

represents an ethyl group,

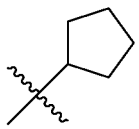 [SMILES: *C1CCCC1]

represents a cyclopentyl group, etc.

The compounds of the present invention may have asymmetric carbon atoms. The carbon-carbonbonds of the compounds of the present invention may be depicted herein using a solid line (-), a solid wedge ( ▬ ), or a dotted wedge ( ..... ). The use of a solid line to depict bonds to asymmetric carbon atoms is meant to indicate that all possible stereoisomers (e.g. specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of the present invention can exist as enantiomers and diastereomers or as racemates and mixtures thereof. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

"R", unless otherwise defined, a substituent "R" may reside on any atom of the ring system, assuming replacement of a depicted, implied, or expressly defined hydrogen from one of the ring atoms, so long as a stable structure is formed.

Conventional techniques for the preparation/isolation of individual enantiomers include chiral synthesis from a suitable optically pure precursor or resolution of the recemate using, for example, chiral high pressure liquid chromatography (HPLC). Alternatively, the racemate (or a racemic precursor) maybe reacted with a suitable optically active compound, for example, an alcohol, or, in the case where the compound contains an acidic or basic moiety, an acid or base such as tartaric acid or 1-phenyl ethyl amine. The resulting diastereomeric mixture may be separated by chromatography and/or fractional crystallization and one or both of the diastereoisomers converted to the corresponding pure enantiomer(s) by means well known to one skilled in the art. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomeric conglomerates may be separated by conventional techniques known to those skilled in the art. See, e.g. "Stereochemistry of Organic Compounds" by E L Eliel (Wiley, New York, 1994), the disclosure of which is incorporated herein by reference in its entirety.

Where a compound of the invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. Examples of tautomerism include keto and enol tautomers. A single compound may exhibit more than one type of isomerism. Included within the scope of the invention are all stereoisomers, geometric isomers and tautomeric forms of the inventive compounds, including compounds exhibiting more than one type of isomerism, and mixtures of one or more thereof. Cis/trans isomers may be separated by conventional techniques well known to those skilled in the art, for example, chromatography and fractional crystallization.

The compounds of the present invention may be administered as prodrugs. Thus certain derivatives of compounds of Formula I which may have little or no pharmacological activity themselves can, when administered to a mammal, be converted into a compound of Formula I having the desired activity, for example, by hydrolytic cleavage. Such derivatives are referred to as "prodrugs". Prodrugs can, for example, be produced by replacing appropriate functionalities present in the compound of Formula I with certain moieties known to those skilled in the art. See, e.g. "Prodrugs as Novel Delivery Systems", Vol. 14, ACS Symposium Series (T Higuchi and W Stella) and "Bioreversible Carriers in Drug Design", Pergamon Press, 1987 (ed. E B Roche, American Pharmaceutical Association), the disclosures of which are incorporated herein by reference in their entireties. Some examples of such prodrugs include: an ester moiety in the place of a carboxylic acid functional group; an ether moiety or an amide moiety in place of an alcohol functional group; and an amide moiety in place of a primary or secondary amino functional group. Further examples of replacement groups are known to those of skill in the art. See, e.g. "Design of Prodrugs" by H Bundgaard (Elsevier, 1985), the disclosure of which is incorporated herein by reference in its entirety. It is also possible that certain compounds of Formula I may themselves act as prodrugs of other compounds of Formula I.

Salts of the present invention can be prepared according to methods known to those of skill in the art. Examples of salts include, but are not limited to, acetate, acrylate, benzenesulfonate, benzoate (such as chlorobenzoate, methylbenzoate, dinitrobenzoate, hydroxybenzoate, and methoxybenzoate), bicarbonate, bisulfate, bisulfite, bitartrate, borate, bromide, butyne-1,4-dioate, calcium edetate, camsylate, carbonate, chloride, caproate, caprylate, clavulanate, citrate, decanoate, hydrochloride, dihydrogenphosphate, edetate, edislyate, estolate, esylate, ethylsuccinate, formate, fumarate, gluceptate, gluconate, glutamate, glycollate, glycollylarsanilate, heptanoate, hexyne-1,6-dioate, hexylresorcinate, hydrabamine, hydrobromide, hydrochloride, γ-hydroxybutyrate, iodide, isobutyrate, isothionate, lactate, lactobionate, laurate, malate, maleate, malonate, mandelate, mesylate, metaphosphate, methanesulfonate, methylsulfate, monohydrogenphosphate, mucate, napsylate, naphthalene-1-sulfonate, naphthalene-2-sulfonate, nitrate, oleate, oxalate, pamoate (embonate), palmitate, pantothenate, phenylacetates, phenylbutyrate, phenylpropionate, phthalate, phospate/diphosphate, polygalacturonate, propanesulfonate, propionate, propiolate, pyrophosphate, pyrosulfate, salicylate, stearate, subacetate, suberate, succinate, sulfate, sulfonate, sulfite, tannate, tartrate, teoclate, tosylate, triethiodode, and valerate salts.

The compounds of the present invention that are basic in nature are capable of forming a wide variety of different salts with various inorganic and organic acids. Although such salts must be pharmaceutically acceptable for administration to animals or humans, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention can be prepared by treating the base compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

Those compounds of the present invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium, calcium, and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

If the inventive compound is a base, the desired salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired salt may be prepared by any suitable method, for example, treatment of the free acid with an inorganic or organic base, such as an amine (primary, secondary or tertiary), an alkali metal hydroxide or alkaline earth metal hydroxide, or the like.

Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds, agents and salts may exist in different crystal or polymorphic forms, all of which are intended to be within the scope of the present invention and specified formulas.

The invention also includes isotopically-labeled compounds of the invention, wherein one or moreatoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, for example, $^2$H increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The compounds of the present invention may be formulated into pharmaceutical compositions as described below in any pharmaceutical form recognizable to the skilled artisan as being suitable. Pharmaceutical compositions of the invention comprise a therapeutically effective amount of at least one compound of the present invention and an inert, pharmaceutically acceptable carrier or diluent.

To treat or prevent diseases or conditions mediated in part or whole by enveloped virus infection, a pharmaceutical composition of the invention is administered in a suitable formulation prepared by combining a therapeutically effective amount (i.e., an enveloped virus GP- or host cell partner-modulating, regulating, or inhibiting amount effective to achieve therapeutic efficacy) of at least one compound of the present invention (as an active ingredient) with one or more pharmaceutically suitable carriers, which may be selected, for example, from diluents, excipients and auxiliaries that facilitate processing of the active compounds into the final pharmaceutical preparations.

The pharmaceutical carriers employed may be either solid or liquid. Exemplary solid carriers are lactose, sucrose, talc, gelatin, agar, pectin, acacia, magnesium stearate, stearic acid and the like. Exemplary liquid carriers are syrup, peanut oil, olive oil, water and the like. Similarly, the inventive compositions may include time-delay or time-release material known in the art, such as glyceryl monostearate or glyceryl distearate alone or with a wax, ethylcellulose, hydroxypropylmethylcellulose, methylmethacrylate or the like. Further additives or excipients may be added to achieve the desired formulation properties. For example, a bioavailability enhancer, such as Labrasol, Gelucire or the like, or formulator, such as CMC (carboxy-methylcellulose), PG (propyleneglycol), or PEG (polyethyleneglycol), may be added. Gelucire®, a semi-solid vehicle that protects active ingredients from light, moisture and oxidation, may be added, e.g., when preparing a capsule formulation.

If a solid carrier is used, the preparation can be tableted, placed in a hard gelatin capsule in powder or pellet form, or formed into a troche or lozenge. The amount of solid carrier may vary, but generally will be from about 25 mg to about 1 g. If a liquid carrier is used, the preparation may be in the form of syrup, emulsion, soft gelatin capsule, sterile injectable solution or suspension in an ampoule or vial or non-aqueous liquid suspension. If a semi-solid carrier is used, the preparation may be in the form of hard and soft gelatin capsule formulations. The inventive compositions are prepared in unit-dosage form appropriate for the mode of administration, e.g. parenteral or oral administration.

To obtain a stable water-soluble dose form, a salt of a compound of the present invention may be dissolved in an aqueous solution of an organic or inorganic acid, such as a 0.3 M solution of succinic acid or citric acid. If a soluble salt form is not available, the agent may be dissolved in a suitable co-solvent or combinations of co-solvents. Examples of suitable co-solvents include alcohol, propylene glycol, polyethylene glycol 300, polysorbate 80, glycerin and the like in concentrations ranging from 0 to 60% of the total volume. In an exemplary embodiment, a compound of the present invention is dissolved in DMSO and diluted with water. The composition may also be in the form of a solution of a salt form of the active ingredient in an appropriate aqueous vehicle such as water or isotonic saline or dextrose solution.

Proper formulation is dependent upon the route of administration selected. For injection, the agents of the compounds of the present invention may be formulated into aqueous solutions, preferably in physiologically compatible buffers such as Hanks solution, Ringer's solution, or physiological saline buffer.

For transmucosal administration, penetrants appropriate to the barrier to be permeated are used in the formulation. Such penetrants are generally known in the art.

For oral administration, the compounds can be formulated by combining the active compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures.

Dyestuffs or pigments may be added to the tablets or dragee coatings for identification or to characterize different combinations of active agents.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

For administration intranasally or by inhalation, the compounds for use according to the present invention may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Alternatively, the active ingredient may be in powder form for constitution with a suitable vehicle, e.g. sterile pyrogen-free water, before use.

In addition to the formulations described above, the compounds of the present invention may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt. A pharmaceutical carrier for hydrophobic compounds is a cosolvent system comprising benzyl alcohol, a non-polar surfactant, a water-miscible organic polymer, and an aqueous phase. The co-solvent system may be a VPD co-solvent system. VPD is a solution of 3% w/v benzyl alcohol, 8% w/v of the non-polar surfactant polysorbate 80, and 65% w/v polyethylene glycol300, made up to volume in absolute ethanol. The VPD co-solvent system (VPD: 5W) contains VPD diluted 1:1 with a 5% dextrose in water solution. This co-solvent system dissolves hydrophobic compounds well, and itself produces low toxicity upon systemic administration. The proportions of a cosolvent system may be suitably varied without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity due to the toxic nature of DMSO. Additionally, the compounds may be delivered using a sustained-release system, such as semipermeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. These carriers and excipients may provide marked improvement in the bioavailability of poorly soluble drugs. Examples of such carriers or excipients include calcium carbonate, calcium phosphate, sugars, starches, cellulose derivatives, gelatin, and polymers such as polyethylene glycols. Furthermore, additives or excipients such as Gelucire®, Capryol®, Labrafil®, Labrasol®, Lauroglycol®, Plurol®, Peceol®, Transcutol® and the like may be used.

Further, the pharmaceutical composition may be incorporated into a skin patch for delivery of the drug directly onto the skin.

It will be appreciated that the actual dosages of the agents of this invention will vary according to the particular agent being used, the particular composition formulated, the mode of administration, and the particular site, host, and disease being treated. Those skilled in the art using conventional dosage determination tests in view of the experimental data for a given compound may ascertain optimal dosages for a given set of conditions. For oral administration, an exemplary daily dose generally employed will be from about 0.001 to about 1000 mg/kg of body weight, with courses of treatment repeated at appropriate intervals.

Furthermore, the pharmaceutically acceptable formulations of the present invention may contain a compound of the present invention, or a salt or solvate thereof, in an amount of about 10 mg to about 2000 mg, or from about 10 mg to about 1500 mg, or from about 10 mg to about 1000 mg, or from about 10 mg to about 750 mg, or from about 10 mg to about 500 mg, or from about 25 mg to about 500 mg, or from about 50 to about 500 mg, or from about 100 mg to about 500 mg.

Additionally, the pharmaceutically acceptable formulations of the present invention may contain a compound of the present invention, or a salt or solvate thereof, in an amount from about 0.5 w/w % to about 95 w/w %, or from about 1 w/w % to about 95 w/w %, or from about 1 w/w % to about 75 w/w %, or from about 5 w/w % to about 75 w/w %, or from about 10 w/w % to about 75 w/w %, or from about 10 w/w % to about 50 w/w %.

The compounds of the present invention, or salts or solvates thereof, may be administered to a mammal, such as a human, suffering from a condition or disease mediated by an enveloped virus, either alone or as part of a pharmaceutically acceptable formulation, once a day, twice a day, three times a day, four times a day, or even more frequently.

The compounds of the present invention, or salts or solvates thereof, may be administered to humans or mammals suffering from a condition or disease mediated by a filovirus, arenavirus, or other enveloped virus in combination with at least one other agent used for treatment, alone or as part of a pharmaceutically acceptable formulation, once a day, twice a day, three times a day, four times a day, or even more frequently.

Those of ordinary skill in the art will understand that with respect to the compounds of the present invention, the particular pharmaceutical formulation, the dosage, and the number of doses given per day to humans or mammals requiring such treatment, are all choices within the knowledge of one of ordinary skill in the art and can be determined without undue experimentation.

Combination Therapy

Compounds of Structural Formula I of the invention may be combined with other therapeutic agents. The inhibitor and other therapeutic agent may be administered simultaneously or sequentially. When the other therapeutic agents are administered simultaneously they can be administered in the same or separate formulations, but are administered at the same time. The other therapeutic agents are administered sequentially with one another and with the inhibitors, when the administration of the other therapeutic agents and the inhibitors is temporally separated. The separation in time between the administration of these compounds may be a matter of minutes or it may be longer. Other therapeutic agents include but are not limited to anti-viral vaccines and anti-viral agents. In some instances the inhibitors are administered with multiple therapeutic agents, i.e., 2, 3, 4 or even more different anti-viral agents.

An anti-viral vaccine is a formulation composed of one or more viral antigens and one or more adjuvants. The viral antigens include proteins or fragments thereof as well as whole killed virus. Adjuvants are well known to those of skill in the art.

Antiviral agents are compounds, which prevent infection of cells by viruses or replication of the virus within the cell. There are many fewer antiviral drugs than antibacterial drugs because viruses are more dependent on host cell factors than bacteria. There are several stages within the process of viral infection, which can be blocked or inhibited by antiviral agents. These stages include, attachment of the virus to the host cell (immunoglobulin or binding peptides), membrane penetration inhibitors, e.g. T-20, uncoating of the virus (e.g. amantadine), synthesis or translation of viral mRNA (e.g. interferon), replication of viral RNA or DNA (e.g. nucleotide analogues), maturation of new virus proteins (e.g. pro-tease inhibitors), and budding and release of the virus.

Nucleotide analogues are synthetic compounds which are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, zidovudine (azidothymidine), imiquimod, resimiquimod, favirpiravir, BCX4430, and GS-5374 or their analogues.

The interferons are cytokines which are secreted by virus-infected cells as well as immune cells. The interferons function by binding to specific receptors on cells adjacent to the infected cells, causing the change in the cell which protects it from infection by the virus. α- and β-interferon also induce the expression of Class I and Class II MHC molecules on the surface of infected cells, resulting in increased antigen presentation for host immune cell recognition. α- and β-interferons are available as recombinant proteins and have been used for the treatment of chronic hepatitis B and C infection. At the dosages that are effective for anti-viral therapy, interferons may have severe side effects such as fever, malaise and weight loss.

Anti-viral agents, which may be useful in combination with Structural Formula I of the invention, include but are not limited to immunoglobulins, amantadine, interferons, nucleotide analogues, small interfering RNAs (siRNAs) and other protease inhibitors (other than the papain-like cysteine protease inhibitors—although combinations of papain-like cysteine protease inhibitors are also useful). Specific examples of anti-viral agents include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; AVI-7537: Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Favipiravir; Fiacitabine; Fialuridine; Fosarilate; Foscarnet Sodium; Fosfonet Sodium; Ganciclovir; Ganciclovir Sodium; Idoxuridine; Kethoxal; Lamivudinc; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; TKM Ebola; Triazavirin; Trifluridine; Valacyclovir Hydrochloride; Vidarabine; Vidarabine Phosphate; Vidarabine Sodium Phosphate; Viroxime; Zalcitabine; Zidovudine; Zinviroxime; and ZMapp.

Specific examples of antiviral agents suitable for combination therapy with the compounds of structural formula I of the invention in the treatment of filovirus including Ebola virus and Marburg virus includes the following compounds; Ribavirin, viral RNA-dependent-RNA polymeras inhibitors including favipiravir, Triazavirin, Remdesivir (GS-5734), monoclonal antibody therapies including, ZMapp, REGN3470-3471-3479, mAb 114, vaccines including, cAd3-EBOZ, rVSV-ZEBOV, small interfering RNAs and microRNAs and other immunomodulators.

Immunoglobulin therapy is used for the prevention of viral infection. Immunoglobulin therapy for viral infections is different than bacterial infections, because rather than being antigen-specific, the immunoglobulin therapy functions by binding to extracellular virions and preventing them from attaching to and entering cells which are susceptible to the viral infection. The therapy is useful for the prevention of viral infection for the period of time that the antibodies are present in the host. In general there are two types of immunoglobulin therapies, normal immunoglobulin therapy and hyper-immunoglobulin therapy. Normal immune globulin therapy utilizes an antibody product which is prepared from the serum of normal blood donors and pooled. This pooled product contains low titers of antibody to a wide range of human viruses, such as hepatitis A, parvovirus, enterovirus (especially in neonates). Hyper-immune globulin therapy utilizes antibodies which are prepared from the serum of individuals who have high titers of an antibody to a particular virus. Those antibodies are then used against a specific virus. Another type of immunoglobulin therapy is active immunization. This involves the administration of antibodies or antibody fragments to viral surface proteins.

In the following Preparations and Examples, "Ac" means acetyl, "Me" means methyl, "Et" means ethyl, "Ph" means phenyl, "Py" means pyridine, "BOC", "Boc" or "boc" means N-tert-butoxycarbonyl, "Ns" means 2-Nitrophenylsulfonyl, "CMMP" means (cyanomethylene) trimethyl phosphorane", "DCM" ($CH_2Cl_2$) means dichloromethane or methylene chloride, "DCE" means dichloroethane or ethylene chloride, "DIAD" means diisopropylazadicarboxylate, "DIPEA" or "DIEA" means diisopropyl ethyl amine, "DMA" means N,N-dimethylacetamide, "DMAP" means 4-dimethylaminopyridine, "DME" means 1,2-dimethoxyethane, "DMF" means N,N-dimethyl formamide, "DMSO" means dimethylsulfoxide, "DPPA" means diphenylphosphorylazide, "DPPP" means 1,3-bis(diphenylphosphino) propane, "EDCl" means 3-(ethyliminomethyleneamino)-N, N-dimethylpropan-1-amine, "EtOAc" means ethyl acetate, "HATU" means 1-[Bis(dimethylamino)methylene]-1H-1,2, 3-triazolo[4,5-b]pyridinium 3-oxid hexafluorophosphate, "HOAt" means 1-hydroxy-7 azabenzotriazole, "HOAc"

means acetic acid, "IPA" means isopropyl alcohol, "LDA" means lithium diisopropylamide, "NMP" means 1-methyl 2-pyrrolidinone, "TEA" means triethyl amine, "TFA" means trifluoroacetic acid, "TOSMIC" means toluenesulfonylmethyl isocyanide, "MgSO$_4$" means magnesium sulphate, "NaHMDS" or "NHMDS" means sodium hexamethyldisilazide, "Na$_2$SO$_4$" means sodium sulphate, "MeOH" means methanol, "Et$_2$O" means diethyl ether, "EtOH" means ethanol, "H$_2$O" means water, "HCl" means hydrochloric acid, "POCl$_3$" means phosphorus oxychloride, "SOCl$_2$" means thionylchloride, "K$_2$CO$_3$" means potassium carbonate, "THF" means tetrahydrofuran, "DBU" means 1,8-diazabicyclo[5.4.0]undec-7-ene, "LAH" means lithium aluminium hydride, "LiHMDS" or "LHMDS" means lithium hexamethyldisilazide, "TBABr" means tetra butyl ammonium bromide, "TBME" or "MTBE" means tert-butyl methyl ether, "TMS" means trimethylsilyl, "PMHS" means polymethylhydrosiloxane, "MCPBA" means 3-chloroperoxy benzoic acid, "N" means Normal, "M" means molar, "mL" means millilitre, "mmol" means millimoles, "µmol" means micromoles, "eq." means equivalent, "° C." means degrees Celsius, "Pa" means pascals, "Xanthphos" means 4,5-bis(diphenylphosphino)-9,9-dimethylxanthene, "rt" means room temperature.

Methods of Preparation.

Compounds of the present invention may be prepared using the reaction routes and synthetic schemes described below, employing the techniques available in the art using starting materials that are readily available. The preparation of certain embodiments of the present invention is described in detail in the following examples, but those of ordinary skill in the art will recognize that the preparations described may be readily adapted to prepare other embodiments of the present invention. For example, the synthesis of non-exemplified compounds according to the invention may be performed by modifications apparent to those skilled in the art, e.g. by appropriately protecting interfering groups, by changing to other suitable reagents known in the art, or by making routine modifications of reaction conditions. Alternatively, other reactions referred to herein or known in the art will be recognized as having adaptability for preparing other compounds of the invention.

In one general synthetic process, compounds of the Structural Formula I where Y is a bond or CR$^4$R$^5$ and X is

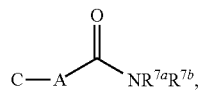

represented by Formula I-a can be prepared according to Scheme 1 by reacting carboxylic acid 1-1 with amine NHR$^{7a}$R$^{7b}$ in the presence of a coupling reagent such as EDCl or HATU and a base such as DIEA or triethylamine in a solvent such as DMF or dichloroethane to provide the desired product of Formula I-a. Alternatively, carboxylic acid 1-1 can react with SOCl$_2$ to form acid chloride 1-2 which can react with amine NHR$^{7a}$R$^{7b}$ in presence of a base such as DIEA or triethylamine in a solvent such as DMF or dichloroethane to form amide I-a. Reduction of the amide I-a with a reducing agent such as lithium aluminium hydride or similar reagents known to those skilled in the arts in a solvent such as THF or dietyl ether can provide a compound of general structure I where Y is a bond or CR$^4$R$^5$ and X is —C-A-CH$_2$NR$^{7a}$R$^{7b}$ represented by Formula I-b.

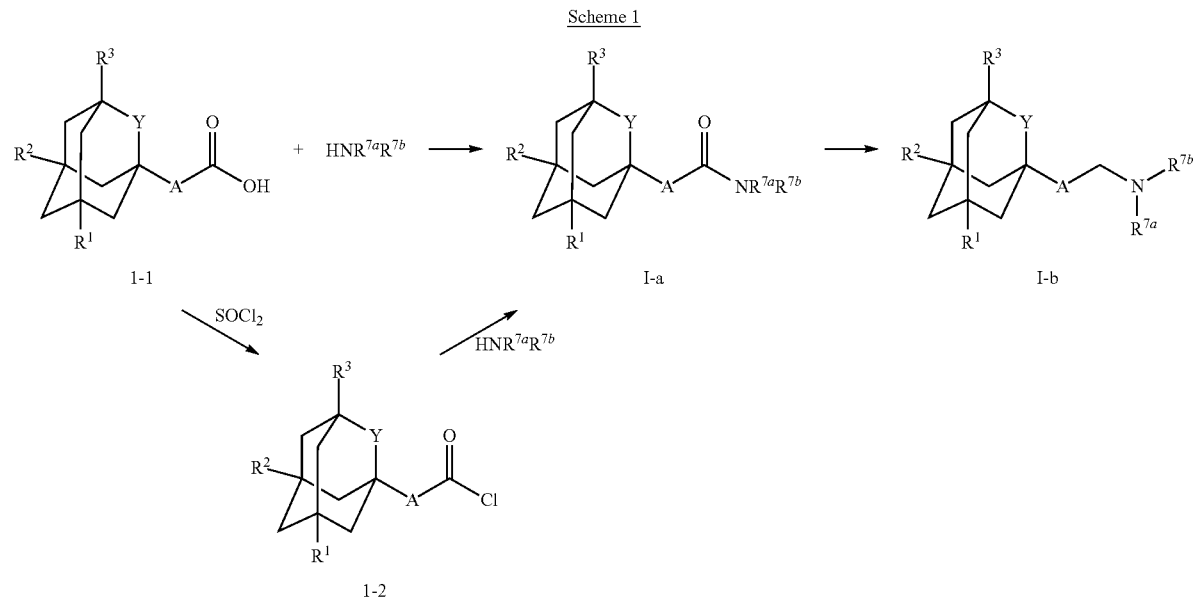

Scheme 1

In another general synthetic process, compounds of the Structural Formula I where Y is a bond or CR$^4$R$^5$ and X is

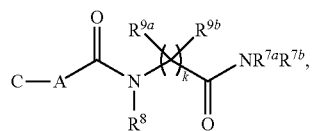

represented by Formula I-c can be prepared according to Scheme 2 by reacting carboxylic acid 2-1 with amine 2-2 in the presence of a coupling reagent such as EDCl or HATU and a base such as trimethylamine in a solvent such as DMF or dichloromethane to provide the desired product of Formula I-c. Alternatively, carboxylic acid 2-1 can react with SOCl$_2$ to form acid chloride 2-3 which can react with amine 2-2 in presence of a base such as DIEA or triethylamine in a solvent such as DMF or dichloroethane to form amide I-c Scheme 2

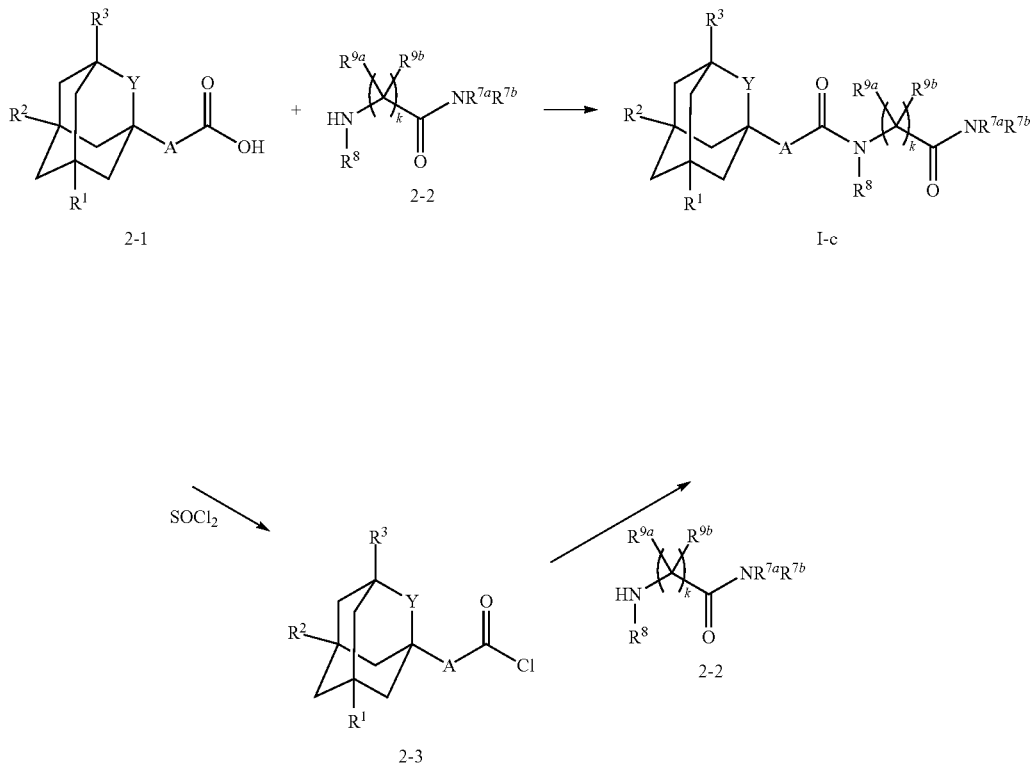

In another general synthetic process, compounds of the Structural Formula I where Y is a bond or $CR^4R^5$ and X is

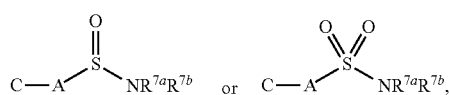

represented by Formula I-d or I-e can be prepared according to Scheme 3 by reacting sulfinyl chloride 3-1 with amine $NHR^{7a}R^{7b}$ in the presence a base such as triethylamine in a solvent such as DMF or dichloromethane to provide the desired product of Formula I-d which can be oxidized with an oxidizing agent such as MCPBA to desired product of formula I-e. Alternatively, sulfonyl chloride 3-2 can be reacted with amine $NHR^{7a}R^{7b}$ in the presence of a base such as triethylamine in a solvent such as DMF or dichloromethane to provide the desired product of Formula I-e.

Scheme 3

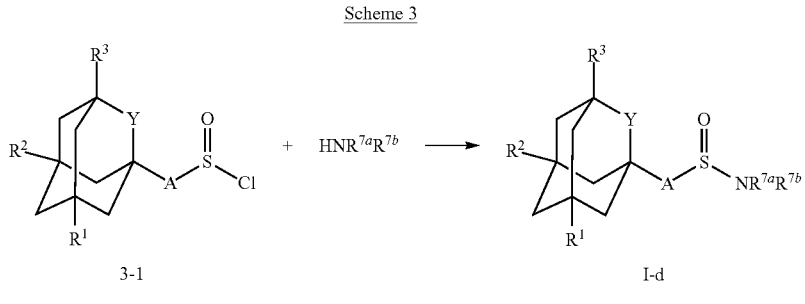

-continued

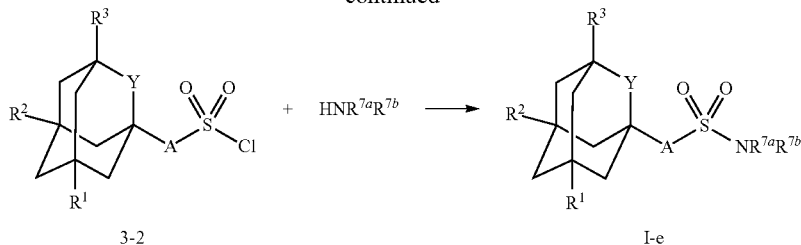

3-2   I-e

In another general synthetic process, compounds of the Structural Formula I where X is $CR^5$, and Y is

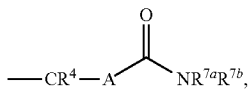

represented by Formula I-f can be prepared according to Scheme 4 by reacting carboxylic acid 4-1 with amine $NHR^{7a}R^{7b}$ in the presence of a coupling reagent such as EDCl or HATU and a base such as DIEA or triethylamine in a solvent such as DMF or dichloroethane to provide the desired product of Formula I-f. Alternatively, carboxylic acid 4-1 can react with $SOCl_2$ to form acid chloride 4-2 which can react with amine $NHR^{7a}R^{7b}$ in presence of a base such as DIEA or triethylamine in a solvent such as DMF or dichloroethane to form amide I-f. Reduction of the amide I-f with a reducing agent such as lithium aluminium hydride or similar reagents known to those skilled in the arts in a solvent such as THE or dietyl ether can provide a compound of general structure I where X is $CR^5$ and Y is $CR^4$-A-$CH_2NR^{7a}R^{7b}$, represented by Formula I-g.

In another general synthetic process, compounds of the Structural Formula I where Y is a bond or $CR^4R^5$, X is C-A-$ZR^{10}$, Z is O, S, or $NR^8$, and $R^{10}$ is

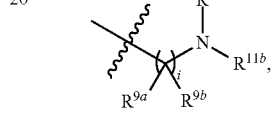

represented by Formula I-h can be prepared according to Scheme 5 by reacting 5-1 with a suitable hydroxy alkane containing a leaving group (LG) such as a halogen or a sulfonate 5-2 to provide 5-3. Treatment of 5-3 with triflic anhydride in a presence of a base such as triethylamine in a solvent such as THE or DCM can provide triflate 4-5 which can be treated with amine $NHR^{11a}R^{11b}$ in a solvent such as THE or DCM to provide a compound of Formula I-h.

Scheme 4

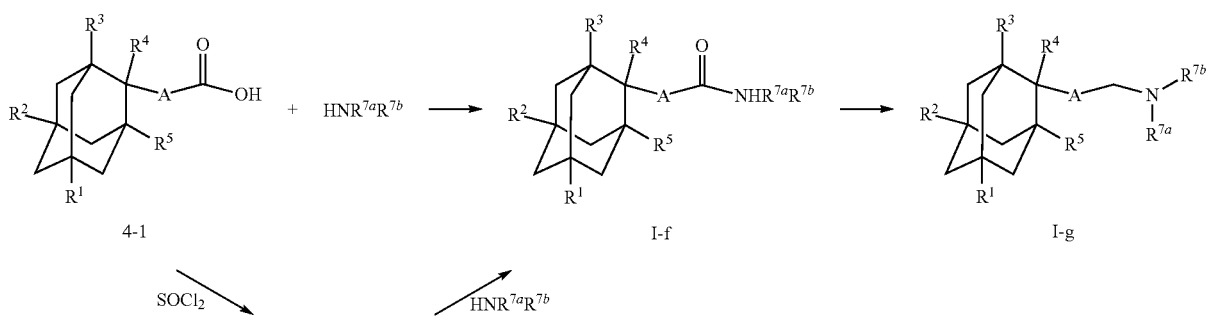

4-1   I-f   I-g

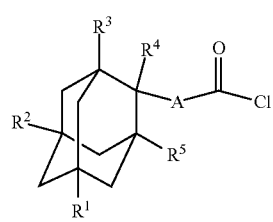

4-2

Scheme 5

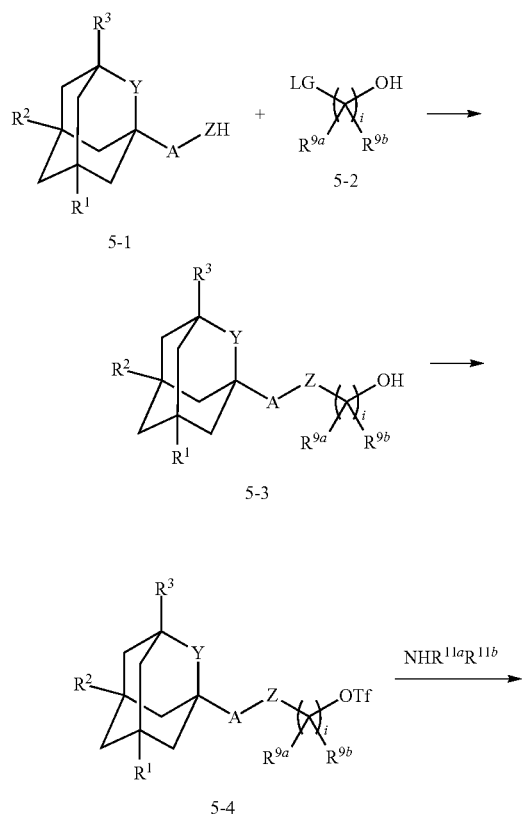

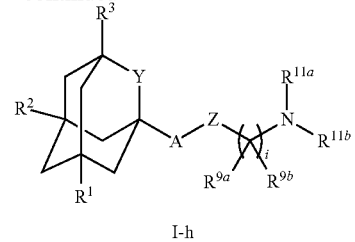

In another general synthetic process, compounds of the Structural Formula I where Y is a bond or $CR^4R^5$, X is C-A-$ZR^{10}$, Z is O, S, or $NR^8$, and $R^{10}$ is

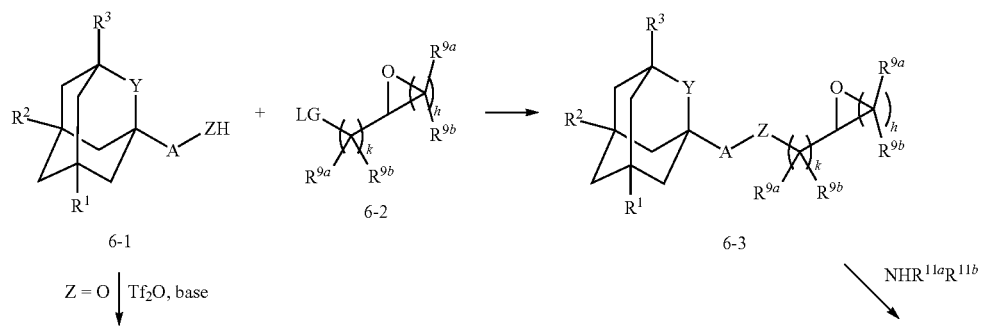

represented by Formula I-i can be prepared according to Scheme 6 by reacting 6-1 with an alkyl oxirane or oxetane 6-2 containing a leaving group (LG) such as a halogen or a sulfonate in the presence of a base such as $K_2CO_3$ in a solvent such as DMF to form oxirane or oxetane 6-3. Alternatively, when Z is oxygen, alcohol 6-1 can be treated with triflic anhydride in the presence of a base such as $NEt_3$ in a solvent such as DCM to form triflate 6-4 which in the presence of a base such sodium hydride in a solvent such as DMF can react with alcohol 6-5 to form 6-3. Treatment of 6-3 with amine $NHR^{11a}R^{11b}$ in a solvent such as isopropanol can provide a compound of Formula I-i.

Scheme 6

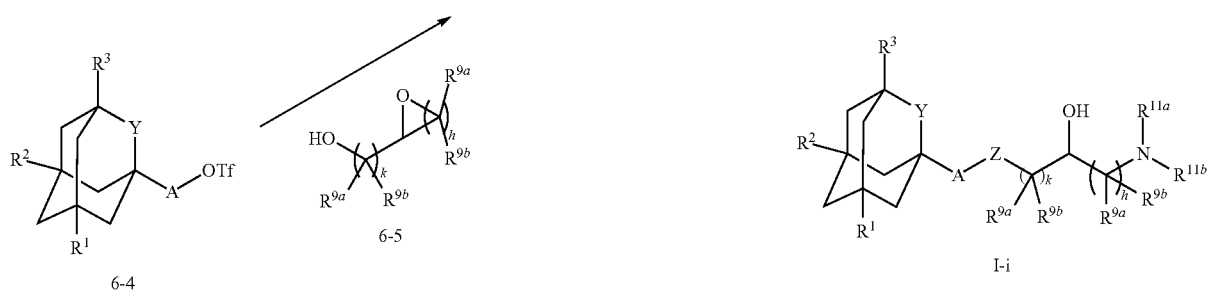

In another general synthetic process, compounds of the Structural Formula I where Y is a bond or $CR^4R^5$, X is $C-A-ZR^{10}$, Z is O, S, or $NR^8$, and $R^{10}$ is

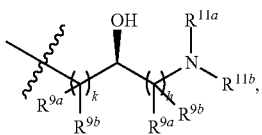

represented by Formula I-j can be prepared according to Scheme 7 by reacting 7-1 with an alkyl oxirane or oxetane 7-2 containing a leaving group (LG) such as a halogen or a sulfonate in the presence of a base such $K_2CO_3$ in a solvent such as DMF to form oxirane or oxetane 7-3. Alternatively, when Z is oxygen, alcohol 7-1 can be treated with triflic anhydride in the presence of a base such as $NEt_3$ in a solvent such as DCM to form triflate 7-4 which in the presence of a base such as sodium hydride in a solvent such as DMF can react with alcohol 7-5 to form 7-3. Treatment of 7-3 with amine $NHR^{11a}R^{11b}$ in a solvent such as isopropanol can provide a compound of Formula I-j.

In another general synthetic process, compounds of the Structural Formula I where Y is a bond or $CR^4R^5$, X is $C-A-ZR^{10}$, Z is O, S, or $NR^8$, and $R^{10}$ is

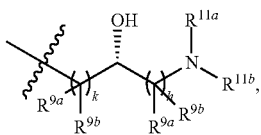

represented by Formula I-k can be prepared according to Scheme 8 by reacting 8-1 with an alkyl oxirane or oxetane 8-2 containing a leaving group (LG) such as a halogen or a sulfonate in the presence of a base such $K_2CO_3$ in a solvent such as DMF to form oxirane or oxetane 8-3. Alternatively, when Z is oxygen, alcohol 8-1 can be treated with triflic anhydride in the presence of a base such as $NEt_3$ in a solvent such as DCM to form triflate 8-4 which in the presence of a base such sodium hydride in a solvent such as DMF can react with alcohol 8-5 to form 8-3. Treatment of 8-3 with amine $NHR^{11a}R^{11b}$ in a solvent such as isopropanol can provide a compound of Formula I-k.

Scheme 7

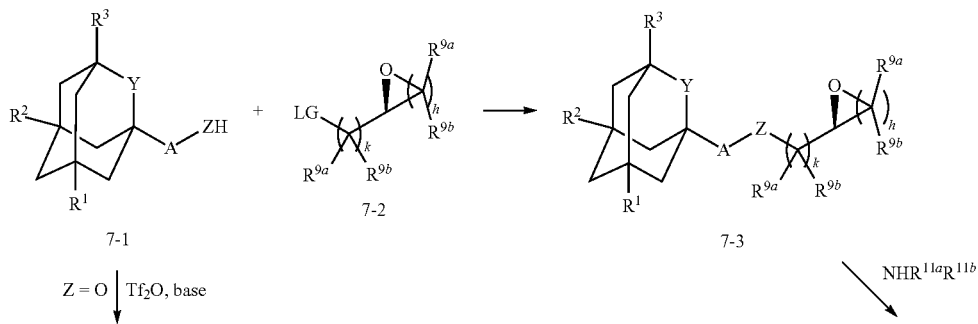

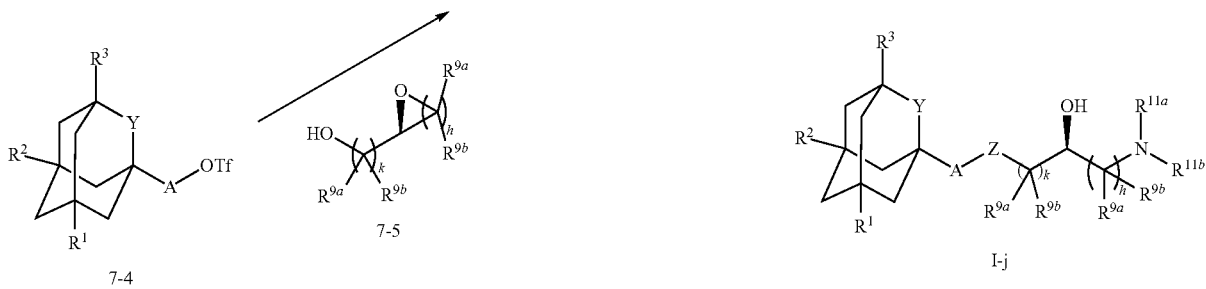

Scheme 8

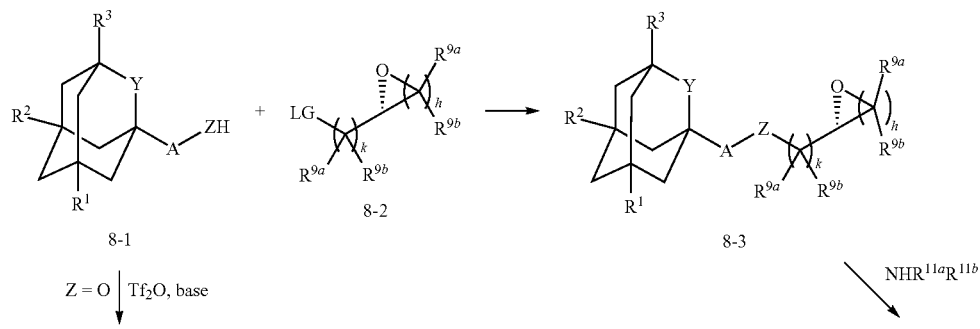

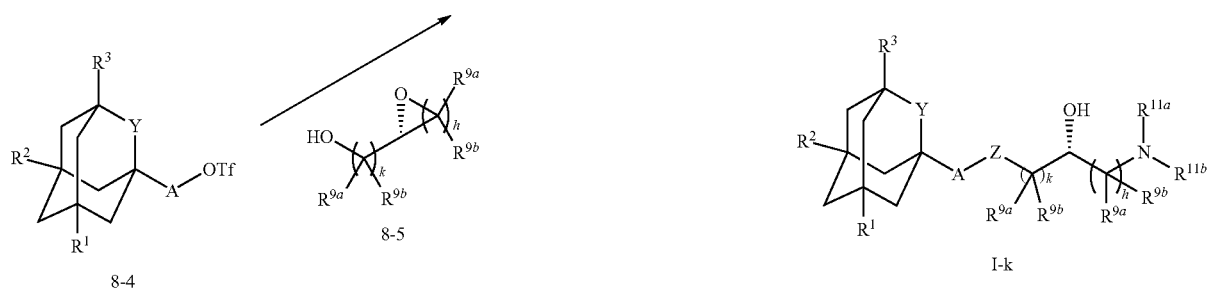

In another general synthetic process, compounds of the Structural Formula I where Y is a bond or $CR^4R^5$, X is C-A-D, A is a bond, and D is

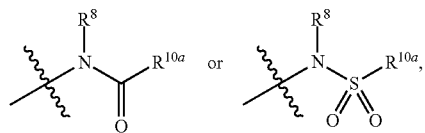

represented by Formula I-l and I-m can be prepared according to Scheme 9 from carboxylic acid 9-1 via a Curtius rearrangement using an azide reagent such as diphenylphosphorylazide to form amine 9-2 which can react with an aldehyde in the presence of a reducing agent such as $NaCNBH_3$ in a solvent such as DCM to form amine 9-3. Reaction of amine with a carboxylic acid $R^{10a}CO_2H$ the presence of a coupling reagent such as EDCl or HATU and a base such as triethylamine in a solvent such as DMF or dichloromethane can provide the desired product of Formula 1-1. Reaction of amine 9-3 with sulfonyl chloride $R^{10a}SO_2Cl$ in the presence of a base such as triethylamine in a solvent such as dichloromethane can provide the desired product of Formula I-m.

Scheme 9

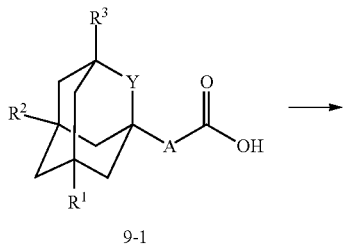

-continued

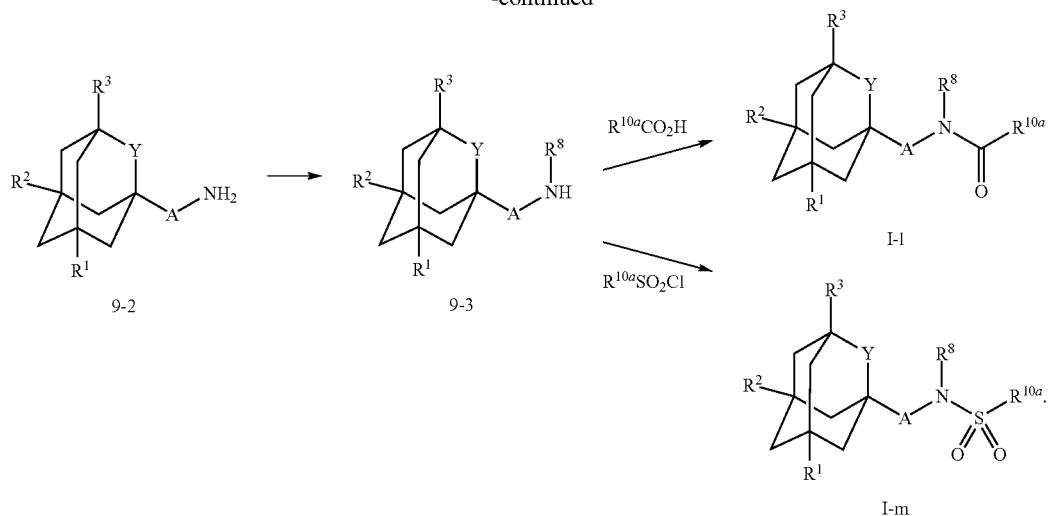

In another general synthetic process, compounds of the Structural Formula I where Y is a bond or $CR^4R^5$, X is C-A-D, A is a bond, and D is

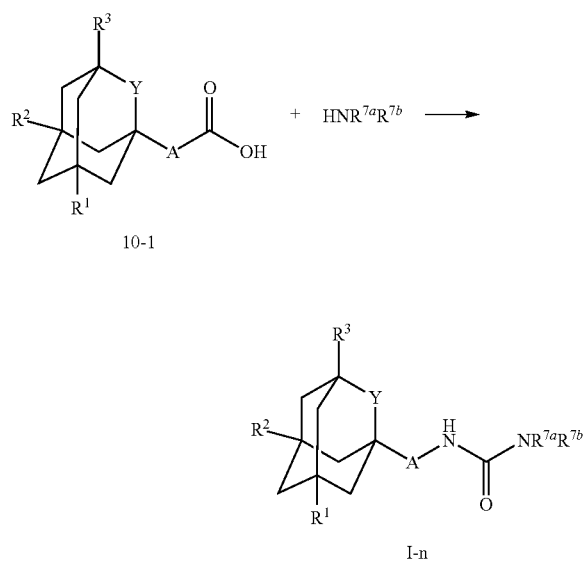

represented by Formula I-n can be prepared according to Scheme 10 from carboxylic acid 10-1 via a Curtius rearrangement using an azide reagent such as diphenylphosphorylazide to form amine 9-2 and reacting the intermediate isocyanate with an amine $NHR^{7a}R^{7b}$ to form the desired product of Formula I-n.

Scheme 10

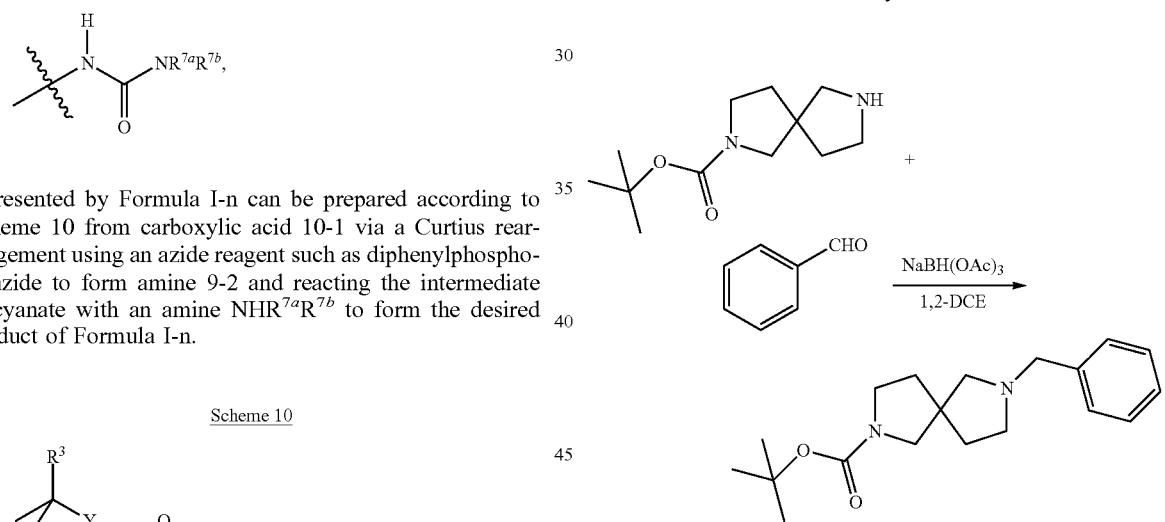

Preparation of Intermediates tert-Butyl 7-benzyl-2,7-diazaspiro[4.4]nonane-2-carboxylate A mixture of tert-butyl 2,7-diazaspiro[4.4]nonane-2-carboxylate (0.15 g, 0.66 mmol) and benzaldehyde (0.07 g, 0.66 mmol) in 3 mL 1,2-dichloroethane was stirred at rt for 0.5 h. Sodium triacetoxy borohydride (0.35 g, 1.65 mmol) was then added and the reaction mixture was stirred at rt for 12 h. The reaction mixture was then diluted with $CH_2Cl_2$ and washed with saturated aq. $NaHCO_3$ solution. The organic phase was dried over $Na_2SO_4$, filtered, and concentrated in vacuo. The residue was purified by $SiO_2$ column chromatography (EtOAc, then $CH_2Cl_2/CH_3OH$ 40:1) to give 0.084 g (40%) of the title compound as a colorless oil. LC/MS m/z: 217.28 (M-Boc+H)$^+$, 261.29 (M-tBu+H)$^+$, 302.31 (M-$CH_3$+H)$^+$, 317.33 (M+H)$^+$, 358.31 (M+H+$CH_3CN$)$^+$.

The following intermediates were prepared in the same manner as described above for tert-butyl 7-benzyl-2,7-diazaspiro[4.4]nonane-2-carboxylate using the appropriate amine and the appropriate aldehyde as starting materials.

| Starting materials | Intermediate/Name | Analytical Data |
|---|---|---|
| tert-butyl 2,7-diazaspiro[4.4]nonane-2-carboxylate<br>methyl 4-(2-formylphenoxymethyl)benzoate | 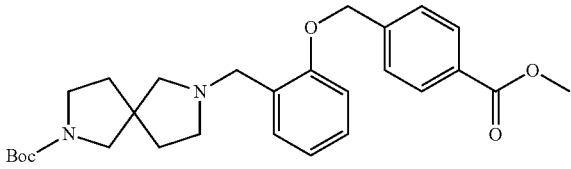<br>tert-butyl 7-[(2-{[4-(methoxycarbonyl)phenyl]methoxy}phenyl)methyl]-2,7-diazaspiro[4.4]nonane-2-carboxylate | LC/MS m/z: 481.36 (M + H)+ |
| tert-butyl piperazine-1-carboxylate<br>methyl 4-(2-formyl phenoxymethyl)benzoate | 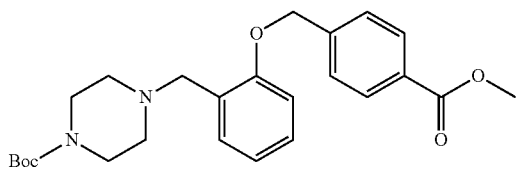<br>tert-butyl 4-[(2-{[4-(methoxycarbonyl)phenyl]ethoxy}phenyl)methyl]piperazine-1-carboxylate | LC/MS m/z: 441.24 (M + H)+ |
| tert-butyl N-(piperidin-4-yl)carbamate<br>methyl 4-(2-formylphenoxymethyl)benozate | 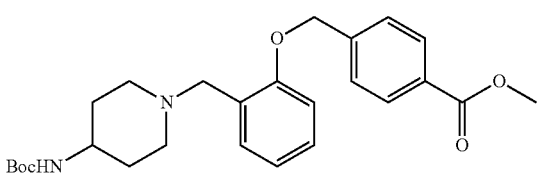<br>methyl 4-{2-[(4-{[tert-butoxy)carbonyl]amino}piperidin-1-yl)methyl]phenoxy methyl}benzoate | LC/MS m/z: 455.28 (M + H)+ |
| tert-butyl 2,5-diazabicyclo[2.2.1]heptane-2-carboxylate<br>methyl 4-(2-formylphenoxymethyl)benzoate | 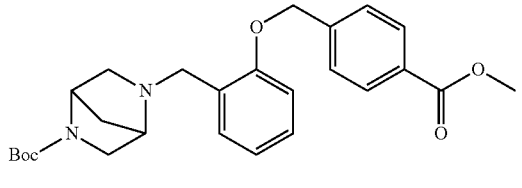<br>tert-butyl 5-[(2-{[4-(methoxycarbonyl)phenyl]methoxy}phenyl)methyl]-2,5-diazabicyclo[2.2.1]heptane-2-carboxylate | LC/MS m/z: 453.28 (M + H)+ |
| tert-butyl 2,6-diazaspiro[3.3]heptane-2-carboxylate<br>benzaldehyde | 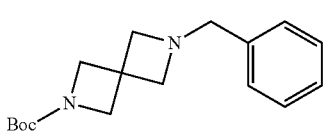<br>tert-butyl 6-benzyl-2,6-diazaspiro[3.3]heptane-2-carboxylate | LC/MS m/z: 233.23 (M − tBu + H)+, 274.23 (M − CH3 + H)+, 289.28 (M + H)+, 330.32 (M + H + CH3CN)+ |
| tert-butyl 2,6-diazaspiro[3.4]octane-2-carboxylate<br>benzaldehyde | 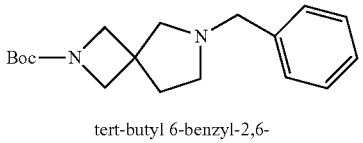<br>tert-butyl 6-benzyl-2,6-diazaspiro[3.4]octane-2-carboxylate | LC/MS m/z: 247.2 (M − tBu + H)+, 288.22 (M − CH3 + H)+, 303.33 (M + H)+, 344.38 (M + H + CH3CN)+ |

101 tert-Butyl-N-(2-{7-benzyl-2,7-diazaspiro[4.4]nonan-2-yl}-2-oxoethyl)carbamate

Step 1: 2-benzyl-2,7-diazaspiro[4.4]nonanedihydrochloride

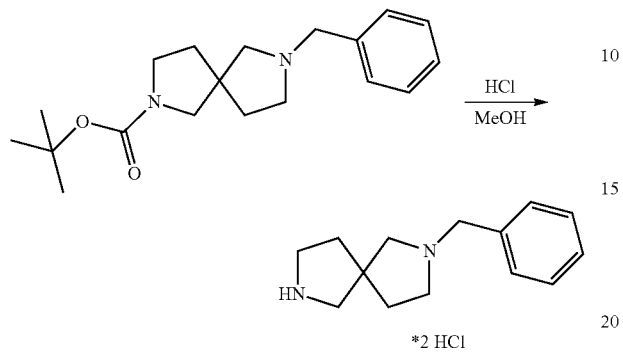

To a solution of tert-butyl 7-benzyl-2,7-diazaspiro[4.4]nonane-2-carboxylate (0.08 g, 0.25 mmol) in 1.5 mL $CH_3OH$ was added 0.75 mL conc. HCl. The reaction mixture was stirred at rt for 12 h, then concentrated in vacuo to give 0.073 g (100%) of the product as a viscous oil, which was used in the next step without further purification. LC/MS m/z: 258.09 $(M+H+CH_3CN)^+$.

Step 2: tert-butyl N-(2-{7-benzyl-2,7-diazaspiro[4.4]nonan-2-yl}-2-oxoethyl)carbamate

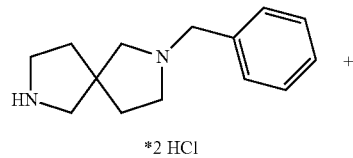

102

To a mixture of 2-benzyl-2,7-diazaspiro[4.4]nonanedihydrochloride (58 mg, 0.2 mmol) in 2 mL anhydrous $CH_2Cl_2$ was added N,N-diisopropylethylamine (116.6 mg, 0.9 mmol), 2-{[(tert-butoxy)carbonyl]amino}acetic acid (35 mg, 0.2 mmol), EDC hydrochloride (50 mg, 0.26 mmol), and 1-hydroxy-7-azabenzotriazole (HOAt, 30 mg, 0.22 mmol). The reaction mixture was stirred at rt for 12 h, then diluted with $CH_2Cl_2$ and washed with saturated aq. $NaHCO_3$ solution. The organic phase was dried over $Na_2SO_4$, filtered, and concentrated in vacuo. The residue was purified by $SiO_2$ column chromatography (EtOAc, then $CH_2Cl_2/CH_3OH$ from 40:1 to 10:1) to give 45 mg (60%) of the product as a colorless oil. LC/MS m/z: 274.44 $(M-Boc+H)^+$, 318.35 $(M-tBu+H)^+$, 374.36 $(M+H)^+$.

The following intermediates I-1 to I-8 were prepared in the same manner as described for the preparation of tert-butyl N-(2-{7-benzyl-2,7-diazaspiro[4.4]nonan-2-yl}-2-oxoethyl)carbamate using the appropriate precursor.

| | Starting materials | Product/Name | Analytical data |
|---|---|---|---|
| I-1 | tert-butyl 7-benzyl-2,7-diazaspiro[4.4]nonane-2-carboxylate | tert-butyl N-(2-{7-benzyl-2,7-diazaspiro[4.4]nonan-2-yl}-2-oxoethyl)carbamate | LC/MS m/z: 274.44 (M − Boc + H)$^+$, 318.35 (M − tBu + H)$^+$, 374.36 (M + H)$^+$ |
| I-2 | tert-butyl 7-[(2-{[4-(methoxycarbonyl)phenyl]methoxy}phenyl)methyl]-2,7-diazaspiro[4.4]nonane-2-carboxylate | methyl 4-(2-{[7-(2-{[(tert-butoxy)carbonyl]amino}acetyl)-2,7-diazaspiro[4.4]nonan-2-yl]methyl}phenoxymethyl)benzoate | LC/MS m/z: 538.38 (M + H)$^+$ |

-continued

| | Starting materials | Product/Name | Analytical data |
|---|---|---|---|
| I-3 | tert-butyl 4-[(2-{[4-(methoxy carbonyl)phenyl]methoxy} phenyl)methyl]piperazine-1-carboxylate | 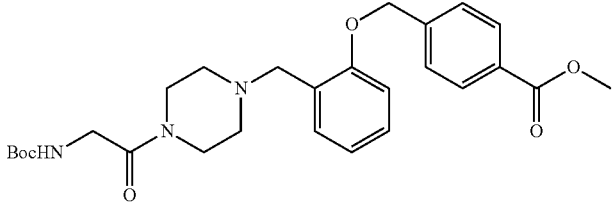<br>methyl 4-(2-{[4-(2-{[(tert-butoxy) carbonyl]amino}acetyl)piperazin-1-yl]methyl}phenoxymethyl) benzoate | LC/MS m/z: 398.3 (M − Boc + H)+, 442.27 (M − tBu + H)+, 498.28 (M + H)+ |
| I-4 | methyl 4-{2-[(4-{[(tert-butoxy)carbonyl]amino} piperidin-1-yl)methyl] phenoxy methyl}benzoate | 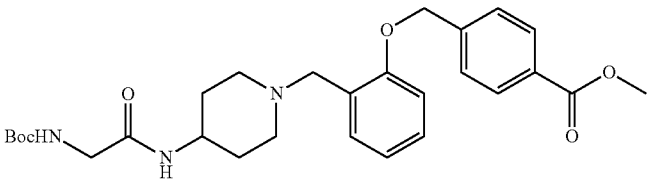<br>methyl 4-(2-{[4-(2-{[(tert-butoxy) carbonyl]amino}acetamido)piperidin-1-yl]methyl}phenoxymethyl) benzoate | LC/MS m/z: 456.27 (M − tBu + H)+, 512.35 (M + H)+ |
| I-5 | tert-butyl 5-[(2-{[4-(methoxycarbo-nyl)phenyl]meth-oxy}phenyl)methyl]-2,5-diazabicyclo[2.2.1]heptane-2-carboxylate | 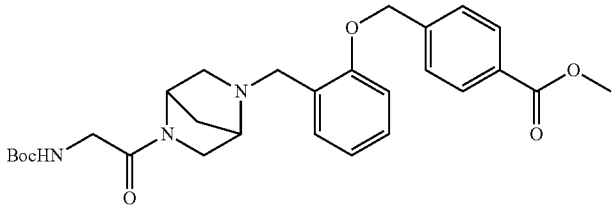<br>methyl 4-(2-{[5-(2-{[(tert-butoxy)carbonyl]amino}acetyl)-2,5-diazabicyclo[2.2.1]heptan-2-yl]methyl}phenoxymethyl)benzoate | LC/MS m/z: 510.3 (M + H)+ |
| I-6 | 1-benzylpiperidin-4-amine | 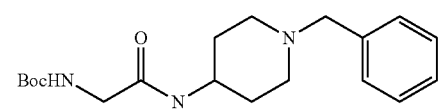<br>tert-butyl N-{[(1-benzylpiperidin-4-yl)carbamoyl]methyl}carbamate | LC/MS m/z: 348.34 (M + H)+, 292.26 (M − tBu + H)+ |
| I-7 | (3R)-1-benzylpyrrolidin-3-amine | 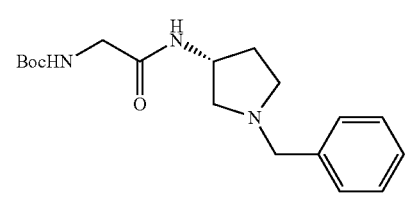<br>tert-butyl N-({[(3R)-1-benzyl pyrrolidin-3-yl]carbamoyl} methyl)carbamate | LC/MS m/z: 334.27 (M + H)+, 278.25 (M − tBu + H)+ |

| Starting materials | Product/Name | Analytical data |
|---|---|---|
| I-8 | 2-benzyl-2,5-diazabicyclo[2.2.]heptane dihydrobromide | tert-butyl N-(2-{5-benzyl-2,5-diazabicyclo[2.2.1]heptan-2-yl}-2-oxoethyl)carbamate | LC/MS m/z: 246.26 (M − Boc + H)+, 290.24 (M − tBu + H)+, 346.32 (M + H)+, 387.33 (M + H + CH3CN)+ |

3-Bromo-5,7-dimethyladamantane-1-carboxylic acid

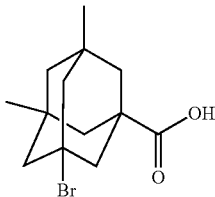 [SMILES: CC12CC3(C)CC(Br)(C1)CC(C(=O)O)(C2)C3]

The title compound was obtained by bromination of 3,5-dimethyladamantane-1-carboxylic acid using the procedure described in patent application US 2013/0096120, published Apr. 18, 2013.

3-Bromo-5-ethyladamantane-1-carboxylic acid

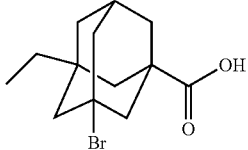 [SMILES: CCC12CC3CC(Br)(C1)CC(C(=O)O)(C3)C2]

The title compound was prepared from 3-ethyladamantane-1-carboxylic acid in the same manner as described for 3-bromo-5,7-dimethyladamantane-1-carboxylic acid.

3,5-Dimethyl-7-phenyladamantane-1-carboxylic acid

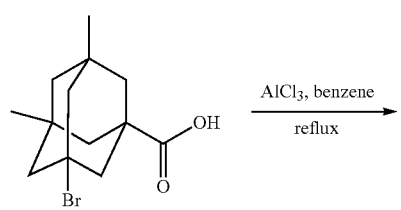

3-Bromo-5,7-dimethyladamantane-1-carboxylic acid (0.033 g, 0.11 mmol) was added to a mixture of AlCl3 (0.018 g, 0.14 mmol) in 1 mL anhydrous benzene. The reaction mixture was heated to reflux for 6 h, then diluted with EtOAc. The organic phase was washed with 0.5 M aq. HCl and brine, dried over Na2SO4, filtered, and concentrated in vacuo to give 0.03 g (91%) of the product as white solid, which was used in the next step without further purification.

3-Ethyl-5-phenyladamantane-1-carboxylic acid

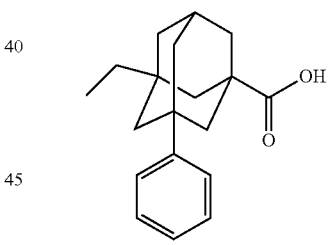

The title compound was prepared from 3-bromo-5-ethyladamantane-1-carboxylic acid and benzene in the same manner as described for 3,5-dimethyl-7-phenyladamantane-1-carboxylic acid.

3-(4-Chlorophenyl)adamantane-1-carboxylic acid

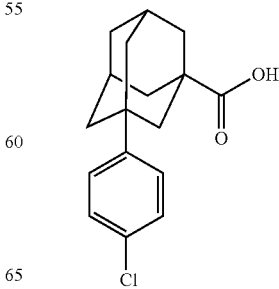

The title compound was prepared from 3-bromoadamantane-1-carboxylic acid and chlorobenzene in the same manner as described for 3,5-dimethyl-7-phenyladamantane-1-carboxylic acid.

3-(4-Fluorophenyl)adamantane-1-carboxylic acid

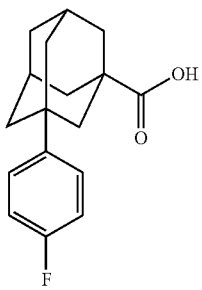 [SMILES: O=C(O)C12CC3CC(C1)CC(c1ccc(F)cc1)(C3)C2]

The title compound was prepared from 3-bromoadamantane-1-carboxylic acid and fluorobenzene in the same manner as described for 3,5-dimethyl-7-phenyladamantane-1-carboxylic acid.

1-Phenyltricyclo[3.3.1.0$^{3,7}$]nonane-3-carboxylic acid

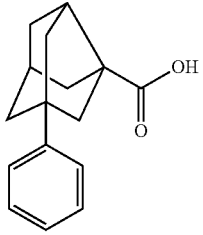 [SMILES: O=C(O)C12CC3CC1CC(c1ccccc1)(C3)C2]

The title compound was prepared following the procedure described in patent application US2013/0345127, published Dec. 26, 2013.

5-Phenyladamantane-2-carboxylic acid

Step 1: 5-phenyladamantan-2-one

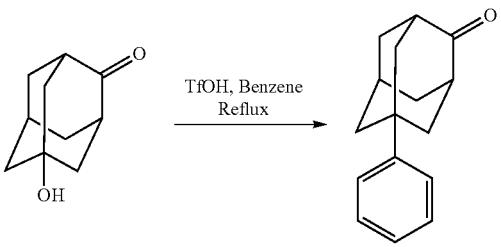 [SMILES: O=C1C2CC3CC1CC(O)(C3)C2 ; "TfOH, BenzeneReflux" ; O=C1C2CC3CC1CC(c1ccccc1)(C3)C2]

To 5-hydroxyadamantan-2-one (5 g, 150 mmol) was added benzene (20 mL) and triflic acid (3 mL). The heterogenous mixture was heated to reflux, at which time all starting materials dissolved, and reflux was continued overnight. The mixture was cooled to room temperature and partitioned between water and tert-butylmethyl ether (50 mL), and the organic phase was washed 3 times with water, followed by saturated NaHCO$_3$ and brine. The organics were dried over Na$_2$SO$_4$ and evaporated to give 4.7 g of crude product. Purification with flash chromatography on silica gel using 8:2 hexanes:ethyl acetate eluent gave 3.7 g of pure product as a white solid. $^1$H NMR (300 MHz, CDCl$_3$) δ: 7.41-7.32 (m, 4H), 7.27-7.21 (m, 1H), 2.70 (br:s, 2H), 2.37-2.03 (m, 11H).

Step 2: cis-5-phenyladamantane-2-carbonitrile and trans-5-phenyladamantane-2-carbonitrile

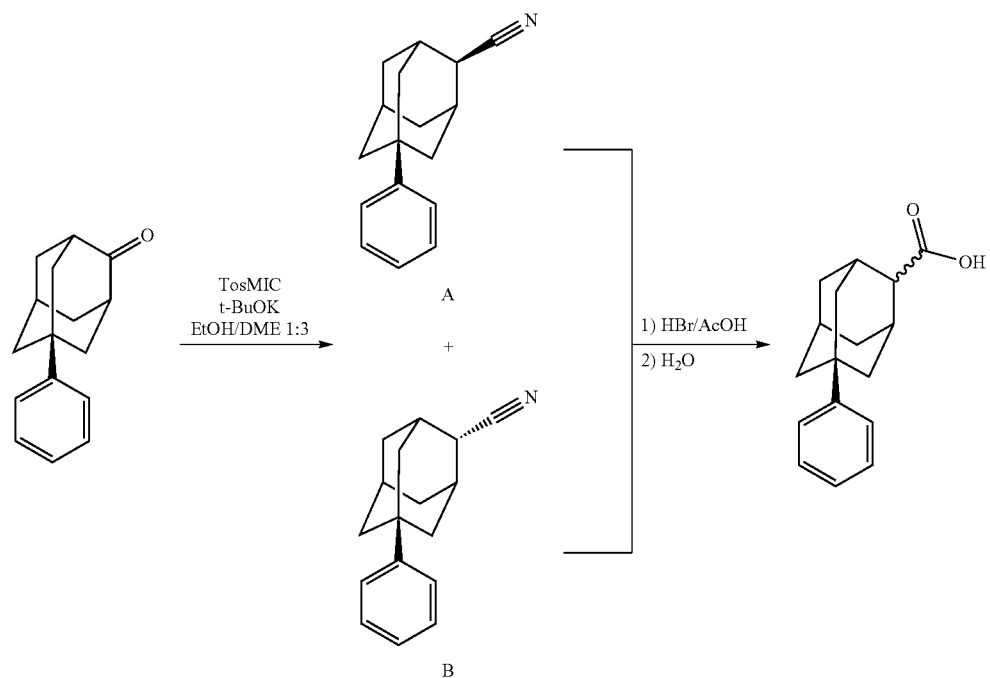

To 5-phenyladamantan-2-one (1.1 g, 4.87 mmol) in a flask with strong stirrer was added dimethoxyethane (20 mL), ethanol (7 mL), and p-toluenesulfonylmethylisocyanide (1.23 g, 6.33 mmol). The mixture was cooled to 0° C., and potassium tert-butoxide (1.31 g, 11.7 mmol) was added in 3 portions (mild exotherm). The reaction mixture was heated to 35° C. overnight and then cooled to room temperature and filtered to remove potassium tosylate. The filtrate was partitioned between water and tert-butylmethyl ether and washed three times with water, then brine, dried ($Na_2SO_4$), and evaporated. The crude residue was purified via flash chromatography on silica gel using 95:5 hexanes:ethyl acetate eluent. Purification gave 200 mg and 234 mg of the less and more polar isomers, respectively, and 410 mg of mixed fractions containing co-eluted meso-isomers A and B. Top isomer on TLC, configuration unknown: $^1$H NMR (500 MHz, $CDCl_3$) δ: 7.38-7.30 (m, 4H), 7.20 (t, 1H), 2.93 (s, 1H), 2.39 (s, 2H), 2.25-2.15 (m, 3H), 2.07 (d, 2H), 1.94 (t, 4H), 1.77 (d, 2H). Bottom isomer on TLC, configuration unknown: $^1$H NMR (500 MHz, $CDCl_3$) δ: 7.38-7.31 (m, 4H), 7.20 (t, 1H), 2.94 (s, 1H), 2.39 (s, 2H), 2.35 (d, 2H), 2.15 (s, 1H), 1.97 (s, 1H), 1.90 (d, 4H), 1.78 (d, 2H).

Step 3: 5-phenyladamantane-2-carboxylic acid

In two separate reactions, 140 mg of the top nitrile on TLC (absolute configuration unknown) and 230 mg of the bottom nitrile on TLC (absolute configuration unknown) were combined with 5 mL of 33% HBr/glacial acetic acid solution. Each reaction was brought to reflux until TLC indicated that the nitriles had hydrolyzed to the primary amide, and the maximum amount of water that does not cause the amide to precipitate was titrated into the reaction mixtures through their condensers. The separate reactions were refluxed overnight and then cooled to room temperature. On cooling, both reactions produced precipitates that were filtered off into sintered glass funnels, washed 3 times with 1 M HCl, and dried on a rotary evaporator to yield fine white crystals. The top nitrile on TLC yielded 105 mg, while the bottom nitrile produced 185 mg. $^{13}$C NMR of both reaction products confirms that both nitriles hydrolyze to identical carboxylic acids, presumably the most thermodynamically stable product. The absolute cis/trans configuration of the single carboxylic acid product is unknown. HPLC and TLC also indicate the formation of a single, identical carboxylic acid isomer from both reactions. $^{13}$C NMR (125 MHz, $CDCl_3$) δ: 180.35, 150.64, 128.45, 125.96, 125.01, 49.04, 48.76, 43.76, 43.33, 39.16, 37.43, 35.83, 32.96, 30.40, 28.41

3-(3-Methylphenyl)adamantane-1-carboxylic acid

Step 1: 3-(2-hydroxy-5-methylphenyl)adamantane-1-carboxylic acid

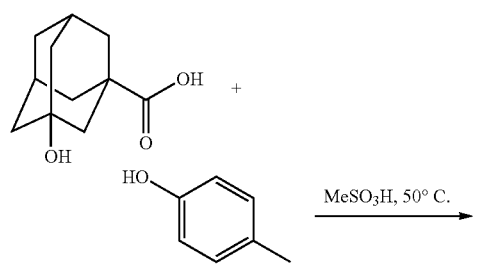

MeSO$_3$H, 50° C.

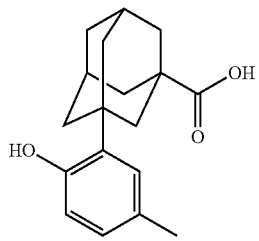

4-Methylphenol (0.25 g, 2.3 mmol) was added to a solution of 3-hydroxyadamantane-1-carboxylic acid (0.5 g, 2.55 mmol) in methanesulfonic acid (2.3 mL) heated to 40° C. under $N_2$ atmosphere (G. Ogawa, M. A. Tius, H. Zhou, S. P. Nikas, A. Halikhedkar, S. Mallipeddi, and A. Makriyannis, *J. Med. Chem.* 2015, 58, 3104-3116). The reaction mixture was stirred at 50° C. for 3 h, then cooled to rt, diluted with $CH_2Cl_2$, poured onto ice-water. The organic layer was separated, and the aqueous layer was extracted with $CH_2Cl_2$. The organic layers were combined, washed with brine, dried over $Na_2SO_4$, filtered, and concentrated in vacuo. The residue was purified by $SiO_2$ column chromatography (hexanes/EtOAc from 7:3 to 1:1) to give 0.34 g (47%) of the product as a colorless oil. $^1$H NMR (500 MHz, $CDCl_3$) δ 6.99 (s, 1H), 6.86 (dd, 1H), 6.53 (d, 1H), 2.28 (br. s, 2H), 2.26 (s, 3H), 2.23-2.19 (m, 2H), 2.13-2.06 (m, 4H), 1.97-1.91 (m, 4H), 1.77-1.70 (m, 2H).

Step 2: methyl 3-(2-hydroxy-5-methylphenyl)adamantane-1-carboxylate

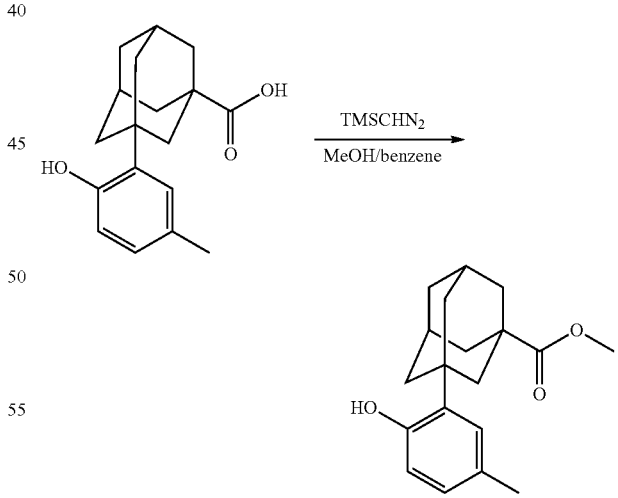

TMSCHN$_2$ (0.51 mL of 2 M in hexanes, 1.02 mmol) was added to a mixture of 3-(2-hydroxy-5-methylphenyl)adamantane-1-carboxylic acid (0.18 g, 0.63 mmol) in benzene (2.5 mL) and MeOH (0.6 mL) at 10° C. The reaction mixture was allowed to warm to rt for 1 h, then concentrated in vacuo to give the product as a colorless oil (0.19 g, 100%), which was used in the next step without further purification.

Step 3: methyl 3-{5-methyl-2-[(trifluoromethane)sulfonyloxy]phenyl}adamantane-1-carboxylate

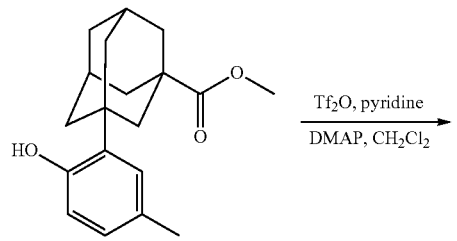

To a mixture of methyl 3-(2-hydroxy-5-methylphenyl)adamantane-1-carboxylate (0.15 g, 0.5 mmol), pyridine (0.12 g, 1.5 mmol) and DMAP (0.6 mg, 0.005 mmol) in CH$_2$Cl$_2$ (2 mL) cooled to 0° C. was added Tf$_2$O (0.17 g, 0.6 mmol) in CH$_2$Cl$_2$ (0.12 mL) dropwise. The reaction mixture was brought to rt gradually and stirred for 3 h, then diluted with CH$_2$Cl$_2$ and washed quickly with water. The organic phase was dried over Na$_2$SO$_4$, filtered, and concentrated in vacuo. The residue was purified by flash chromatography on SiO$_2$ (hexanes/EtOAc from 8:1 to 7:1) to give 0.11 g (52%) of the title compound as a colorless oil.

Step 4: methyl 3-(3-methylphenyl)adamantane-1-carboxylate

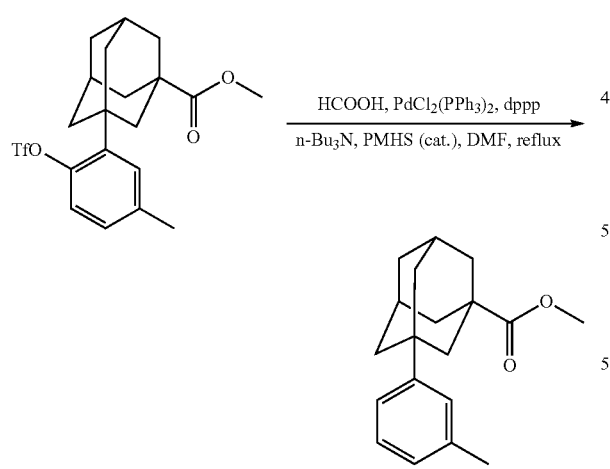

To a solution of methyl 3-{5-methyl-2-[(trifluoromethane)sulfonyloxy]phenyl}adamantane-1-carboxylate (0.11 g, 0.25 mmol) in dry DMF (1 mL) were added PdCl$_2$(PPh$_3$)$_2$ (9 mg, 0.013 mmol), dppp (10 mg, 0.024 mmol), n-Bu$_3$N (0.23 g, 1.27 mmol), HCOOH (0.03 g, 0.63 mmol), and catalytic polymethylhydrosiloxane (PMHS) under N$_2$ atmosphere. The reaction mixture was stirred at 95° C. overnight, then cooled to rt, diluted with MTBE and 1 N HCl, stirred for 10 min, filtered through a plug of Celite. The organic layer was separated, and the aqueous layer was extracted with MTBE. The organic layers were combined, dried over Na$_2$SO$_4$, filtered, and concentrated in vacuo. The residue was purified by flash chromatography on SiO$_2$ (hexanes/EtOAc from 9:1 to 8:1) to give 54 mg (75%) of the title compound as a colorless oil. $^1$H NMR (500 MHz, CDCl$_3$) δ 7.20 (t, 1H), 7.18-7.14 (m, 2H), 7.00 (d, 1H), 3.66 (s, 3H), 2.34 (s, 3H), 2.24-2.20 (m, 2H), 2.03 (br. s, 2H), 1.95-1.87 (m, 8H), 1.75-1.71 (m, 2H).

Step 5: 3-(3-methylphenyl)adamantane-1-carboxylic acid

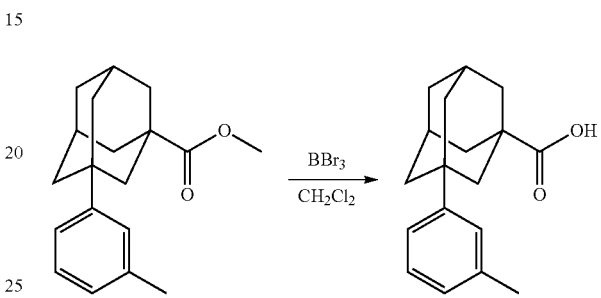

To a solution of methyl 3-(3-methylphenyl)adamantane-1-carboxylate (30 mg, 0.105 mmol) in CH$_2$Cl$_2$ (1 mL) cooled to 0° C. was added BBr$_3$ (0.2 mL of 1 M in CH$_2$Cl$_2$, 0.2 mmol) dropwise under N$_2$ atmosphere. The reaction mixture was gradually warmed to rt over 3 h, diluted with CH$_2$Cl$_2$, then quenched with ice. The organic layer was separated, and the aqueous layer was extracted with EtOAc. The organic layers were combined, dried over Na$_2$SO$_4$, filtered, and concentrated in vacuo to give 25 mg (90%) of the title compound as a white solid, which was used in the next step without further purification.

3-(Propan-2-yl)adamantane-1-carboxylic acid

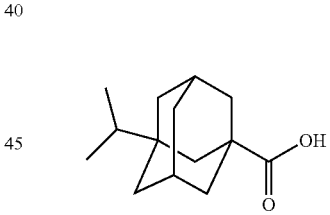

The title compound was prepared by isomerization of 2-(adamantan-1-yl)propan-2-ol into 3-(propan-2-yl)adamantan-1-ol in trifluoroacetic acid, followed by carboxylation of the formed alcohol using Koch-Haaf conditions (V. V. Kovalev, A. K. Rozov, and E. A. Shokova, *Tetrahedron* 1996, 52, 3983-3990).

3-Hydroxy-5-(propan-2-yl)adamantane-1-carboxylic acid

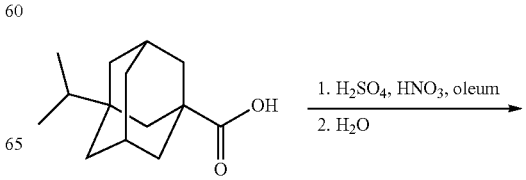

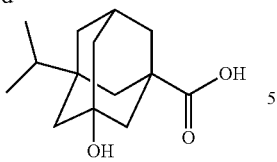

To a suspension of 3-(propan-2-yl)adamantane-1-carboxylic acid (90 mg, 0.4 mmol) in fuming nitric acid (0.25 mL) cooled to 0° C. was added sulfuric acid (0.41 mL) (L. Wanka, C. Cabrele, M. Vanejews and P. R. Schreiner, *Eur. J. Org. Chem.* 2007, 1474-1490). The reaction mixture was stirred at 0° C. for 10 min. Then, oleum (0.14 mL, 25% $SO_3$) was added, and the reaction mixture was stirred for 1 h at 0° C. and 3 h at rt, poured onto ice. The aqueous layer was extracted with EtOAc. The organic layer was dried over $Na_2SO_4$, filtered, and concentrated in vacuo to give 90 mg (94%) of the crude product as a white solid, which was used in the next step without further purification.

3-phenyl-5-(propan-2-yl)adamantane-1-carboxylic acid

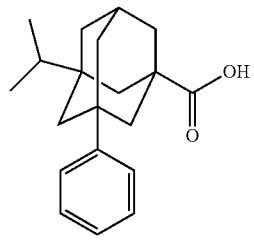 [SMILES: CC(C)C12CC3CC(C(=O)O)(CC(c4ccccc4)(C3)C1)C2]

The title compound was prepared from 3-hydroxy-5-(propan-2-yl)adamantane-1-carboxylic acid and benzene in the same manner as described above for 5-phenyladamantan-2-one. $^1$H NMR (500 MHz, $CDCl_3$) δ 7.39-7.35 (m, 2H), 7.34-7.29 (m, 2H), 7.19 (t, 1H), 2.34-2.30 (m, 1H), 2.01 (br. s, 2H), 1.89-1.81 (m, 4H), 1.72-1.65 (m, 2H), 1.63-1.58 (m, 2H), 1.54-1.48 (m, 2H), 1.39-1.34 (m, 1H), 0.86 (d, 6H).

3-Ethoxyadamantane-1-carboxylic acid

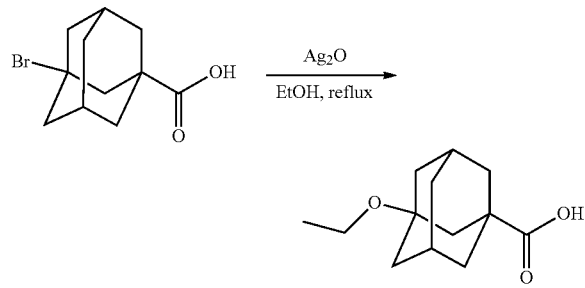

To a solution of 3-bromoadamantane-1-carboxylic acid (0.2 g, 0.77 mmol) in dry ethanol (2 mL) was added silver (I) oxide (0.18 g, 0.77 mmol) (H. Stetter and J. Mayer, *Chem. Ber.* 1962, 95, 667-672). The reaction mixture was refluxed for 3 h, then cooled to rt, diluted with EtOAc. Solids were filtered and washed with 5% AcOH in EtOAc. Volatiles were concentrated in vacuo to give 0.13 g (76%) of the title compound as a colorless oil, which was used in the next step without further purification.

1,3-Dimethyl 5-phenyladamantane-1,3-dicarboxylate

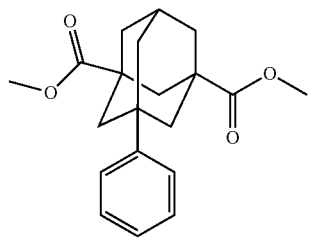

The title compound was prepared from 1,3-dimethyl 5-hydroxyadamantane-1,3-dicarboxylate and benzene in the same manner as described above for 5-phenyladamantan-2-one. $^1$H NMR (500 MHz, $CDCl_3$) δ 7.37-7.30 (m, 4H), 7.20 (t, 1H), 3.67 (s, 6H), 2.38-2.35 (m, 1H), 2.07 (br. s, 2H), 2.05-1.99 (m, 4H), 1.92-1.85 (m, 6H).

3-(Methoxycarbonyl)-5-phenyladamantane-1-carboxylic acid

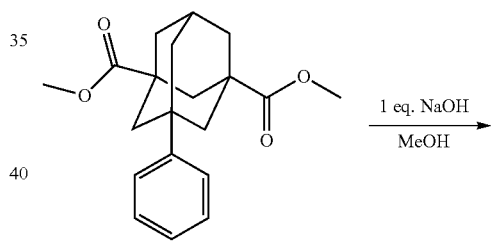

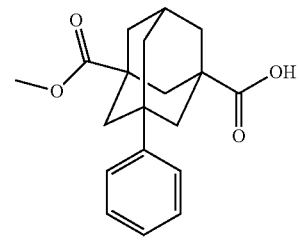

To a solution of 1,3-dimethyl 5-phenyladamantane-1,3-dicarboxylate (0.12 g, 0.37 mmol) in MeOH (1 mL) was added NaOH (15 mg, 0.37 mmol). The reaction mixture was stirred at 50° C. overnight, then concentrated in vacuo without heating. The residue was dissolved in water, acidified with 1 N HCl, and extracted with EtOAc. The organic layer was dried over $Na_2SO_4$, filtered, and concentrated in vacuo to give 80 mg (68%) of the crude product as a colorless oil, which was used in the next step without further purification.

115

Methyl 3-phenyl-5-[(pyrrolidin-1-yl)carbonyl]adamantane-1-carboxylate

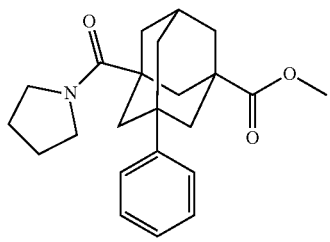 [SMILES: COC(=O)C12CC3CC(C(=O)N4CCCC4)(C1)CC(c1ccccc1)(C3)C2]

The title compound was prepared from 3-(methoxycarbonyl)-5-phenyladamantane-1-carboxylic acid and pyrrolidine in the same manner as described for 2-benzyl-7-[(3-phenyladamantan-1-yl)carbonyl]-2,7-diazaspiro[4.4]nonane (example A1, Step 2). LC/MS m/z: 368.32 (M+H)+, 735.54 (2M+H)+.

3-Phenyl-5-[(pyrrolidin-1-yl)carbonyl]adamantane-1-carboxylic acid

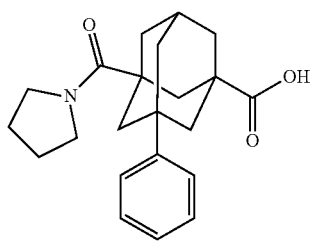 [SMILES: O=C(O)C12CC3CC(C(=O)N4CCCC4)(C1)CC(c1ccccc1)(C3)C2]

The title compound was prepared from methyl 3-phenyl-5-[(pyrrolidin-1-yl)carbonyl]adamantane-1-carboxylate using excess of NaOH in the same manner as described above for 3-(methoxycarbonyl)-5-phenyladamantane-1-carboxylic acid Example A1: 2-benzyl-7-[(3-phenyladamantan-1-yl)carbonyl]-2,7-diazaspiro[4.4]nonane

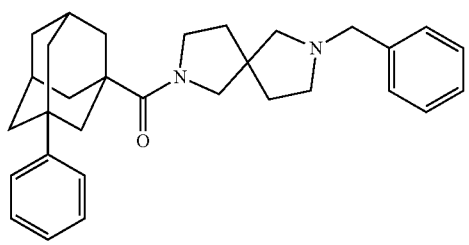 [SMILES: O=C(N1CCC2(CCN(Cc3ccccc3)C2)C1)C12CC3CC(C1)CC(c1ccccc1)(C3)C2]

116

Step 1: 2-benzyl-2,7-diazaspiro[4.4]nonanedihydrochloride

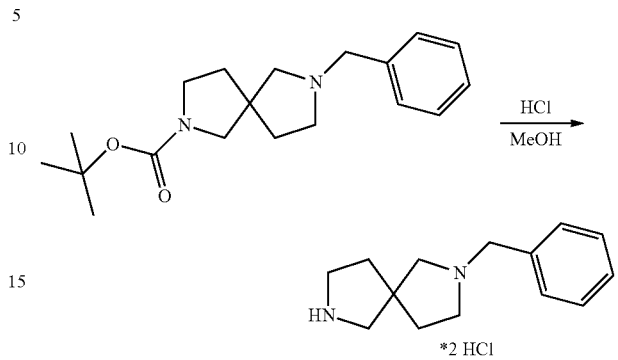

To a solution of tert-butyl 7-benzyl-2,7-diazaspiro[4.4]nonane-2-carboxylate (0.08 g, 0.25 mmol) in 1.5 mL $CH_3OH$ was added 0.75 mL conc. HCl. The reaction mixture was stirred at rt for 12 h, then concentrated in vacuo to give 0.073 g (100%) of the product as a viscous oil, which was used in the next step without further purification. LC/MS m/z: 258.09 (M+H+$CH_3$CN)+.

Step 2: 2-benzyl-7-[(3-phenyladamantan-1-yl)carbonyl]-2,7-diazaspiro[4.4]nonane

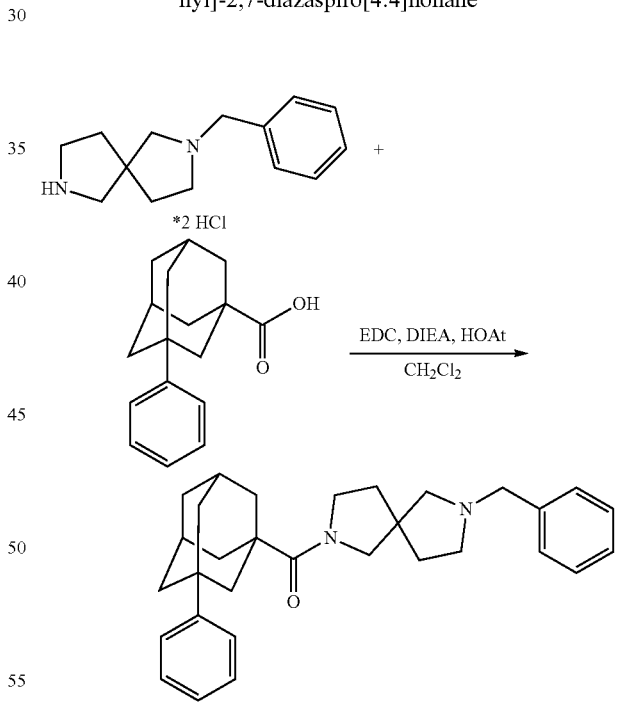

To a mixture of 2-benzyl-2,7-diazaspiro[4.4]nonane dihydrochloride (12.5 mg, 0.043 mmol) in 1 mL anhydrous $CH_2Cl_2$ was added N,N-diisopropylethylamine (25 mg, 0.19 mmol), 3-phenyl-adamantane-1-carboxylic acid (11 mg, 0.043 mmol), EDO hydrochloride (11 mg, 0.057 mmol), and 1-hydroxy-7-azabenzotriazole (HOAt, 6.5 mg, 0.048 mmol). The reaction mixture was stirred at rt for 12 h, then diluted with $CH_2Cl_2$ and washed with saturated aq. $NaHCO_3$ solution. The organic phase was dried over $Na_2SO_4$, filtered, and concentrated in vacuo. The residue was purified by $SiO_2$ column chromatography (EtOAc, then CH₂Cl₂/CH₃OH from 40:1 to 30:1) to give 10 mg (51%) of the product as a colorless oil. LC/MS m/z: 455.40 (M+H)⁺, 496.43 (M+H+CH₃CN)⁺.

Examples A2 to A14 were prepared in the same manner as described for example A1, Steps 1 and 2 starting from the appropriate Boc-protected amine and the appropriate carboxylic acid.

Examples A15 to A48 were prepared in the same manner as described for example A1, Step 2 using the appropriate commercially available amine and carboxylic acid as starting materials.

| Ex. | Starting materials | Product/Name | Analytical Data |
|---|---|---|---|
| A2 | tert-butyl N-(2-{7-benzyl-2,7-diazaspiro[4.4]nonan-2-yl}-2-oxoethyl)carbamate 3-phenyl-adamantane-1-carboxylic acid | N-(2-{7-benzyl-2,7-diazaspiro[4.4]nonan-2-yl}-2-oxoethyl)-3-phenyladamantane-1-carboxamide | LC/MS m/z: 512.42 (M + H)⁺, 553.47 (M + H + CH₃CN)⁺ |
| A3 | methyl 4-(2-{[4-(2-{[(tert-butoxy)carbonyl]amino}acetyl)piperazin-1-yl]methyl}phenoxymethyl)benzoate 3-phenyl-adamantane-1-carboxylic acid | methyl 4-{2-[(4-{2-[(3-phenyl adamantan-1-yl)formamido]acetyl}piperazin-1-yl)methyl]phenoxy methyl}benzoate | LC/MS m/z: 636.48 (M + H)⁺ |
| A4 | methyl 4-(2-{[4-(2-{[(tert-butoxy)carbonyl]amino}acetyl)piperazin-1-yl]methyl}phenoxymethyl)benzoate 2-(3-phenyl-adamantan-1-yl)acetic acid | methyl 4-{2-[(4-{2-[2-(3-phenyl adamantan-1-yl)acetamido]acetyl}piperazin-1-yl)methyl]phenoxymethyl}benzoate | LC/MS m/z: 650.44 (M + H)⁺ |

-continued

| Ex. | Starting materials | Product/Name | Analytical Data |
|---|---|---|---|
| A5 | methyl 4-(2-{[4-(2-{[(tert-butoxy)carbonyl]amino}acetyl)piperazin-1-yl]methyl}phenoxymethyl)benzoate tricyclo[3.3.1.0³,⁷]nonane-3-carboxylic acid | methyl 4-(2-{[4-(2-{tricyclo[3.3.1.0³,⁷]nonan-3-ylformamido}acetyl)piperazin-1-yl]methyl}phenoxymethyl)benzoate | LC/MS m/z: 546.35 (M + H)⁺ |
| A6 | tert-butyl N-{[(1-benzylpiperidin-4-yl)carbamoyl]methyl}carbamate 3-phenyl-adamantane-1-carboxylic acid | N-(1-benzylpiperidin-4-yl)-2-[(3-phenyl adamantan-1-yl)formamido]acetamide | LC/MS m/z: 486.41 (M + H)⁺ |
| A7 | tert-butyl N-({[(3R)-1-benzyl pyrrolidin-3-yl]carbamoyl}methyl)carbamate 3-phenyl-adamantane-1-carboxylic acid | N-[(3R)-1-benzylpyrrolidin-3-yl]-2-[(3-phenyladamantan-1-yl)formamido]acetamide | LC/MS m/z: 472.40 (M + H)⁺ |
| A8 | tert-butyl N-(2-{5-benzyl-2,5-diazabicyclo[2.2.1]heptan-2-yl}-2-oxoethyl)carbamate 3-phenyl-adamantane-1-carboxylic acid | N-(2-{5-benzyl-2,5-diazabicyclo[2.2.1]heptan-2-yl}-2-oxoethyl)-3-phenyl adamantane-1-carboxamide | LC/MS m/z: 484.3 (M + H)⁺ |

-continued

| Ex. | Starting materials | Product/Name | Analytical Data |
|---|---|---|---|
| A9 | tert-butyl 6-benzyl-2,6-diaza-spiro[3.3]heptane-2-carboxylate 3-phenyl-adamantane-1-carboxylic acid | 2-benzyl-6-[(3-phenyl adamantan-1-yl)carbonyl]-2,6-diazaspiro[3.3]heptane | LC/MS m/z: 427.45 (M + H)+, 468.34 (M + H + CH$_3$CN)+ |
| A10 | tert-butyl 6-benzyl-2,6-diaza-spiro[3.4]octane-2-carboxylate 3-phenyl-adamantane-1-carboxylic acid | 6-benzyl-2-[(3-phenyl adamantan-1-yl)carbonyl]-2,6-diazaspiro[3.4]octane | LC/MS m/z: 441.31 (M + H)+, 482.36 (M + H + CH$_3$CN)+ |
| A11 | tert-butyl N-(2-{7-benzyl-2,7-diazaspiro[4.4]nonan-2-yl}-2-oxo-ethyl)carbamate 2-(3-phenyl-adamantan-1-yl)acetic acid | N-(2-{7-benzyl-2,7-diazaspiro[4.4]nonan-2-yl}-2-oxoethyl)-2-(3-phenyl adamantan-1-yl)acetamide | LC/MS m/z: 526.45 (M + H)+ |
| A12 | tert-butyl N-{[(1-benzylpiperidin-4-yl)carbamoyl]methyl}carbamate 2-(3-phenyl-adamantan-1-yl)acetic acid | N-{[(1-benzylpiperidin-4-yl)carbamoyl]methyl}-2-(3-phenyladamantan-1-yl)acetamide | LC/MS m/z: 500.46 (M + H )+ |

-continued

| Ex. | Starting materials | Product/Name | Analytical Data |
|---|---|---|---|
| A13 | tert-butyl N-({[(3R)-1-benzyl pyrrolidin-3-yl]carbamoyl}methyl)carbamate 2-(3-phenyl-adamantan-1-yl)acetic acid | 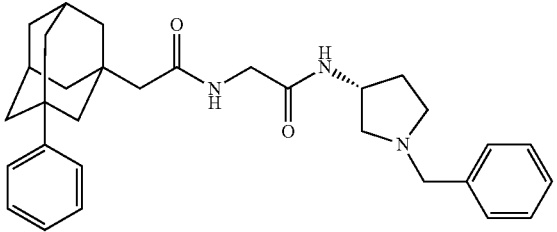<br>N-({[(3R)-1-benzylpyrrolidin-3-yl]carbamoyl}methyl)-2-(3-phenyladamantan-1-yl) acetamide | LC/MS m/z: 486.43 (M + H)+ |
| A14 | tert-butyl N-(2-{5-benzyl-2,5-diazabicyclo[2.2.1]heptan-2-yl}-2-oxoethyl)carbamate 2-(3-phenyl-adamantan-1-yl)acetic acid | 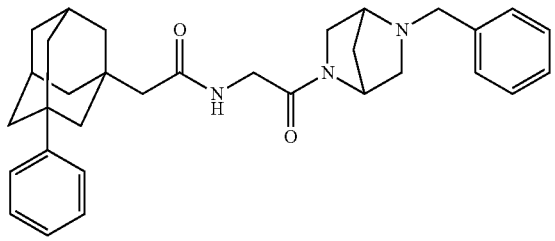<br>N-(2-{5-benzyl-2,5-diaza-bicyclo[2.2.1]heptan-2-yl}-2-oxoethyl)-2-(3-phenyl-adamantan-1-yl)acetamide | LC/MS m/z: 498.39 (M + H)+ |
| A15 | (3S)-1-benzyl-pyrrolidin-3-amine 3-phenyl-adamantane-1-carboxylic acid | 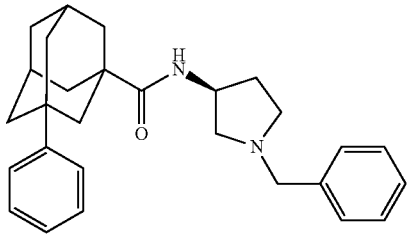<br>N-[(3S)-1-benzylpyrrolidin-3-yl]-3-phenyladamantane-1-carboxamide | LC/MS m/z: 415.33 (M + H)+, 456.41 (M + H + CH3CN)+ |
| A16 | 2-amino-1-(4-benzyl piperazin-1-yl)ethan-1-one dihydrochloride 3-phenyl-adamantane-1-carboxylic acid | 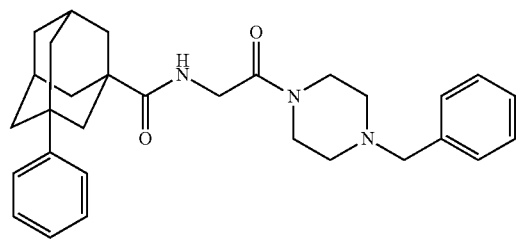<br>N-[2-(4-benzylpiperazin-1-yl)-2-oxoethyl]-3-phenyl adamantane-1-carboxamide | LC/MS m/z: 472.33 (M + H)+ |

-continued

| Ex. | Starting materials | Product/Name | Analytical Data |
|---|---|---|---|
| A17 | 2-amino-1-(4-benzyl piperazin-1-yl)ethan-1-one dihydrochloride 2-(3-phenyl-adamantan-1-yl)acetic acid | 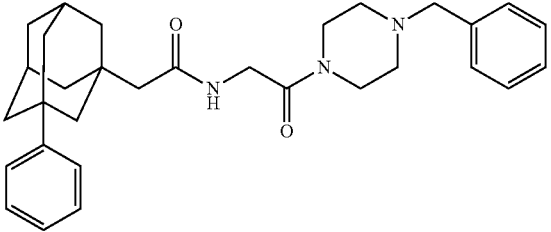<br>N-[2-(4-benzylpiperazin-1-yl)-2-oxoethyl]-2-(3-phenyl-adamantan-1-yl)acetamide | LC/MS m/z: 486.33 (M + H)+ |
| A18 | 2-amino-1-(4-benzyl piperazin-1-yl)ethan-1-one dihydrochloride tricyclo[3.3.1.0$^{3,7}$]nonane-3-carboxylic acid | 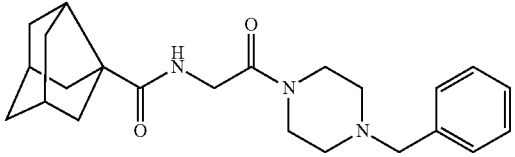<br>N-[2-(4-benzylpiperazin-1-yl)-2-oxoethyl]tricyclo[3.3.1.0$^{3,7}$] nonane-3-carboxamide | LC/MS m/z: 382.33 (M + H)+ |
| A19 | (3R)-1-benzyl-pyrrolidin-3-amine 3-phenyl-adamantane-1-carboxylic acid | 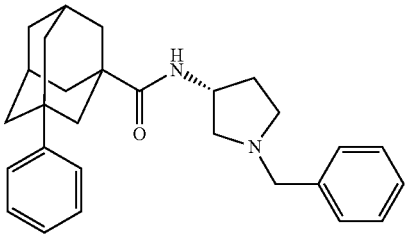<br>N-[(3R)-1-benzylpyrrolidin-3-yl]-3-phenyladamantane-1-carboxamide | LC/MS m/z: 415.44 (M + H)+ |
| A20 | 2-benzyl-2,5-diaza bicyclo[2.2.1]heptane dihydrobromide 3-phenyl-adamantane-1-carboxylic acid | 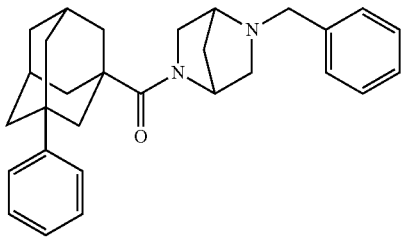<br>2-benzyl-5-[(3-phenyl-adamantan-1-yl)carbonyl]2,5-diazabicyclo[2.2.1]heptane | LC/MS m/z: 427.36 (M + H)+, 468.36 (M + H + CH$_3$CN)+ |

-continued

| Ex. | Starting materials | Product/Name | Analytical Data |
|---|---|---|---|
| A21 | 1-benzylpiperidin-4-amine tricyclo[3.3.1.0³,⁷]nonane-3-carboxylic acid | 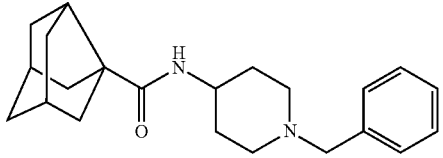<br>N-(1-benzylpiperidin-4-yl) tricyclo[3.3.1.0³,⁷]nonane-3-carboxamide | LC/MS m/z: 339.38 (M + H)⁺ |
| A22 | benzyl(methyl)[2-(methylamino)ethyl]amine 3-phenyl-adamantane-1-carboxylic acid | 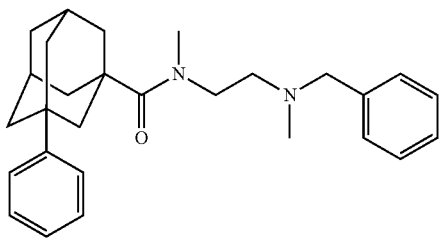<br>N-{2-[benzyl(methyl)amino]ethyl}-N-methyl-3-phenyl adamantane-1-carboxamide | LC/MS m/z: 417.35 (M + H)⁺ |
| A23 | 1-benzyl-N-methyl piperidin-4-amine 3-phenyl-adamantane-1-carboxylic acid | 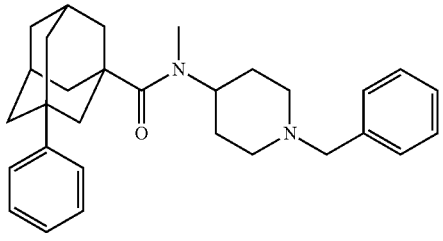<br>N-(1-benzylpiperidin-4-yl)-N-methyl-3-phenyl adamantane-1-carboxamide | LC/MS m/z: 443.39 (M + H)⁺ |
| A24 | (3R)-1-benzyl-pyrrolidin-3-amine 2-(3-phenyl-adamantan-1-yl)acetic acid | 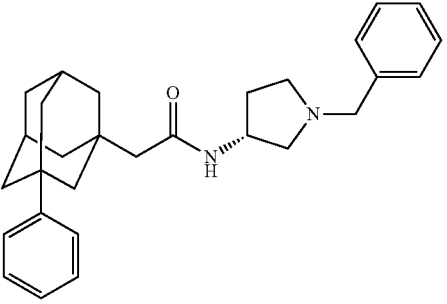<br>N-[(3R)-1-benzylpyrrolidin-3-yl]-2-(3-phenyladamantan-1-yl) acetamide | LC/MS m/z: 429.26 (M + H)⁺ |

-continued

| Ex. | Starting materials | Product/Name | Analytical Data |
|---|---|---|---|
| A25 | 1-methylpiperazine 3-phenyl-adamantane-1-carboxylic acid | 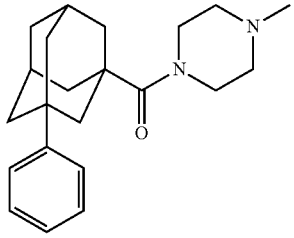<br>1-methyl-4-{(3-phenyl adamantan-1-yl)carbonyl] piperazine | LC/MS m/z: 339.27 (M + H)+ |
| A26 | 1-methylpiperidin-4-amine 3-phenyl-adamantane-1-carboxylic acid | 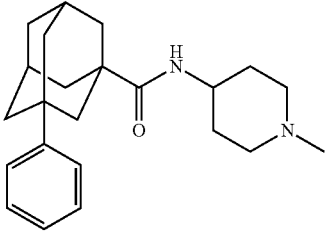<br>N-(1-methylpiperidin-4-yl)-3-phenyladamantane-1-carboxamide | $^1$H NMR (300 MHz, CDCl$_3$) δ 7.26-7.38 (m, 4H) 7.14-7.21 (m, 1H) 5.67 (d, 1H) 3.83-4.01 (m, 1H) 3.22 (d, 2H) 2.57 (s, 4H) 2.25 (br. s., 2H) 1.98 (br. s., 3H) 1.79-1.95 (m, 10H) 1.72 (br. s., 2H); LC/MS m/z: 353.37 (M + H)+ |
| A27 | N,1-dimethyl-piperidin-4-amine 3-phenyl-adamantane-1-carboxylic acid | 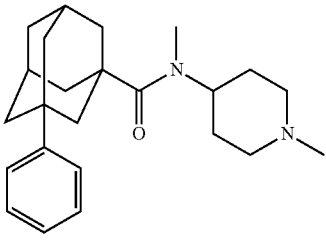<br>N-methyl-N-(1-methylpiperidin-4-yl)-3-phenyl adamantane-1-carboxamide | LC/MS m/z: 367.36 (M + H)+ |
| A28 | 1-benzylpiperazine tricyclo[3.3.1.0$^{3,7}$] nonane-3-carboxylic acid | 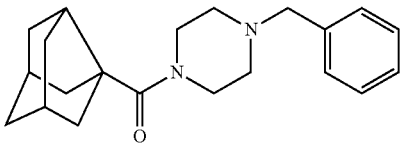<br>1-benzyl-4-({tricyclo [3.3.1.0$^{3,7}$]nonan-3-yl}carbonyl)piperazine | LC/MS m/z: 325.35 (M + H)+, 366.41 (M + H + CH$_3$CN)+ |

| Ex. | Starting materials | Product/Name | Analytical Data |
|---|---|---|---|
| A29 | 1-benzylpiperazine 3-phenyl-adamantane-1-carboxylic acid | 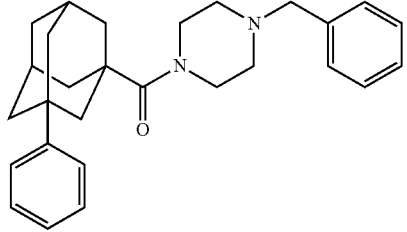<br>1-benzyl-4-[(3-phenyl-adamantan-1-yl)carbonyl]piperazine | LC/MS m/z: 415.34 (M + H)+ |
| A30 | 1-benzylpiperazine 2-(3-phenyl-adamantan-1-yl)acetic acid | 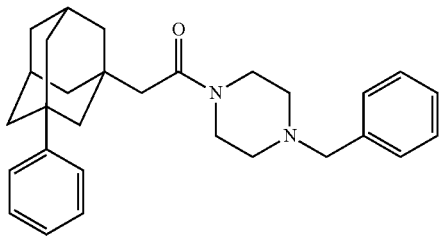<br>1-(4-benzylpiperazin-1-yl)-2-(3-phenyladamantan-1-yl)ethan-1-one | LC/MS m/z: 429.30 (M + H)+, 470.49 (M + H + CH$_3$CN)+ |
| A31 | 1-benzylpiperazine adamantane-2-carboxylic acid | 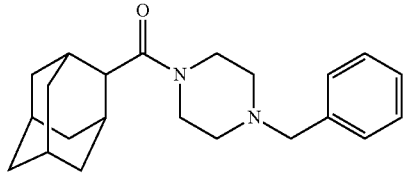<br>1-[(adamantan-2-yl)carbonyl]-4-benzylpiperazine | LC/MS m/z: 339.33 (M + H)+, 380.28 |
| A32 | 1-benzylpiperidin-4-amine 2-(3-phenyl-adamantan-1-yl)acetic acid | 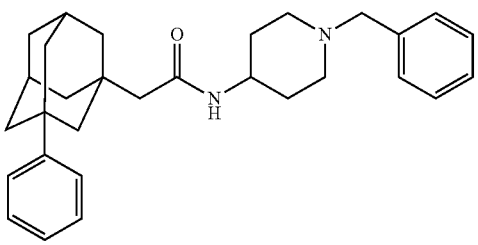<br>N-(1-benzylpiperidin-4-yl)-2-(3-phenyladamantan-1-yl)acetamide | LC/MS m/z: 443.42 (M + H)+ |

-continued

| Ex. | Starting materials | Product/Name | Analytical Data |
|---|---|---|---|
| A33 | 2-benzyl-2,5-diazabicyclo[2.2.1]heptane dihydrobromide 2-(3-phenyl-adamantan-1-yl)acetic acid | 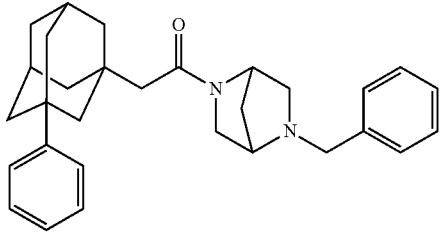<br>1-{5-benzyl-2,5-diazabicyclo[2.2.1]heptan-2-yl}-2-(3-phenyl-adamantan-1-yl)ethan-1-one | LC/MS m/z: 441.34 (M + H)+, 482.40 (M + H + CH$_3$CN)+ |
| A34 | (3R)-1-benzyl-piperidin-3-amine 3-phenyl-adamantane-1-carboxylic acid | 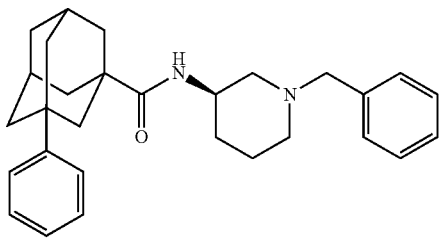<br>N-[(3R)-1-benzylpiperidin-3-yl]-3-phenyladamantane-1-carboxamide | LC/MS m/z: 429.33 (M + H)+, 470.56 (M + H + CH$_3$CN)+ |
| A35 | 1-methylazetidin-3-amine 3-phenyl-adamantane-1-carboxylic acid | 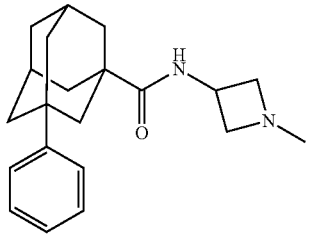<br>N-(1-methylazetidin-3-yl)-3-phenyladamantane-1-carboxamide | LC/MS m/z: 325.35 (M + H)+ |
| A36 | 1-benzylazetidin-3-amine 3-phenyl-adamantane-1-carboxylic acid | 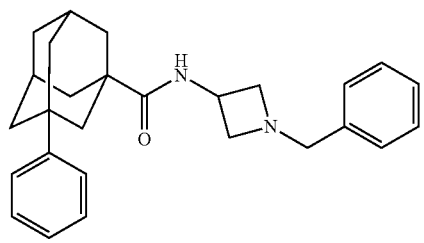<br>N-(1-benzylazetidin-3-yl)-3-phenyl admantane-1-carboxamide | LC/MS m/z: 401.25 (M + H)+ |

-continued

| Ex. | Starting materials | Product/Name | Analytical Data |
|---|---|---|---|
| A37 | (3R)-1-methyl-pyrrolidin-3-amine 3-phenyl-adamantane-1-carboxylic acid | 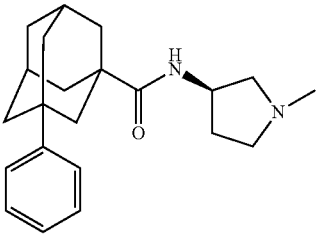<br>N-[(3R)-1-methylpyrrolidin-3-yl]-3-phenyladamantane-1-carboxamide | LC/MS m/z: 339.29 (M + H)+ |
| A38 | (3R)-1-methyl-piperidin-3-amine 3-phenyl-adamantane-1-carboxylic acid | 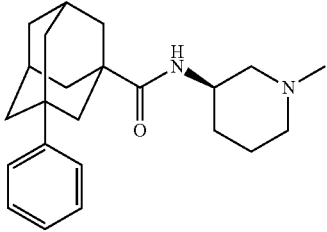<br>N-[(3R)-1-methylpiperidin-3-yl]-3-phenyladamantane-1-carboxamide | LC/MS m/z: 353.33 (M + H)+ |
| A39 | 1-methylazetidin-3-amine 2-(3-phenyl-adamantan-1-yl)acetic acid | 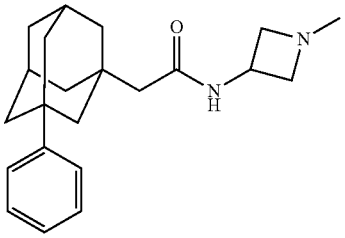<br>N-(1-methylazetidin-3-yl)-2-(3-phenyladamantan-1-yl)acetamide | LC/MS m/z: 339.38 (M + H)+ |
| A40 | (3R)-1-methyl-pyrrolidin-3-amine 2-(3-phenyl-adamantan-1-yl)acetic acid | 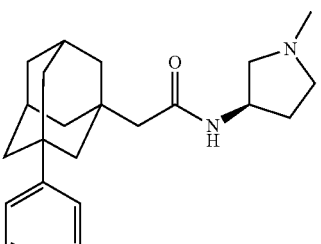<br>N-[(3R)-1-methylpyrrolidin-3-yl]-2-(3-phenyladamantan-1-yl)acetamide | LC/MS m/z: 353.34 (M + H)+ |

-continued

| Ex. | Starting materials | Product/Name | Analytical Data |
|---|---|---|---|
| A41 | (3R)-1-methyl-pyrrolidin-3-amine 3-methyl-5-phenyl adamantane-1-carboxylic acid | 3-methyl-N-[(3R)-1-methyl pyrrolidin-3-yl]-5-phenyl adamantane-1-carboxamide | $^1$H NMR (300 MHz, CDCl$_3$) δ 7.38-7.28 (m, 4H), 7.20-7.15 (m, 1H), 6.66-6.56 (m, 1H), 4.68-4.58 (m, 1H), 3.22-3.17 (m, 1H), 2.89 (d, 1H), 2.64 (dd, 1H), 2.50 (s, 3H), 2.43-2.35 (m, 2H), 2.33-2.26 (m, 1H), 1.95-1.86 (m, 2H), 1.85-1.72 (m, 5H), 1.64-1.55 (m, 4H), 1.46 (br. s, 2H), 0.92 (s, 3H). LC/MS m/z: 353.3 (M + H)$^+$, 394.43 (M + H + CH$_3$CN)$^+$ |
| A42 | 1-methylazetidin-3-amine 3-methyl-5-phenyladamantane-1-carboxylic acid | 3-methyl-N-(1-methyl azetidin-3-yl)-5-phenyl adamantane-1-carboxamide | LC/MS m/z: 339.4 (M + H)$^+$ |
| A43 | 1-[3-(pyrrolidin-1-yl)propyl]-1,4-diazepane 3-methyl-5-phenyladamantane-1-carboxylic acid | 1-[(3-methyl-5-phenyl adamantan-1-yl)carbonyl]-4-[3-(pyrrolidin-1-yl)propyl]-1,4-diazepane | LC/MS m/z: 464.43 (M + H)$^+$ |
| A44 | (3S)-1-azabicyclo[2.2.2]octan-3-amine 3-methyl-5-phenyladamantane-1-carboxylic acid | N-[(3S)-1-azabicyclo[2.2.2]octan-3-yl]-3-methyl-5-phenyl adamantane-1-carboxamide | $^1$H NMR (500 MHz, MeOH-d4) δ 7.39 (d, 2H), 7.30 (t, 2H), 7.15 (t, 1H), 4.07 (m, 1H), 3.45 (t, 1H), 3.2-3.12 (m, 1H), 3.12-2.98 (m, 3H), 2.95-2.88 (m, 1H), 2.31-2.29 (m, 1H), 2.1-2.05 (m, 1H), 1.99-1.78 (m, 9H), 1.70-1.58 (m, 5H), 1.53 (br:s, 2H), 0.97 (s, 3H). LC/MS m/z: 379.42 (M + H)$^+$, 420.30 (M + H + CH$_3$CN) |

-continued

| Ex. | Starting materials | Product/Name | Analytical Data |
|---|---|---|---|
| A45 | (3R)-1-azabicyclo[2.2.2]octan-3-amine 3-methyl-5-phenyladamantane-1-carboxylic acid | N-[(3R)-1-azabicyclo[2.2.2]octan-3-yl]-3-methyl-5-phenyl adamantane-1-carboxamide | $^{1}$H NMR (300 MHz, CDCl$_3$) δ 7.41 (d, 2H), 7.33 (t, 2H), 7.20 (t, 1H), 4.33 (br:s. 1H), 3.85-3.66 (m, 2H), 3.36 (t, 1H), 3.26-2.88 (m, 4H), 2.31 (br:s, 2H), 2.09-1.40 (m, 15H), 0.95 (s, 3H). LC/MS m/z: 379.33 (M + H)$^{+}$, 420.35 (M + H + CH$_3$CN) |
| A46 | (2-aminoethyl)dimethylamine 3-methyl-5-phenyladamantane-1-carboxylic acid | N-[2-(dimethylamino)ethyl]-3-methyl-5-phenyl adamantane-1-carboxamide | LC/MS m/z: 341.37 (M + H)$^{+}$ |
| A47 | 4-methylpiperazin-1-amine 3-methyl-5-phenyladamantane-1-carboxylic acid | 3-methyl-N-(4-methyl piperazin-1-yl)-5-phenyl adamantane-1-carboxamide | LC/MS m/z: 368.40 (M + H)$^{+}$ |
| A48 | 2-(morpholin-4-yl)ethan-1-amine 3-methyl-5-phenyladamantane-1-carboxylic acid | 3-methyl-N-[2-(morpholin-4-yl)ethyl]-5-phenyl adamantane-1-carboxamide | LC/MS m/z: 383.39 (M + H)$^{+}$ |

Example A49: N-Benzyl-1-[(3-phenyladamantan-1-yl)carbonyl]piperidin-4-amine

Step 1: tert-butyl N-{1-[(3-phenyladamantan-1-yl)carbonyl]piperidin-4-yl}carbamate The title compound was prepared in the same manner as described for example A1, Step 2 using tert-butyl N-(piperidin-4-yl)carbamate instead of 2-benzyl-2,7-diazaspiro[4.4]nonane. LC/MS m/z: 383.31 (M–tBu+H)⁺, 439.34 (M+H)⁺, 877.74 (2M+H)⁺

Step 2: N-benzyl-1-[(3-phenyladamantan-1-yl)carbonyl]piperidin-4-amine

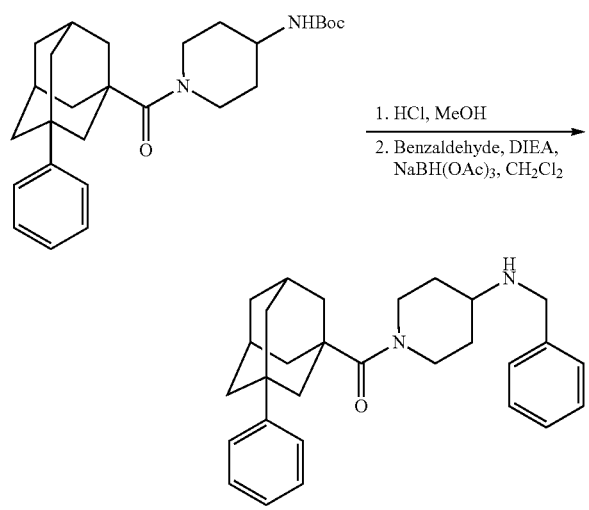

To a solution of tert-butyl N-{1-[(3-phenyladamantan-1-yl)carbonyl]piperidin-4-yl}carbamate (74 mg, 0.17 mmol) in 1 mL CH₃OH was added 0.5 mL conc. HCl. The reaction mixture was stirred at rt for 12 h, then concentrated in vacuo to give 64 mg (100%) of HCl salt as a viscous oil. To a mixture of the obtained HCl salt (24 mg, 0.064 mmol) in 1 mL CH₂Cl₂ was added N,N-diisopropylethylamine (8.2 mg, 0.064 mmol) followed by benzaldehyde (6.8 mg, 0.064 mmol). The resulting mixture was stirred at rt for 1 h. Sodium triacetoxyborohydride (34 mg, 0.16 mmol) was then added and the reaction mixture was stirred at rt for 12 h. The reaction mixture was then diluted with CH₂Cl₂ and washed with saturated aq. NaHCO₃ solution. The organic phase was dried over Na₂SO₄, filtered, and concentrated in vacuo. The residue was purified by SiO₂ column chromatography (EtOAc, then CH₂Cl₂/CH₃OH from 40:1 to 20:1) to give 6 mg (22%) of the title compound as a colorless oil. LC/MS m/z: 429.28 (M+H)+.

Example A50: 2-(Adamantan-1-yl)-1-{7-benzyl-2,7-diazaspiro[4.4]nonan-2-yl}ethan-1-one

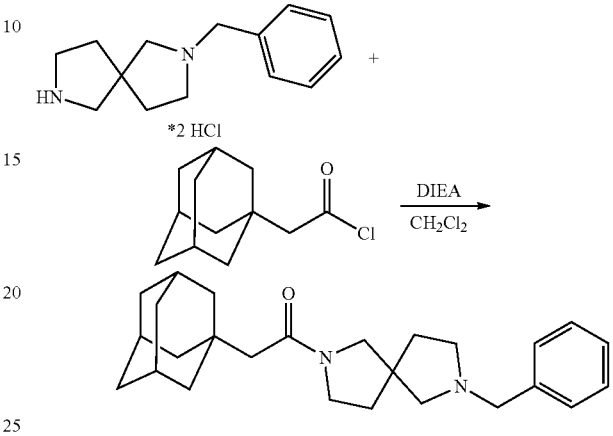

To a mixture of 2-benzyl-2,7-diazaspiro[4.4]nonane dihydrochloride (21 mg, 0.073 mmol) in 0.75 mL CH₂Cl₂ was added N,N-diisopropylethylamine (37 mg, 0.29 mmol), followed by 1-adamantaneacetyl chloride (15 mg, 0.073 mmol). The reaction mixture was stirred at rt for 3 h, then diluted with CH₂Cl₂ and washed with saturated aq. NaHCO₃ solution. The organic phase was dried over Na₂SO₄, filtered, and concentrated in vacuo. The residue was purified by preparative HPLC. The obtained TFA salt was dissolved in methanol and filtered through an Agilent Stratopheres PL-HCO₃ ion exchange resin. The filtrate was concentrated to afford 16 mg (56%) of the product as a colorless oil. LC/MS m/z: 393.42 (M+H)⁺, 434.42 (M+H+CH₃CN)⁺.

Examples A51 to A53 were prepared in the same manner as described above for 2-(adamantan-1-yl)-1-{7-benzyl-2,7-diazaspiro[4.4]nonan-2-yl}ethan-1-one using the appropriate commercially available amine and 1-adamantaneacetyl chloride as starting materials.

Starting amines in Examples A54 to A59 were prepared from the appropriate Boc-protected amines in the same manner as described above for 2-benzyl-2,7-diazaspiro[4.4]nonane dihydrochloride (Example A1, Step 1), and used in the next step without further purification.

Examples A54 to A59 were prepared in the same manner as described above for 2-(adamantan-1-yl)-1-{7-benzyl-2,7-diazaspiro[4.4]nonan-2-yl}ethan-1-one using the appropriate amine and 1-adamantaneacetyl chloride as starting materials.

| Ex. | Starting amine | Product/Name | Analytical Data |
| --- | --- | --- | --- |
| A51 | 1-benzylpiperidin-4-amine | 2-(adamantan-1-yl)-N-(1-benzylpiperidin-4-yl)acetamide | LC/MS m/z: 367.36 (M + H)⁺ |

-continued

| Ex. | Starting amine | Product/Name | Analytical Data |
|---|---|---|---|
| A52 | (3R)-1-benzyl-pyrrolidin-3-amine | 2-(adamantan-1-yl)-N-[(3R)-1-benzyl pyrrolidin-3-yl]acetamide | LC/MS m/z: 353.25 (M + H)⁺ |
| A53 | 2-benzyl-2,5-diaza-bicyclo[2.2.1]heptane dihydrobromide | 2-(adamantan-1-yl)-1-{5-benzyl-2,5-diaza bicyclo[2.2.1]heptan-2-yl}ethan-1-one | LC/MS m/z: 365.35 (M + H)⁺, 406.35 (M + H + CH₃CN)⁺ |
| A54 | 2-amino-N-(1-benzyl piperidin-4-yl)acetamide dihydrochloride | 2-(adamantan-1-yl)-N-{[(1-benzyl piperidin-4-yl)carbamoyl]methyl}acetamide | LC/MS m/z: 424.29 (M + H)⁺ |
| A55 | methyl 4-(2-{[4-(2-amino acetamido)piperidin-1-yl]methyl}phenoxy-methyl) benzoate hydrochloride | methyl 4-{2-[(4-{2-[2-(adamantan-1-yl)acetamido]acetamido}piperidin-1-yl)methyl]phenoxymethyl}benzoate | LC/MS m/z: 588.45 (M + H)⁺ |
| A56 | 2-amino-N-[(3R)-1-benzylpyrrolidin-3-yl]acetamide dihydrochloride | 2-(adamantan-1-yl)-N-({[(3R)-1-benzylpyrrolidin-3-yl]carbamoyl}methyl) acetamide | LC/MS m/z: 410.31 (M + H)⁺ |

Analytical Data column LC/MS values reproduced as shown.

The chemical structures for A52–A56 are depicted in the Product/Name column (adamantyl-acetamide derivatives with the listed amine substituents).

Expressed with LaTeX for ion notation: $(M+H)^+$, $(M+H+CH_3CN)^+$.

-continued

| Ex. | Starting amine | Product/Name | Analytical Data |
|---|---|---|---|
| A57 | methyl 4-(2-{2,5-diaza bicyclo[2.2.1]heptan-2-ylmethyl}phenoxymethyl) benzoate hydrochloride | 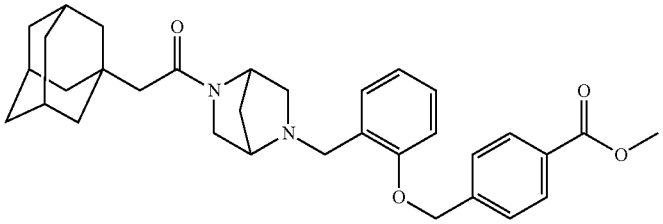<br>methyl 4-[2-({5-[2-(adamantan-1-yl)acetyl]-2,5-diazabicyclo[2.2.1]heptan-2-yl}methyl)phenoxymethyl]benzoate | LC/MS m/z: 529.36 (M + H)⁺ |
| A58 | methyl 4-(2-{[5-(2-aminoacetyl)-2,5-diazabicyclo[2.2.1]heptan-2yl]methyl}phenoxy methyl)benzoate dihydrochloride | 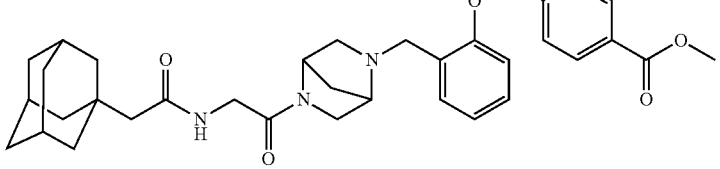<br>methyl 4-{2-[(5-{2-[2-(adamantan-1-yl)acetamido]acetyl}-2,5-diaza bicycle [2.2.1]heptan-2-yl)methyl]phenoxy methyl}benzoate | LC/MS m/z: 586.40 (M + H)⁺ |
| A59 | methyl 4-(2-{[7-(2-aminoacetyl)-2,7-diazaspiro[4.4]nonan-2-yl]methyl}phenoxymethyl) benozate hydrochloride | 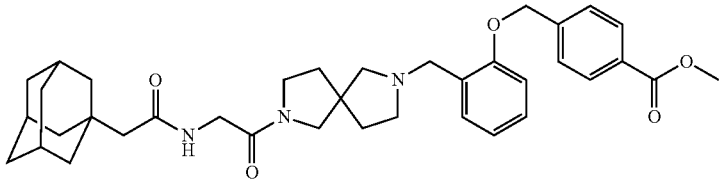<br>methyl 4-{2-[(7-{2-[2-(adamantan-1-yl)acetamido]acetyl}-2,7-diazaspiro [4.4]nonan-2-yl)methyl]phenoxymethyl} benzoate | LC/MS m/z: 614.43 (M + H)⁺ |

Examples A60 to A115 were prepared in the same manner as described for example A1, Steps 1 and 2 starting from the appropriate Boc-protected amine (Step 2) and the appropriate carboxylic acid followed by Boc-deprotecting as described for Step 1.

| Ex. | Starting materials | Product/Name | Analytical Data |
|---|---|---|---|
| A60 | tert-butyl piperazine-1-carboxylate 3-phenyl-adamantane-1-carboxylic acid | 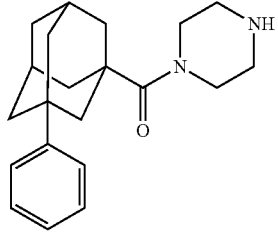<br>1-[(3-phenyladamantan-1-yl)carbonyl]piperazine | LC/MS m/z: 325.24 (M + H)⁺ |

-continued

| Ex. | Starting materials | Product/Name | Analytical Data |
|---|---|---|---|
| A61 | tert-butyl N-(piperidin-4-yl)carbamate 3-phenyl-adamantane-1-carboxylic acid | 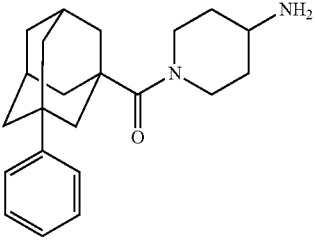<br>1-[(3-phenyladamantan-1-yl)carbonyl]piperidin-4-amine | LC/MS m/z: 339.34 (M + H)⁺ |
| A62 | tert-butyl octahydro pyrrolo[3,4-b]pyrrole-1-carboxylate 3-phenyl-adamantane-1-carboxylic acid | 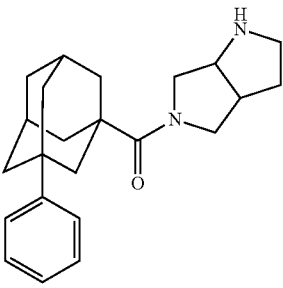<br>5-[(3-phenyladamantan-1-yl)carbonyl]-octahydro pyrrolo[3,4-b]pyrrole | LC/MS m/z: 351.83 (M + H)⁺, 392.03 (M + H + CH$_3$CN)⁺ |
| A63 | tert-butyl 4-aminopiperidine-1-carboxylate 3-phenyl-adamantane-1-carboxylic acid | 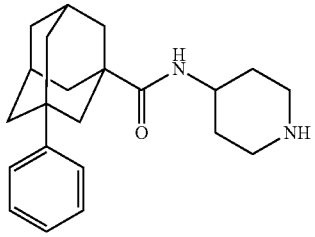<br>3-phenyl-N-(piperidin-4-yl)adamantane-1-carboxamide | $^1$H NMR (300 MHz, CDCl$_3$) δ 9.58 (br. s., 1H) 7.28-7.37 (m, 4H) 7.15-7.22 (m, 1H) 5.66 (d, 0.5 H) 5.46 (d, 0.5H) 4.28 (d, 1H) 4.01 (dd, 1H) 3.49 (d, 1H) 2.84-3.11 (m, 2 H) 2.26 (br. s., 2 H) 2.10 (d, 1H) 1.99 (br. s., 1H) 1.78-1.95 (m, 10H) 1.72 (br. s., 2H). LC/MS m/z: 339.45 (M + H)⁺ |
| A64 | tert-butyl 2,7-diazaspiro[4.4]nonane-2-carboxylate 3-phenyl-adamantane-1-carboxylic acid | 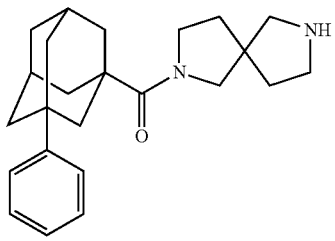<br>2-[(3-phenyladamantan-1-yl)carbonyl]-2,7-diazaspiro[4.4]nonane | LC/MS m/z: 365.32 (M + H)⁺ |

| Ex. | Starting materials | Product/Name | Analytical Data |
|---|---|---|---|
| A65 | 2-[1-(tert-butoxy)ethenyl]-2,5-diazabicyclo [2.2.1] heptane-3-phenyl-adamantane-1-carboxylic acid | 2-[(3-phenyladamantan-1-yl)carbonyl]-2,5-diaza bicyclo[2.2.1]heptane | LC/MS m/z: 337.30 (M + H)+ |
| A66 | tert-butyl 1,4-diazepane-1-carboxylate 3-phenyl-adamantane-1-carboxylic acid | 1-[(3-phenyladamantan-1-yl)carbonyl]-1,4-diazepane | LC/MS m/z: 339.38 (M + H)+ |
| A67 | tert-butyl 4-aminopiperidine-1-carboxylate 3-(4-methoxyphenyl) adamantane-1-carboxylic acid | 3-(4-methoxyphenyl)-N-(piperidin-4-yl)adamantae-1-carboxamide | LC/MS m/z: 369.35 (M + H)+, 410.36 (M + H + CH$_3$CN)+ |
| A68 | tert-butyl 4-amino piperidine-1-carboxylate 3-methyl-5-phenyladamantane-1-carboxylic acid | 3-methyl-5-phenyl-N-(piperidin-4-yl)adamantane-1-carboxamide | $^1$H NMR (300 MHz, CDCl$_3$) δ 7.37-7.29 (m, 4H), 7.21-7.16 (m, 1H), 5.73 (d, 0.6H), 5.50 (dd, 0.4H), 4.28 (d, 0.4H), 4.07-3.91 (m, 1H), 3.60 (d, 0.6H), 3.42 (d, 1H), 3.03-2.86 (m, 2H), 2.30 (br. s, 1H), 2.23-2.00 (m, 2H), 1.91-1.71 (m, 8H), 1.61 (br. s, 2H), 1.55 (br. s, 2H), 1.47 (br. s, 2H), 0.93 (s, 3H). LC/MS m;z: 353.39 (M + H)+, 394.33 (M + H + CH$_3$CN)+ |

-continued

| Ex. | Starting materials | Product/Name | Analytical Data |
|---|---|---|---|
| A69 | tert-butyl 4-amino piperidine-1-carboxylate 3-(4-chlorophenyl) adamantane-1-carboxylic acid | 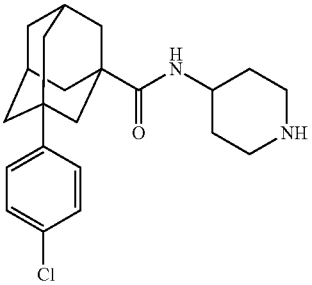<br>3-(4-chlorophenyl)-N-(piperidin-4-yl)adamantane-1-carboxamide | LC/MS m/z: 373.31 (M + H)$^+$, 414.31 (M + H + CH$_3$CN)$^+$ |
| A70 | tert-butyl 4-aminopiperidine-1-carboxylate 2-(3-phenyladamantan-1-yl)acetic acid | 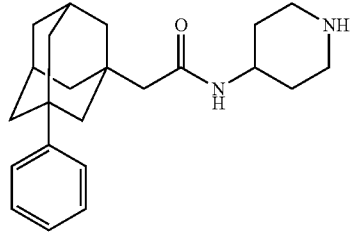<br>2-(3-phenyladamantan-1-yl)-N-(piperidin-4-yl)acetamide | LC/MS m/z: 353.39 (M + H)$^+$ |
| A71 | tert-butyl piperazine-1-carboxylate 3-methyl-5-phenyladamantane-1-carboxylic acid | 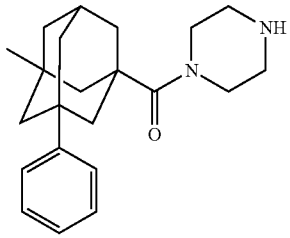<br>1-[(3-methyl-5-phenyl adamantan-1-yl)carbonyl] piperazine | LC/MS m/z: 339.42 (M + H)$^+$, 380.34 (M + H + CH$_3$CN)$^+$, 677.63 (2M + H)$^+$ |
| A72 | tert-butyl 3-aminoazetidine-1-carboxylate 3-methyl-5-phenyladamantane-1-carboxylic acid | 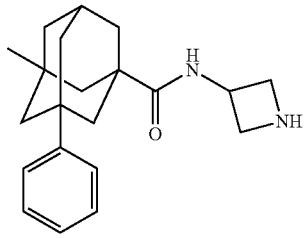<br>N-(azetidin-3-yl)-3-methyl-5-phenyl adamantane-1-carboxamide | LC/MS m/z: 325.32 (M + H)$^+$, 366.39 (M + H + CH$_3$CN)$^+$, 649.59 (2M + H)$^+$ |

| Ex. | Starting materials | Product/Name | Analytical Data |
|---|---|---|---|
| A73 | tert-butyl 4-aminopiperidine-1-carboxylate 3,5-dimethyl-7-phenyladamantane-1-carboxylic acid | 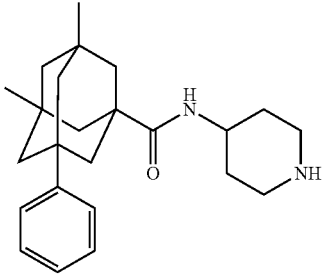<br>3,5-dimethyl-7-phenyl-N-(piperidin-4-yl)adamantane-1-carboxamide | LC/MS m/z: 367.36 (M + H)$^+$, 408.35 (M + H + CH$_3$CN)$^+$ |
| A74 | tert-butyl 4-aminopiperidine-1-carboxylate 3-(4-hydroxyphenyl)adamantane-1-carboxylic acid | 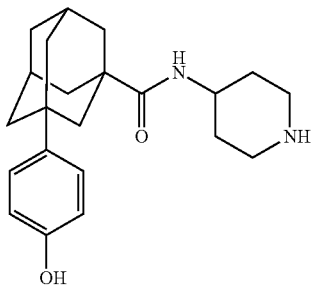<br>3-(4-hydroxyphenyl)-N-(piperidin-4-yl)adamantane-1-carboxamide | LC/MS m/z: 355.31 (M + H)$^+$, 396.30 (M + H + CH$_3$CN)$^+$ |
| A75 | tert-butyl 4-aminopiperidine-1-carboxylate 3-(4-fluorophenyl)adamantane-1-carboxylic acid | 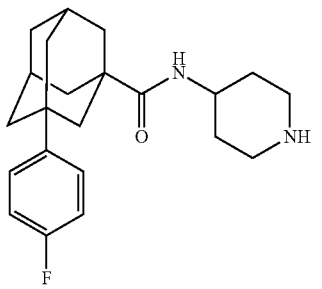<br>3-(4-fluorophenyl)-N-(piperidin-4-yl)adamantane-1-carboxamide | LC/MS m/z: 357.29 (M + H)$^+$, 398.45 (M + H + CH$_3$CN)$^+$ |
| A76 | tert-butyl 4-aminopiperidine-1-carboxylate 3-(4-nitrophenyl)adamantane-1-carboxylic acid | 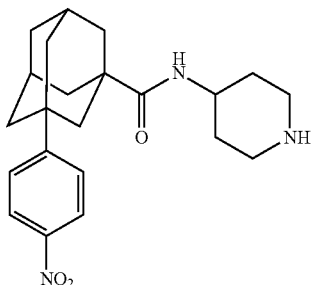<br>3-(4-nitrophenyl)-N-(piperidin-4-yl)adamantane-1-carboxamide | LC/MS m/z: 384.30 (M + H)$^+$, 425.32 (M + H + CH$_3$CN)$^+$ |

-continued

| Ex. | Starting materials | Product/Name | Analytical Data |
|---|---|---|---|
| A77 | cis-tert-butyl N-(4-aminocyclohexyl)carbamate 3-methyl-5-phenyl adamantane-1-carboxylic acid | cis-N-(4-aminocyclohexyl)-3-methyl-5-phenyl adamantane-1-carboxamide | $^1$H NMR (500 MHz, MeOH-d$_4$) δ 7.37 (d, 2H), 7.28 (t, 2H), 7.16 (t, 1H), 3.80 (m, 1H), 3.04 (m, 1H), 2.29 (m, 1H), 1.90 (t, 3H), 1.82 (t, 3H), 1.75-1.67 (m, 4H), 1.66-1.58 (m, 8H), 1.51 (br.s., 2H), 0.96 (s, 3H). LC/MS m/z: 367.43 (M + H)$^+$, 408.30 (M + H + CH$_3$CN)$^+$ |
| A78 | trans-tert-butyl N-(4-aminocyclohexyl)carbamate 3-methyl-5-phenyladamantane-1-carboxylic acid | trans-N-(4-aminocyclohexyl)-3-methyl-5-phenyl adamantane-1-carboxamide hydrochloride | $^1$H NMR (500 MHz, DMSO-d$_6$) δ 8.00 (br. s., 3H), 7.36 (d, 2H), 7.30 (t, 2H), 7.20 (d, 1H), 7.16 (t, 1H), 3.54-3.47 (m, 1H), 2.91-2.86 (m, 1H), 2.20-2.15 (m, 1H), 1.97-1.90 (m, 2H), 1.81-1.64 (m, 8H), 1.54-1.44 (m, 4H), 1.40 (br. s, 2H), 1.37-1.22 (m, 4H), 0.87 (s, 3H). LC/MS m/z: 367.42 (M + H)$^+$, 408.36 (M + H + CH$_3$CN)$^+$, 733.73 (2M + H)$^+$ |
| A79 | tert-butyl N-(2-aminoethyl)carbamate 3-methyl-5-phenyladamantane-1-carboxylic acid | N-(2-aminoethyl)-3-methyl-5-phenyladamantane-1-carboxamide | LC/MS m/z: 313.47 (M + H)$^+$, 354.01 (M + H + CH$_3$CN)$^+$ |
| A80 | tert-butyl 4-aminopiperidine-1-carboxylate 3-ethyl-5-phenyladamantane-1-carboxylic acid | 3-ethyl-5-phenyl-N-(piperidin-4-yl)adamantane-1-carboxamide | $^1$H NMR (300 MHz, CDCl$_3$) δ 7.40-7.29 (m, 4H), 7.22-7.16 (m, 1H), 5.70 (d, 0.7H), 5.48 (d, 0.3H), 4.29 (d, 0.3H), 4.08-3.84 (m, 1H), 3.48 (d, 0.7H), 3.40-3.21 (m, 1H), 3.03-2.88 (m, 1.4H), 2.68-2.53 (m, 0.6H), 2.32 (br. s, 1H), 2.15-2.05 (m, 1H), 2.00-1.75 (m, 9H), 1.59 (br. s, 2H), 1.56-1.52 (m, 2H), 1.46 (br. s, 2H), 1.26 (q, 2H), 0.84 (t, 3H). LC/MS m/z: 367.40 (M + H)$^+$, 408.51 (M + H + CH$_3$CN)$^+$ |

| Ex. | Starting materials | Product/Name | Analytical Data |
|---|---|---|---|
| A81 | tert-butyl 4-amino piperidine-1-carboxylate 5-phenyladamantane-2-carboxylic acid | 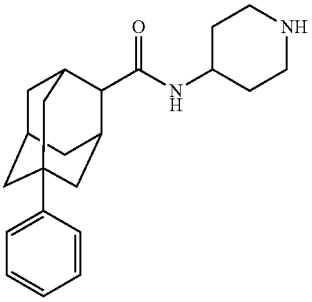<br>5-phenyl-N-(piperidin-4-yl) adamantane-2-carboxamide | $^1$H NMR (500 MHz, MeOH-d$_4$) δ 7.36 (d, 1H), 7.34-7.23 (m, 3H), 7.13 (q, 1H), 4.04-3.93 (m, 1H), 3.46-3.37 (m, 2H), 3.09 (q, 2H), 2.57 (d, 1H), 2.40 (br:s, 2H), 2.22 (d, 1H), 2.13-1.83 (m, 10H), 1.81-1.67 (m, 3H), 1.63 (d, 1H). LC/MS m/z: 339.34 (M + H)$^+$ |
| A82 | tert-butyl (2S)-2-methylpiperazine-1-carboxylate 3-methyl-5-phenyladamantane-1-carboxylic acid | 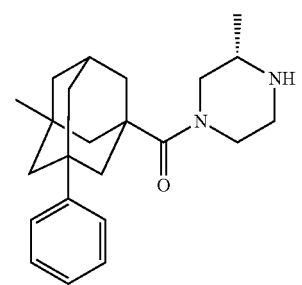<br>(3S)-3-methyl-1-[(3-methyl-5-phenyladamantan-1-yl)carbonyl]piperazine | $^1$H NMR (300 MHz, CDCl$_3$) δ 10.03 (br:s. 1H), 9.53 (br:s, 1H), 7.36 (d, 4H), 7.27-7.20 (m, 1H), 4.52 (d, 2H), 3.50 (d, 2H), 3.45-3.32 (m, 1H), 3.19-3.07 (m, 1H), 3.06-2.88 (m, 1H), 2.35 (br:s, 1H), 2.03 (br:s, 1H), 1.89 (d, 4H), 1.68 (d, 4H), 1.51 (br:s, 2H), 1.39 (d, 3H), 0.97 (s, 3H). LC/MS m/z: 353.41 (M + H)$^+$, 394.38 (M + H + CH$_3$CN)$^+$ |
| A83 | tert-butyl (3S)-3-methyl piperazine-1-carboxylate 3-methyl-5-phenyladamantane-1-carboxylic acid | 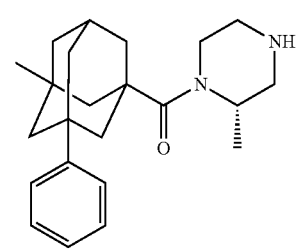<br>(2S)-2-methyl-1-[(3-methyl-5-phenyladamantan-1-yl)carbonyl]piperazine | LC/MS m/z: 353.34 (M + H)$^+$, 394.38 (M + H + CH$_3$CN)$^+$ |
| A84 | trans-tert-butyl N-(4-amino cyclohexyl)carbamate 5-phenyladamantane-2-carboxylic acid | 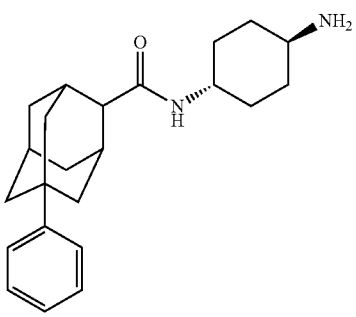<br>trans-N-(4-aminocyclo hexyl)-5-phenyl adamantane-2-carboxamide | $^1$H NMR (500 MHz, MeOH-d$_4$) δ 7.36 (d, 2H), 7.33-7.24 (m, 2H), 7.14 (t, 1H), 3.77-3.67 (m, 1H), 3.13-3.03 (m, 1H), 2.54 (d, 1H), 2.39 (br:s, 2H), 2.13-1.88 (m, 13H), 1.63 (d, 2H), 1.51 (q, 2H), 1.40 (q, 2H). LC/MS m/z: 353.41 (M + H)$^+$, 394.39 (M + H + CH$_3$CN)$^+$ |

| Ex. | Starting materials | Product/Name | Analytical Data |
|---|---|---|---|
| A85 | trans-tert-butyl N-(4-amino cyclohexyl)carbamate 3-ethyl-5-phenyladamantane-1-carboxylic acid | trans-N-(4-aminocyclo hexyl)-3-ethyl-5-phenyl adamantane-1-carboxamide | $^1$H NMR (300 MHz, CDCl$_3$) δ 8.33 (br. s, 2H), 7.38-7.27 (m, 4H), 7.21-7.15 (m, 1H), 5.73-5.63 (m, 0.6H), 5.40-5.32 (d, 0.4H), 3.79-3.65 (m, 1H), 3.36-3.06 (m, 1H), 2.33-2.21 (m, 2H), 2.02-1.76 (m, 11H), 1.60-1.50 (m, 4H), 1.48-1.40 (m, 2H), 1.30-1.14 (m, 4H), 0.82 (td, 3H). LC/MS m/z: 381.35 (M + H)$^+$, 422.30 (M + H + CH$_3$CN)$^+$ |
| A86 | tert-butyl (2R,6S)-2,6-dimethylpiperazine-1-carboxylate 3-methyl-5-phenyladamantane-1-carboxylic acid | (3R,5S)-3,5-dimethyl-1-[(3-methyl-5-phenyladamantan-1-yl)carbonyl]piperazine | LC/MS m/z: 367.41 (M + H)$^+$, 408.41 (M + H + CH$_3$CN)$^+$ |
| A87 | trans-tert-butyl N-(4-aminocyclohexyl) carbamate 1-phenyltricyclo [3.3.1.0$^{3,7}$]nonane-3-carboxylic acid | trans-N-(4-aminocyclo hexyl)-1-phenyl tricyclo [3.3.1.0$^{3,7}$]nonane-3-carboxamide | LC/MS m/z: 339.42 (M + H)$^+$ |
| A88 | tert-butyl 4-aminopiperidine-1-carboxylate 1-phenyltricyclo [3.3.1.0$^{3,7}$]nonane-3-carboxylic acid | 1-phenyl-N-(piperidin-4-yl)tricyclo[3.3.1.0$^{3,7}$] nonane-3-carboxamide | LC/MS m/z: 325.32 (M + H)$^+$ |

-continued

| Ex. | Starting materials | Product/Name | Analytical Data |
|---|---|---|---|
| A89 | tert-butyl 6-amino-2-azaspiro[3.3]heptane-2-carboxylate<br>3-methyl-5-phenyladamantane-1-carboxylic acid | 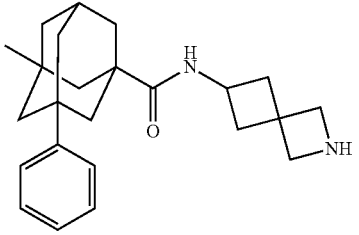<br>N-{2-azaspiro]3.3]heptan-6-yl}-3-methyl-5-phenyl adamantane-1-carboxamide | LC/MS m/z: 365.41 (M + H)⁺ |
| A90 | tert-butyl N-{6-aminospiro[3.3]heptan-2-yl}carbamate<br>3-methyl-5-phenyladamantane-1-carboxylic acid | 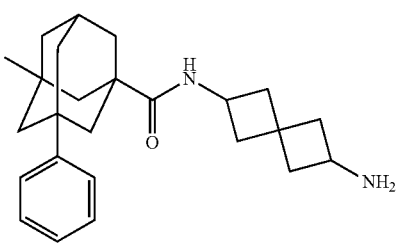<br>N-{6-aminospiro[3.3]heptan-2-yl}-3-methyl-5-phenyladamantane-1-carboxamide | ¹H NMR (300 MHz, CDCl₃) δ 8.28 (br. s, 2H), 7.37-7.27 (m, 4H), 7.21-7.14 (m, 1H), 6.25-6.14 (m, 0.6H), 5.76-5.69 (m, 0.4H), 4.32-4.13 (m, 1H), 3.88-3.72 (m, 1H), 2.55-2.27 (m, 7H), 1.94-1.76 (m, 8H), 1.61-1.51 (m, 4H), 1.49-1.41 (m, 2H), 0.93 (s, 1.2H), 0.91 (s, 1.8H). LC/MS m/z: 379.31 (M + H)⁺, 420.36 (M + H + CH₃CN)⁺ |
| A91 | tert-butyl N-{2-azaspiro[3.3]heptan-6-yl}carbamate<br>3-methyl-5-phenyl adamantane-1-carboxylic acid | 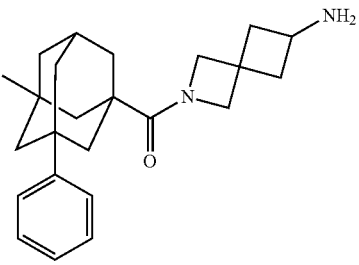<br>2-[(3-methyl-5-phenyl adamantan-1-yl)carbonyl]-2-azaspiro]3.3]heptan-6-amine | ¹H NMR (300 MHz, CDCl₃) δ 7.36-7.27 (m, 4H), 7.21-7.12 (m, 1H), 4.46-4.19 (m, 2H), 4.11-3.86 (m, 2H), 3.78-3.64 (m, 1H), 2.70-2.48 (m, 3H), 2.29-2.20 (m, 1H), 2.04-1.71 (m, 7H), 1.61-1.51 (m, 4H), 1.43 (br. s, 2H), 0.90 (s, 3H). LC/MS m/z: 365.35 (M + H)⁺, 406.41 (M + H + CH₃CN)⁺, 729.67 (2M + H)⁺ |
| A92 | exo-3-amino-8-Boc-8-azabicyclo[3.2.1]octane<br>3-methyl-5-phenyladamantane-1-carboxylic acid | 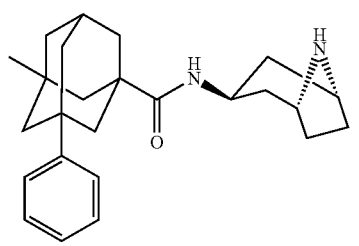<br>exo-N-8-azabicyclo[3.2.1]octan-3-yl]-3-methyl-5-phenyladamantane-1-carboxamide | LC/MS m/z: 379.41 (M + H)⁺ |

-continued

| Ex. | Starting materials | Product/Name | Analytical Data |
| --- | --- | --- | --- |
| A93 | exo-3-(Boc-amino)-8-azabicyclo[3.2.1]octane<br>3-methyl-5-phenyladamantane-1-carboxylic acid | exo-8-[(3-methyl-5-phenyl adamantan-1-yl)carbonyl]-8-azabicyclo[3.2.1]octan-3-amine | LC/MS m/z: 379.35 (M + H)+ |
| A94 | trans-tert-butyl N-(4-aminocyclo-hexyl)carbamate<br>3-(trifluoromethyl) adamantane-1-carboxylic acid | trans-N-(4-aminocyclo hexyl)-3-(trifluoromethyl) adamantane-1-carboxamide | LC/MS m/z: 328.31 (M − F + H)+, 345.25 (M + H)+, 386.33 (M + H + CH$_3$CN)+, 689.51 (2M + H)+ |
| A95 | tert-butyl 4-(aminomethyl)piperidine-1-carboxylate<br>3-methyl-5-phenyladamantane-1-carboxylic acid | 3-methyl-5-phenyl-N-(piperidin-4-ylmethyl) adamantane-1-carboxamide | LC/MS m/z: 367.38 (M + H)+, 733.62 (2M + H)+ |
| A96 | trans-tert-butyl N-[(4-aminocyclohexyl)methyl] carbamate<br>3-methyl-5-phenyladamantane-1-carboxylic acid | trans-N-[4-(aminomethyl) cyclohexyl]-3-methyl-5-phenyladamantane-1-carboxamide | $^1$H NMR (300 MHz, CDCl$_3$) δ 8.17 (br. s, 2H), 7.37-7.27 (m, 4H), 7.21-7.15 (m, 1H), 5.72 (d, 0.7H), 5.45 (d, 0.3H), 3.78-3.61 (m, 1H), 3.00-2.91 (m, 2H), 2.90-2.80 (m, 1H), 2.33-2.24 (m, 1H), 2.01-1.69 (m, 10H), 1.61-1.51 (m, 4H), 1.49-1.41 (m, 2H), 1.24-1.07 (m, 4H), 0.93 (s, 0.9H), 0.91 (s, 2.1H). LC/MS m/z: 381.39 (M + H)+, 422.34 (M + H + CH$_3$CN)+ |

-continued

| Ex. | Starting materials | Product/Name | Analytical Data |
|---|---|---|---|
| A97 | trans-tert-butyl N-(4-aminocyclohexyl)carbamate 2-(2-phenyl adamantan-2-yl)acetic acid | 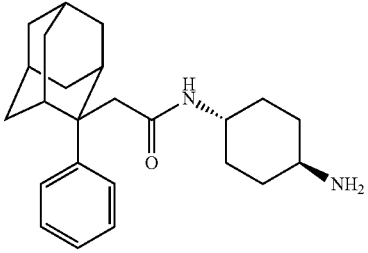<br>trans-N-(4-aminocyclo hexyl)-2-(2-phenyl adamantan-2-yl)acetamide | LC/MS m/z: 367.3 (M + H)$^+$ |
| A98 | cis-tert-butyl N-(4-amino cyclohexyl)carbamate 2-(2-phenyl adamantan-2-yl)acetic acid | 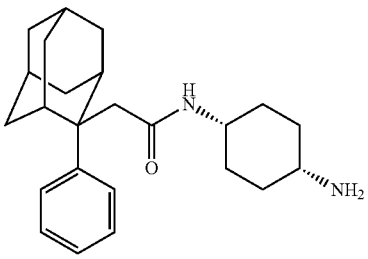<br>cis-N-(4-aminocyclohexyl)-2-(2-phenyladamantan-2-yl) acetamide | LC/MS m/z: 367.38 (M + H)$^+$ |
| A99 | tert-butyl 4-aminopiperidine-1-carboxylate 2-(2-phenyl adamantan-2-yl)acetic acid | 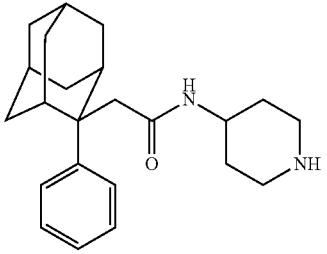<br>2-(2-phenyladamantan-2-yl)-N-(piperidin-4-yl)acetamide | LC/MS m/z: 353.34 (M + H)$^+$ |
| A100 | trans-tert-butyl N-(4-aminocyclohexyl)carbamate 3-(3-methylphenyl)adamantane-1-carboxylic acid | 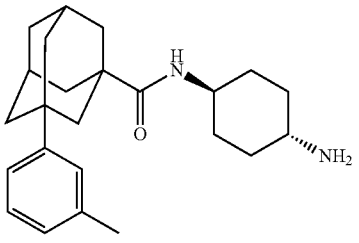<br>trans-N-(4-aminocyclo hexyl)-3-(3-methylphenyl)adamantane-1-carboxamide | LC/MS m/z: 367.63 (M + H)$^+$, 408.41 (M + H + CH$_3$CN)$^+$, 733.79 (2M + H)$^+$ |

-continued

| Ex. | Starting materials | Product/Name | Analytical Data |
|---|---|---|---|
| A101 | tert-butyl 3-amino-3-hydroxyazetidine-1-carboxylate<br>3-methyl-5-phenyladamantane-1-carboxylic acid | N-(3-hydroxyazetidin-3-yl)-3-methyl-5-phenyl adamantane-1-carboxamide | LC/MS m/z: 355.36 (M + H)$^+$ |
| A102 | tert-butyl (1R,5S,6S)-6-amino-3-azabicyclo[3.1.0]hexane-3-carboxylate<br>3-methyl-5-phenyladamantane-1-carboxylic acid | N-[(1R,5S)-3-azabicyclo[3.1.0]hexan-6-yl]-3-methyl-5-phenyladamantane-1-carboxamide | LC/MS m/z: 351.29 (M + H)$^+$,<br>392.40 (M + H + CH$_3$CN)$^+$ |
| A103 | tert-butyl N-[(4-aminophenyl)methyl]carbamate<br>3-methyl-5-phenyladamantane-1-carboxylic acid | N-[4-(amionmethyl)phenyl]-3-methyl-5-phenyladamantane-1-carboxamide | $^1$H NMR (500 MHz, DMSO-d$_6$) δ 9.11 (s, 1H), 7.54 (d, 2H), 7.41 (dd, 2H), 7.31 (t, 2H), 7.21 (d, 2H), 7.18 (t, 1H), 3.64 (s, 2H), 2.27-2.22 (m, 1H), 1.95 (q, 2H), 1.87-1.80 (m, 3H), 1.75-1.70 (m, 1H), 1.66-1.54 (m, 4H), 1.48-1.43 (m, 2H), 0.92 (s, 3H).<br>LC/MS m/z: 416.35 (M + H + CH$_3$CN)$^+$ |
| A104 | tert-butyl 4-(methylamino)piperidine-1-carboxylate<br>3-methyl-5-phenyladamantane-1-carboxylic acid | N,3-dimethyl-5-phenyl-N-(piperidin-4-yl)adamantane-1-carboxamide | LC/MS m/z: 367.36 (M + H)$^+$ |

-continued

| Ex. | Starting materials | Product/Name | Analytical Data |
|---|---|---|---|
| A105 | trans-tert-butyl N-(4-aminocyclohexyl)carbamate 3-methyl-5-phenyladamantane-1-carboxylic acid | 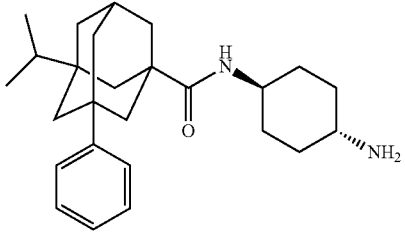<br>trans-N-(4-aminocyclohexyl)-3-phenyl-5-(propan-2-yl)adamantane-1-carboxamide | LC/MS m/z: 395.39 (M + H)$^+$, 436.21 (M + H + CH$_3$CN)$^+$, 789.67 (2M + H)$^+$ |
| A106 | 1-tet-butyl 2-methyl (2R)-piperazine-1,2-dicarboxylate 3-methyl-5-phenyladamantane-1-carboxylic acid | 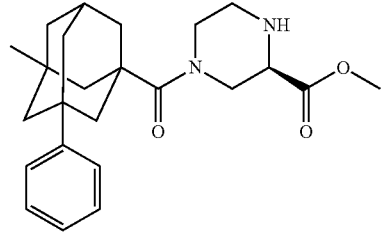<br>methyl (2R)-4-[(3-methyl-5-phenyladamantan-1-yl)carbonyl]piperazine-2-carboxylate | LC/MS m/z: 397.35 (M + H)$^+$, 438.37 (M + H + CH$_3$CN)$^+$ |
| A107 | trans-tert-butyl-4-amino-2-methylpiperidine-1-carboxylate 3-methyl-5-phenyladamantane-1-carboxylic acid | 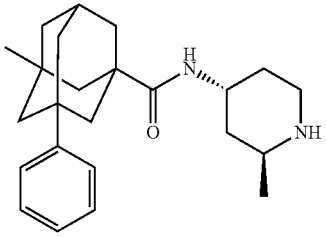<br>trans-3-methyl-N-[(2S,4R)-2-methylpiperidin-4-yl]-5-phenyladamantane-1-carboxamide | $^1$H NMR (300 MHz, CDCl$_3$) δ 7.26-7.37 (m, 4H) 7.14-7.21 (m, 1H) 5.78 (d, 1H) 4.17 (dt, 1 H) 3.44 (s, 3H) 2.70-3.02 (m, 3H) 2.29 (dt, 1H) 2.22 (br. s., 2H) 1.52-1.90 (m, 9H) 1.38-1.51 (m, 2H) 1.10 (d, 2H) 0.93 (s, 3H). LC/MS m/z: 367.35 (M + H)$^+$ |
| A108 | trans-tert-butyl-4-amino-3-fluoropiperidine-1-carboxylate 3-methyl-5-phenyladamantane-1-carboxylic acid | 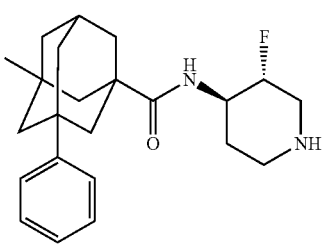<br>trans-N-3-fluoropiperidin-4-yl]-3-methyl-5-phenyladamantane-1-carboxamide | $^1$H NMR (300 MHz, CDCl$_3$) δ .26-7.39 (m, 4H) 7.13-7.22 (m, 1H) 5.62 (d, 1 H) 4.19-4.37 (m, 0.5H) 4.05-4.17 (m, 0.5H) 3.98-4.03 (m, 1H) 3.22-3.86 (m, 1H) 2.84-2.98 (m, 1H) 2.59-2.84 (m, 1H) 2.25-2.34 (m, 1H) 1.99-2.17 (m, 2H) 1.70-1.93 (m, 6H) 1.51-1.67 (m, 4H) 1.19-1.40 (m, 2H) 0.93 (s, 3H). LC/MS m/z: 371.40 (M + H)$^+$ |

| Ex. | Starting materials | Product/Name | Analytical Data |
|---|---|---|---|
| A109 | tert-butyl 4-amino-3,3-difluoropiperidine-1-carboxylate<br>3-methyl-5-phenyladamantane-1-carboxylic acid | 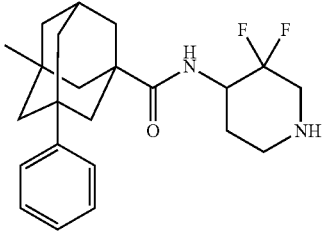<br>N-(3,3-difluoropiperidin-4-yl)-3-methyl-5-phenyladamantane-1-carboxamide | $^1$H NMR (300 MHz, CDCl$_3$) δ 10.65 (br. s., 0.5H) 10.00 (br. s., 0.5H) 7.27-7.38 (m, 4H) 7.14-7.22 (m, 1H) 6.04 (d, 0.5H) 5.78 (d, 0.5H) 4.57-4.76 (m, 1H) 4.41 (d, 1H) 3.83 (br. s., 1 H) 3.02-3.38 (m, 2H) 2.31 (d, 1H) 2.14 (br. s., 1H) 1.71-1.97 (m, 3H) 1.51-1.70 (m, 6 H) 1.47 (br. s., 2H) 0.93 (s, 3 H). LC/MS m/z: 389.32 (M + H)$^+$ |
| A110 | cis-tert-butyl-4-amino-2-methylpiperidine-1-carboxylate<br>3-methyl-5-phenyladamantane-1-carboxylic acid | 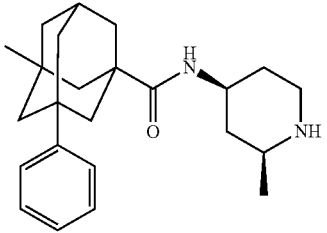<br>cis-3-methyl-N-2-methylpiperidin-4-yl]-5-phenyladamantane-1-carboxamide | $^1$H NMR (300 MHz, CDCl$_3$) δ 7.37-7.29 (m, 4H), 7.21-7.16 (m, 1H), 5.50 (d, 0.8H), 5.38 (d, 0.2H), 4.09-3.85 (m, 1H), 3.32-2.96 (m, 3H), 2.92-2.84 (m, 1H), 2.78 (td, 1H), 2.34-2.25 (m, 1H), 2.03-1.76 (m, 8H), 1.61 (br. s, 2H), 1.55 (br. s, 2H), 1.50-1.44 (m, 2H), 1.34 (d, 0.6H), 1.22 (d, 2.4H), 0.93 (s, 3H). LC/MS m/z: 367.34 (M + H)$^+$ |
| A111 | tert-butyl 4-amino-3,3-dimethylpiperidine-1-carboxylate<br>3-methyl-5-phenyladamantane-1-carboxylic acid | 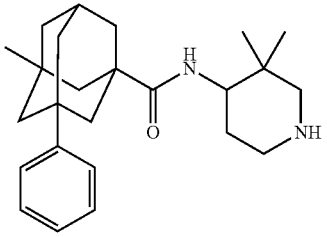<br>N-(3,3-dimethylpiperidin-4-yl)-3-methyl-5-phneyladamantane-1-carboxamide | $^1$H NMR (300 MHz, CDCl$_3$) δ 7.26-7.38 (m, 4H) 7.13-7.22 (m, 1H) 5.44 (d, 1H) 3.84 (ddd, 1H) 3.45 (s, 2H) 3.08 (d, 1H) 2.61-2.75 (m, 2H) 2.47-2.57 (m, 1H) 2.29 (dt, 1 H) 2.17 (br. s., 3H) 1.95 (br. s., 3H) 1.69-1.85 (m, 3 H) 1.56 (s, 3H) 1.40-1.52 (m, 3 H) 0.93 (d, 3H) 0.80-0.87 (m, 2H). LC/MS m/z: 381.40 (M + H)$^+$ |
| A112 | tert-butyl 4-amino-3-methylpiperidine-1-carboxylate<br>3-methyl-5-phenyladamantane-1-carboxylic acid | 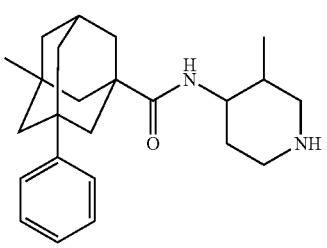<br>N-(3-methylpiperidin-4-yl)-3-methyl-5-phenyladamantane-1-carboxamide | $^1$H NMR (300 MHz, CDCl$_3$) δ 7.26-7.38 (m, 4H) 7.14-7.22 (m, 1H) 5.57 (d, 1H) 4.04-4.20 (m, 0.5H) 3.53-3.77 (m, 0.5H) 3.45 (s, 3H) 3.13-3.28 (m ,1H) 2.61-2.99 (m, 2H) 2.35-2.53 (m, 4 H) 1.64-2.00 (m, 8H) 1.51-1.63 (m, 2H) 1.41-1.51 (m, 2H) 0.93 (s, 3H). LC/MS m/z: 367.43 (M + H)$^+$ |

-continued

| Ex. | Starting materials | Product/Name | Analytical Data |
|---|---|---|---|
| A113 | tert-butyl 4-amino piperidine-1-carboxylate 3-ethoxyadamantane-1-carboxylic acid | 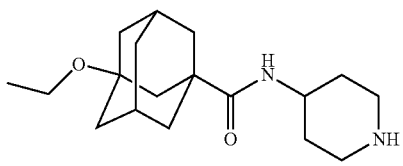<br>3-ethoxy-N-(piperidin-4-yl)adamantane-1-carboxamide | LC/MS m/z: 307.34 (M + H)+, 613.65 (2M + H)+ |
| A114 | trans-tert-butyl N-(4-aminocyclohexyl)carbamate 3-phenyl-5-[(pyrrolidin-1-yl)carbonyl]adamantane-1-carboxylic acid | 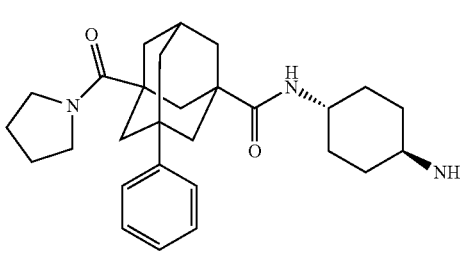<br>trans-N-(4-aminocyclohexyl)-3-phenyl-5[(pyrrolidin-1-yl)carbonyl]adamantane-1-carboxamide | LC/MS m/z: 450.42 (M + H)+ |
| A115 | trans-tert-butyl N-(4-aminocyclohexyl)carbamate 3-(methoxycarbonyl)-5-phenyladamantane-1-carboxylic acid | 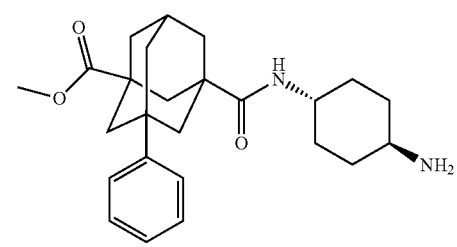<br>methyl 3-[trans-(4-aminocyclohexyl)carbamoyl]-5-phenyladamantane-1-carboxylate | LC/MS m/z: 411.27 (M + H)+, 452.2 (M + H + CH$_3$CN)+, 821.63 (2M + H)+ |

Example A116: trans-N-(4-aminocyclohexyl)-3-(hydroxymethyl)-5-phenyladamantane-1-carboxamide

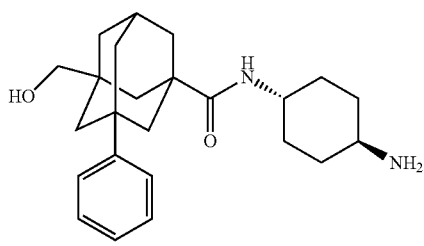 [SMILES: N[C@H]1CC[C@H](NC(=O)C23CC4CC(CO)(C2)CC(c2ccccc2)(C4)C3)CC1]

Step 1: methyl 3-[trans-(4-{[(tert-butoxy)carbonyl]amino}cyclohexyl)carbamoyl]-5-phenyladamantane-1-carboxylate

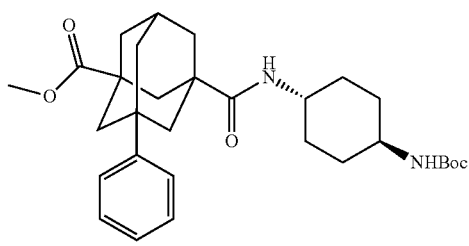 [SMILES: COC(=O)C12CC3CC(C(=O)N[C@H]4CC[C@H](NC(=O)OC(C)(C)C)CC4)(C1)CC(c1ccccc1)(C3)C2]

The title compound was prepared from 3-(methoxycarbonyl)-5-phenyladamantane-1-carboxylic acid and trans-tert-butyl N-(4-aminocyclohexyl)carbamate in the same manner as described above for 2-benzyl-7-[(3-phenyladamantan-1-yl)carbonyl]-2,7-diazaspiro[4.4]nonane (example A1, Step 2). LC/MS m/z: 455.32 (M−tBu+H)⁺, 496.35 (M−Me+H)⁺, 511.41 (M+H)⁺, 552.44 (M+H+CH₃CN)⁺.

Step 2: tert-butyl trans-N-{4-[3-(hydroxymethyl)-5-phenyladamantane-1-amido]cyclohexyl}carbamate

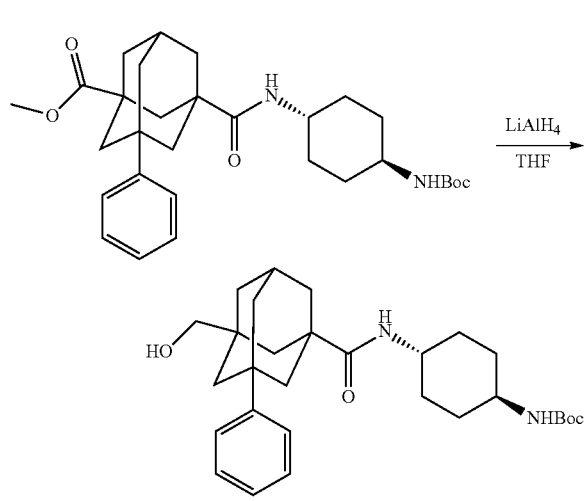

To a solution of methyl 3-[trans-(4-{[(tert-butoxy)carbonyl]amino}cyclohexyl)carbamoyl]-5-phenyladamantane-1-carboxylate (15 mg, 0.03 mmol) in THF (0.5 mL) was added dropwise 2.4 M solution of LiAlH₄ in THF (0.012 mL, 0.03 mmol) at 0° C. The reaction mixture was stirred at ambient temperature for 2 h, then cooled in an ice-bath, and quenched with saturated aqueous Na₂SO₄ solution. After stirring for 0.5 h, the mixture was diluted with THF, filtered through Celite, and concentrated in vacuo to give 11 mg (78%) of the title compound as a white solid, which was used in the next step without further purification. LC/MS m/z: 427.34 (M−tBu+H)⁺, 483.38 (M+H)⁺, 965.75 (2M+H)⁺.

Step 3: trans-N-(4-aminocyclohexyl)-3-(hydroxymethyl)-5-phenyladamantane-1-carboxamide

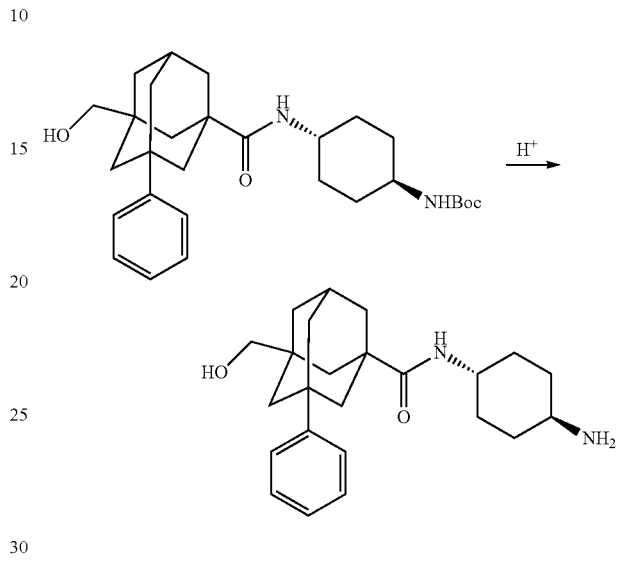

The title compound was prepared from tert-butyl trans-N-{4-[3-(hydroxymethyl)-5-phenyladamantane-1-amido]cyclohexyl}carbamate in the same manner as described above for 2-benzyl-2,7-diazaspiro[4.4]nonanedihydrochloride (example A1, Step 1). LC/MS m/z: 366.35 (M−OH+H)⁺, 383.38 (M+H)⁺, 424.3 (M+H+CH₃CN)⁺.

Examples A201 to A203 were prepared in the same manner as described for example A1, Step 2 using the appropriate commercially available amine and carboxylic acid as starting materials.

| | | | |
|---|---|---|---|
| A201 | pyridin-4-amine<br>3-methyl-5-phenyl adamantane-1-carboxylic acid | 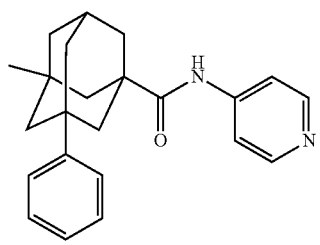 [SMILES: CC12CC3CC(C(=O)Nc4ccncc4)(C1)CC(c1ccccc1)(C3)C2]<br>3-methyl-5-phenyl-N-(pyridin-4-yl)adamantane-1-carboxamide | LC/MS m/z: 347.36 (M + H)⁺, 388.24 (M + H + CH₃CN)⁺ |
| A202 | 1H-imidazol-2-ylmethanamine<br>3-methyl-5-phenyl adamantane-1-carboxylic acid | 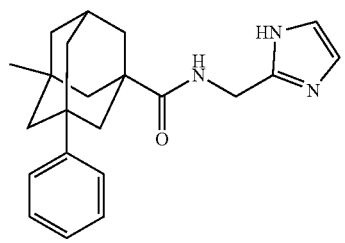 [SMILES: CC12CC3CC(C(=O)NCc4ncc[nH]4)(C1)CC(c1ccccc1)(C3)C2]<br>N-(1H-imidazol-2-ylmethyl)-3-methyl-5-phenyladamantane-1-carboxamide | LC/MS m/z: 350.24 (M + H)⁺, 391.29 (M + H + CH₃CN)⁺ |

| | | |
|---|---|---|
| A203 | pyridine-2,4-diamine 3-methyl-5-phenyladamantane-1-carboxylic acid 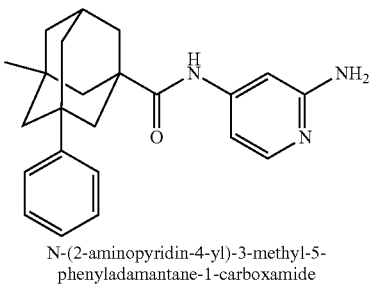 N-(2-aminopyridin-4-yl)-3-methyl-5-phenyladamantane-1-carboxamide | LC/MS m/z: 362.28 (M + H)+ |

Example A204: N-(piperidin-4-yl)adamantane-1-sulfinamide

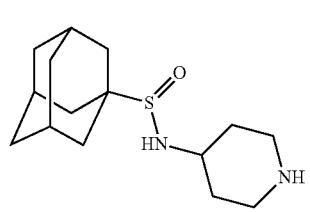

Step 1: tert-butyl 4-(((-adamantan-1-yl)sulfinyl)amino)piperidine-1-carboxylate

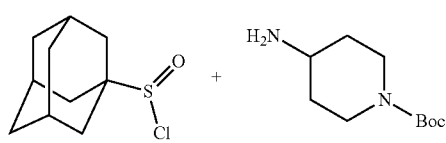

To a solution of adamantane-1-sulfinyl chloride (50 mg, 0.23 mmol) in DCM (1 mL) was added triethylamine (64 uL, 0.46 mmol) and 4-dimethylaminopyridine (3 mg), followed by tert-butyl 4-aminopiperidine-1-carboxylate (56 mg, 0.28 mmol). The mixture was stirred overnight, diluted with DCM, washed 1× with 1 M HCl, dried with brine and sodium sulfate, and evaporated. The crude product was purified via silica gel flash column using 5% MeOH in DCM as eluent to afford 49 mg of the title compound as a clear, viscous oil. LC/MS m/z: 383.35 (M+H)+, 765.68 (2M+H)+

Step 2: N-(piperidin-4-yl)adamantane-1-sulfinamide

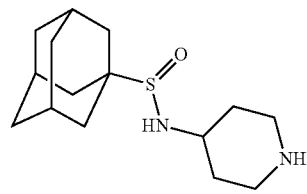 [SMILES: O=S(NC1CCNCC1)C12CC3CC(CC(C3)C1)C2]

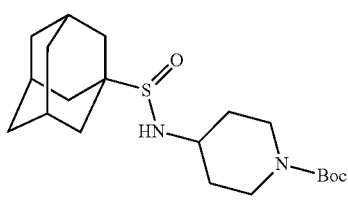

To a solution of tert-butyl 4-(((-adamantan-1-yl)sulfinyl)amino)piperidine-1-carboxylate (20 mg) in DCM (0.5 mL) was added TFA (0.5 mL), and the mixture was stirred for 2 hours at room temperature. All volatiles were evaporated and the residue dissolved in methanol and passed through an Agilent PL-HCO3 ion exchange column. The filtrate was evaporated to afford 15 mg of the title compound as a clear oil which requires no further purification. LC/MS m/z: 283.33 (M+H)+

Example A205: N-(piperidin-4-yl)adamantane-1-sulfonamide

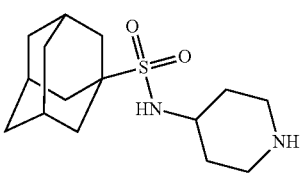 [SMILES: O=S(=O)(NC1CCNCC1)C12CC3CC(CC(C3)C1)C2]

Step 1: tert-butyl 4-(adamantane-1-sulfonamido)piperidine-1-carboxylate

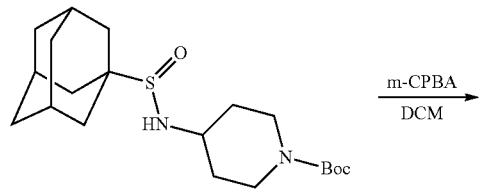

To a solution of tert-butyl 4-(((-adamantan-1-yl)sulfinyl)amino)piperidine-1-carboxylate (30 mg, 0.08 mmol) in DCM (1 mL) was added m-CPBA (20 mg, 0.1 mmol), and the mixture was stirred at room temperature for 3 hours. After completion, the reaction was diluted with DCM and washed 2× with saturated NaHCO₃, dried over sodium sulfate, and evaporated. The crude product was purified via silica gel flash column using 50:50 hexanes:ethyl acetate as eluent to afford 23 mg of the title compound as a white solid. LC/MS m/z: 399.33 (M+H)⁺, 343.27 (M+H−(t-butyl))⁺

Step 2: N-(piperidin-4-yl)adamantane-1-sulfonamide

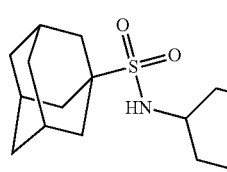

The title compound was prepared from tert-butyl 4-(adamantane-1-sulfonamido)piperidine-1-carboxylate using the procedure described for example A204, Step 2. LC/MS m/z: 299.26 (M+H)⁺, 597.48 (2M+H)⁺

Example C1: 1-Methyl-4-(3-phenyladamantan-1-yl)methyl)piperazine

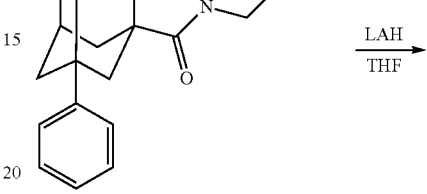

To a suspension of LAH (0.030 g, 0.78 mmol) in THF (1 mL) cooled to 0° C. was added a solution of (4-tert-butoxycarbonylpiperazin-1-yl)(3-phenyladamantan-1-yl)methanone (0.060 g, 0.14 mmol) in THF (1 mL) dropwise. The resulting reaction mixture was brought to room temperature and then refluxed for 6 h, cooled to 0° C. and quenched with sat. aq. Na₂SO₄ solution, filtered and the solvent was evaporated to give a crude residue that was purified using preparative HPLC to give the title compound as pale yellow syrup. Yield: 0.012 g (28%). LC/MS m/z: 325.28 (M+H)⁺ ¹H NMR (300 MHz, CDCl₃) δ 7.26-7.38 (m, 4H) 7.17 (d, 1H) 2.63 (br. s., 7H) 2.39 (s, 3H) 2.14 (br. s., 2H) 2.06 (s, 2H) 1.83 (br. s., 4H) 1.66 (d, 2H) 1.60 (s, 2H) 1.45-1.52 (m, 3H)

The following examples were prepared from the appropriate amide using the same procedure as for example C1.

| Ex. | amide | Product/Name | Analytical Data |
|---|---|---|---|
| C2 | 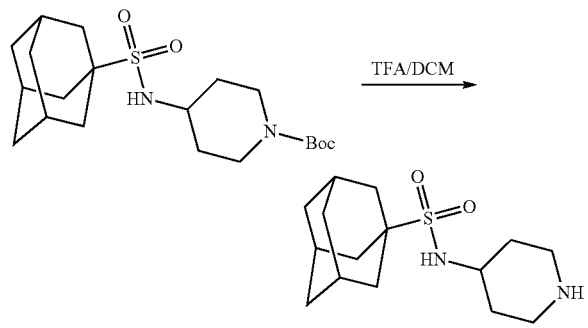 | N-((3-phenyladamantan-1-yl)methyl)piperidin-4-amine | ¹H NMR (300 MHz, CDCl₃) δ 7.26-7.38 (m, 4 H) 7.12-7.20 (m, 1 H) 3.19-3.33 (m, 1 H) 3.13 (s, 1 H) 2.68-2.88 (m, 3 H) 2.54-2.68 (m, 1 H) 2.25-2.37 (m, 2 H) 2.16 (br. s., 2 H) 1.99 (d, 1 H) 1.75-1.92 (m, 4 H) 1.38-1.75 (m, 10 H). LC/MS m/z: 325.34 (M + H)⁺ |

| Ex. | amide | Product/Name | Analytical Data |
|---|---|---|---|
| C3 | 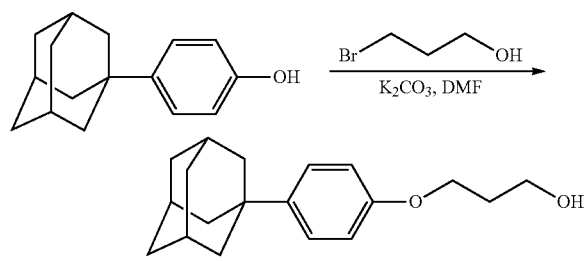 | 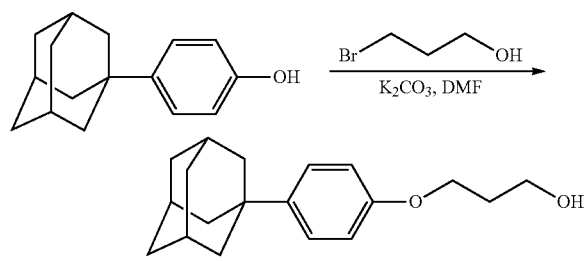  N-((3-methyl-5-phenyladamantan-1-yl)methyl)piperidin-4-amine | $^1$H NMR (300 MHz, CDCl$_3$) δ 7.25-7.38 (m, 4H) 7.11-7.19 (m, 1 H) 3.13 (dt, 2H) 2.57-2.71 (m, 2H) 2.41 - 2.55 (m, 1 H) 2.34 (s, 2H) 2.16-2.26 (m, 1H) 1.83-1.94 (m, 2H) 1.77 (br.s., 2H) 1.47-1.63 (m, 4 H) 1.37-1.47 (m, 4H) 1.15-1.36 (m,4H) 0.88 (s,3H). LC/MS m/z: 339.38 (M + H)$^+$ |

Example C4: 1-(3-(4-(adamantan-1-yl)phenoxy)propyl)-4-methylpiperidine

Step 1: 3-(4-(adamantan-1-yl)phenoxy)propan-1-ol

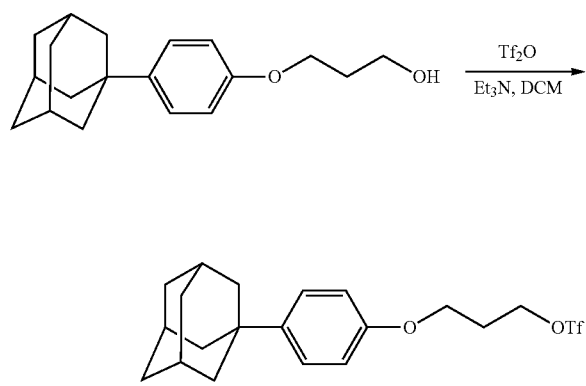

To a solution of 4-(adamantan-1-yl)phenol (0.456 g, 2 mmol) in DMF (2 mL) was added 1-bromopropanol (0.305 g, 2.2 mmol) followed by K$_2$CO$_3$ (0.414 g, 3 mmol) and resulting reaction mixture was stirred at 80° C. for 6 h. Solvent was evaporated, and residue was extracted with ethyl acetate (2×10 mL) and washed with water (1×10 mL). Dried (Na$_2$SO$_4$), filtered and evaporation of solvent under vacuum gave crude residue, which was purified by SiO$_2$ column chromatography to give the title compound as a white solid. Yield: 0.253 g (44%).

Step 2: 3-(4-(adamantan-1-yl)phenoxy)propyl trifluoromethanesulfonate

To a solution of 3-(4-(adamantan-1-yl)phenoxy)propan-1-ol (0.143 g, 0.5 mmol) in DCM (5 mL) was added Et$_3$N (0.101 g, 1 mmol) and cooled to 0° C. Then Tf$_2$O (0.225 g, 0.8 mmol) was added dropwise. Brought to room temperature gradually and stirred overnight. Reaction mixture was washed quickly with water (2 mL). Dried (Na$_2$SO$_4$), filtered and evaporation of solvent gave crude product as syrup, which was used as such in the next step. Yield: 0.208 g (100%).

Step 3: 1-(3-(4-(adamantan-1-yl)phenoxy)propyl)-4-methylpiperidine

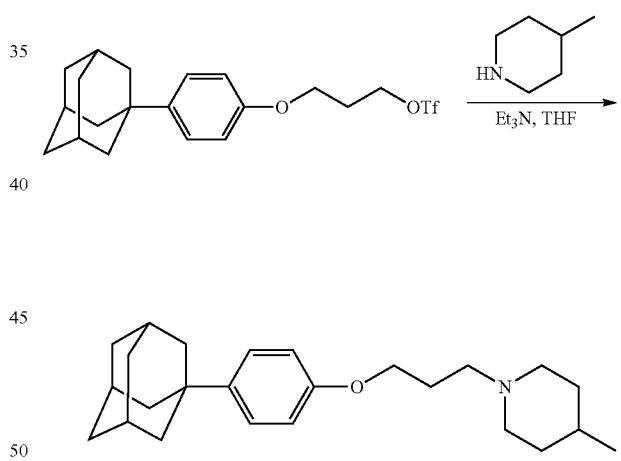

To a solution of 3-(4-(adamantan-1-yl)phenoxy)propyl trifluoromethanesulfonate (0.021 g, 0.05 mmol) in THF (0.5 mL) was added 4-methylpiperidine (0.010 g, 1 mmol) followed by Et$_3$N (0.010 g, 1 mmol) and resulting reaction mixture was stirred at room temperature for 12 h. Solvent was evaporated, and residue was purified using preparative HPLC to give the title compound as pale yellow syrup. Yield 0.007 g (39%). LC/MS m/z: 368.36 (M+H)$^+$ $^1$H NMR (300 MHz, CDCl$_3$) δ 7.19-7.28 (m, 2H) 6.78-6.85 (m, 2H) 3.98 (t, 2H) 3.03 (d, 2H) 2.62 (t, 2H) 2.06 (br. s., 6H) 1.86 (d, 6H) 1.59-1.80 (m, 8H) 1.39 (br. s., 2H) 0.93 (d, 3H).

The following examples were prepared as described for examples C4 using the appropriate amines.

| Ex. | Amine | Structure/Name | Analytical Data |
|---|---|---|---|
| C5 | (piperidine) | (structure) 1-(3-(4-(adamantan-1-yl)phenoxy)propyl)piperidine | $^1$H NMR (300 MHz, CDCl$_3$) δ 7.21 (d, 2 H) 6.81 (d, 2 H) 3.99 (t, 2 H) 2.61-2.81 (m, 4 H) 2.10-2.23 (m, 2 H) 2.06 (br. s., 3 H) 1.83-1.89 (m, 6H) 1.65-1.83 (m, 10 H) 1.52 (br. s., 2 H). LC/MS m/z: 354.41(M + H)$^+$ |
| C6 | (N-methylpiperazine) | (structure) 1-(3-(4-(adamantan-1-yl)phenoxy)propyl)-4-methylpiperazine | $^1$H NMR (300 MHz, CDCl$_3$) δ 7.24 (d, 2 H) 6.81 (d, 2 H) 3.98 (t, 2 H) 2.78 (br. s., 6 H) 2.66 (t, 2 H) 2.49 (s, 3 H) 1.93-2.10 (m, 5 H) 1.82-1.89 (m, 6 H) 1.73 (br. s., 6 H). LC/MS m/z: 369.37 (M + H)$^+$ |

Example C7: 4-(4-(adamantan-1-yl)phenoxy)-1-(4-methylpiperidin-1-yl)butan-2-ol

Step 1: 2-(2-(4-(adamantan-1-yl)phenoxy)ethyl)oxirane

Step 2: 4-(4-(adamantan-1-yl)phenoxy)-1-(4-methylpiperidin-1-yl)butan-2-ol

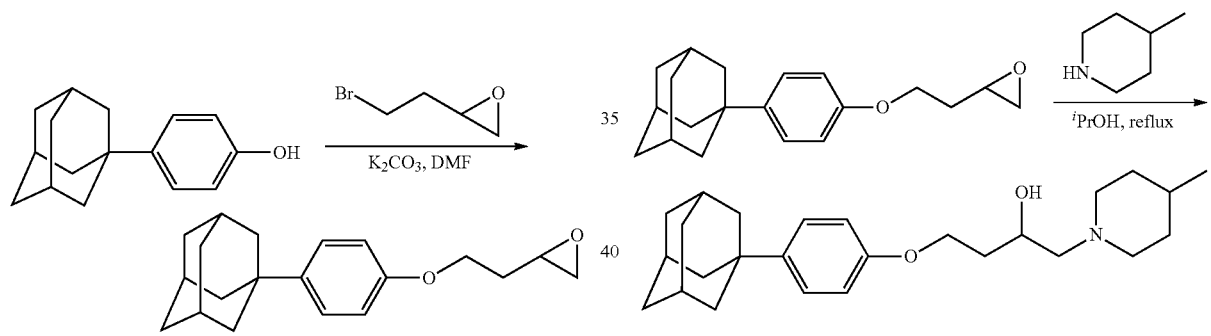

To a solution of 4-(adamantan-1-yl)phenol (0.228 g, 1 mmol) in DMF (2 mL) was added K$_2$CO$_3$ (0.276 g, 2 mmol) followed by 2-(2-bromoethyl)oxirane (0.151 g, 1 mmol) and reaction mixture was stirred at 80° C. for 12 h. Solvent was evaporated, and residue was extracted with ethyl acetate (2×5 mL) and washed with water (1×5 mL). Dried (Na$_2$SO$_4$), filtered and evaporation of solvent under vacuum gave crude residue, which was purified by SiO$_2$ column chromatography to give the title compound as a white solid. Yield: 0.224 g (75%).

To a solution of 2-(2-(4-(adamantan-1-yl)phenoxy)ethyl)oxirane (0.015 g, 0.05 mmol) in $^i$PrOH (0.5 mL) was added 4-methylpiperidine (0.010 g, 1 mmol) and resulting reaction mixture was stirred under reflux for 12 h. Solvent was evaporated, and residue was purified using preparative HPLC to give the title compound as an off-white solid. Yield: 0.007 g (36%). LC/MS m/z: 398.43 (M+H)$^+$ The following examples were prepared as described for examples C7, step 2 using the appropriate amines.

| Ex | Amine | Product/Name | Analytical Data |
|---|---|---|---|
| C8 | (piperidine) | (structure) 4-(4-(adamantan-1-yl)phenoxy)-1-(piperidin-1-yl)butan-2-ol | $^1$H NMR (300 MHz, CDCl$_3$) δ 7.21-7.27 (m, 2 H) 6.80-6.87 (m, 2 H) 4.11 (t, 2 H) 3.99-4.08 (m, 1 H) 2.75 (d, 2 H) 2.44-2.58 (m, 3 H) 2.06 (br. s., 3 H) 1.80-1.90 (m, 8 H) 1.61-1.80 (m, 10 H) 1.41-1.53 (m, 2 H). LC/MS m/z: 384.41 (M + H)$^+$ |

| Ex | Amine | Product/Name | Analytical Data |
|---|---|---|---|
| C9 | (structure: N-methylpiperazine with free NH) | (structure) 4-(4-(adamantan-1-yl)phenoxy)-1-(4-methylpiperazin-1-yl)butan-2-ol | LC/MS m/z: 399.39 (M + H)+ |

(3-Phenyladamantan-1-yl)methanol

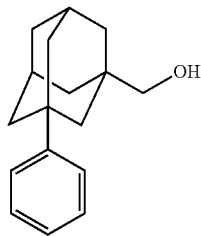 [SMILES: OCC12CC3CC(C1)CC(c1ccccc1)(C3)C2]

The title compound was prepared by LAH reduction of 3-phenyladamantane-1-carboxylic acid (A. Koperniku, I. Papanastasiou, G. B. Foscolos, A. Tsotinis, M. C. Taylor, and J. M. Kelly, *Med. Chem. Commun.* 2013, 4, 856-859).

2-(3-Phenyladamantan-1-yl)ethan-1-ol

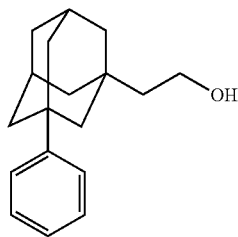 [SMILES: OCCC12CC3CC(C1)CC(c1ccccc1)(C3)C2]

The title compound was prepared from 2-(3-phenyladamantan-1-yl)acetic acid in the same manner as described for (3-phenyladamantan-1-yl)methanol.

(3-Phenyladamantan-1-yl)methyltrifluoromethanesulfonate

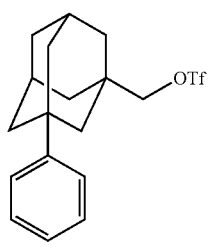 [SMILES: O=S(=O)(OCC12CC3CC(C1)CC(c1ccccc1)(C3)C2)C(F)(F)F]

The title compound was prepared from (3-phenyladamantan-1-yl)methanol in the same manner as described for Example C4, Step 2.

2-(3-Phenyladamantan-1-yl)ethyltrifluoromethanesulfonate

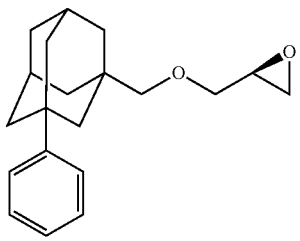

The title compound was prepared from 2-(3-phenyladamantan-1-yl)ethan-1-ol in the same manner as described for Example C4, Step 2.

(2S)-2-{[(3-phenyladamantan-1-yl)methoxy]methyl}oxirane

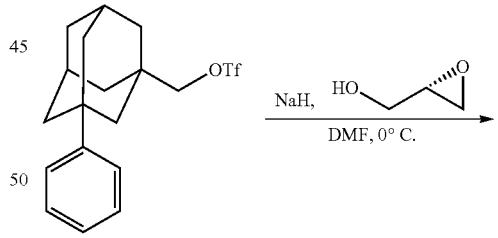

To a solution of (2S)-oxiran-2-ylmethanol (5.7 mg, 0.061 mmol) in 0.5 mL anhydrous DMF, under N₂ was added NaH (60% w/w in mineral oil, 4 mg, 0.092 mmol) at 0° C., and the resulting mixture was stirred for 1 h. Then (3-phenyladamantan-1-yl)methyltrifluoromethanesulfonate (23 mg, 0.061 mmol) in 0.3 mL anhydrous DMF was added at 0° C. The reaction mixture was stirred at 50° C. overnight, then diluted with EtOAc and washed with water. The organic phase was dried over Na₂SO₄, filtered, and concentrated in vacuo. The residue was purified by SiO₂ column chromatography (hexanes/EtOAc from 6:1 to 4:1) to give 5 mg (28%) of the product as a colorless oil.

(2R)-2-{[(3-phenyladamantan-1-yl)methoxy]methyl}oxirane

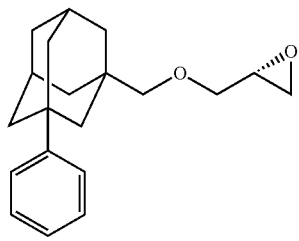 [SMILES: c1ccc(C23CC4CC(CC(COC[C@H]5CO5)(C4)C2)C3)cc1]

The title compound was prepared from (3-phenyladamantan-1-yl)methyltrifluoromethanesulfonate and (2R)-oxiran-2-ylmethanol in the same manner as described above for (2S)-2-{[(3-phenyladamantan-1-yl)methoxy]methyl}oxirane.

(2S)-2-{[2-(3-phenyladamantan-1-yl)ethoxy]methyl}oxirane

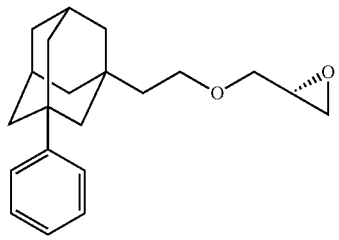 [SMILES: c1ccc(C23CC4CC(CC(CCOC[C@@H]5CO5)(C4)C2)C3)cc1]

The title compound was prepared from 2-(3-phenyladamantan-1-yl)ethyltrifluoromethanesulfonate and (2S)-oxiran-2-ylmethanol in the same manner as described above for (2S)-2-{[(3-phenyladamantan-1-yl)methoxy]methyl}oxirane.

(2R)-2-{[2-(3-phenyladamantan-1-yl)ethoxy]methyl}oxirane

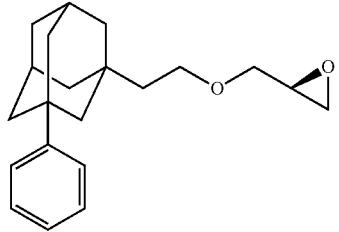 [SMILES: c1ccc(C23CC4CC(CC(CCOC[C@H]5CO5)(C4)C2)C3)cc1]

The title compound was prepared from 2-(3-phenyladamantan-1-yl)ethyltrifluoromethanesulfonate and (2R)-oxiran-2-ylmethanol in the same manner as described above for (2S)-2-{[(3-phenyladamantan-1-yl)methoxy]methyl}oxirane.

Example C10: (2S)-1-(4-methylpiperidin-1-yl)-3-[(3-phenyladamantan-1-yl)methoxy]propan-2-ol

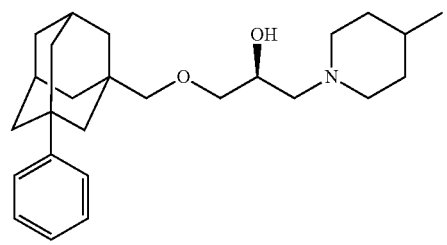 [SMILES: CC1CCN(C[C@H](O)COCC23CC4CC(C2)CC(c2ccccc2)(C4)C3)CC1]

The title compound was prepared from (2S)-2-{[(3-phenyladamantan-1-yl)methoxy]methyl}oxirane and 4-methylpiperidine in the same manner as described for Example C7, Step 2. LC/MS m/z: 398.36 (M+H)⁺.

Example C11: (2R)-1-(4-methylpiperidin-1-yl)-3-[(3-phenyladamantan-1-yl)methoxy]propan-2-ol

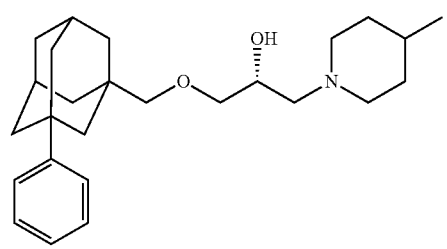 [SMILES: CC1CCN(C[C@@H](O)COCC23CC4CC(C2)CC(c2ccccc2)(C4)C3)CC1]

The title compound was prepared from (2R)-2-{[(3-phenyladamantan-1-yl)methoxy]methyl}oxirane and 4-methylpiperidine in the same manner as described for Example C7, Step 2. LC/MS m/z: 398.38 (M+H)⁺.

Example C12: (2S)-1-(4-methylpiperidin-1-yl)-3-[2-(3-phenyladamantan-1-yl)ethoxy]propan-2-ol

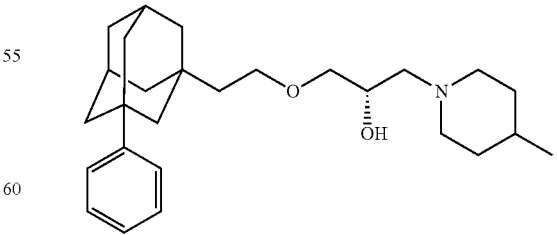

The title compound was prepared from (2S)-2-{[2-(3-phenyladamantan-1-yl)ethoxy]methyl}oxirane and 4-methylpiperidine in the same manner as described for Example C7, Step 2. LC/MS m/z: 412.32 (M+H)⁺.

Example C13: (2R)-1-(4-methylpiperidin-1-yl)-3-[2-(3-phenyladamantan-1-yl)ethoxy]propan-2-ol

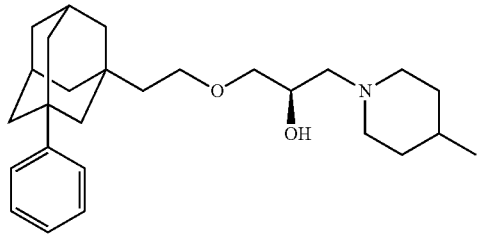 [SMILES: CC1CCN(C[C@@H](O)COCCC23CC4CC(C2)CC(c2ccccc2)(C4)C3)CC1]

The title compound was prepared from (2R)-2-{[2-(3-phenyladamantan-1-yl)ethoxy]methyl}oxirane and 4-methylpiperidine in the same manner as described for Example C7, Step 2. LC/MS m/z: 412.29 (M+H)$^+$.

Example C14: 6-{[(3-phenyladamantan-1-yl)methyl]amino}-N-(piperidin-4-yl)pyridine-3-carboxamide

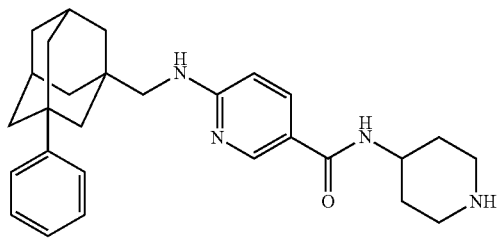 [SMILES: O=C(NC1CCNCC1)c1ccc(NCC23CC4CC(C2)CC(c2ccccc2)(C4)C3)nc1]

Step 1: 3-phenyladamantane-1-carboxamide

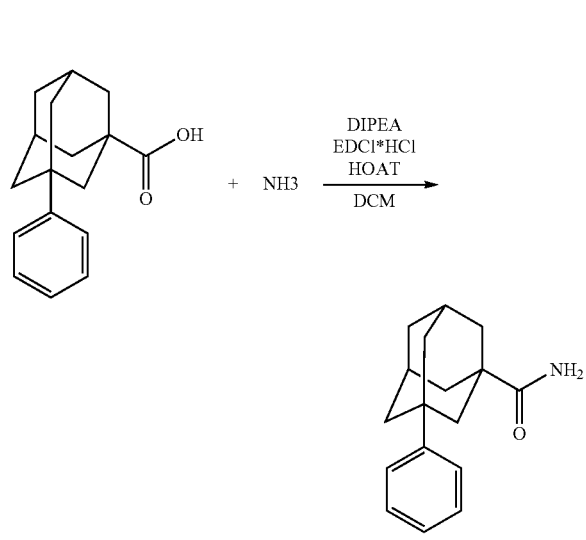

To a solution of 3-phenyladamantane-1-carboxylic acid (300 mg, 1.17 mmol) in dichloromethane (5 mL) is added diisopropylethylamine (610 mg, 3.51 mmol), HOAT (206 mg, 1.52 mmol), and EDCl*HCl (290 mg, 1.52 mmol). Finally, 2.8 mL of a 0.5 M solution of ammonia (1.4 mmol) in dioxane is added, and the mixture is stirred overnight. The mixture is then diluted with DCM, washed 3× with 1 M HCl, dried over sodium sulfate, and evaporated. The crude product is purified via flash column using ethyl acetate as the eluent to give 180 mg of the title compound as a white solid. LC/MS m/z: 256.18 (M+H)$^+$, 297.27 (M+H+CH$_3$CN)$^+$, 511.39 (2M+H)$^+$ Step 2: (3-phenyladamantan-1-yl)methanamine

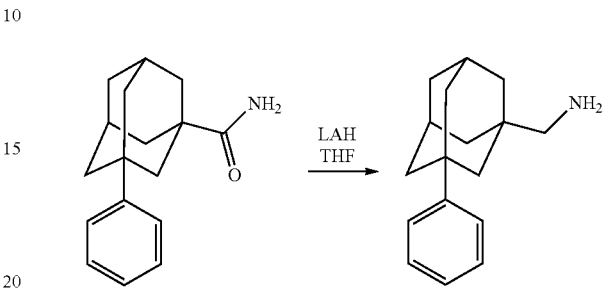

To a solution of 3-phenyladamantane-1-carboxamide (180 mg, 0.71 mmol) in THF (5 mL) was slowly added 0.9 mL of a 2.4M solution of lithium aluminum hydride in THF. The mixture was heated to reflux and stirred overnight. After completion, the reaction was cooled in an ice bath and 80 uL water, followed by 80 uL 15% NaOH, and finally 0.24 mL water were added successively, and stirring was continued for one hour at room temperature. The formed precipitate was filtered off and the filtrate was evaporated, giving 165 mg of the title compound as clear oil that was not purified further. LC/MS m/z: 242.22 (M+H)$^+$, 283.26 (M+H+CH$_3$CN)$^+$ Step 3: methyl 6-(((−3-phenyladamantan-1-yl)methyl)amino)nicotinate

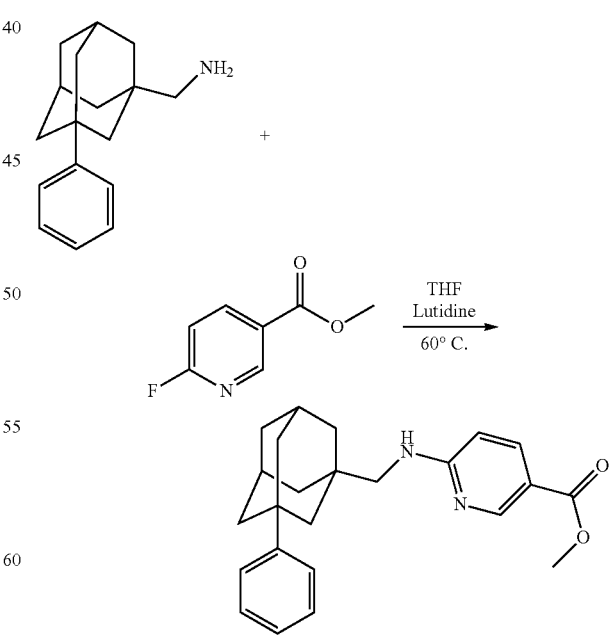

To a solution of (3-phenyladamantan-1-yl)methanamine (30 mg, 0.12 mmol) in THF (1 mL) was added 23 mg (0.15 mmol) of methyl 6-fluoronicotinate and 0.021 mL (0.18 mmol) of 2,6-lutidine. The mixture was heated to reflux and stirred overnight, then diluted with ethyl acetate and washed 2× with water, dried with brine and sodium sulfate, and evaporated to give the crude product. Purification on flash column using 1:1 hexanes:ethyl acetate eluent gave 41 mg of the title compound as a white solid. LC/MS m/z: 377.33 (M+H)$^+$, 418.29 (M+H+CH$_3$CN)$^+$ Step 4: 6-(((-3-phenyladamantan-1-yl)methyl)amino)nicotinic acid

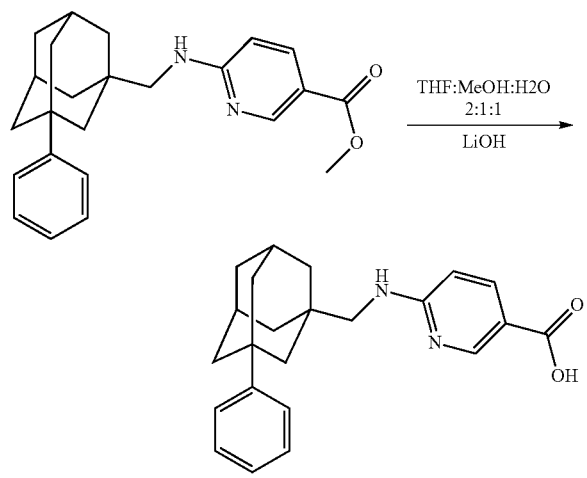

To 40 mg of methyl 6-(((-3-phenyladamantan-1-yl)methyl)amino)nicotinate was added 1 mL of solvent THF:MeOH:water (2:1:1) mixture, followed by 10 mg of LiOH. Stirring was continued for 2 hours and all solvents are then evaporated. The residue was dissolved in 1M HCl and extracted 4× with ethyl acetate. The organics were dried with sodium sulfate and evaporated to give 35 mg of the title compound as a white solid, requiring no further purification. LC/MS m/z: 363.27 (M+H)$^+$, 404.35 (M+H+CH$_3$CN)$^+$ Step 5: tert-butyl 4-(6-(((-3-phenyladamantan-1-yl)methyl)amino)nicotinamido)piperidine-1-carboxylate

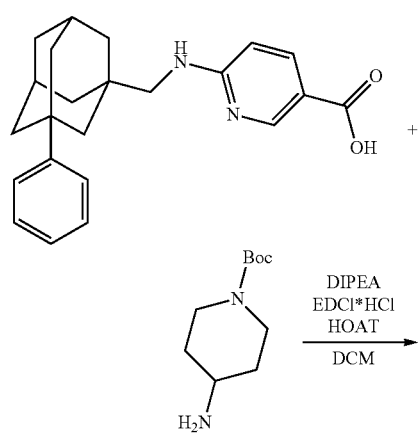

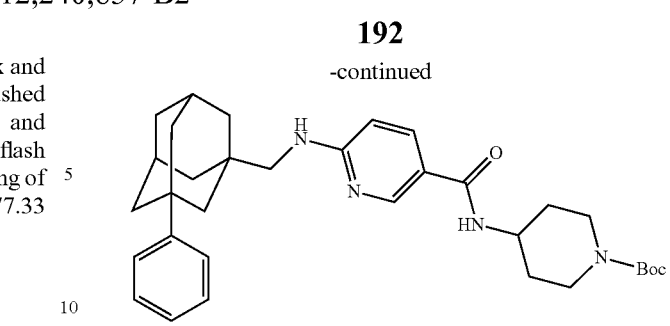

To a solution of 6-(((-3-phenyladamantan-1-yl)amino)nicotinic acid (15 mg, 0.04 mmol) in dichloromethane (1 mL) was added diisopropylethylamine (0.022 mL, 0.13 mmol), HOAT (7 mg, 0.052 mmol), and EDCl*HCl (10 mg, 0.052 mmol). Finally, tert-butyl 4-aminopiperidine-1-carboxylate (10 mg, 0.052 mmol) was added, and the mixture was stirred overnight. The reaction was then diluted with DCM, washed 2× with water, dried over sodium sulfate, and evaporated. The crude product was purified via flash column using 1:1 hexanes:ethyl acetate as eluent, giving 18 mg of the title compound as a white solid. LC/MS m/z: 545.48 (M+H)$^+$, 586.47 (M+H+CH$_3$CN)$^+$ Step 6: 6-(((-3-phenyladamantan-1-yl)methyl)amino)-N-(piperidin-4-yl)nicotinamide

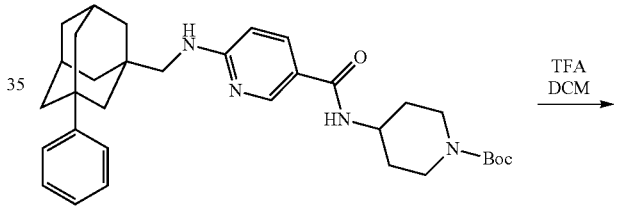

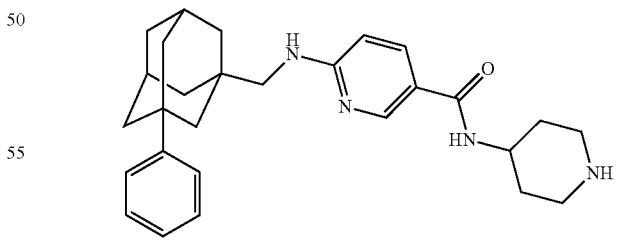

To 18 mg of the protected amine was added 0.25 mL of dichloromethane and 0.25 mL of TFA. The mixture was stirred for 2 h and all volatiles are evaporated. The residue was dissolved in methanol, passed through an Agilent PL-HCO3 ion exchange column to remove remaining TFA, and evaporated to give 10.5 mg of the title compound requiring no further purification. LC/MS m/z: 445.39 (M+H)$^+$

193

Example C15: N-[(3-phenyladamantan-1-yl)methyl]-5-(piperidin-1-ylmethyl)pyridin-2-amine

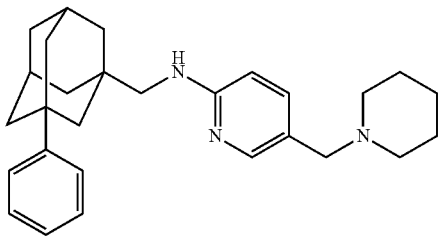 [SMILES: c1ccc(C23CC4CC(CC(CNc5ccc(CN6CCCCC6)cn5)(C4)C2)C3)cc1]

Step 1: (6-(((3-phenyladamantan-1-yl)methyl)amino)pyridin-3-yl)(piperidin-1-yl)methanone

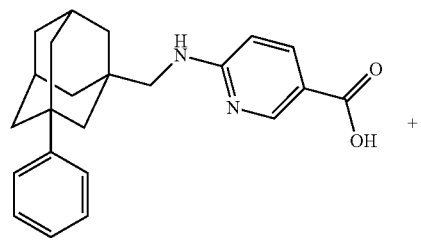

The title compound was prepared from 6-(((-3-phenyladamantan-1-yl)methyl)amino)nicotinic acid and piperidine using the procedure from example C14, Step 5. LC/MS m/z: 430.37 (M+H)+, 471.49 (M+H+CH3CN)+, 859.75 (2M+H)+

Step 2: N-[(3-phenyladamantan-1-yl)methyl]-5-(piperidin-1-ylmethyl)pyridin-2-amine

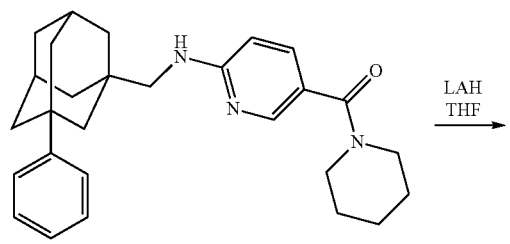

194

-continued

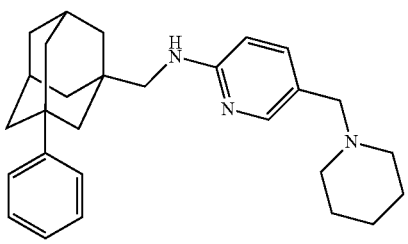

The title compound was prepared from (6-(((3-phenyladamantan-1-yl)methyl)amino)pyridin-3-yl)(piperidin-1-yl)methanone using the procedure from example C14, Step 2. LC/MS m/z: 416.31 (M+H)+

Example C16: 5-(aminomethyl)-N-[(3-phenyladamantan-1-yl)methyl]pyridin-2-amine

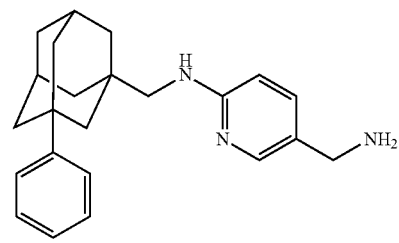 [SMILES: NCc1ccc(NCC23CC4CC(C2)CC(c2ccccc2)(C4)C3)nc1]

Step 1: 6-(((-3-phenyladamantan-1-yl)methyl)amino)nicotinamide

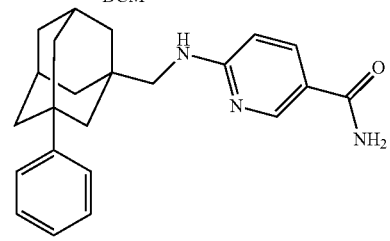

The title compound was prepared from 6-(((-3-phenyladamantan-1-yl)methyl)amino)nicotinic acid and ammonia using the procedure for example C14, Step 1. LC/MS m/z: 362.17 (M+H)+, 403.39 (M+H+CH3CN)+,

Step 2: 5-(aminomethyl)-N-((3-phenyladamantan-1-yl)methyl)pyridin-2-amine

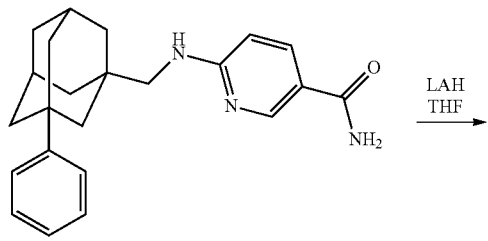

LAH
THF
→

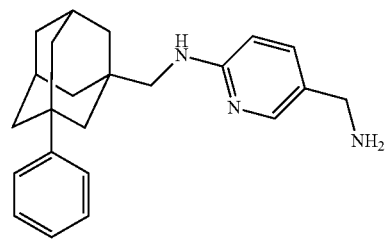

The title compound was prepared from 6-(((–3-phenyladamantan-1-yl)methyl)amino)nicotinamide using the procedure from example C14, Step 2. LC/MS m/z: 348.26 (M+H)⁺

Example C17: {4-[(3-phenyladamantan-1-yl)methoxy]phenyl}methanamine

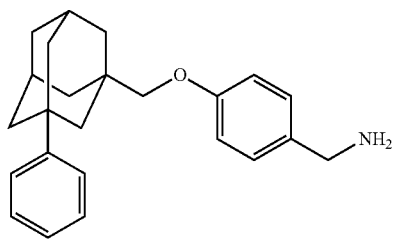 [SMILES: NCc1ccc(OCC23CC4CC(C2)CC(c2ccccc2)(C4)C3)cc1]

Step 1: methyl 4-((–3-phenyladamantan-1-yl)methoxy)benzoate

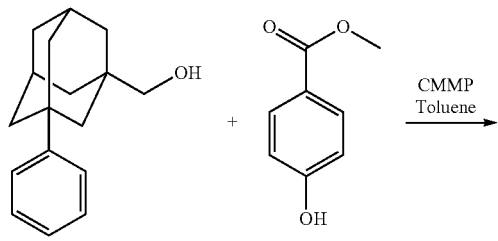

CMMP
Toluene
→

-continued

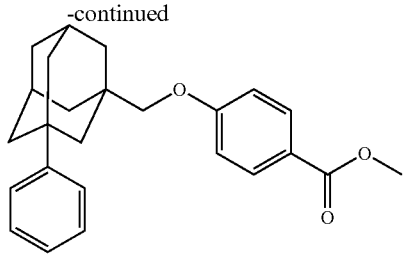

To a flame dried flask was added toluene (1 mL), (3-phenyladamantan-1-yl)methanol (30 mg, 0.12 mmol), methyl-4-hydroxybenzoate (20 mg, 0.12 mmol), and 0.5 mL of a 0.5M (cyanomethylene) trimethyl phosphorane solution in THF. The mixture was brought to reflux and stirred overnight, then diluted with ethyl acetate, washed 2× with water, dried with brine and sodium sulfate, and evaporated. The crude residue was purified by flash column using 9:1 hexanes:ethyl acetate as eluent to give 22 mg of the title compound as a clear oil. ¹H NMR (500 MHz, CDCl₃) δ: 7.98 (d, 2H), 7.39 (d, 2H), 7.33 (t, 2H), 7.19 (t, 1H), 6.91 (d, 2H), 3.88 (s, 3H), 3.64 (s, 2H), 2.25 (br:s, 1H), 1.93 (q, 4H), 1.83 (br:s, 2H), 1.76 (d, 5H)

Step 3: 4-((–3-phenyladamantan-1-yl)methoxy)benzoic acid

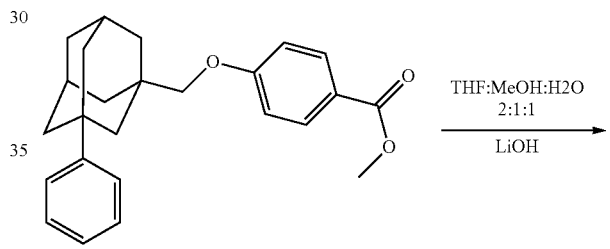

THF:MeOH:H2O
2:1:1
LiOH
→

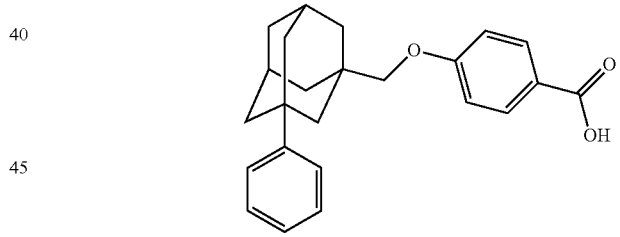

The title compound was prepared from methyl 4-((–3-phenyladamantan-1-yl)methoxy)benzoate using the procedure from example C14, Step 4.

Step 4: 4-((–3-phenyladamantan-1-yl)methoxy)benzamide

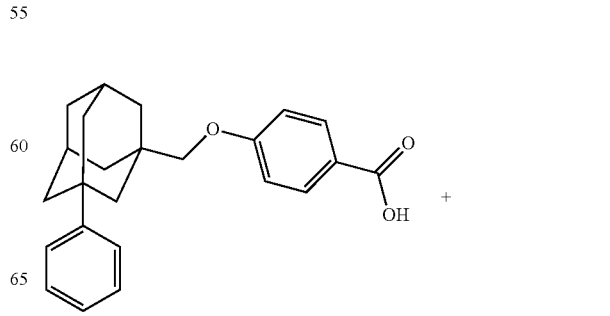

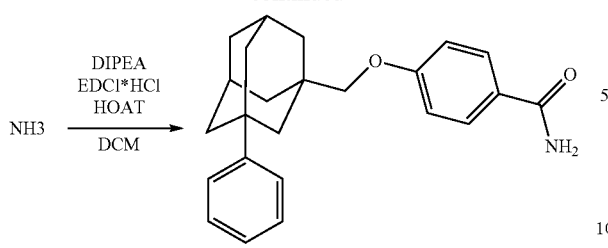

The title compound was prepared from 4-((–3-phenyladamantan-1-yl)methoxy)benzoic acid using the procedure from example C14, Step 1. LC/MS m/z: 362.07 (M+H)+, 403.30 (M+H+CH₃CN)+

Step 5: {4-[(3-phenyladamantan-1-yl)methoxy]phenyl}methanamine

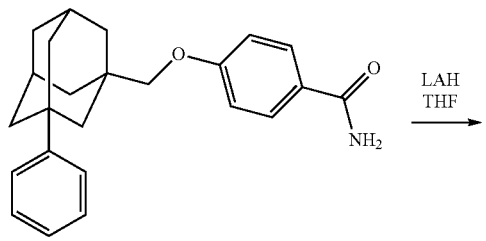

The title compound was prepared from 4-((–3-phenyladamantan-1-yl)methoxy)benzamide using the procedure from example C14, Step 2. LC/MS m/z: 348.30 (M+H)+, 331.31 (M–NH2)+

Example C18: (2S)-1-(4-methylpiperidin-1-yl)-3-[4-(3-phenyladamantan-1-yl)phenoxy]propan-2-ol

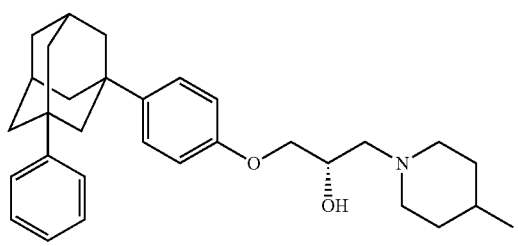

Step 1: 1-bromo-3-phenyladamantane

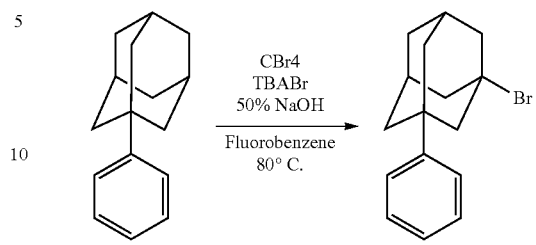

To a solution of phenyladamantane (100 mg, 0.47 mmol) in fluorobenzene (1.5 mL) was added carbon tetrabromide (240 mg) and tetrabutylammonium bromide (10 mg). The mixture is stirred until homogenous, and 1 mL of a 50% (w/w) aqueous NaOH solution is added. The mixture is heated to 80° C. overnight, cooled to rt, and diluted with water. The mixture is extracted 3× with DCM, and the organic layer dried with brine and sodium sulfate. The crude product is purified by flash column with pure hexanes as eluent to give 48 mg of the title compound as an off-brown solid. $^{13}$C NMR (125 MHz, CDCl₃) δ: 148.93, 128.57, 126.37, 124.90, 66.21, 54.57, 48.66, 41.50, 34.96, 32.91

Step 2: 4-(3-phenyladamantan-1-yl)phenol

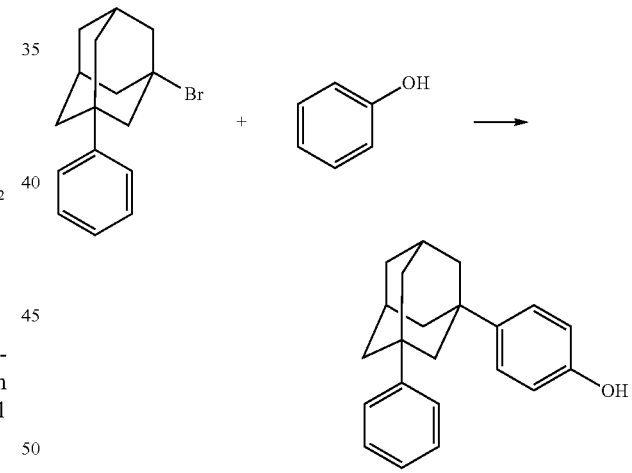

To 50 mg (0.17 mmol) of 1-bromo-3-phenyladamantane was added phenol (160 mg, 1.7 mmol). The reaction was then heated to 120° C. with vigorous stirring for 14 hours and allowed to cool to room temperature. The solid residue was dissolved in methanol, cooled to 0° C., and water was added until a precipitate forms. The formed solid is filtered off, washed with ice cold methanol and water, and dried by air suction giving 20 mg of the title compound as an off-brown solid. $^{1}$H NMR (500 MHz, CDCl₃) δ 7.39 (d, 2H), 7.327 (t, 2H), 7.27 (d, 2H), 7.19 (t, 1H) 6.79 (d, 2H), 4.62 (br:s, 1H), 2.3 (br:s, 2H), 2.0 (s, 2H), 1.94 (dd, 9H), 1.78 (br:s, 2H)

Step 3: (2S)-2-[4-(3-phenyladamantan-1-yl)phenoxymethyl]oxirane

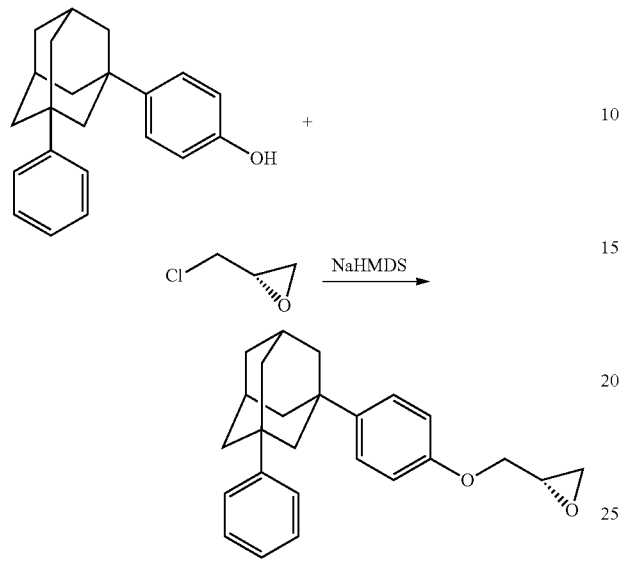

To a solution of 4-(3-phenyladamantan-1-yl)phenol (32 mg, 0.1 mmol) in THF (1 mL) is added NaHMDS (22 mg, 0.12 mmol). The mixture is brought to reflux for 10 minutes, and (S)-epichlorohydrin (50 mg, 0.50 mmol) is added in one portion. Reflux is continued overnight, and then all volatiles are evaporated. The residue was partitioned between ethyl acetate and water, washed 2× with water, then brine, dried over sodium sulfate, and evaporated. The crude product was purified by silica gel flash column with 90:10 hexanes:ethyl acetate as eluent, giving 20 mg of the title compound as a yellow oil. $^1$H NMR (500 MHz, CDCl$_3$) δ: 7.40 (d, 2H), 7.32 (t, 4H), 7.19 (t, 1H), 6.88 (d, 2H), 4.18 (dd, 1H), 3.99-3.95 (m, 1H), 3.34 (m, 1H), 2.90 (t, 1H), 2.76-2.74 (m, 1H), 2.31 (br:s, 2H), 2.01 (s, 2H), 1.94 (dd, 9H), 1.78 (br:s, 2H)

Step 4: (2S)-1-(4-methylpiperidin-1-yl)-3-[4-(3-phenyladamantan-1-yl)phenoxy]propan-2-ol

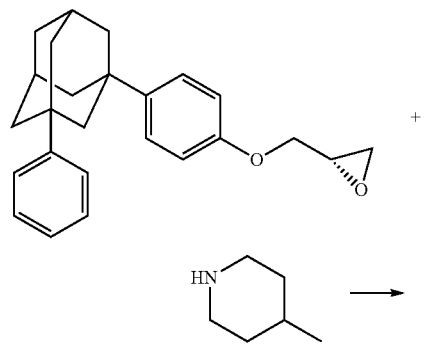

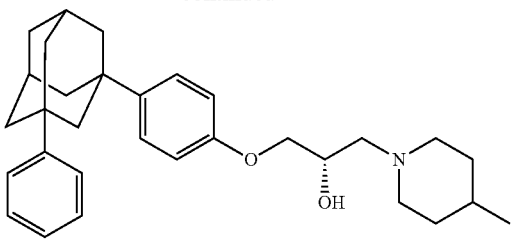 [SMILES: CC1CCN(C[C@H](O)COc2ccc(C34CC5CC(CC(c6ccccc6)(C5)C3)C4)cc2)CC1]

To a solution of (2S)-2-[4-(3-phenyladamantan-1-yl)phenoxymethyl]oxirane (20 mg, 0.056 mmol) in isopropanol (1 mL) is added triethylamine (0.012 mL, 0.083 mmol) and 4-methylpiperidine (10 uL, 0.083 mmol). The mixture was brought to reflux and stirred overnight. After cooling, all volatiles are evaporated and the crude residue is added directly to a small silica flash column using first ethyl acetate and then 95:5 DCM:MeOH as eluents, giving 10.8 mg of the title compound as a viscous oil. LC/MS m/z: 460.41 (M+H)$^+$

Example C19: (S)-1-(4-(−3-ethyladamantan-1-yl)phenoxy)-3-(4-methylpiperidin-1-yl)propan-2-ol

Step 1: 1-bromo-3-ethyladamantane

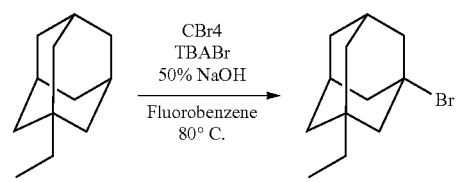

The title compound was prepared from ethyladamantane using the procedure from example C18, Step 1.

Step 2: 4-(3-ethyladamantan-1-yl)phenol

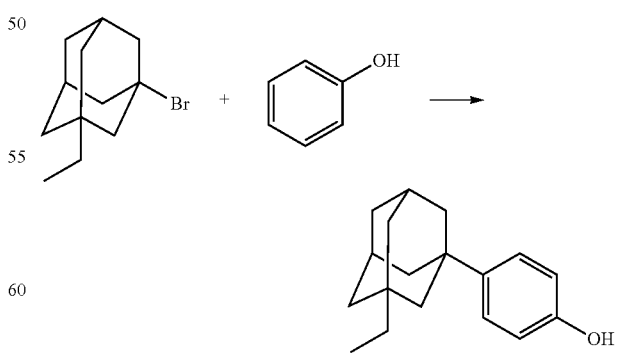

The title compound was prepared from 1-bromo-3-ethyladamantane and phenol using the procedure from example C18, Step 2.

Step 3: (S)-2-((4-(3-ethyladamantan-1-yl)phenoxy)methyl)oxirane

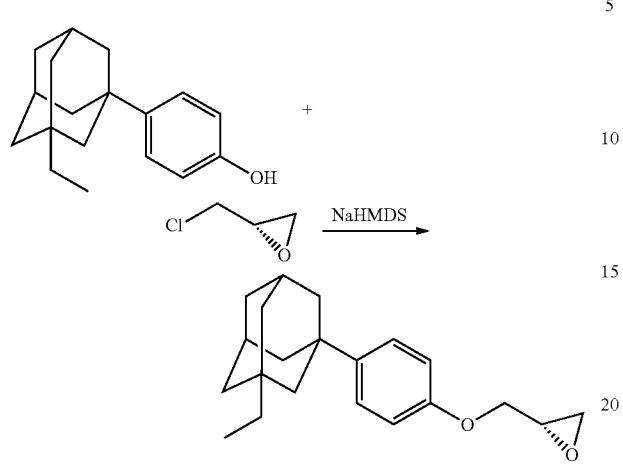

The title compound was prepared from 4-(3-ethyladamantan-1-yl)phenol and (s)-epichlorohydrin using the procedure from example C18, Step 3.

Step 4: (S)-1-(4-(-3-ethyladamantan-1-yl)phenoxy)-3-(4-methylpiperidin-1-yl)propan-2-ol

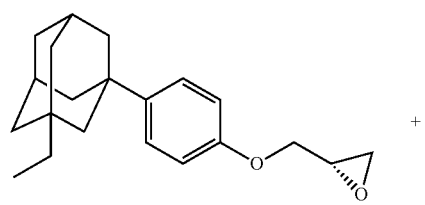

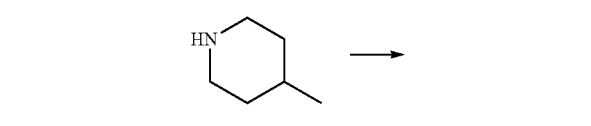

The title compound was prepared from (S)-2-((4-(3-ethyladamantan-1-yl)phenoxy)methyl)oxirane and 4-methylpiperidine using the procedure from example C18, step 4. LC/MS m/z: 412.36 (M+H)+

Example E1: 3-(3-phenyladamantan-1-yl)-1-(piperidin-4-yl)urea

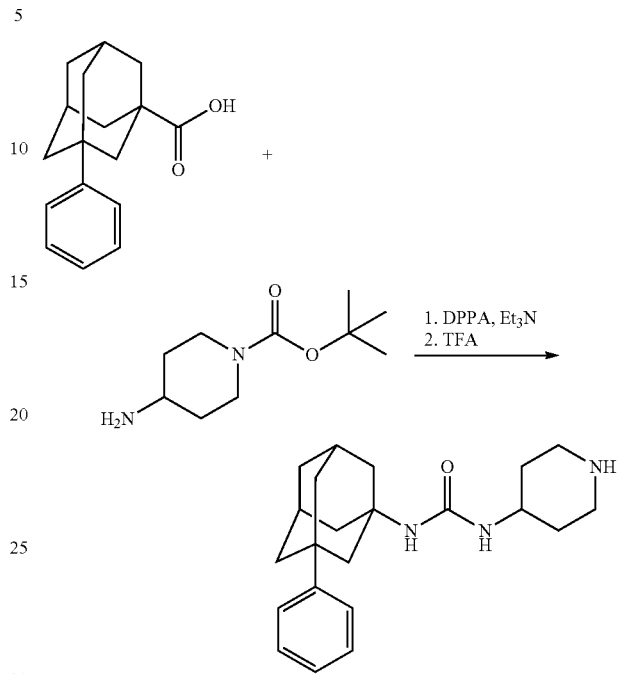

To a solution of 3-phenyladamantane-1-carboxylic acid (0.064 g, 0.25 mmol) in toluene (0.75 mL) was added Et₃N (0.04 ml, 0.29 mmol) followed by diphenylphosphorylazide (0.060 ml, 0.28 mmol) and the resulting reaction mixture was stirred at 70° C. for 2 h. It was cooled to room temperature, then tert-butyl-4-aminopiperidine-1-carboxylate (0.050 g, 0.25 mmol) was added and the mixture was stirred at room temperature overnight. The solvent was evaporated, and the residue was dissolved in DCM (0.5 mL). TFA (0.2 mL) was added and the mixture was stirred for 2 h. The solvent was evaporated and the crude residue was purified by preparative HPLC to give the title compound as an off-white solid. Yield: 9.1 mg (10.3%). LC/MS m/z: 354.36 (M+H)+

Example E2: 1-(4-aminocyclohexyl)-3-(3-phenyladamantan-1-yl)urea

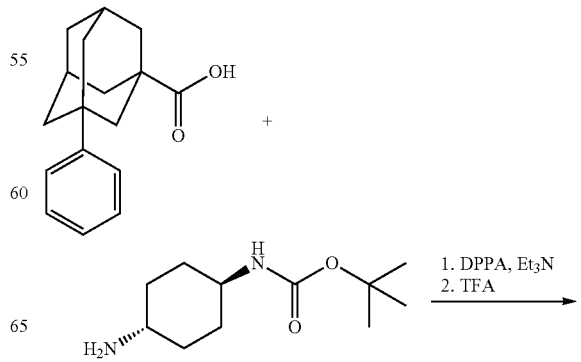

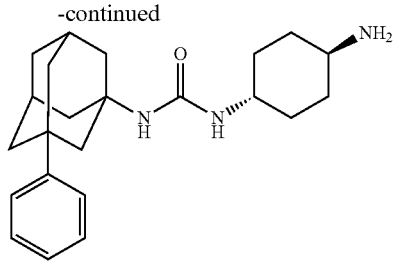

The title compound was prepared following the same procedure as described for example E1, using the appropriate amine. Yield: 10.1 mg (11%). LC/MS m/z: 409.19 (M+H+CH$_3$CN)$^+$ Example E3:
N-(3-phenyladamantan-1-yl)piperidine-4-carboxamide Step 1: 3-phenyladamantan-1-amine

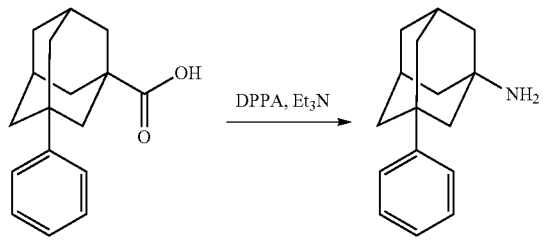 [SMILES: O=C(O)C12CC3CC(C1)CC(c1ccccc1)(C3)C2 ; NC12CC3CC(C1)CC(c1ccccc1)(C3)C2]

To a solution of 3-phenyladamantane-1-carboxylic acid (0.064 g, 0.25 mmol) in toluene (0.75 mL) was added Et$_3$N (0.04 ml, 0.29 mmol) followed by diphenylphosphorylazide (0.060 ml, 0.28 mmol) and the resulting reaction mixture was stirred at 70° C. for 2 h. After cooling rt, aq. NaHCO$_3$ solution was added and the mixture was stirred for 0.5 h, and extracted with ethyl acetate (2 mL). The organic extract was dried (Na$_2$SO$_4$), filtered and concentrated to give the title compound which was used without purification in the next step.

Step 2:
N-(3-phenyladamantan-1-yl)piperidine-4-carboxamide

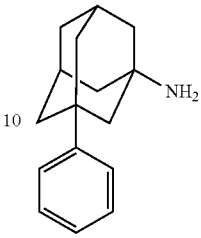

+

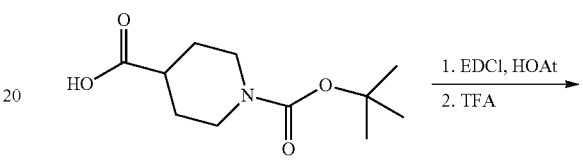

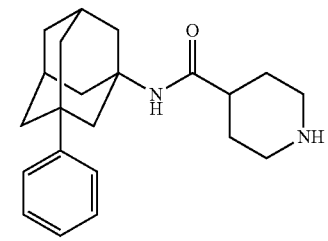

To a solution of N—BOC-piperidine-4-carboxylic acid (0.057 g, 0.25 mmol) in DCM (1 mL) was added EDCl·HCl (0.059 g, 0.30 mmol) followed by DIEA (0.06 ml, 0.29 mmol). The mixture was stirred for 0.5 h, then 3-phenyl-adamantane-1-amine obtained from step 1 was added and the resulting mixture was stirred for 3 h, then TFA was added and stirring was continued for 2 h. The solvent was evaporated and the crude residue was purified by preparative HPLC to give the title compound as a syrup. Yield: 1.5 mg (1.8%). LC/MS m/z: 339.40 (M+H)$^+$ Examples E4 to E6 were prepared as described for example E3 using the appropriate amine and carboxylic acid.

| Ex. | Starting materials | Product | Analytical Data |
|---|---|---|---|
| E4 | 3-phenyladamantan-1-amine<br>2-{1-(tert-butoxy)carbonyl]piperidin-4-yl}acetic acid | N-(3-phenyladamantan-1-yl)-2-(piperidin-4-yl)acetamide | $^1$H NMR (300 MHz, CDCl$_3$) δ 7.26-7.37 (m, 4 H) 7.13-7.21 (m, 1 H) 5.16 (br. s., 1 H) 4.29 (d, 1 H) 3.47 (s, 0.5 H) 3.05 (s, 0.5 H) 2.84 (d, 1 H) 2.27 (br. s., 2 H) 2.13 (s, 2 H) 2.02 (d, 4 H) 1.72-1.96 (m, 6 H) 1.68 (br. s., 3 H) 1.59 (s, 4 H). LC/MS m/z: 353.49 (M + H)$^+$ |

-continued

| Ex. | Starting materials | Product | Analytical Data |
|---|---|---|---|
| E5 | 3-phenyladamantan-1-amine<br>trans-4-{[(tert-butoxy)carbonyl]amino}cyclohexane-1-carboxylic acid | trans-4-amino-N-(3-phenyl adamantan-1-yl)cyclo hexane-1-carboxamide | $^1$H NMR (300 MHz, CDCl$_3$) δ 8.22 (br. s., 2 H) 7.25-7.36 (m, 4 H) 7.12-7.20 (m, 1 H) 3.05-3.41 (m, 1 H) 2.15-2.36 (m, 3 H) 1.96-2.15 (m, 10 H) 1.71-1.96 (m, 3 H) 1.34-1.71 (m, 6 H). LC/MS m/z: 394.48 (M + H + CH$_3$CN)$^+$ |
| E6 | (3-phenyladamantan-1-yl)methanamine<br>1-[(tert-butoxy)carbonyl]piperidine-4-carboxylic acid | N-[(3-phenyladamantan-1-yl)methyl]piperidine-4-carboxamide | LC/MS m/z: 353.37 (M + H)$^+$ |

In some embodiments, the invention provides for methods of treating infection by members of the Filoviridae family, which includes without limitation Ebolavirus, Marburgvirus, Cuevavirus, or any newly emerging filovirus genera. Five species of Ebolavirus have been identified: Zaire (EBOV), Bundibugyo (BDBV), Tai Forest (TAFV), Sudan (SUDV), and Reston (RESTV). Two species of Marburgvirus have been identified: (MARV) and Ravn (RAVV). One species of Cuervavirus has currently been identified: Lloviu virus (LLOV).

In some embodiments, the compounds of the invention can selectively inhibit Ebolavirus infection. Infection by Ebolavirus in humans leads to Ebola Hemorrhagic Fever (EHF), the clinical manifestations of which are severe and/or fatal. The incubation period varies between four and sixteen days. The initial symptoms are generally a severe frontal and temporal headache, generalized aches and pains, malaise, and by the second day the victim will often have a fever. Later symptoms include watery diarrhea, abdominal pain, nausea, vomiting, a dry sore throat, and anorexia. By day seven of the symptoms, the patient will often have a maculopapular (small slightly raised spots) rash. At the same time the person may develop thrombocytopenia and hemorrhagic manifestations, particularly in the gastrointestinal tract, and the lungs, but it can occur from any orifice, mucous membrane or skin site. Ebolavirus infections may cause lesions in almost every organ, although the liver and spleen are the most noticeably affected. Both are darkened and enlarged with signs of necrosis. The cause of death (>75% in most outbreaks) is normally shock, associated with fluid and blood loss into the tissues. The hemorrhagic and connective tissue complications of the disease are not well understood, but may be related to onset of disseminated intra-vascular coagulation. Infectious virus may linger in some tissues of some infected individuals for weeks and months after the initial infection.

In some embodiments, the compounds of the invention may inhibit Marburgvirus infection. Marburg hemorrhagic fever (MHF) is a severe type of hemorrhagic fever associated with Marburgvirus infection, which affects both humans and non-human primates. The case-fatality rate for MHF was approximately 70% in a recent Angola outbreak. After an incubation period of 5-10 days, the onset of the disease is sudden and is marked by fever, chills, headache, and myalgia. Around the fifth day after the onset of symptoms, a maculopapular rash, most prominent on the trunk (chest, back, stomach), may occur. Nausea, vomiting, chest pain, a sore throat, abdominal pain, and diarrhea then may appear. Symptoms become increasingly severe and may include jaundice, inflammation of the pancreas, severe weight loss, delirium, shock, liver failure, massive hemorrhaging, and multi-organ dysfunction.

In some embodiments, the compounds of the invention may inhibit Cuervavirus infection or infections with any newly emerging filovirus.

In some embodiments, the compounds of the invention may inhibit infection by any virus, whether native or engineered, whose cell entry process is mediated by filovirus or hybrid filovirus glycoproteins.

Exemplary Kits

The invention also includes kits. The kit has a container housing an inhibitor of the invention and optionally additional containers with other therapeutics such as antiviral agents or viral vaccines. The kit also includes instructions for administering the component(s) to a subject who has or is at risk of having an enveloped viral infection.

In some aspects of the invention, the kit can include a pharmaceutical preparation vial, a pharmaceutical preparation diluent vial, and inhibitor. The vial containing the diluent for the pharmaceutical preparation is optional. The diluent vial contains a diluent such as physiological saline for diluting what could be a concentrated solution or lyophilized powder of inhibitor. The instructions can include instructions for mixing a particular amount of the diluent with a particular amount of the concentrated pharmaceutical preparation, whereby a final formulation for injection or infusion is prepared. The instructions may include instructions for use in an oral formulation, inhaler, intravenous injection or any other device useful according to the invention. The instructions can include instructions for treating a patient with an effective amount of inhibitor. It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

Protocol A for pseudotype inhibitory testing of compounds.

Utilizing a VSV pseudotype system, EBOV or BDBV mucin-domain-deleted glycoproteins were expressed along with the *Renilla* luciferease reporter gene to screen a library collection of small molecule compounds to identify individual compounds that inhibit infectivity of these VSV filovirus-GP pseudotyped viruses and not VSV expressing the native VSV glycoprotein [Cote, M.; Misasi, J.; Ren, T.; Bruchez, A.; Lee, K.; Filone, C. M.; Hensley, L.; Li, Q.; Ory, D.; Chandran, K.; Cunningham, J. *Small molecule inhibitors reveal Niemann-Pick C1 is essential for Ebola virus infection*, Nature (2011) 477: 344-348; Chandran, K.; Sullivan, N. J.; Felbor, U.; Whelan, S. P.; Cunningham, J. M. *Endosomal proteolysis of the Ebola virus glycoprotein is necessary for infection*, Science 2005 308:1643-1645]. For select compounds, similar pseudotyped viruses expressing full-length EBOV [Genbank: AAB81004], SUDV [Genbank: YP_138523.1], MARV [Genbank: AAC40460] or Lassa virus [Genbank: NP_694870](a member of the Arenaviridae family of viruses) glycoproteins were also tested to further determine the specificity of action of our compounds against full length glycoproteins within and between different virus families. Vero cells (ATCC: CCL-81) were grown in clear 384 well plates (3000 cells/well) in DMEM media with 10% FBS, 1× Pen-Strep, non-essential amino acids and L-glutamine. After incubating overnight at 37° C. and 5% $CO_2$, cells were treated with compounds at desired concentrations and pseudotyped virus in assay media. VSV viruses expressing the full-length VSV glycoprotein, as well as all pseudotyped VSV viruses expressing the other viral glycoproteins, were generated in cultured HEK-293T cells (ATCC CRL-3216) grown in 10 cm dishes in DMEM supplemented with 10% FBS, 1× Pen-Strep, non-essential amino acids, L-glutamine and 500 μg/mL G418 antibiotic. When cells reached approximately 80% confluency, they were transfected with a mixture of 15 μg of the pCAGGS plasmid encoding one of the desired glycoproteins and 45 μl of PEI (polyethylenimine) transfection reagent. The cells were incubated with the solution for 5 hours at 37° C. at 5% $CO_2$. The cells were then washed and the mixture replaced with supplemented DMEM and incubated at 37° C. at 5% $CO_2$ for approximately 16-18 hours. Subsequently cells were infected with approximately 50 μl of VSV parent pseudotype virus lacking VSV glycoprotein and containing the gene for luciferase. The cells were infected for 1 hour, then washed 1× with PBS and incubated in supplemented media. 24 hours post-infection, supernatant was collected, aliquoted and stored at −80° C. For VSV-Luciferase pseudotypes, one aliquot was thawed and tested in a serial dilution for luminescence activity in Vero cells as described in the Luciferase assay protocol (below). Each of the viral supernatants generated was diluted (from 1:100 to 1:2000) to give similar luminescence signal/background values of ≥200 and stored at −80° C. as aliquots for later use. Assay media consisted of 50% Opti-MEM, 50% DMEM, with 1% FBS, Pen-Strep, non-essential amino acids and L-glutamine. Final DMSO concentration in the compound testing wells was kept ≤1% and control wells were treated with assay media and 1% DMSO. Cells were incubated for 24 hours at 37° C. and 5% $CO_2$. The compound-virus mixture was aspirated off the cells 24 hours post-infection and washed 1× with PBS. Cells were lysed using 20 μl of lysis buffer from a Luciferase kit diluted according to manufacturer's (Thermo Scientific) instructions. After incubating for approximately 20 minutes, 5 μl of cell lysate was transferred to an opaque white plate and mixed with 12.5 μl of Coelenterazine diluted in buffer. This mixture was incubated at room temperature for 10 minutes on a plate shaker, and then the luminescence was read using a plate reader (Beckman Coulter DTX 880 multimode detector with an emission of 535 nm) Luminescence signals were obtained for compound containing and control wells to determine % activity (inhibition of luciferase signal) for each compound.

To identify filovirus inhibitors a library collection of commercial compounds was initially tested at a 5 or 10 μM concentration against the EBOV pseudotype virus and selected compounds were tested against BDBV pseudotyped viruses to facilitate identification of broader-spectrum filovirus inhibitors. In order to distinguish between inhibitory activities of the compounds on filovirus cell entry from those potentially resulting from cellular cytotoxicity and/or inhibition of the replication of VSV viruses or luciferase reporter, selected compounds were tested in cytotoxicity assays (see cytotoxicity assay methods below) and/or against parent VSV virus, which expresses the native VSV glycoprotein (rather than a filovirus glycoprotein). Compounds exhibiting inhibitory activity against the EBOV and BDBV pseudotype viruses at concentrations (≥5-10 fold) below those observed in cytotoxicity and/or parental VSV assays were thereby identified as filovirus cell entry inhibitors. A number of these compounds were selected for prosecution in dose-response experiments and/or additional functional assays (see below) to further characterize their potency and antiviral spectrum of activity.

Tables 5-9. Examples. Example (Ex.) compounds from chemical series A, B, C, D, and E including their inhibitory activities ($EC_{50}$ values; the concentration at half-maximal inhibition) are shown against the indicated pseudotyped viruses (EBOV and BDBV) or parental VSV and/or for cytotoxicity, which was evaluated as the % cell viability (% CV) at 3, 5 and/or 10 μM compound or as the $CC_{50}$ (the concentration inducing half-maximal cell death). Vero cells were infected with dilutions of the viral stocks of the luciferase-expressing EBOV or BDBV pseudotyped viruses, or VSV native viruses (to rule out inhibitors of VSV non-glycoprotein gene products or the luciferase reporter) and incubated for 24 h with or without the example compounds; cells were lysed and luciferase activity read on a Beckman Coulter DTX 880 detector. Compound cytotoxicity was determined to rule out potential false-positive inhibitory activity on filovirus pseudotyped virus cell entry. Compounds exhibiting potential activity against the EBOV and BDBV pseudotyped viruses were more fully characterized in cytotoxicity and/or dose response experiments to confirm activity and determine EC$_{50}$ values. Compounds exhibiting activity against one or more pseudotyped filoviruses without comparable VSV activity or cytotoxicity, indicates they are of potential therapeutic interest to treat filovirus infection. Compounds were serially diluted and added to Vero cells (4000 cells/well) with final DMSO concentration maintained at 1% in growth media consisting of minimal essential media (MEM) with 2% FBS. The plates were incubated at 37° C. for 7 days, and then dead cells were removed by washing with Phosphate buffered saline (PBS). Cells were stained with neutral red vital dye for 1 hour and then de-stained with a solution of 50% ethanol/1% acetic acid solution. Absorbance was read at 540 nm and 690 nm on a Spectramax Plus 384 spectrophotometer. Data were analyzed as (540 nm-690 nm) and then compared to untreated controls to obtain % cell viability.

TABLE 5

| Ex. | Structure | Name | EC$_{50}$ (μM) EBOV | EC$_{50}$ (μM) BDBV | VSV % inh. at 5 μM | % cell viability at 3 μM | % cell viability at 5 μM | % cell viability at 10 μM |
|---|---|---|---|---|---|---|---|---|
| B1 | | N-(1-benzylpiperidin-4-yl)-3-phenyladamantane-1-carboxamide | 0.44 | 0.77 | <20 | ND | 62 | ND |
| B2 | | N-{[4-(2-methylpropyl)morpholin-2-yl]methyl}-3-phenyladamantane-1-carboxamide | 0.57 | 0.93 | ND | 100 | ND | 97 |
| B3 | | 1-phenyl-4-[(3-phenyl adamantan-1-yl)carbonyl]piperazine | 0.61 | >5 | ND | ND | 83 | ND |
| B4 | | N-[2-methyl-2-(morpholin-4-yl)propyl]-3-phenyladamantane-1-carboxamide | 0.69 | 2.69 | ND | 100 | ND | 114 |

TABLE 5-continued

| Ex. | Structure | Name | EC$_{50}$ (μM) EBOV | EC$_{50}$ (μM) BDBV | VSV % inh. at 5 μM | % cell viability at 3 μM | % cell viability at 5 μM | % cell viability at 10 μM |
|---|---|---|---|---|---|---|---|---|
| B5 | 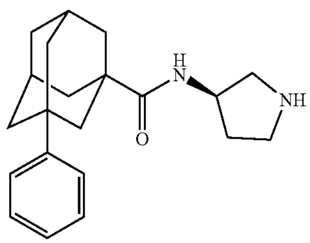 [SMILES: O=C(N[C@@H]1CCNC1)C12CC3CC(C1)CC(c1ccccc1)(C3)C2] | 3-phenyl-N-[(3R)-pyrrolidin-3-yl] adamantane-1-carboxamide | 0.79 | 0.56 | <20 | ND | 97 | ND |
| B6 | 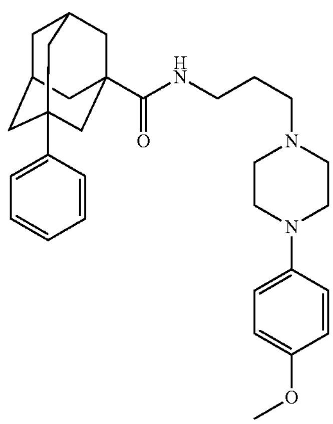 [SMILES: COc1ccc(N2CCN(CCCNC(=O)C34CC5CC(C3)CC(c3ccccc3)(C5)C4)CC2)cc1] | N-{3-[4-(4-methoxy phenyl)piperazin-1-yl] propyl}-3-phenyl adamantane-1-carboxamide | 0.92 | 1.6 | ND | 75 | ND | 25 |
| B7 | 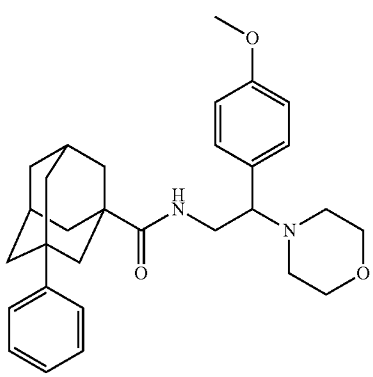 [SMILES: COc1ccc(C(CNC(=O)C23CC4CC(C2)CC(c2ccccc2)(C4)C3)N2CCOCC2)cc1] | N-[2-(4-methoxy phenyl)-2-(morpholin-4-yl)ethyl]-3-phenyl adamantane-1-carboxamide | 3.2 | 3.1 | ND | 112 | ND | 95 |
| B8 | 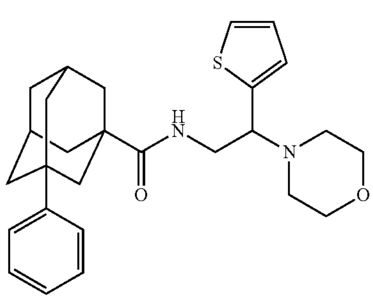 [SMILES: O=C(NCC(c1cccs1)N1CCOCC1)C12CC3CC(C1)CC(c1ccccc1)(C3)C2] | N-[2-(morpholin-4-yl)-2-(thiophen-2-yl)ethyl]-3-phenyladamantane-1-carboxamide | 3.6 | 4.6 | ND | 103 | ND | 90 |

TABLE 5-continued

| Ex. | Structure | Name | EC$_{50}$ (μM) EBOV | EC$_{50}$ (μM) BDBV | VSV % inh. at 5 μM | % cell viability at 3 μM | % cell viability at 5 μM | % cell viability at 10 μM |
|---|---|---|---|---|---|---|---|---|
| B9 | 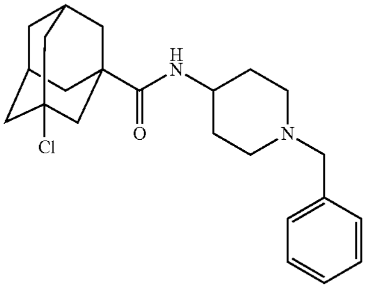 | N-(1-benzylpiperidin-4-yl)-3-chloro adamantane-1-carboxamide | 3.8 | 3.1 | ND | 112 | ND | 104 |
| B10 | 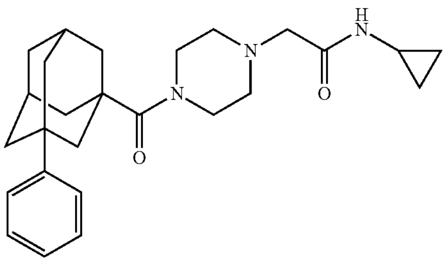 [SMILES: O=C(CN1CCN(C(=O)C23CC4CC(C2)CC(c2ccccc2)(C4)C3)CC1)NC1CC1] | N-cyclopropyl-2-{4-[(3-phenyladamantan-1-yl)carbonyl]piperazin-1-yl}acetamide | <5 | ND | <20 | ND | ND | ND |
| B11 | 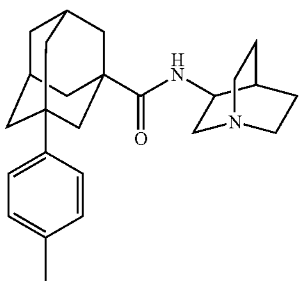 [SMILES: Cc1ccc(C23CC4CC(CC(C(=O)NC5CN6CCC5CC6)(C4)C2)C3)cc1] | N-{1-azabicyclo[2.2.2]octan-3-yl}-3-(4-methylphenyl)adamantane-1-carboxamide | <5 | ND | <20 | ND | 92 | ND |
| B12 | 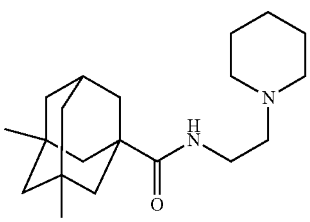 [SMILES: CC12CC3CC(C)(C1)CC(C(=O)NCCN1CCCCC1)(C3)C2] | 3,5-dimethyl-N-[2-(piperidin-1-yl)ethyl]adamantane-1-carboxamide | 50 | ND | <20 | ND | 90 | ND |
| B13 | 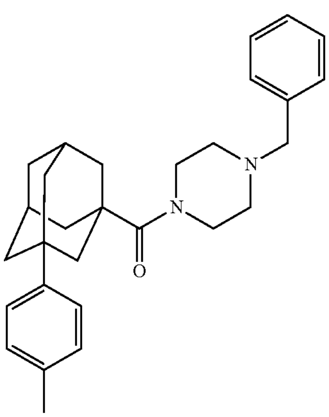 [SMILES: Cc1ccc(C23CC4CC(CC(C(=O)N5CCN(Cc6ccccc6)CC5)(C4)C2)C3)cc1] | 1-benzyl-4-{[3-(4-methylphenyl)adamantan-1-yl]carbonyl}piperazine | >5 | >5 | <20 | ND | ND | ND |

TABLE 5-continued

| Ex. | Structure | Name | EC$_{50}$ (μM) EBOV | EC$_{50}$ (μM) BDBV | VSV % inh. at 5 μM | % cell viability at 3 μM | % cell viability at 5 μM | % cell viability at 10 μM |
|---|---|---|---|---|---|---|---|---|
| B14 | 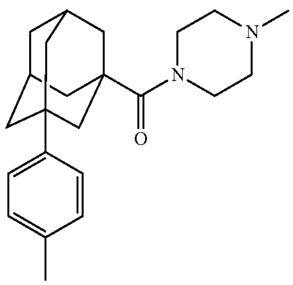 [SMILES: Cc1ccc(C23CC4CC(CC(C(=O)N5CCN(C)CC5)(C4)C2)C3)cc1] | 1-methyl-4-{[3-(4-methylphenyl)adamantan-1-yl]carbonyl}piperazine | 5.6 | ND | <20 | ND | 95 | ND |
| B15 | 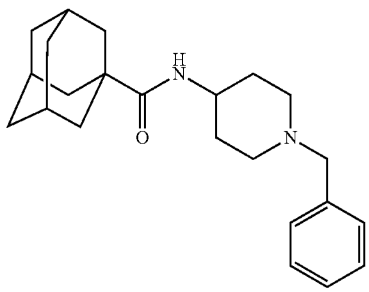 [SMILES: O=C(NC1CCN(Cc2ccccc2)CC1)C12CC3CC(CC(C3)C1)C2] | N-(1-benzylpiperidin-4-yl)adamantane-1-carboxamide | 5.9 | 3.9 | ND | 99 | ND | 98 |
| B16 | 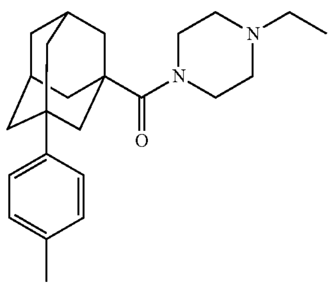 [SMILES: CCN1CCN(C(=O)C23CC4CC(C2)CC(c2ccc(C)cc2)(C4)C3)CC1] | 1-ethyl-4-{[3-(4-methylphenyl)adamantan-1-yl]carbonyl}piperazine | 1.0 | 0.9 | ND | ND | ND | ND |
| B17 | 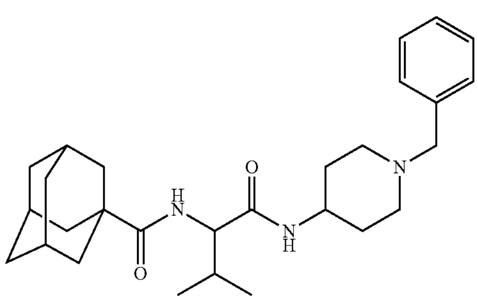 [SMILES: CC(C)C(NC(=O)C12CC3CC(CC(C3)C1)C2)C(=O)NC1CCN(Cc2ccccc2)CC1] | 2-(adamantan-1-ylformamido)-N-(1-benzylpiperidin-4-yl)-3-methylbutanamide | >5 | <5 | ND | ND | ND | ND |
| B18 | 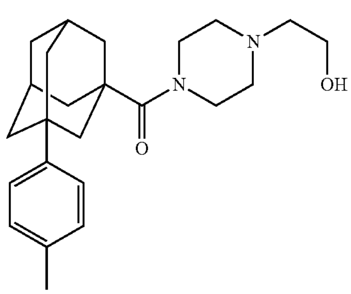 [SMILES: Cc1ccc(C23CC4CC(CC(C(=O)N5CCN(CCO)CC5)(C4)C2)C3)cc1] | 2-(4-{[3-(4-methylphenyl)adamantan-1-yl]carbonyl}piperazin-1-yl)ethan-1-ol | >5 | >5 | ND | ND | ND | ND |

TABLE 5-continued

| Ex. | Structure | Name | EC$_{50}$ (μM) EBOV | EC$_{50}$ (μM) BDBV | VSV % inh. at 5 μM | % cell viability at 3 μM | % cell viability at 5 μM | % cell viability at 10 μM |
|---|---|---|---|---|---|---|---|---|
| B19 | 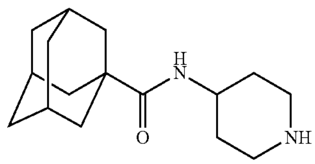 [SMILES: O=C(NC1CCNCC1)C12CC3CC(CC(C3)C1)C2] | N-(piperidin-4-yl)adamantane-1-carboxamide | 1.1 | >1 | ND | ND | ND | ND |

TABLE 6

| Ex. | EC$_{50}$ (μM) EBOV | EC$_{50}$ (μM) BDBV | CC$_{50}$ (μM) |
|---|---|---|---|
| A1 | 0.22 | 0.25 | 5.8 |
| A2 | 0.30 | 0.39 | 8.5 |
| A3 | 0.03 | 1.24 | >3 |
| A4 | 0.19 | 1.24 | >3 |
| A5 | 1.4 | 3.9 | >3 |
| A6 | 0.21 | 0.25 | 16.8 |
| A7 | 0.48 | 0.84 | >10 |
| A8 | 0.19 | 0.22 | >10 |
| A9 | 0.23 | 0.29 | 10.8 |
| A10 | 0.24 | 0.21 | 6.9 |
| A11 | 0.2 | 0.23 | ND |
| A12 | 0.36 | 0.43 | 2.5 |
| A13 | 0.32 | 0.32 | 2.3 |
| A14 | 0.2 | 0.23 | 6.2 |
| A15 | 1.7 | 2.6 | >10 |
| A16 | 0.11 | 0.35 | 12.9 |
| A17 | 0.93 | 0.48 | >10 |
| A18 | >10 | >10 | ND |
| A19 | 0.29 | 0.44 | 3.9 |
| A20 | 0.49 | 0.41 | 10.6 |
| A21 | >10 | >10 | ND |
| A22 | 0.26 | 0.22 | ND |
| A23 | 0.21 | 0.17 | ND |
| A24 | 0.29 | 0.29 | 7.2 |
| A25 | 0.45 | 0.19 | >10 |
| A26 | 0.12 | 0.09 | 34 |
| A27 | 0.28 | 0.14 | >10 |
| A28 | >10 | >10 | >10 |
| A29 | 0.34 | 0.27 | 5.8 |
| A30 | 0.34 | 0.22 | 7.5 |
| A31 | >10 | >10 | >10 |
| A32 | 0.2 | 0.26 | 1.6 |
| A33 | 0.32 | 0.3 | 2.2 |
| A34 | 0.17 | 0.22 | 1.1 |
| A35 | 0.28 | 0.22 | >10 |
| A36 | 0.51 | 0.3 | 4.3 |
| A37 | 0.23 | 0.24 | >10 |
| A38 | 0.25 | 0.19 | >10 |
| A39 | 0.51 | 0.21 | 19.1 |
| A40 | 0.31 | 0.16 | ND |
| A41 | 0.103 | 0.18 | 13.6 |
| A42 | 0.121 | 0.19 | 13.9 |
| A43 | 0.14 | 0.08 | 1.2 |
| A44 | 0.09 | 0.19 | 11.0 |
| A45 | 0.06 | 0.14 | 7.2 |
| A46 | 0.18 | 0.21 | 13.5 |
| A47 | 0.07 | 0.17 | 36.2 |
| A48 | 1.04 | 2.0 | 54.9 |
| A49 | 0.21 | 0.29 | 10 |
| A50 | 2.9 | 3.3 | 54.9 |
| A51 | 9.0 | >10 | 10 |
| A52 | 4.9 | 4.0 | >10 |
| A53 | 9.2 | 9.0 | ND |
| A54 | 4.0 | 10.0 | >10 |
| A55 | 2.9 | 2.6 | >10 |
| A56 | 3.1 | 10.0 | >10 |
| A57 | 2.9 | >10 | ND |
| A58 | 0.65 | 8.0 | >10 |
| A59 | 1.1 | 1.5 | ND |
| A60 | 0.21 | 0.17 | ND |
| A61 | 0.14 | 0.08 | >10 |
| A62 | 0.16 | 0.11 | 30 |
| A63 | 0.08 | 0.08 | >10 |
| A64 | 0.71 | 0.18 | >10 |
| A65 | 0.09 | 0.09 | >10 |
| A66 | 0.16 | 0.10 | >10 |
| A67 | 0.39 | 0.41 | >10 |
| A68 | 0.035 | 0.16 | >10 |
| A69 | 0.22 | 0.24 | 22.4 |
| A70 | 0.49 | 0.19 | >50 |
| A71 | 0.13 | 0.13 | 4.6 |
| A72 | 0.28 | 0.29 | 17.4 |
| A73 | 0.32 | 0.37 | 13.0 |
| A74 | 1.72 | >1 | 14.0 |
| A75 | 0.3 | 0.3 | 17.7 |
| A76 | 1.05 | 1.06 | ND |
| A77 | 0.12 | 0.22 | 8.7 |
| A78 | 0.02 | 0.09 | ND |
| A79 | 0.26 | 0.29 | 4.2 |
| A80 | 0.01 | 0.05 | 10.0 |
| A81 | 0.18 | 0.11 | 13.9 |
| A82 | 0.13 | 0.16 | 4.5 |
| A83 | 0.1 | 0.18 | 12.9 |
| A84 | 0.146 | 0.11 | 9.0 |
| A85 | 0.013 | 0.096 | 12.1 |
| A86 | 0.155 | 0.18 | 3.9 |
| A87 | 0.14 | 0.19 | 1.4 |
| A88 | 0.36 | 0.50 | 12.5 |
| A89 | 0.25 | 0.88 | 40.7 |
| A90 | 0.05 | 0.20 | 59.0 |
| A91 | 0.12 | 0.19 | 17.4 |
| A92 | 0.19 | 0.7 | 10.8 |
| A93 | 0.21 | 0.36 | 12.2 |
| A94 | 1.0 | 0.88 | 5.1 |
| A95 | 0.49 | 0.97 | 23.1 |
| A96 | 0.03 | 0.08 | 11.6 |
| A97 | 0.34 | 0.25 | 100 |
| A98 | 1.16 | 0.58 | 11.3 |
| A99 | 0.69 | 0.19 | 26.7 |
| A100 | 0.22 | 0.18 | 6.3 |
| A101 | >1 | >1 | ND |
| A102 | 0.12 | 0.21 | 29 |
| A103 | 0.07 | 0.28 | 7.9 |
| A104 | 0.06 | 0.22 | 66 |
| A105 | 0.14 | 1.05 | 35 |
| A106 | >1 | >1 | ND |
| A107 | 0.046 | 0.30 | 14.7 |
| A108 | 0.025 | 0.21 | 16.5 |
| A109 | 0.080 | 0.93 | 37 |
| A110 | 0.021 | 0.19 | 17.5 |
| A111 | 0.018 | 0.15 | 10.7 |
| A112 | 0.037 | 0.26 | 7.2 |
| A113 | >1 | >1 | ND |
| A114 | >1 | >1 | ND |

TABLE 6-continued

| | EC$_{50}$ (µM) | | CC$_{50}$ |
|---|---|---|---|
| Ex. | EBOV | BDBV | (µM) |
| A115 | 0.98 | >1 | 59 |
| A116 | >1 | >1 | >100 |
| A201 | 1.1 | >1 | 16.4 |
| A202 | 0.59 | 0.96 | 41.5 |
| A203 | 0.91 | 1.02 | 3.9 |
| A204 | >1 | >1 | >100 |
| A205 | >1 | >1 | 37 |
| C1 | 0.18 | 0.206 | 5.8 |
| C2 | 0.25 | 0.2 | 3.6 |
| C3 | 0.234 | 0.21 | 1.8 |
| C4 | 0.14 | 0.4 | 7.2 |
| C5 | 0.14 | 0.55 | 14.3 |
| C6 | 0.12 | 0.64 | 3.8 |
| C7 | 0.47 | 0.77 | 4.1 |
| C8 | 0.14 | 0.29 | 1.3 |
| C9 | 0.66 | 0.99 | 8.3 |
| C10 | 0.19 | 0.17 | 3.6 |
| C11 | 0.18 | 0.11 | 3.6 |
| C12 | 0.27 | 0.19 | 1.2 |
| C13 | 0.17 | 0.11 | 3.6 |
| C14 | >1 | 1 | 3.9 |
| C15 | >1 | 0.98 | 3.9 |
| C16 | 0.98 | 0.75 | 8.0 |
| C17 | >1 | 1.2 | ND |
| C18 | 0.08 | 0.26 | 2.7 |
| C19 | 0.11 | 0.20 | >100 |
| E1 | >1 | 0.77 | 18.3 |
| E2 | 0.87 | 0.61 | 12.6 |
| E3 | >1 | 0.27 | 36.3 |
| E4 | 1.08 | 0.79 | 23.1 |
| E5 | 0.68 | 0.23 | 13.3 |
| E6 | 0.71 | 0.20 | 11.9 |

TABLE 7

| Ex. | Structure | Name | EC$_{50}$(µM) EBOV | BDBV | CC$_{50}$ (µM) |
|---|---|---|---|---|---|
| D1 | | 1-{[3-(4-methylphenyl)adamantan-1-yl]}methyl}piperidine | 1.3 | 0.61 | >10 |
| D2 | | (adamantan-1-ylmethyl)[3-(2-tert-butyl-4-methoxyphenoxy)-2-hydroxypropyl]amine | 0.68 | 0.62 | ND |
| D3 | | [1-(adamantan-1-yl)propyl]({2-hydroxy-3[2-(propan-2-yl)phenoxy]propylamine | 1.29 | ND | ND |
| D4 | | [2-(adamantan-1-yl)ethyl][(4-methoxyphenyl)methyl]amine | 2.19 | 2.72 | >10 |
| D5 | | 1-(adamantan-1-ylmethyl)-4-(2-ethoxyethyl)piperazine | 4.6 | 1.8 | >10 |

TABLE 7-continued

| Ex. | Structure | Name | EC50(μM) EBOV | EC50(μM) BDBV | CC50 (μM) |
|---|---|---|---|---|---|
| D6 | 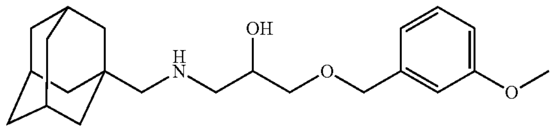 [SMILES: COc1cccc(COCC(O)CNCC23CC4CC(CC(C4)C2)C3)c1]  | (adamantan-1-ylmethyl)({2-hydroxy-3-[(3-methoxyphenyl)methoxy]propyl}amine | 3.45 | 1.5 | ND |
| D7 | 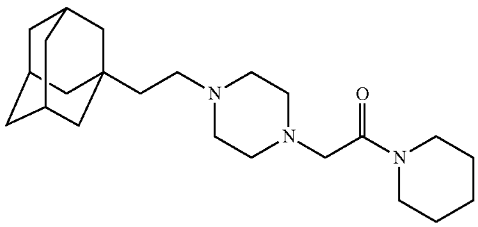 [SMILES: O=C(CN1CCN(CCC23CC4CC(CC(C4)C2)C3)CC1)N1CCCCC1]  | 2-{4-[2-(adamantan-1-yl)ethyl]piperazin-1-yl}-1-(piperidin-1-yl)ethan-1-one | 6.0 | 2.6 | ND |
| D8 | 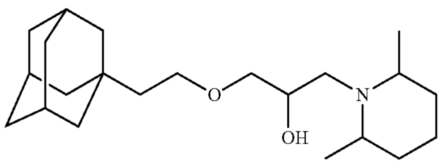 [SMILES: CC1CCCC(C)N1CC(O)COCCC12CC3CC(CC(C3)C1)C2]  | 1-[2-(adamantan-1-yl)ethoxy]-3-(2,6-dimethylpiperidin-1-yl)propan-2-ol | 0.21 | 0.08 | 3.8 |
| D9 | 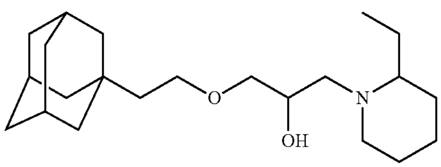 [SMILES: CCC1CCCCN1CC(O)COCCC12CC3CC(CC(C3)C1)C2]  | 1-[2-(adamantan-1-yl)ethoxy]-3-(2-ethylpiperidin-1-yl)propan-2-ol hydrochloride | 0.25 | 0.21 | ND |
| D10 | 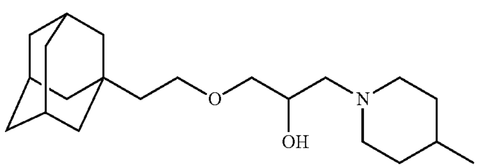 [SMILES: CC1CCN(CC(O)COCCC23CC4CC(CC(C4)C2)C3)CC1]  | 1-[2-(adamantan-1-yl)ethoxy]-3-(4-methylpiperidin-1-yl)propan-2-ol | 0.32 | 0.14 | 15.5 |
| D11 | 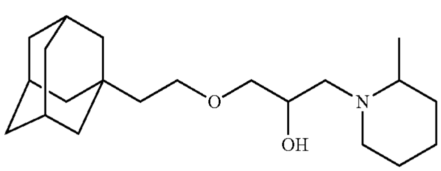 [SMILES: CC1CCCCN1CC(O)COCCC12CC3CC(CC(C3)C1)C2]  | 1-[2-(adamantan-1-yl)ethoxy]-3-(2-methyl piperidin-1-yl)propan-2-ol | 0.44 | 0.19 | 7.5 |
| D12 | 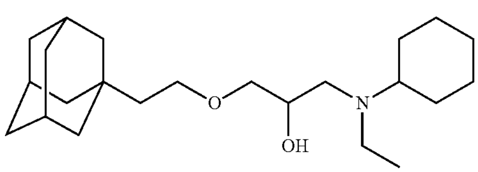 [SMILES: CCN(CC(O)COCCC12CC3CC(CC(C3)C1)C2)C1CCCCC1]  | N-{3-[2-(adamantan-1-yl)ethoxy]-2-hydroxypropyl}-N-ethylcyclohexanamine | 0.61 | 0.49 | >3 |
| D13 | 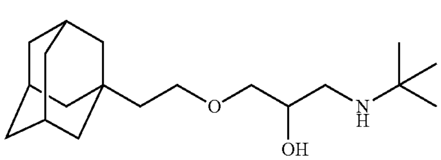 [SMILES: CC(C)(C)NCC(O)COCCC12CC3CC(CC(C3)C1)C2]  | {3-[2-(adamantan-1-yl)ethoxy]-2-hydroxypropyl}(tert-butyl)amine | 0.63 | 0.67 | >10 |
| D14 | 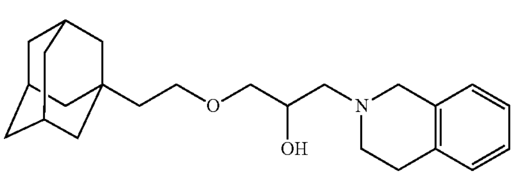 [SMILES: OC(COCCC12CC3CC(CC(C3)C1)C2)CN1CCc2ccccc2C1]  | 1-[2-(adamantan-1-yl)ethoxy]-3-(1,2,3,4-tetrahydroisoquinolin-2-yl)propan-2-ol | 2.1 | 2.67 | ND |

TABLE 7-continued

| Ex. | Structure | Name | EC$_{50}$(μM) EBOV | EC$_{50}$(μM) BDBV | CC$_{50}$ (μM) |
|---|---|---|---|---|---|
| D15 | 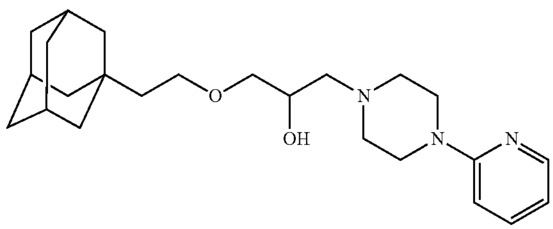 [SMILES: OC(COCCC12CC3CC(CC(C3)C1)C2)CN1CCN(c2ccccn2)CC1] | 1-[2-(adamantan-1-yl)ethoxy]-3-[4-(pyridin-2-yl)piperazin-1-yl]propan-2-ol | 2.9 | 2.8 | ND |
| D16 | 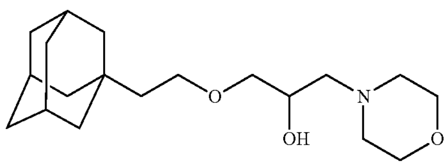 [SMILES: OC(COCCC12CC3CC(CC(C3)C1)C2)CN1CCOCC1] | 1-[2-(adamantan-1-yl)ethoxy]-3-(morpholin-4-yl)propan-2-ol | 3.8 | 3.2 | >10 |
| D17 | 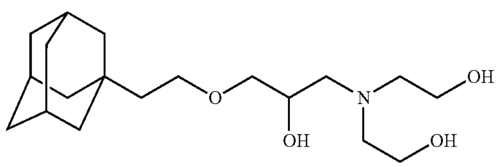 [SMILES: OCCN(CCO)CC(O)COCCC12CC3CC(CC(C3)C1)C2] | 2-({3-[2-(adamantan-1yl)ethoxy]-2-hydroxypropyl}(2-hydroxyethyl)amino)ethan-1-ol | 8.8 | 0.6 | ND |
| D18 | 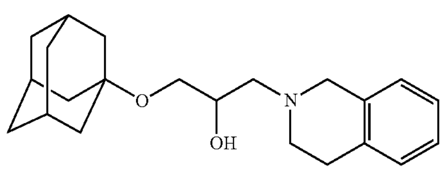 [SMILES: OC(COC12CC3CC(CC(C3)C1)C2)CN1CCc2ccccc2C1] | 1-(adamantan-1-yloxy)-3-(1,2,3,4-tetrahydroisoquinolin-2-yl)propan-2-ol | >10 | ND | ND |
| D19 | 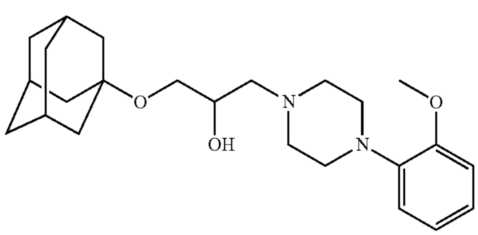 [SMILES: COc1ccccc1N1CCN(CC(O)COC23CC4CC(CC(C4)C2)C3)CC1] | 1-(adamantan-1-yloxy)-3-[4-(2-methoxyphenyl)piperazin-1-yl]propan-2-ol | >10 | ND | ND |
| D20 | 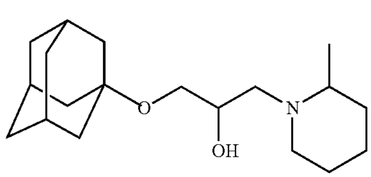 | 1-(adamantan-1-yloxy)-3-(2-methylpiperidin-1-yl)propan-2-ol | >10 | ND | ND |
| D21 | 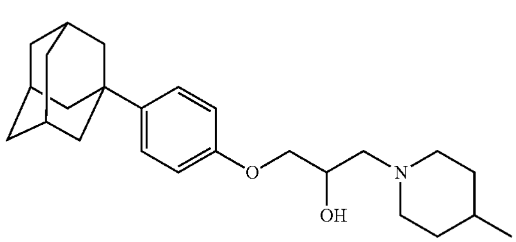 [SMILES: CC1CCN(CC(O)COc2ccc(C34CC5CC(CC(C5)C3)C4)cc2)CC1] | 1-[4-(adamantan-1-yl)phenoxy]-3-(4-methylpiperidin-1-yl)propan-2-ol | 0.05 | 0.11 | 1.1 |

TABLE 7-continued

| Ex. | Structure | Name | EC₅₀(μM) EBOV | EC₅₀(μM) BDBV | CC₅₀ (μM) |
|---|---|---|---|---|---|
| D22 | 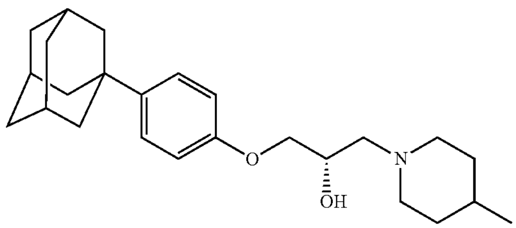 [SMILES: CC1CCN(C[C@H](O)COc2ccc(C34CC5CC(CC(C5)C3)C4)cc2)CC1] | (2S)-1[4-(adamantan-1-yl)phenoxy]-3-(4-methylpiperidin-1-yl)propan-2-ol | 0.052 | 0.085 | 8.5 |
| D23 | 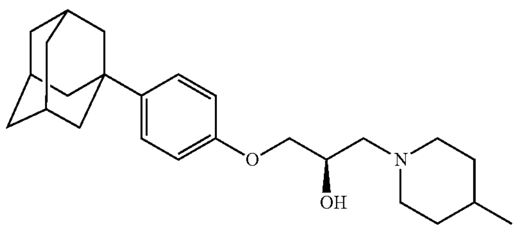 [SMILES: CC1CCN(C[C@@H](O)COc2ccc(C34CC5CC(CC(C5)C3)C4)cc2)CC1] | (2R)-1-[4-(adamantan-1-yl)phenoxy]-3-(4-methylpiperidin-1-yl)propan-2-ol | 0.06 | 0.077 | 3.9 |
| D24 | 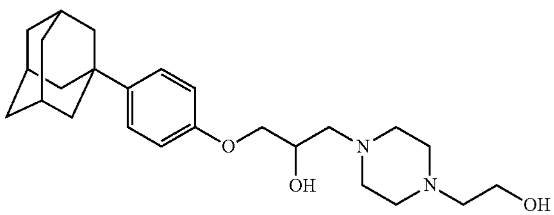 [SMILES: OCCN1CCN(CC(O)COc2ccc(C34CC5CC(CC(C5)C3)C4)cc2)CC1] | 1[4-(adamantan-1-yl)phenoxy]-3[4-(2-hydroxyethyl)piperazin-1-yl]propan-2-ol | 0.08 | 0.27 | 4.3 |
| D25 | 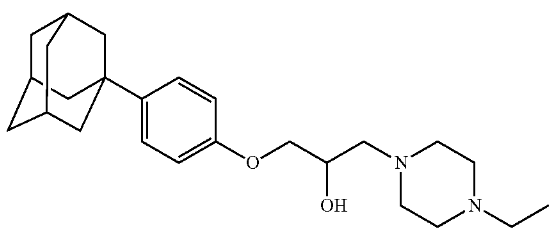 [SMILES: CCN1CCN(CC(O)COc2ccc(C34CC5CC(CC(C5)C3)C4)cc2)CC1] | 1-[4-(adamantan-1-yl)phenoxy]-3-(4-ethylpiperazin-1-yl)propan-2-ol | 0.09 | 0.24 | 3.1 |
| D26 | 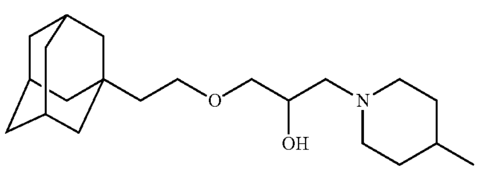 [SMILES: CC1CCN(CC(O)COCCC23CC4CC(CC(C4)C2)C3)CC1] | 1-[4-(adamantan-1-yl)phenoxy]-3-(piperidin-1-yl)propan-2-ol | 0.11 | 0.75 | 2.3 |
| D27 | 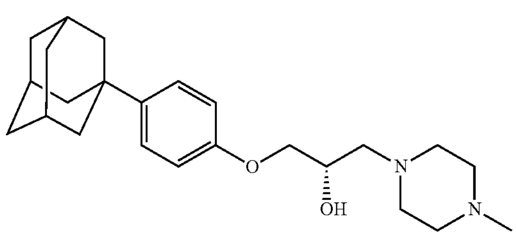 | ((2S)-1-[4-(adamantan-1-yl)phenoxy]-3-(4-methylpiperazin-1-yl)propan-2-ol | 0.13 | 0.19 | 3.5 |
| D28 | 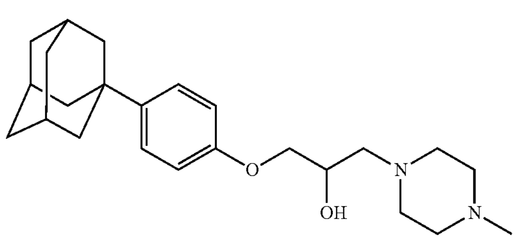 [SMILES: CN1CCN(CC(O)COc2ccc(C34CC5CC(CC(C5)C3)C4)cc2)CC1] | 1-[4-(adamantan-1-yl)phenoxy]-3-(4-methylpiperazin-1-yl)propan-2-ol | 0.15 | 0.21 | 4.2 |

TABLE 7-continued

| Ex. | Structure | Name | EC₅₀(μM) EBOV | EC₅₀(μM) BDBV | CC₅₀ (μM) |
|---|---|---|---|---|---|
| D29 | 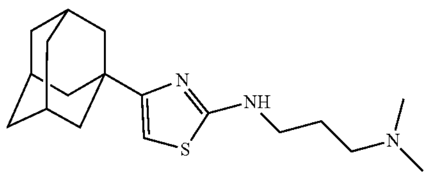 [SMILES: CN(C)CCCNc1nc(C23CC4CC(CC(C4)C2)C3)cs1] | (3-{[4-(adamantan-1-yl)-1,3-thiazol-2-yl]amino}propyl)dimethylamine | 0.17 | 0.16 | 9.4 |
| D30 | 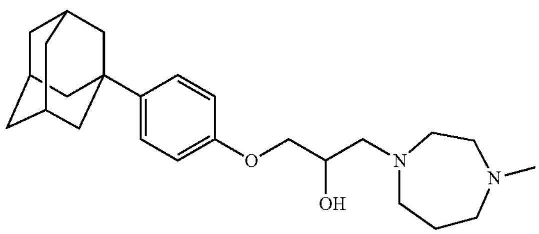 [SMILES: CN1CCCN(CC(O)COc2ccc(C34CC5CC(CC(C5)C3)C4)cc2)CC1] | 1-[4-(adamantan-1-yl)phenoxy]-3-(4-methyl-1,4-diazepan-1-yl)propan-2-ol | 0.19 | 0.47 | ND |
| D31 | 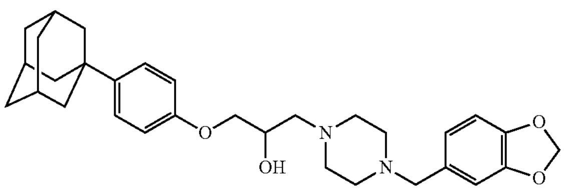 [SMILES: OC(COc1ccc(C23CC4CC(CC(C4)C2)C3)cc1)CN1CCN(Cc2ccc3c(c2)OCO3)CC1] | 1-[4-(adamantan-1-yl)phenoxy]-3-[4-(2H-1,3-benzodioxol-5-ylmethyl)piperazin-1-yl]propan-2-ol | 0.23 | 1.03 | ND |
| D32 | 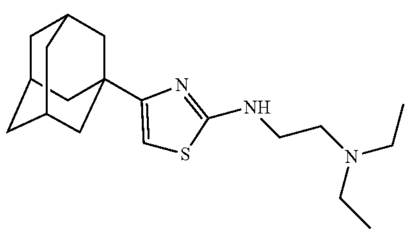 [SMILES: CCN(CC)CCNc1nc(C23CC4CC(CC(C4)C2)C3)cs1] | (2-{[4-(adamantan-1-yl)-1,3-thiazol-2-yl]amino}ethyl)diethylamine | 0.23 | 0.17 | 9.0 |
| D33 | 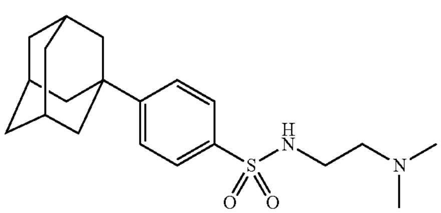 [SMILES: CN(C)CCNS(=O)(=O)c1ccc(C23CC4CC(CC(C4)C2)C3)cc1] | 4-(adamantan-1-yl)-N-[2-(dimethylamino)ethyl]benzene-1-sulfonamide | 0.44 | 0.42 | ND |
| D34 | 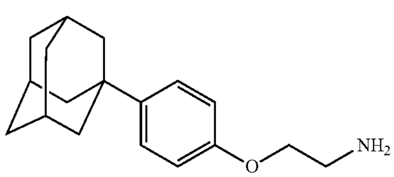 [SMILES: NCCOc1ccc(C23CC4CC(CC(C4)C2)C3)cc1] | 1-[4-(2-aminoethoxy)phenyl]adamantane | 0.43 | 1.16 | 3.7 |
| D35 | 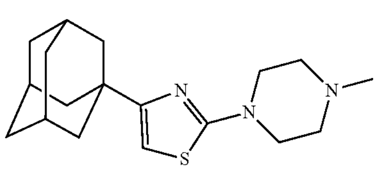 [SMILES: CN1CCN(c2nc(C34CC5CC(CC(C5)C3)C4)cs2)CC1] | 1-[4-(adamantan-1-yl)-1,3-thiazol-2-yl]-4-methylpiperazine | 0.44 | 0.62 | ND |

TABLE 7-continued

| Ex. | Structure | Name | EC₅₀(μM) EBOV | EC₅₀(μM) BDBV | CC₅₀ (μM) |
|---|---|---|---|---|---|
| D36 | 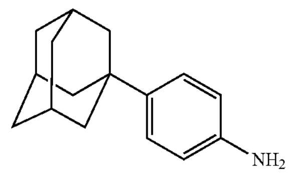 [SMILES: Nc1ccc(C23CC4CC(CC(C4)C2)C3)cc1] | 4-(adamantan-1-yl)aniline | 4.2 | 6.2 | >10 |
| D37 | 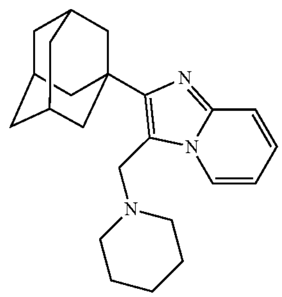 [SMILES: c1ccn2c(CN3CCCCC3)c(C34CC5CC(CC(C5)C3)C4)nc2c1] | 1-{[2-(adamantan-1-yl)imidazo1,2-a]pyridin-3-yl]methyl}piperidine | 8.9 | 3.2 | ND |
| D38 | 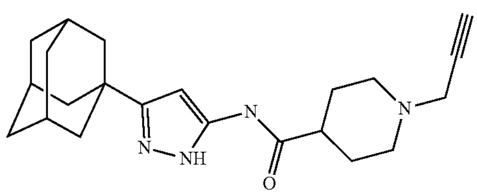 [SMILES: C#CCN1CCC(C(=O)Nc2cc(C34CC5CC(CC(C5)C3)C4)n[nH]2)CC1] | N-[5-(adamantan-1-yl)-1H-pyrazol-3-yl]-1-(prop-2-yn-1-yl)piperidine-4-carboxamide | 3.7 | 6.8 | ND |
| D39 | 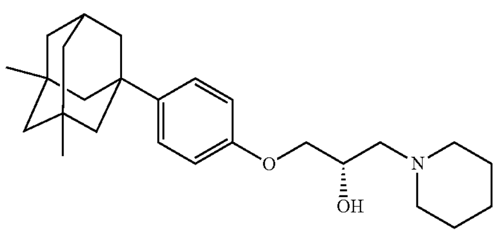 [SMILES: CC12CC3CC(C)(C1)CC(c1ccc(OC[C@@H](O)CN4CCCCC4)cc1)(C3)C2] | (2S)-1-[4-(3,5-dimethyladamantan-1-yl)phenoxy]-3-(piperidin-1-yl)propan-2-ol | 0.12 | 0.25 | 3.2 |
| D40 | 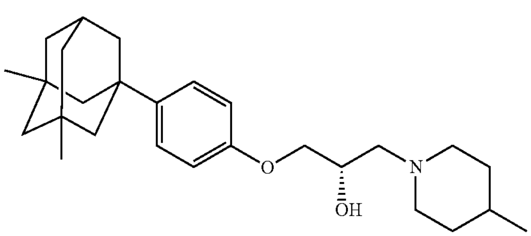 | (2S)-1-[4-(3,5-dimethyladamantan-1-yl)phenoxy]-3-(4-methylpiperidin-1-yl)propan-2-ol | 0.19 | 0.46 | 2.5 |
| D41 | 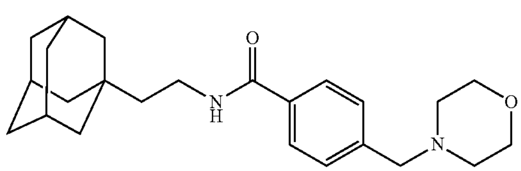 [SMILES: O=C(NCCC12CC3CC(CC(C3)C1)C2)c1ccc(CN2CCOCC2)cc1] | N-[2-(adamantan-1-yl)ethyl]-4-(morpholin-4-ylmethyl)benzamide | 2.3 | 9.7 | >3 |
| D42 | 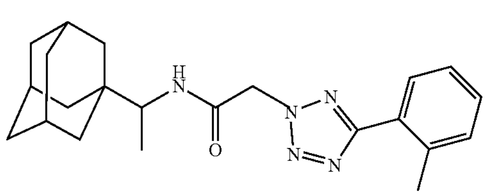 | N-[1-(adamantan-1-yl)ethyl]-2-[5-(2-methylphenyl)-2H-1,2,3,4-tetrazol-2-yl]acetamide | 3.2 | 3.9 | >10 |

TABLE 7-continued

| Ex. | Structure | Name | EC$_{50}$(μM) EBOV | EC$_{50}$(μM) BDBV | CC$_{50}$ (μM) |
|---|---|---|---|---|---|
| D43 | 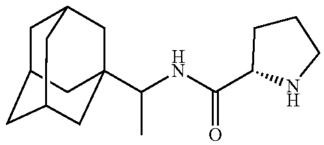 [SMILES: CC(NC(=O)[C@@H]1CCCN1)C12CC3CC(CC(C3)C1)C2] | (2R)-N-[1-(adamantan-1-yl)ethyl] pyrrolidine-2-carboxamide | 4.6 | 2.5 | ND |
| D44 | 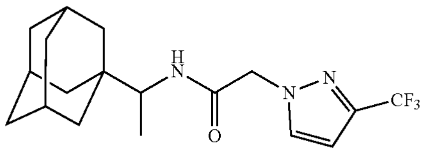 [SMILES: CC(NC(=O)Cn1ccc(C(F)(F)F)n1)C12CC3CC(CC(C3)C1)C2] | N[1-(adamantan-1-yl)ethyl]-2-[3-(trifluoromethyl)-1H-pyrazol-1-yl] acetamide | 5.8 | 2.7 | >10 |
| D45 | 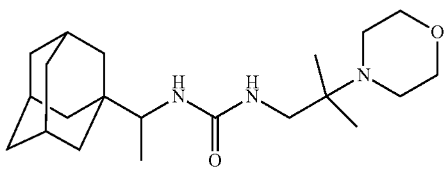 [SMILES: CC(NC(=O)NCC(C)(C)N1CCOCC1)C12CC3CC(CC(C3)C1)C2] | 1-[1-(adamantan-1-yl)ethyl]-3-[2-methyl-2-(morpholin-4-yl) propyl]urea | 6.5 | 4.6 | >10 |
| D46 | 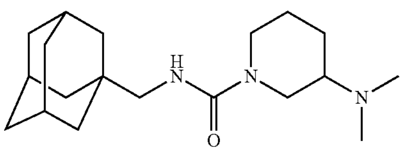 [SMILES: CN(C)C1CCCN(C(=O)NCC23CC4CC(CC(C4)C2)C3)C1] | N-(adamantan-1-ylmethyl)-3-(dimethylamino)piperidine-1-carboxamide | 6.7 | 4.3 | >10 |
| D47 | 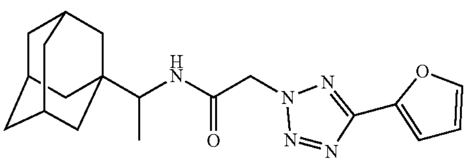 [SMILES: CC(NC(=O)Cn1nnc(-c2ccco2)n1)C12CC3CC(CC(C3)C1)C2] | N-[1-(adamantan-1-yl)ethyl]-2-[5-(furan-2-yl)-2H-1,2,3,4-tetrazol-2-yl]acetamide | 9.3 | 5.4 | >10 |

As mentioned above, the EBOV and BDBV glycoproteins expressed in pseudotyped virus assays were missing the mucin domain given that it can contribute to cellular toxicity [Francica, J. R.; Matukonis, M. K.; Bates, P. *Requirements for cell rounding and surface protein down-regulation by Ebola virus glycoprotein*, Virology (2009), 383:237-247]. However, because native Ebolaviruses express glycoproteins that include the mucin domain, we further tested the compounds against native full-length EBOV glycoproteins in pseudotyped viruses (also expressing the *Renilla* luciferase gene). A representative subset of the compounds exhibiting potent inhibition of the EBOV and BDBV pseudotyped viruses relative to parental VSV (and/or cytotoxicity) were therefore tested against pseudotyped viruses expressing full-length EBOV and SUDV GP to confirm activity against these full length filovirus glycoproteins. In addition, these compounds were also tested against a VSV pseudotyped virus expressing full-length LASV glycoprotein to further define the antiviral activity spectrum of the compounds against both distinct filovirus species as well as other virus families expressing other class I fusion glycoproteins (LASV). As shown in Table 8, compounds of the invention exhibited inhibition of Ebolavirus glycoprotein pseudotyped viruses but did not exhibit similar inhibition of the parental VSV or pseudotyped LASV viruses (data are a average+/− sd, n=3 or 4). However, the compound inhibition EC$_{50}$ values obtained against full-length EBOV and SUDV pseudotyped viruses are comparable to those found for the mucin-deleted EBOV and BDBV pseudotyped viruses. These data further indicate that compounds of the series described herein are inhibitors of filovirus cell entry and as such are inhibitors of filovirus infection.

TABLE 8

| | EC$_{50}$ (μM) Pseudotype Assays | | | | | | | Cytotox |
|---|---|---|---|---|---|---|---|---|
| Ex. | EBOV | *EBOV_FL | BDBV | SUDV | *MARV | VSV | LASV | CC$_{50}$ uM |
| D8 | 0.21 | 0.30 | 0.08 | ND | 0.59 | 3.8 | 4.9 | 4 |
| A60 | 0.26 | 0.28 | 0.21 | ND | 7.9 | >10 | >10 | >10 |
| A68 | 0.04 | 0.04 | 0.17 | 0.41 | 2.8 | >10 | >10 | >10 |
| A78 | 0.02 | 0.05 | 0.09 | 0.21 | 3.5 | >10 | >10 | >10 |
| A80 | 0.02 | 0.04 | 0.06 | 0.4 | 1.1 | >10 | >10 | >10 |
| D32 | 0.23 | 0.20 | 0.17 | ND | 0.61 | >10 | >10 | >10 |

TABLE 8-continued

| | EC$_{50}$ (µM) Pseudotype Assays | | | | | | | Cytotox |
|---|---|---|---|---|---|---|---|---|
| Ex. | EBOV | *EBOV_FL | BDBV | SUDV | *MARV | VSV | LASV | CC$_{50}$ uM |
| D24 | 0.09 | 0.08 | 0.27 | 2.43 | >10 | >10 | >10 | >10 |
| D29 | 0.17 | 0.18 | 0.16 | 1.44 | 0.66 | >10 | >10 | >10 |
| A45 | 0.061 | 0.12 | 0.16 | ND | 0.29 | >10 | >10 | >10 |
| D21 | 0.05 | 0.11 | 0.11 | 0.41 | 0.36 | 3.7 | 3.0 | 3.7 |
| A26 | 0.12 | 0.16 | 0.09 | ND | 2.7 | >10 | >10 | >10 |
| A63 | 0.08 | 0.04 | 0.08 | ND | 2.8 | >10 | >10 | >10 |

*EBOV_FL: full-length Ebola Zaire GP, MARV, LASV and VSV are also full-length glycoproteins As described above, the amino acid homology of full-length MARV and Ebolavirus glycoproteins is ≥30%. To better understand the potential spectrum of activity within the Filoviridae family, including the potential activity of compounds against filoviruses more distantly related than EBOV, BDBV and SUDV the compounds listed in Table 8 were tested against the full-length Marburgvirus (MARV) pseudotyped virus. In contrast to the nearly equivalent activities and EC$_{50}$ values observed against EBOV, BDBV and SUDV pseudotyped viruses, most of the compounds exhibited less inhibition against pseudotyped viruses expressing the more distantly related MARV GP. However, at least some compounds inhibited MARV pseudotyped virus with sub-micromolar EC$_{50}$ concentrations (e.g., compounds D8, D32, D29, A45 and D21). Some compounds such as D8 and D21 appeared to inhibit non-filovirus GP pseudotype viruses including VSV (class III GP) and LASV (class I GP) but only at higher (>10 fold) cytotoxic concentrations. In addition, compounds of the invention, although containing an adamantyl or adamantyl-like group as found in influenza drugs amantadine and rimantidine [Wanka L, Iqbal K and Schreiner PR, *The Lipophilic Bullet Hits the Targets: Medicinal Chemistry of Adamantane Derivatives*, Chem Rev (2013), 113: 3516-3604] did not exhibit any activity against the influenza M2 ion channel or live influenza virus at concentrations of 10 uM or greater. The results indicate that the compounds and chemical series described herein inhibit the cell entry of a broad range of filoviruses and/or viruses expressing filovirus glycoproteins while exhibiting no similar activity against the glycoproteins from the other enveloped viruses examined.

Protocol B—Native Ebola plaque and viral yield reduction assays. Biosafety Safety Level 2 (BSL2) pseudotyped viruses expressing filovirus GPs were used (above) as surrogates to facilitate the identification of inhibitors of wild-type Biosafety safety level 4 (BSL4) filoviruses, which may only be studied in highly specialized containment facilities. To confirm activity against native BSL4 Ebola virus example compounds were tested against EBOV (Mayinga) in both plaque forming and viral yield reduction (VYR) assay formats (Table 9) under stringent BSL4 testing requirements. In the plaque assay format confluent or near confluent (Vero) cell culture monolayers in 12-well disposable cell culture plates are prepared. Cells are maintained in MEM or DMEM supplemented with 10% FBS. For antiviral assays the same medium is used but with FBS reduced to 2% or less and supplemented with 1% penicillin/streptomycin. The test compound is prepared at four log$_{10}$ final concentrations in 2×MEM or 2×DMEM. The virus only and cytotoxicity (compound only) controls are run in parallel with each tested compound. Further, a known active drug (favipiravir) is tested as a positive control drug with each test run. Test compounds and positive controls are tested in biological triplicates. The assay is initiated by first removing growth media from the 12-well plates of cells, and infecting cells with 0.01 MOI of virus or about 50 to 100 plaque forming units (pfu). Cells are incubated for 60 min: 100 µl inoculum/well, at 37° C., 5% $CO_2$ with constant gentle rocking. Virus inoculum is removed, cells washed and overlaid with either 1% agarose or 1% methylcellulose diluted 1:1 with 2×MEM and supplemented with 2% FBS and 1% penicillin/streptomycin and supplemented with the corresponding drug concentration. Cells are incubated at 37° C. with 5% $CO_2$ for 10 days. The overlay is removed and plates stained with 0.05% crystal violet in 10% buffered formalin for approximately twenty minutes at room temperature. The plates are washed, dried and the number of plaques counted. The number of plaques in each set of compound dilution is converted to a percentage relative to the untreated virus control. The 50% effective (EC$_{50}$ virus-inhibitory) concentration is calculated by linear regression analysis. The cytotoxicity assay (In vitro Toxicology Assay Kit, Neutral red based; Sigma) is being performed in parallel in 96-well plates following the manufacturer's instructions. Briefly, growth medium is removed from confluent cell monolayers and replaced with fresh medium (total of 100 µl) containing the test compound with the concentrations as indicated for the primary assay. Control wells contain medium with the positive control or medium devoid of compound. A total of up to five replicates are performed for each condition. Plates are incubated for 3, 5, or 10 days at 37° C. with 5% $CO_2$. The plates are stained with 0.033% neutral red for approximately two hours at 37° C. in a 5% $CO_2$ incubator. The neutral red medium is removed by complete aspiration, and the cells rinsed 1× with phosphate buffered solution (PBS) to remove residual dye. The PBS is completely removed and the incorporated neutral red eluted with 1% acetic acid/50% ethanol for at least 30 minutes. Neutral red dye penetrates into living cells: the more intense the red color, the larger the number of viable cells present in the wells. The dye content in each well is quantified using a 96-well spectrophotometer at 540 nm wavelength and 690 nm wavelength (background reading). The 50% cytotoxic (CC$_{50}$, cell-inhibitory) concentrations are then calculated by linear regression analysis. The quotient of CC$_{50}$ divided by EC50 gives the selectivity index (SI$_{50}$) value. The viral yield reduction (VYR) assay format involves similar methodology to that described for the plaque assay format using 12-well plates of cells. Cells are infected and treated with test compound prepared at eight half-log$_{10}$ final concentration and applied in 1 ml of total volume of liquid media. In parallel compounds are added under similar conditions in the absence of virus for CC$_{50}$ determination. To quantify virus particles produced tissue culture supernatant (TCS) aliquots are collected at 72 hours, serially diluted in 10-fold increments and added to fresh monolayer of cells overlaid with 1% agarose mixed 1:1 with 2×MEM supplemented with 2% FBS and 1% penicillin, and the number of plaques determined. Test compounds and a positive control (favipiravir) are tested in biological triplicates. Plotting the $\log_{10}$ of the inhibitor concentration versus $\log_{10}$ of virus produced at each concentration allows calculation of the 90% (one $\log_{10}$) effective concentration or $EC_{90}$ by linear regression. The quotient of $CC_{50}$ divided by $EC_{90}$ gives the $SI_{90}$ selectivity index.

In the plaque assay example compounds showed half-maximal activity ($EC_{50}$) against the native filovirus (EBOV) at sub (0.89) to low (1.1) micromolar concentrations (Table 9). The $SI_{50}$ selectivity index (=$CC_{50}/EC_{50}$) is typically used to determine whether a compound is exhibiting true antiviral inhibitory in vitro. Since $SI_{50}$ values >10 are accepted as confirmation of bona fide inhibitory activity against the virus, rather than artifactual activity reflecting cellular cytotoxicity, the data confirm the compounds as inhibitors of live filovirus. As a further test for antifilovirus inhibitory activity the compounds were then tested in a VYR assay where $EC_{90}$ values (concentration at which 90% virus inhibition is observed) were determined. Compounds exhibiting $SI_{90}$ (=$CC_{50}/EC_{50}$) values approaching 10 are thought to represent compounds that are sufficiently active to provide inhibition of viruses in living mammals. As shown in Table 9 the example compounds tested in the VYR assay exhibit 90% of the live BSL4 EBOV (Mayinga) virus at low micromolar (5.6 and 8.9 uM) concentrations while exhibiting $SI_{90}$ values approaching 10. By comparison the positive control drug compound favipiravir exhibited $EC_{90}$ and $SI_{90}$ values of 333 uM and 3, respectively. The data from the two independent live virus antiviral assays for the example compounds validate the utilization of pseudotyped virus assays to identify bona fide filovirus inhibitors compatible with administration in mammals in vivo as a method of treatment for filovirus infection.

TABLE 9

| Example | Assay Format | $EC_{50}$ (uM) | $SI_{50}$ ($CC_{50}/EC_{50}$) | $EC_{90}$ (uM) | $SI_{90}$ ($CC_{50}/EC_{90}$) |
|---|---|---|---|---|---|
| A78 | Plaque | 1.1 | 41.5 | — | — |
|  | VYR | — | — | 5.6 | 8.2 |
| A80 | Plaque | 0.89 | 95.6 | — | — |
|  | VYR | — | — | 8.9 | 9.6 |

Ebola entry inhibitors identified from pseudotype virus cell assays were tested for efficacy against wild-type Ebola Zaire and Sudan Gulu species (Table 10). Briefly, HeLa cells were inoculated with virus at 1000 pfus along with different doses of compound. On a separate plate, cells were dosed only with compound but no virus to determine cytotoxic $CC_{50}$ values. Virus infection was determined by immunostaining for virus glycoprotein and $EC_{50}$ determined using a high-throughput confocal imaging system. Stained nuclei combined with imaging was used to determine $CC_{50}$.

TABLE 10

| | Ebola Zaire | | Sudan Gulu | |
|---|---|---|---|---|
| Example | $EC_{50}$ uM | SI ($CC_{50}/EC_{50}$) | $EC_{50}$ uM | SI ($CC_{50}/EC_{50}$) |
| D29 | 0.92 | 66.1 | 0.30 | 203 |
| D21 | 0.15 | 48.1 | 0.19 | 38.2 |
| A63 | 0.39 | >16 | ND | ND |
| D24 | 0.44 | 45.6 | 0.26 | 78.7 |
| A68 | 0.18 | 134 | 0.13 | 181 |
| A71 | 0.87 | >6 | ND | ND |
| C2 | 0.25 | 25.3 | 0.06 | 109 |
| A43 | 0.18 | 36.3 | 0.06 | 104 |
| A78 | 0.21 | 268.2 | 0.21 | 264.3 |

TABLE 10-continued

| | Ebola Zaire | | Sudan Gulu | |
|---|---|---|---|---|
| Example | $EC_{50}$ uM | SI ($CC_{50}/EC_{50}$) | $EC_{50}$ uM | SI ($CC_{50}/EC_{50}$) |
| A45 | 0.38 | >28 | ND | ND |
| A80 | 0.13 | 137 | 0.14 | 130 |
| A81 | 1.11 | 48.9 | 0.21 | 266 |
| A85 | 0.10 | 112 | 0.18 | 64 |
| A47 | 0.71 | >8.5 | ND | ND |

Testing compound efficacy in vitro against BSL-4 Ebola viruses while necessary for validation, is a challenge due to the limited sites approved to work with these viruses. However, there is a reasonable translation between BSL-2 pseudotype virus assays and wild-type BSL-4 efficacy that supports the use of pseudotype virus system to drive compound SAR (structure activity relationship) and ranking compounds for testing top candidates for in vitro efficacy against wild-type Ebola viruses.

Examples 11-13. In addition to the ability of compounds to inhibit live filoviruses in vitro, compounds must also have certain drug-like properties for them to be used to inhibit filoviruses and provide methods of treatment for filovirus infection in mammals in vivo. Such compounds may exhibit drug-like properties including but not limited to chemical stability against degradation by and lack of inhibition of liver microsomal CYP p450 enzymes, cell permeability and oral bioavailability (if the drug is to delivered orally) and lack of inhibition of the hERG ion channel, which is associated with cardiac safety [Kerns, E. H. Li, D. *Drug-like Properties: Concepts, Structure Design and Methods from ADME to Toxicity Optimization*, (2008) Academic Press, Burlington MA]. To characterize drug-like properties of the chemical series example compounds were evaluated for metabolic stability in human, mouse and monkey liver microsome assays (Table 11). Compounds exhibiting half-lives ($T_{1/2}$) >60 minutes indicate attractive chemical stability. The demonstration of good microsomal stability in human and nonhuman species facilitates the ability to test and optimize compounds in preclinical animal studies. To reduce or prevent serious/life-threatening conditions caused by exposure to lethal or permanently disabling toxic agents where human efficacy trials are not feasible or ethical (such as filovirus infection) the FDA has provided an approach to test and approve drugs using the Animal Efficacy Rule; whereby the FDA can rely on evidence from animal studies to provide substantial evidence of product effectiveness. In the absence of an epidemic filovirus outbreak in humans with a sufficiently large patient population efficacy data for new methods of treatment for filovirus infection may only be obtained from relevant animal models (e.g., mouse and monkey efficacy studies). Thus the translation of drug like-properties from one species to another significantly facilitates the testing and development of filovirus inhibitor compounds.

TABLE 11

| | Microsomal stability $T_{1/2}$ (min) | | |
|---|---|---|---|
| Ex. | human | Mouse | Monkey |
| A63 | 258 | >210 | 237 |
| A68 | 187 | >240 | 142 |
| A80 | 103 | >120 | 89 |
| A78 | 462 | 267 | >120 |
| A85 | >120 | >120 | 84 |

To further characterize compounds of the invention for the inhibition of filoviruses in mammals in vivo additional drug-like properties of an example compound (compound A78) were determined including solubility, Caco-2 cell permeability, protein binding, Cyp-p450 ambition and hERG ion channel inhibition (Table 12). The example compound was not an inhibitor of human Cyp-p450 enzymes 1A2, 2B6, 2C9, 2C19, 2D6 while for 3A4 it exhibited an $IC_{50}$ of ~28 uM for one substrate and >100 uM for another. The data indicate little if any metabolic liabilities related to Cyp-p450 inhibition (formation of metabolites was measured by LC/MS). In addition, the $IC_{50}$ for compound A78 against the hERG ion channel was >10 uM (the highest concentration tested), which indicates attractive cardiac safety properties. Compound A78 exhibits high protein binding (5 uM test concentration) in PBS, which will factor in for in vivo efficacy studies and therapeutic dosing while its solubility at neutral pH is >500 uM, which will facilitate formulation and dissolution in vivo. To help determine the potential for oral administration we evaluated the permeability of compound A78 (5 uM test concentration in PBS in absence or presence of P-gp inhibitor Verapamil) in the Caco-2 in vitro model where it demonstrated permeability but was found to be effluxed (ratio of B>A/A>B was 4.32) by P-gP; the addition of verapamil, a known P-gP pump inhibitor, inhibited the efflux to a ratio of less than 1.

TABLE 12

| Turbidimetric solubility (uM) | | |
|---|---|---|
| Caco-2 Permeability | Mean A > B | 3.61 |
| $P_{aap}$ ($10^{-6}$ cm s$^{-1}$) | Mean B > A | 15.6 |
| | Efflux ratio | 4.32 |
| P-gp substrate ID | Mean A > B | 8.47 |
| Caco-2 Permeability | Mean B > A | 7.45 |
| (+Verapamil) | Efflux ratio | 0.88 |
| $P_{aap}$ ($10^{-6}$ cm s$^{-1}$) | | |
| PPB fraction bound | Human | 97.5% |
| | Mouse | 98.6% |
| | 1A2, 2B6, 2C9, 2C19, 2D9 | 90 to >100 |
| | 3A4 (Testosterone) | 28 |
| | 3A4 (Midazolam) | >100 |
| hERG $IC_{50}$ (uM) | | >10 |

While the P-gP efflux of compound A78 was not ideal, there remained sufficient absorption to justify exploration of an IV/PO PK (intravenous/oral pharmacokinetic) study in mice of compound A78, When administered to mice (Table 13 and FIG. 1), as either 1 mg/kg IV or 10 mg/kg PO, with analysis of blood plasma samples obtained over a 24 hr period, the example compound was found to demonstrate excellent oral bioavailability (72%), clearance was less than hepatic blood flow and the compound exhibited a half-life of 7.1 hrs and volume of distribution of 14 L/kg. These values are consistent with single or twice daily oral dosing.

drug-like property characterization of example compounds indicate: iii) attractive microsome stability in human, mouse and monkey (potential efficacy models for application of the Animal Efficacy Rule), and other drug-like properties and; iv) mouse PK properties for an example compound were characterized by a long half-life, low clearance and excellent oral bioavailability. These data indicate that the compounds of the invention have sufficient potency and drug-like properties to inhibit filoviruses in mammals in vivo as a method of treatment for filovirus infection.

This is further supported by comparisons between favipiravir and compounds of the invention. Favipiravir is a drug that has been evaluated in human clinical trials during the 2014-16 Ebola outbreak with 111 patients in Guinea as a method of treatment for Ebola virus infection. Although this study was not powered to define efficacy and tolerability the results indicated that patients with moderate levels of viremia (below $10^8$ genome copies/mL) responded to the drug (3-4 log drop in viral load) while those with higher levels (>$10^8$ genome copies/mL) of viremia did not [Sissoko, D. *Experimental Treatment with Favipiravir for Ebola Virus Disease (the J/K/Trial): A Historically Controlled, Single-Arm Proof-of-Concept Trial in Guinea.* (2016) PLoS Med. 2016 Mar. 1; 13(3):e1001967]. While efficacy was limited to those in early stages of infection it was likely limited by certain specific properties including potency and chemical stability, i.e., favipiravirs weak potency against EBOV and short half-life in humans (1-4 hr). In this context it is useful to compare the potency and dosing characteristics of favipiravir with compounds of the current invention to gauge the potential for their efficacy in inhibiting EBOV infection in mammals including humans. The published $EC_{50}$ for favipiravir against native EBOV virus has been reported as 67 uM values [Oestereich, L. et al. *Successful treatment of advanced Ebola virus infection with T-705 (favipiravir) in a small animal model.* Antiviral Res. (2014) 105:17-21] whereas $EC_{50}$ values for example compounds of the invention are ~1 uM (67 times more potent than favipiravir). Furthermore, while we have not tested our compounds in humans and cannot yet compare the bioavailability and pharmacokinetic properties of the two compounds in humans to date comparisons of the half-life of favipiravir (1.8 h with 150 mg/kg twice daily oral dosing) [Mentre, F., et al. *Dose regimen of favipiravir for Ebola virus disease.* Lancet Infect. Dis. (2015) 15(2):150-1] versus example compounds of the invention (7 hr half-life with 10 mg/kg single dosing, for compound A78) indicate that compounds of the current invention are significantly more potent than

TABLE 13

| Dose (mg/kg) | $t_{1/2}$ (h) | $T_{max}$ (h) | Cmax (ng/ml) | $AUC_{last}$ (h · ng/ml) | $AUC_{inf}$ (h · ng/ml) | Cl (ml/h · kg) | Vz (ml/kg) | F (%) |
|---|---|---|---|---|---|---|---|---|
| 1 (IV) | 5.4 | 0.083 | 129 ± 40 | 539 ± 23 | 561 | 1783 | 13900 | NA[a] |
| 10 (PO) | 7.1 | 6 | 239 ± 46 | 3590 ± 576 | 4040 | NC[b] | NC[b] | 72 |

[a]NA, not applicable;
[b]NC, not calculated.

In summary, example compounds of the invention exhibit potencies of i) low nanomolar $EC_{50}$ activity against pseudotyped viruses expressing a range of filovirus glycoproteins and ii) sub to low uM $EC_{50}$ and low uM $EC_{90}$ activities against native BSL4 filovirus with selectivity indices that confirm them as bona fide filovirus inhibitors. In addition, favipiravir and have greater potential to reach higher plasma concentrations in mammals. These comparisons provide compelling support for the utilization of compounds of the invention to inhibit filoviruses including in vitro in mammals and as methods of treatment for filovirus infection in humans.

249
-continued
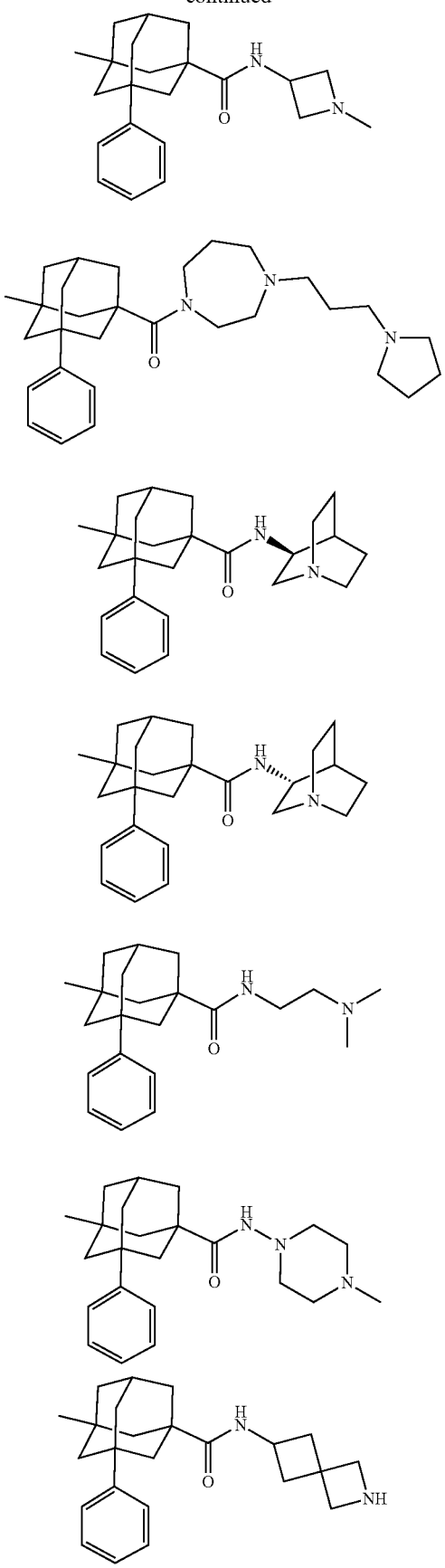
250
-continued
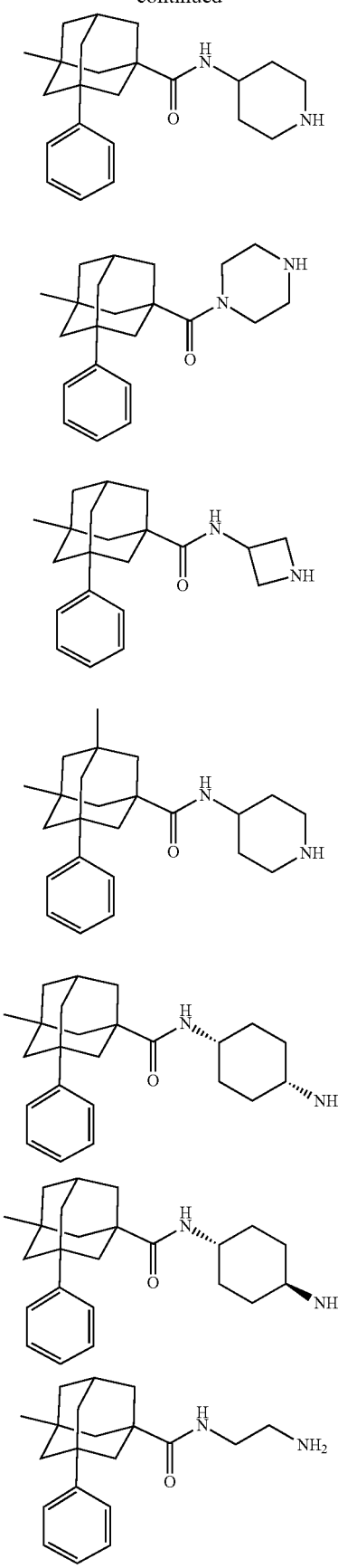

251
-continued
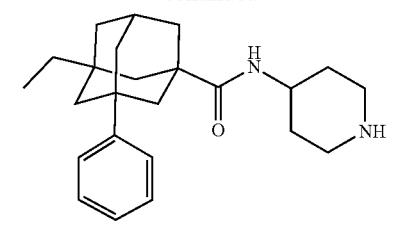
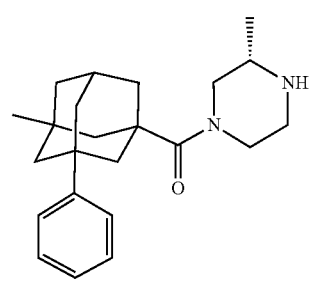
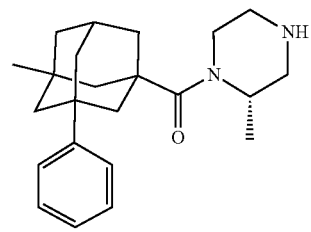
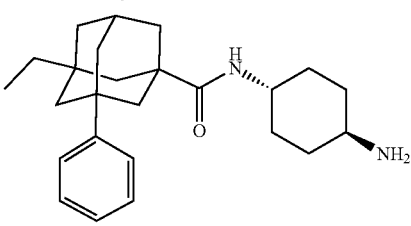
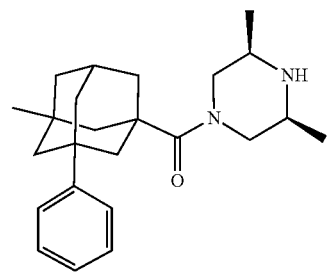
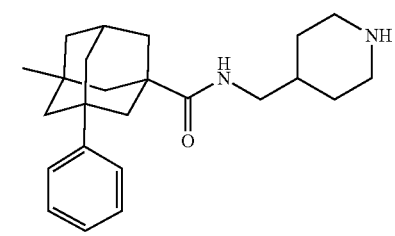
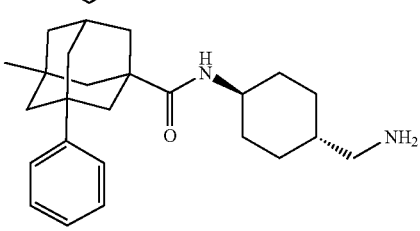
252
-continued
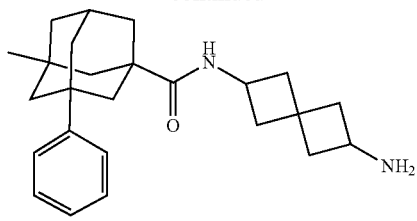
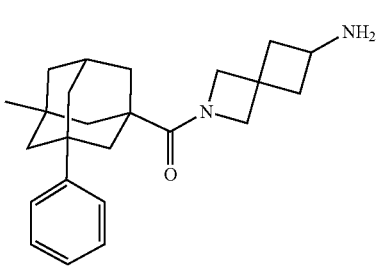
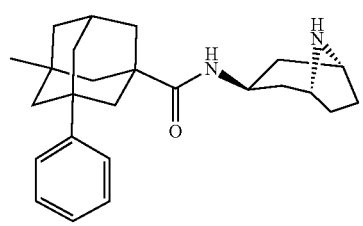
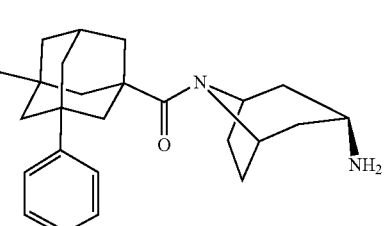
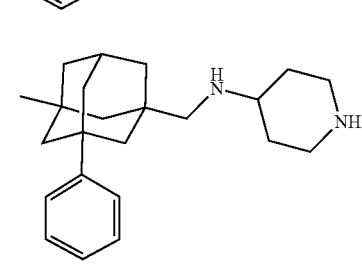
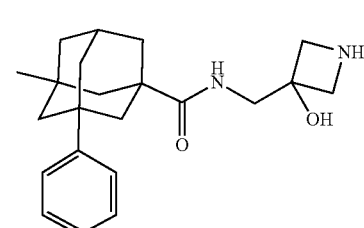
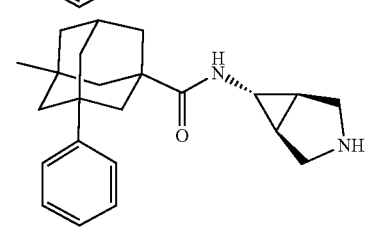

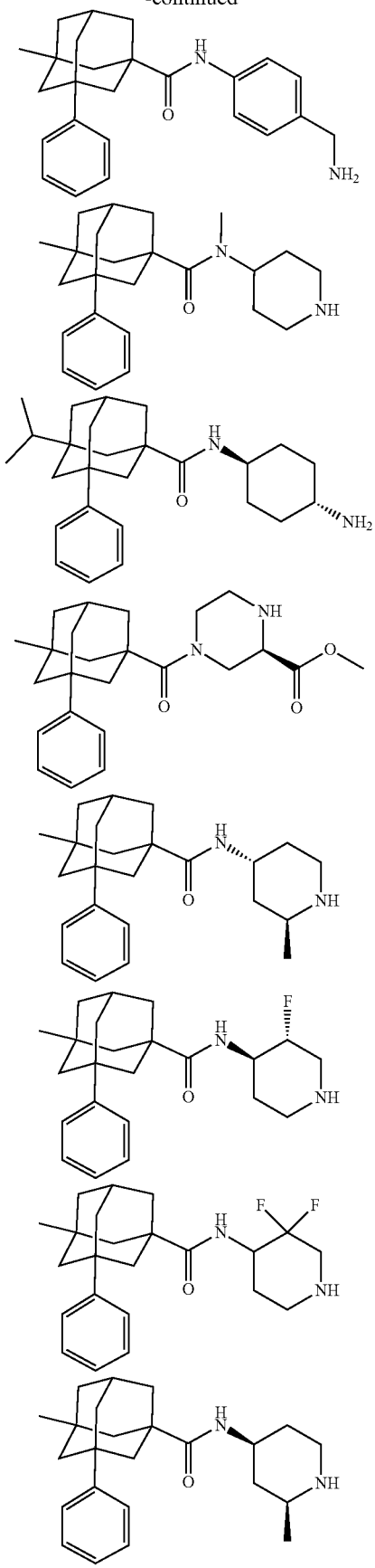
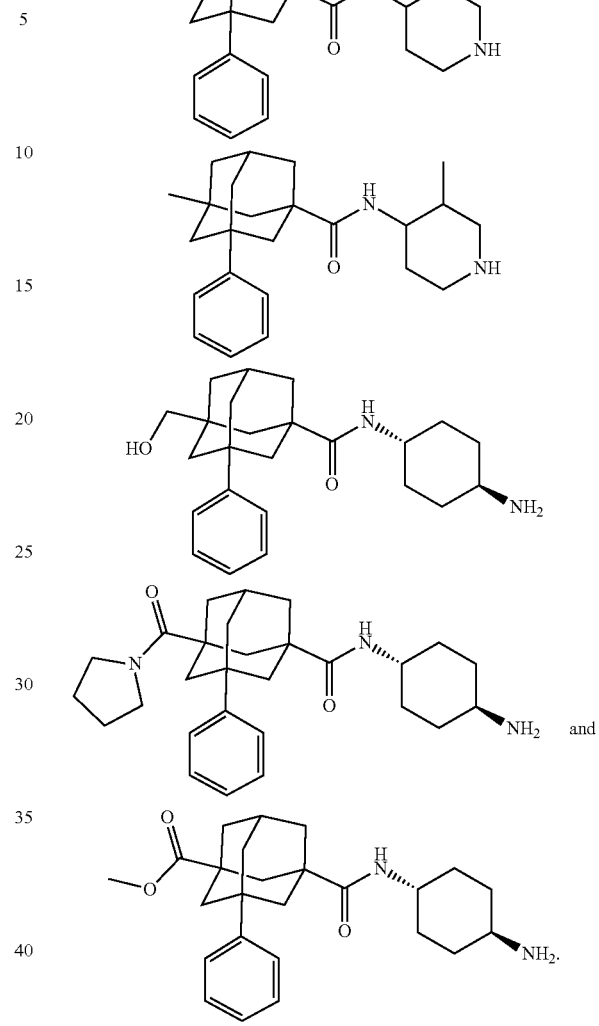
20. The compound of claim 19 selected from the group consisting of
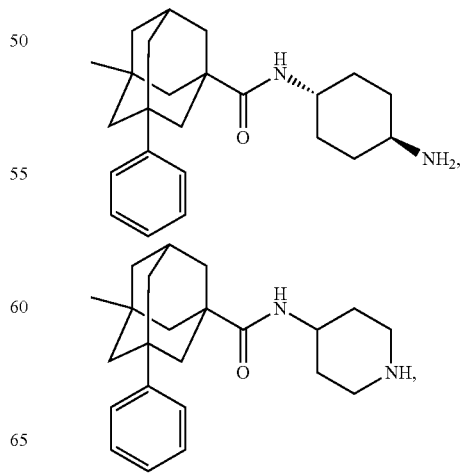

-continued
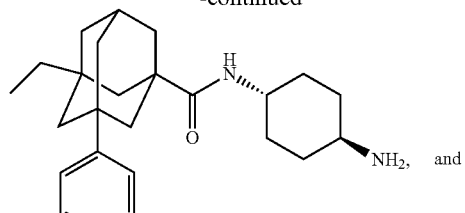
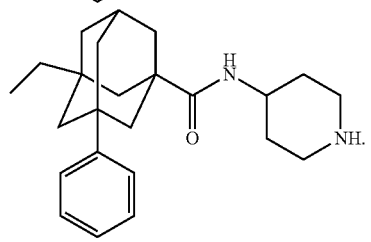

What is claimed is:

1. A method of treating infections associated with Filoviridae enveloped virus, or any virus expressing filovirus glycoproteins to mediate cell entry, comprising administering to a subject in need thereof a composition comprising a therapeutically effective amount of a compound of Structural Formula I

I or a pharmaceutically acceptable salt thereof, and a pharmaceutically acceptable carrier, diluent, or vehicle, wherein:

X is C-D, and Y is a bond;
D is selected from the group consisting of $R^1$ is ($C_6$ to $C_{10}$) aryl, wherein (C to $C_{10}$) aryl is optionally substituted with at least one $R^{13}$ group;

$R^2$ is selected from ($C_1$ to $C_{10}$) alkyl, ($C_1$ to $C_{10}$) alkoxy, and —C(O)O$R^{12}$, wherein ($C_1$ to $C_{10}$) alkyl is optionally substituted with at least one $R^{13}$ group;

$R^3$ is selected from hydrogen and ($C_1$ to $C_{10}$) alkyl;

each $R^8$ is independently selected from hydrogen and ($C_1$ to $C_{10}$) alkyl;

each of the $R^{9a}$ and $R^{9b}$ is independently selected from hydrogen, halogen, ($C_1$ to $C_{10}$) alkyl, and —C(O)O$R^{12}$;

$R^{12}$ is ($C_1$ to $C_{10}$) alkyl;

each $R^{13}$ is independently selected from hydrogen, OH, nitro, ($C_1$ to $C_{10}$) alkyl, and ($C_1$ to $C_{10}$) alkoxy;

j is independently selected from 0 or 1.

2. The method of claim 1, wherein the infection associated with Filoviridae enveloped virus is selected from the group consisting of Ebolavirus and Marburgvirus.

3. The method of claim 2, where infection associated with Filoviridae enveloped virus is is Ebolavirus.

4. The method of claim 3, further comprising administering a therapeutic amount of a therapeutic agent selected from the group consisting of ribavirin viral RNA-dependent-RNA polymerase inhibitors, monoclonal antibody therapies, vaccines, small interfering RNAs, microRNAs, and immunomodulators.

5. The method of claim 4, wherein the viral RNA-dependent-RNA polymerase inhibitors are selected from the group consisting of favipiravir, triazavirin, and remdesivir.

6. The method of claim 4, wherein the monoclonal antibody therapies are selected from the group consisting of ZMapp, REGN3470-3471-3479, and mAb 114.

7. The method of claim 4, wherein the vaccines are selected from the group consisting of cAd3-EBOZ and rVSV-ZEBOV.

8. The method of claim 4, wherein Ebolavirus glycoprotein is inhibited.

9. A method of treating infections associated with Filoviridae A enveloped virus, or any virus expressing filovirus glycoproteins to mediate cell entry, comprising administering to a subject in need thereof, composition comprising a therapeutically effective amount of a compound or a pharmaceutically acceptable salt thereof, and a pharmaceutically acceptable A carrier, diluent, or vehicle, wherein the compound is selected from the group consisting of:

241
-continued
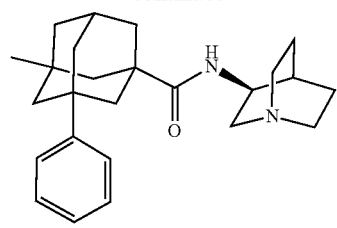
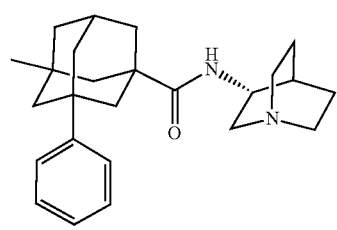
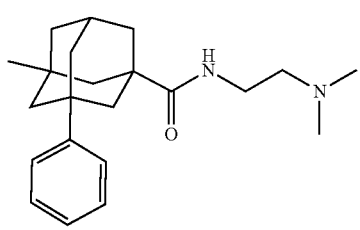
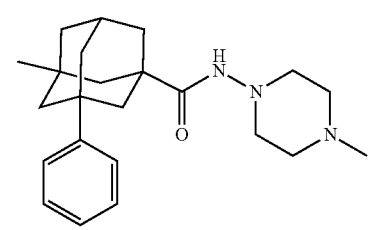
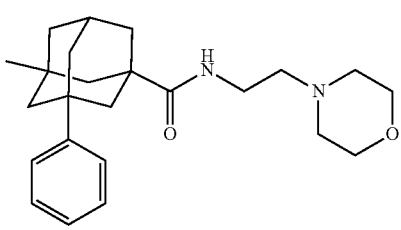
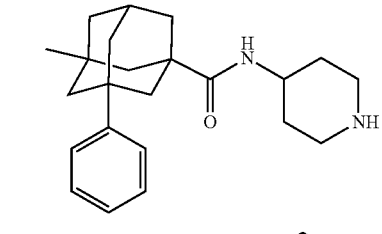
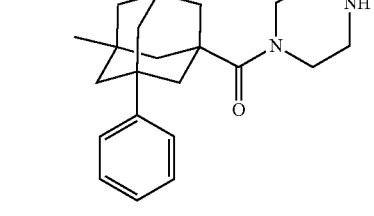
242
-continued
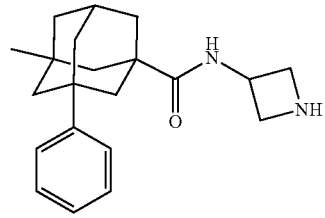
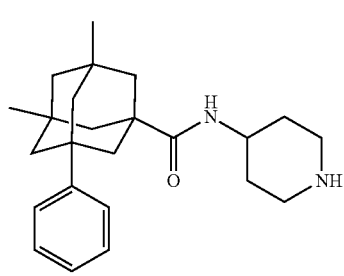
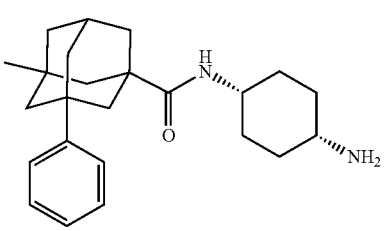
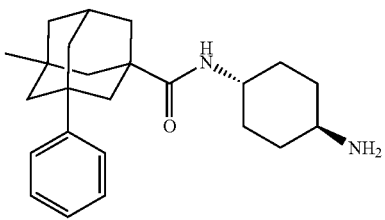
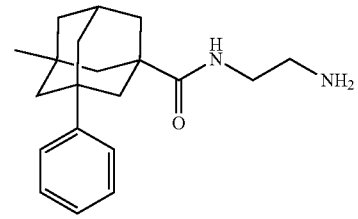
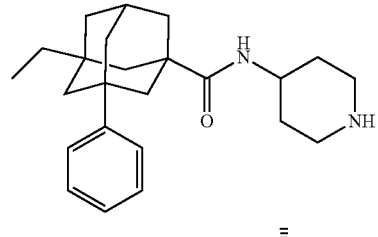
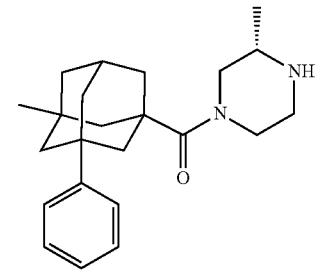

243
-continued
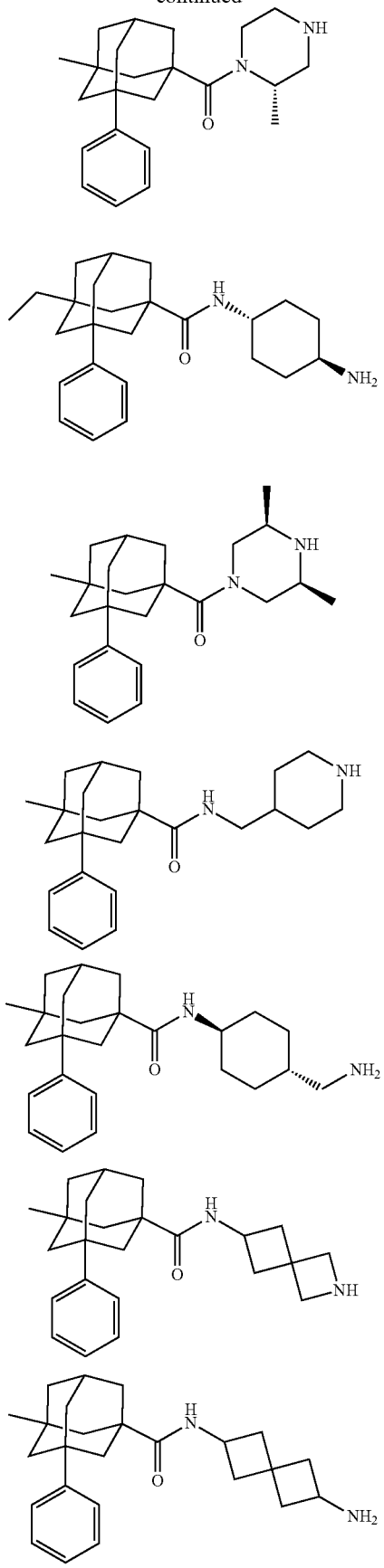
244
-continued
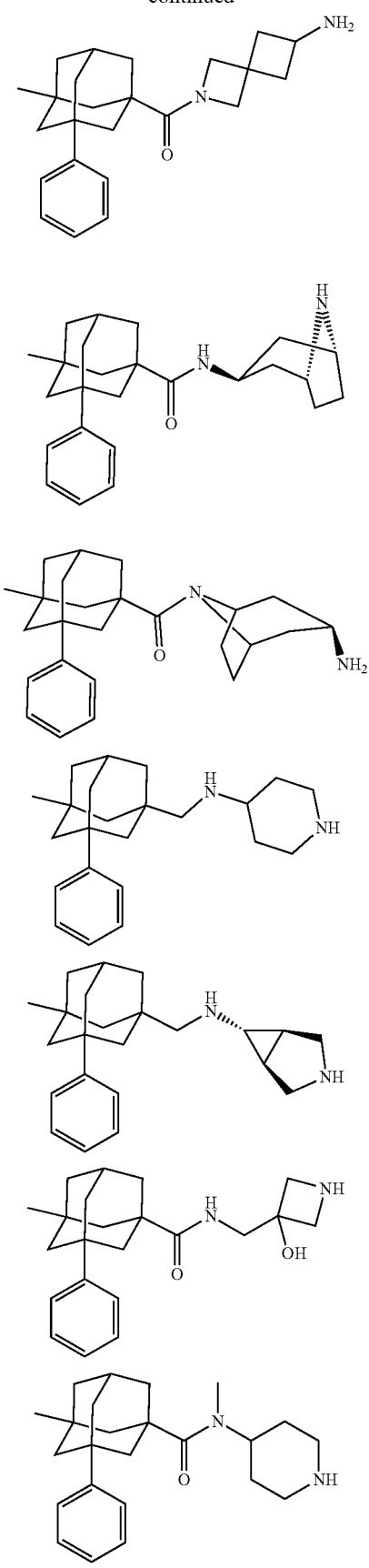

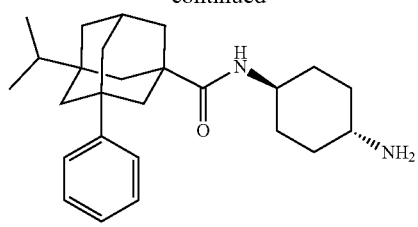
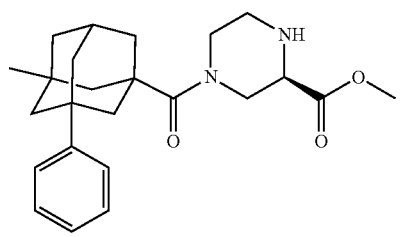
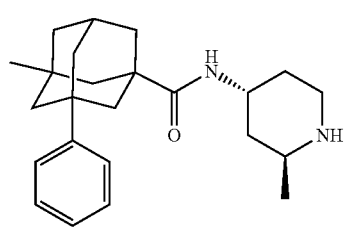
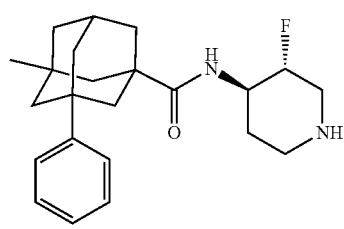
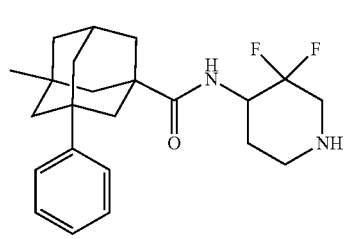
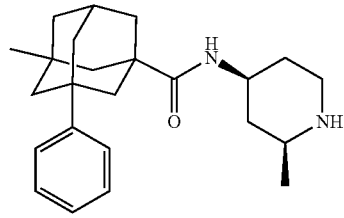
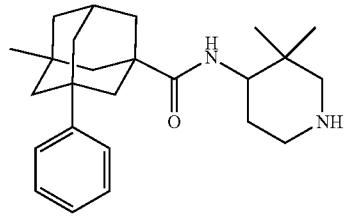
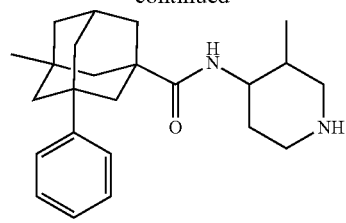
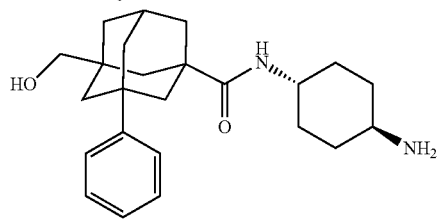
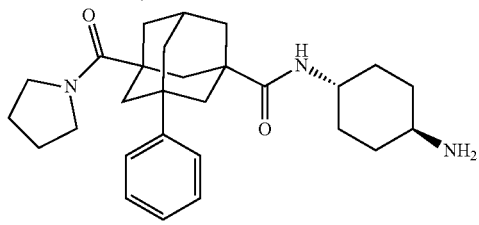
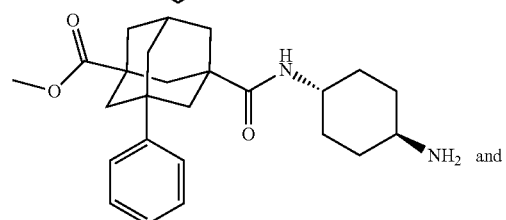
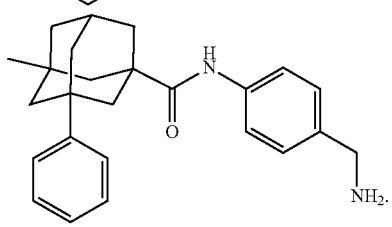
10. The method of claim 9, wherein the compound is selected from the group consisting of:
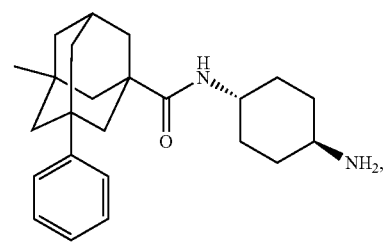
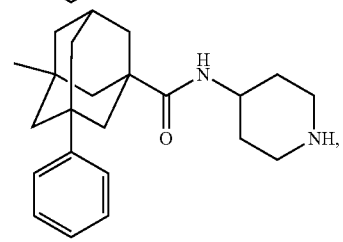

11. The method of claim 10, wherein the infections associated with Filoviridae enveloped virus is selected from the group consisting of Ebolavirus and Marburgvirus.

12. The method of claim 11, wherein the the infection associated with Filoviridae enveloped virus is Ebolavirus.

13. The method of claim 12, further comprising administering a therapeutic amount of a therapeutic agent selected from the group consisting of ribavirin viral RNA-dependent-RNA polymerase inhibitors, monoclonal antibody therapies, vaccines, small interfering RNAs, microRNAs, and immunomodulators.

14. The method of claim 13, wherein the viral RNA-dependent-RNA polymerase inhibitors are selected from the group consisting of favipiravir, triazavirin, and remdesivir.

15. The method of claim 13, wherein the monoclonal antibody therapies are selected from the group consisting of ZMapp, REGN3470-3471-3479, and mAb 114.

16. The method of claim 13, wherein the vaccines are selected from the group consisting of cAd3-EBOZ and rVSV-ZEBOV.

17. A compound represented by Structural Formula I or a pharmaceutically acceptable salt, and a pharmaceutically acceptable carrier, diluent, or vehicle thereof, wherein:

X is C-D, and Y is a bond;

D is selected from the group consisting of $R^1$ is selected from (C to $C_{10}$) aryl, wherein (C to $C_{10}$) aryl is optionally substituted with at least one $R^{13}$ group;

$R^2$ is selected from ($C_1$ to $C_{10}$) alkyl, ($C_1$ to $C_{10}$) alkoxy, and —C(O)O$R^{12}$, wherein ($C_1$ to $C_{10}$) alkyl is optionally substituted with at least one $R^{13}$ group;

$R^3$ is selected from hydrogen and ($C_1$ to $C_{10}$) alkyl;

each $R^8$ is independently selected from hydrogen and ($C_1$ to $C_{10}$) alkyl;

each of the $R^{9a}$ and $R^{9b}$ is independently selected from hydrogen, halogen, ($C_1$ to $C_{10}$) alkyl, and —C(O)O$R^{12}$;

each of the $R^{12}$ is independently selected from ($C_1$ to $C_{10}$) alkyl;

each $R^{13}$ is independently selected from hydrogen, OH, nitro, ($C_1$ to $C_{10}$) alkyl, and ($C_1$ to $C_{10}$) alkoxy;

j is independently selected from 0 or 1.

18. The compound of claim 17, wherein:

$R^3$ is hydrogen.

19. A compound selected from the group consisting of: